US006903102B2

(12) United States Patent
Guzi et al.

(10) Patent No.: US 6,903,102 B2
(45) Date of Patent: Jun. 7, 2005

(54) 17β-HYDROXYSTEROID DEHYDROGENASE TYPE 3 INHIBITORS FOR THE TREATMENT OF ANDROGEN DEPENDENT DISEASES

(75) Inventors: Timothy J. Guzi, Chatham, NJ (US); Kamil Paruch, Cranford, NJ (US); Alan K. Mallams, Mallams, NJ (US); Jocelyn D. Rivera, Monmouth Junction, NJ (US); Ronald J. Doll, Convent Station, NJ (US); Viyyoor M. Girijavallabhan, Parsippany, NJ (US); Jonathan A. Pachter, Maplewood, NJ (US); Yi-Tsung Liu, Morris Township, NJ (US); Anil K. Saksena, Upper Montclair, NJ (US)

(73) Assignee: Schering Corporation, Kenilworth, NJ (US)

( * ) Notice: Subject to any disclaimer, the term of this patent is extended or adjusted under 35 U.S.C. 154(b) by 161 days.

(21) Appl. No.: 10/235,627

(22) Filed: Sep. 5, 2002

(65) Prior Publication Data

US 2004/0132736 A1 Jul. 8, 2004

Related U.S. Application Data

(60) Provisional application No. 60/317,715, filed on Sep. 6, 2001.

(51) Int. Cl.[7] .................... A61K 31/497; C07D 401/00; C07D 403/00; C07D 405/00; C07D 409/00
(52) U.S. Cl. .......................... 514/253.01; 514/253.13; 544/360; 544/364
(58) Field of Search .................. 514/253.01, 253.13; 544/360, 364

(56) References Cited

U.S. PATENT DOCUMENTS

| | | | |
|---|---|---|---|
| 5,350,852 A | 9/1994 | Emonds-Alt et al. | 544/336 |
| 5,432,175 A | 7/1995 | Piwinski et al. | 514/252 |
| 5,620,989 A | 4/1997 | Harrison et al. | 514/317 |
| 5,654,316 A | 8/1997 | Carruthers et al. | 514/307 |
| 5,665,735 A | 9/1997 | Friary et al. | 514/318 |
| 5,688,960 A | 11/1997 | Shankar | 546/202 |
| 5,691,362 A | 11/1997 | McCormick et al. | 514/339 |
| 5,696,267 A | 12/1997 | Reichard et al. | 546/217 |
| 5,719,156 A | 2/1998 | Shue et al. | 514/255 |
| 5,760,018 A | 6/1998 | Baker et al. | 514/63 |
| 5,783,579 A | 7/1998 | McCormick | 514/255 |
| 5,789,422 A | 8/1998 | Reichard et al. | 514/327 |
| 5,840,725 A | 11/1998 | Reichard et al. | 514/252 |
| 5,945,428 A | 8/1999 | Shih et al. | 514/278 |
| 5,968,929 A | 10/1999 | Blythin et al. | 514/215 |
| 6,063,926 A | 5/2000 | Reichard et al. | 546/187 |
| 6,204,265 B1 | 3/2001 | Reichard et al. | 514/235.8 |
| 6,391,865 B1 * | 5/2002 | Baroudy et al. | 514/63 |

FOREIGN PATENT DOCUMENTS

| | | | |
|---|---|---|---|
| JP | 1 122 242 A1 | 9/1999 | C07D/213/74 |
| WO | WO86/01105 | 2/1986 | |
| WO | WO90/10462 | 9/1990 | |
| WO | WO91/00731 | 1/1991 | |
| WO | WO91/00733 | 1/1991 | |
| WO | WO94/10165 | 5/1994 | |
| WO | WO94/13639 | 6/1994 | |
| WO | WO94/26767 | 11/1994 | |
| WO | WO94/29309 | 12/1994 | |
| WO | WO95/19344 | 7/1995 | |
| WO | WO96/26201 | 8/1996 | |
| WO | WO97/11162 | 3/1997 | |
| WO | WO00/43008 | 7/2000 | |
| WO | WO 01/58891 A2 | 8/2001 | C07D/401/04 |

OTHER PUBLICATIONS

Hawley's Condensed Chemical Dictionary, 12th ed., Richard J. Lewis, Sr. , © 1993 by Van Nostrand Reinhold. p. 594.*
Concise Chemical Dictionary, edited by Drs. Hans–Dieter Jakubke and Hans Jeschkeit, © 1993 by Walter de Gruyter & Co., p. 490.*
McGraw–Hill Dictionary of Chemical Terms, 3rd ed. edited by Sybil P. Parker, © 1984 McGraw–Hill, Inc., p. 200.*
Mallams et al, J. Med. Chem. vol. 41, pp. 877–893 (1998).*
Poirier, Donald, "Inhibitors of 17–beta–Hydroxysteroid Dehydrogenases" Current Medicinal Chemistry, vol. 10, pp. 453–477 (2003).*

(Continued)

*Primary Examiner*—James O. Wilson
*Assistant Examiner*—Zachary C. Tucker
(74) *Attorney, Agent, or Firm*—Palaiyur S. Kalyanaraman; Allan N. Kutzenco; Margaret M. Albanese

(57) ABSTRACT

There are disclosed compounds of the formula (I):

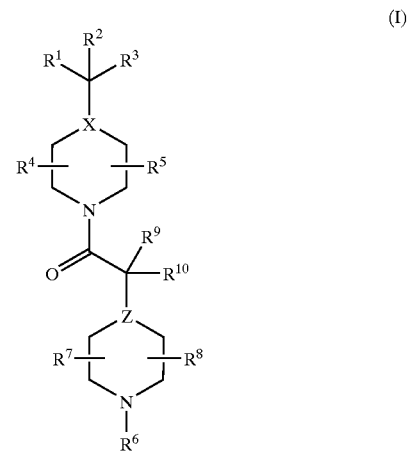

prodrugs thereof, or pharmaceutically acceptable salts of the compounds or of said prodrugs which are useful as inhibitors of Type 3 17β-Hydroxysteroid Dehydrogenase. Also disclosed are pharmaceutical compositions containing said compounds and their use for the treatment or prevention of androgen dependent diseases.

29 Claims, No Drawings

OTHER PUBLICATIONS

Goodman & Gilman's The Pharmacological Basis of Therapeutics, 10th ed., pp. 1635–1648, McGraw–Hill Medical Publishing Division © 2001.*

The Merck Manual, 16th ed., pp. 1092–1093, 2277–2278 and 2429–2431, Merck Research Laboratories, Merck & Co., Rahway, NJ © 1992.*

Smith et al, "Inhibitors of steroidogenesis as agents for the treatment of hormone–dependent cancers" Expert Opinion on Therapeutic Patents, vol. 11(5), pp. 789–824 (2001).*

Debeljuk, L., Lasaga, M., *Modulation of the hypothalamo- -pituitary–gonadal axis and the pineal gland by neurokinin A, neuropeptide K and neuropeptide γ*, Peptides 20 (1999), 285–299.

* cited by examiner

17β-HYDROXYSTEROID DEHYDROGENASE TYPE 3 INHIBITORS FOR THE TREATMENT OF ANDROGEN DEPENDENT DISEASES

CROSS-REFERENCE TO RELATED APPLICATION

This application claims priority to U.S. Provisional Application No. 60/317,715, filed 6 Sep. 2001.

BACKGROUND

1. Field of the Invention

The invention relates to novel inhibitors of Type 3 17β-Hydroxysteroid Dehydrogenase, pharmaceutical compositions containing the compounds and the use of the compounds for the treatment or prevention of androgen dependent diseases.

2. Description of Related Art

Androgen dependent diseases, i.e. diseases whose onset or progress is aided by androgenic activity, are well known. These diseases include but are not limited to prostate cancer, benign prostatic hyperplasia, acne, seborrhea, hirsutism, androgenic alopecia, precocious puberty, adrenal hyperplasia and polycystic ovarian syndrome. Estrogen dependent diseases, i.e. diseases whose onset or progress is aided by estrogenic activity are also well known. These include but are not limited to breast cancer, endometriosis, leiomyoma and precocious puberty.

Androgenic and estrogenic activity may be suppressed by administering androgen receptor antagonists or estrogen receptor antagonists respectively. See e.g. WO 94/26767 and WO 96/26201. Androgenic and estrogenic activity may also be reduced by suppressing androgen or estrogen biosynthesis using inhibitors of enzymes that catalyze one or more steps of such biosynthesis. Type 3 17β-Hydroxysteroid Dehydrogenase (17β-HSD3) is the primary enzyme that converts androstenedione to testosterone in the testes. Androgenic and estrogenic activity may also be reduced by suppressing ovarian or testicular secretions by known methods. See e.g. WO 90/10462, WO 91/00731, WO 91/00733, and WO 86/01105. Type 5 17B-Hydroxysteroid Dehydrogenase is described in WO 97/11162. Novel inhibitors of both Type 3 and Type 5 17B-Hyroxysteroid Dehydrogenase are described in WO 99/46279.

U.S. Pat. No. 5,665,735 discloses compounds useful in the treatment of asthma, allergy and inflammation, which are of the formula:

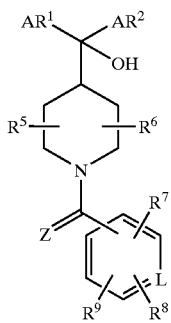

or a pharmaceutically acceptable salt or solvate thereof, wherein:

$AR^1$ (or $Ar^1$) represents

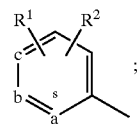

$AR^2$ (or $Ar^2$) represents

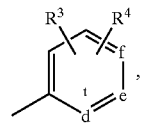

or a five-membered heterocyclic aromatic group selected from the group consisting of Formulas I to XII:

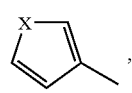

(I)

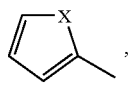

(II)

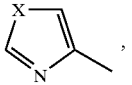

(III)

(IV)

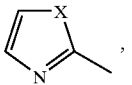

(V)

(VI)

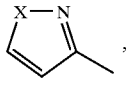

(VII)

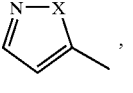

(VIII)

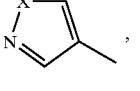

(IX)

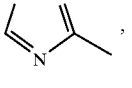

(X)

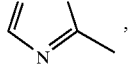

(XI)

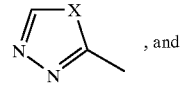

, and (XII)

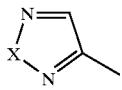

wherein X represents O, S.

U.S. Pat. No. 5,432,175 discloses compounds which posess anti-allergic and anti-inflammatory activity and are of the formula:

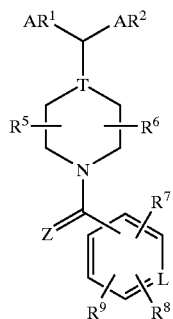

wherein:

$AR^1$ represents

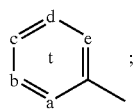

$AR^2$ represents

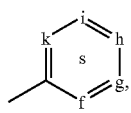

or a five-membered heterocyclic aromatic group containing at least one

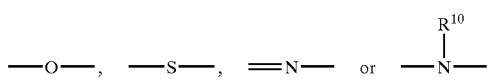

in the ring structure,

T represents CH, C or N.

Current therapies for the treatment of androgenic and estrogenic dependent diseases include the use of glucocorticoids to block adrenal secretions, and luteinizing hormone releasing hormone (LHRH) agonists which cause medical castration. Both therapies are associated with undesirable side effects. An improved therapy would include compounds that specifically inhibit type 3 17β-Hydroxysteroid dehydrogenase, while avoiding inhibition of other 17β-Hydroxysteroid dehydrogenases. Such an improvement is provided by this invention.

SUMMARY OF THE INVENTION

The invention provides novel compounds represented by Formula (I):

(I)

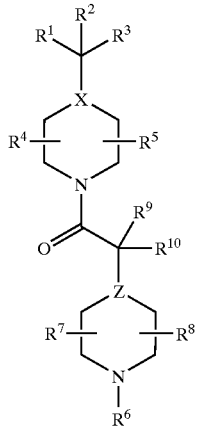

a prodrug thereof, or a pharmaceutically acceptable salt or solvate of the compound or of said prodrug wherein, $R^1$ and $R^2$ are the same or different and are independently selected from the group consisting of aryl, heteroaryl, arylalkyl, and heteroarylalkyl, each optionally substituted with one to six groups selected from the group consisting of:

a) halogen;
b) —$OCF_3$ or —$OCHF_2$;
c) —$CF_3$;
d) —CN;
e) alkyl or $R^{18}$-alkyl;
f) heteroalkyl or $R^{18}$-heteroalkyl;
g) aryl or $R^{18}$-aryl;
h) heteroaryl or $R^{18}$-heteroaryl;
i) arylalkyl or $R^{18}$-arylalkyl;
j) heteroarylalkyl or $R^{18}$-heteroarylalkyl;
k) hydroxy;
l) alkoxy;
m) aryloxy;
n) —$SO_2$-alkyl;
o) —$NR^{11}R^{12}$;
p) —$N(R^{11})C(O)R^{13}$,
q) methylenedioxy;
r) difluoromethylenedioxy;
s) trifluoroalkoxy;
t) —$SCH_3$ or —$SCF_3$; and
u) —$SO_2CF_3$ or —$NHSO_2CF_3$;

$R^3$ is H, —OH, alkoxy or alkyl, provided that when X is N, $R^3$ is not —OH or alkoxy;

$R^4$, $R^5$, $R^7$ and $R^8$ are the same or different and are independently selected from the group consisting of: H, —OH, —$OR^{14}$, —$NR^{11}R^{12}$, —$N(R^{11})C(O)R^{13}$, alkyl, aryl, cycloalkyl, arylalkyl, heteroalkyl, heteroaryl, heteroarylalkyl, heterocycloalkyl,

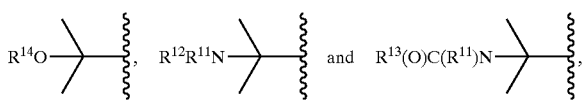

provided that when Z and/or X is N, then $R^4$, $R^5$, $R^7$ and $R^8$ are each not —OH, —$OR^{14}$, —$NR^{11}R^{12}$ or —$N(R^{11})C(O)R^{13}$;

$R^6$ is selected from the group consisting of —C(O)$R^{15}$ and —SO$_2$$R^{15}$;

$R^9$ and $R^{10}$ are the same or different and are independently selected from the group consisting of: H, F, —CF$_3$, alkyl, cycloalkyl, arylalkyl, heteroalkyl, heteroarylalkyl, heterocycloalkyl, hydroxy, alkoxy, aryloxy, —NR$^{11}$R$^{12}$ and —N(R$^{11}$)C(O)R$^{13}$; provided that when Z is N, then $R^9$ and $R^{10}$ are each not F, hydroxy, alkoxy, aryloxy, —NR$^{11}$R$^{12}$ or —N(R$^{11}$)C(O)R$^{13}$;

$R^{11}$ is selected from the group consisting of H, alkyl, aryl and heteroaryl;

$R^{12}$ is selected from the group consisting of H, alkyl, aryl and heteroaryl;

$R^{13}$ is selected from the group consisting of alkyl, alkoxy and aryloxy;

$R^{14}$ is selected from the group consisting of H, alkyl, aryl and heteroaryl;

$R^{15}$ is selected from the group consisting of: —NR$^{16}$R$^{17}$, —OR$^{16}$, alkyl, cycloalkyl, heterocycloalkyl, aryl, arylalkyl and heteroarylalkyl, each optionally substituted with $R^{18}$;

$R^{16}$ and $R^{17}$ are the same or different and are independently selected from the group consisting of: H, alkyl, aryl, arylalkyl, heteroalkyl and heteroaryl, each optionally substituted with $R^{18}$, provided that when $R^{15}$ is —OR$^{16}$, $R^{16}$ is not H;

$R^{18}$ is one to four substituents each independently selected from the group consisting of: lower alkyl, halo, cyano, nitro, haloalkyl, hydroxy, alkoxy, alkoxy carbonyl, carboxy, carboxyalkyl, carboxamide, mercapto, amino, alkylamino, dialkylamino, sulfonyl, sulfonamido, cycloalkyl, heterocycloalkyl, heterocycloalkylalkyl, aryl and heteroaryl; and X and Z are the same or different and are independently selected from the group consisting of C and N.

One aspect of the present invention relates to a pharmaceutical composition comprising a compound of formula (I) in combination or association with a pharmaceutically acceptable carrier or diluent.

Another aspect of the present invention relates to a method of inhibiting type 3 17β-hydroxysteroid dehydrogenase in a mammal, e.g. a human, which comprises administering to a patient in need thereof of an effective amount, i.e. a therapeutically effective amount, of a compound of formula (I), or a pharmaceutically acceptable salt or solvate thereof.

In another aspect, the present invention provides a method of treating or preventing androgen or estrogen dependent diseases in a mammal, e.g. a human, which comprises administering to a patient in need thereof of a therapeutically effective amount of a compound of formula (I), or a pharmaceutically acceptable salt or solvate thereof.

In yet another aspect, the present invention provides a method of treating or preventing prostate cancer, and other androgen-dependent neoplasms, benign prostatic hyperplasia, prostatic intraepithelial neoplasia, androgenic alopecia (i.e. pattern baldness in both male and female patients), hirsutism, polycystic ovary syndrome and acne in a mammal, e.g. a human, which comprises administering to a patient in need thereof, a therapeutically effective amount of a compound of formula (I), or a pharmaceutically acceptable salt or solvate thereof.

Also, the present invention provides a method of treating or preventing androgen-dependent diseases comprising administering to a mammal in need thereof an effective amount of a compound of the invention in combination with at least one anti-androgenic agent (i.e. agents that decrease androgen synthesis or activity).

This invention also provides a method of treating or preventing benign prostatic hyperplasia comprising administering an effective amount of a compound of the invention in combination with at least one agent useful in the treatment or prevention of benign prostatic hyperplasia.

This invention further provides a method of treating or preventing hair loss, comprising administering an effective amount of a compound of the invention in combination with at least one agent useful in the treatment or prevention of alopecia, e.g., potassium channel agonists or 5α-reductase inhibitors.

The present invention also provides a method of treating or preventing proliferative diseases, especially cancers (tumors), comprising administering an effective amount (e.g., a therapeutically effective amount) of (1) a compound of the invention, described herein, to a mammal (e.g., a human) in need of such treatment in combination with (2) an effective amount of an anti-cancer agent i.e., a chemotherapeutic agent, biological agent, and/or surgery, e.g., prostatectomy and/or radiation therapy.

DETAILED DESCRIPTION OF THE PREFERRED EMBODIMENTS

Unless where indicated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", etc.

Unless otherwise known, stated or shown to be to the contrary, the point of attachment for a multiple term substituent (multiple terms that are combined to identify a single moiety) to a subject structure is through the last named term of the multiple term. For example, a cycloalkylalkyl substituent attaches to a targeted through the latter "alkyl" portion of the substituent (e.g., Structure-alkyl-cycloalkyl).

When any variable (e.g., aryl, $R^2$) occurs more than one time in any constituent, its definition on each occurrence is independent of its definition at every other occurrence. Also, combinations of substituents and/or variables are permissible only if such combinations result in stable compounds.

Unless stated, shown or otherwise known to be the contrary, all atoms illustrated in chemical formulas for covalent compounds possess normal valencies. Thus, hydrogen atoms, double bonds, triple bonds and ring structures need not be expressly depicted in a general chemical formula.

Double bonds, where appropriate, may be represented by the presence of parentheses around an atom in a chemical formula. For example, a carbonyl functionality, —CO—, may also be represented in a chemical formula by —C(O)— or —C(=O)—. Similarly, a double bond between a sulfur atom and an oxygen atom may be represented in a chemical formula by —SO—, —S(O)— or —S(=O)—. One skilled in the art will be able to determine the presence or absence of double (and triple bonds) in a covalently-bonded molecule. For instance, it is readily recognized that a carboxyl functionality may be represented by —COOH, —C(O)OH, —C(=O)OH or —CO$_2$H.

The term "substituted," as used herein, means the replacement of one or more atoms or radicals, usually hydrogen atoms, in a given structure with an atom or radical selected from a specified group. In the situations where more than one atom or radical may be replaced with a substituent selected from the same specified group, the substituents may be, unless otherwise specified, either the same or different at every position. Radicals of specified groups, such as alkyl, cycloalkyl, heterocycloalkyl, aryl and heteroaryl groups, independently of or together with one another, may be substituents on any of the specified groups, unless otherwise indicated.

"Alkyl" represents a straight or branched saturated hydrocarbon chain having the designated number of carbon atoms. Preferably the number of carbon atoms is 1 to 20, more preferably 1 to 10, most preferably the number of carbon atoms is 1 to 6. Where the number of carbon atoms is not specified, 1 to 20 carbons are intended. "Lower alkyl" represents a straight or branched hydrocarbon chain having 1 to 6 carbon atoms.

The term "chemically-feasible" is usually applied to a ring structure present in a compound and means that the ring structure would be expected to be stable by a skilled artisan.

The term "cycloalkyl" or "cycloalkane," as used herein, means an unsubstituted or substituted, saturated, stable, non-aromatic, chemically-feasible carbocyclic ring, having, preferably, from three to fifteen carbon atoms, more preferably, from three to eight carbon atoms. The cycloalkyl carbon ring radical is saturated and may be fused, for example, benzofused, with one to two cycloalkyl, aromatic, heterocyclic or heteroaromatic rings. The cycloalkyl may be attached at any endocyclic carbon atom that results in a stable structure. Preferred carbocyclic rings have from five to six carbons. Examples of cycloalkyl radicals include cyclopropyl, cyclobutyl, cyclopentyl, cyclohexyl, cycloheptyl, and the like.

The term "heterocycloalkyl" refers to a cycloalkyl group which has at least one heteroatom.

The term "halogen" or "Halo" (halogen) is intended to include fluorine, chlorine, bromine or iodine.

The term "alkoxy," as used herein, means an oxygen atom bonded to a hydrocarbon chain, such as an alkyl group (—O-alkyl). Representative alkoxy groups include methoxy, ethoxy and isopropoxy groups.

The term "aryloxy" as used herein, means an oxygen atom bonded to an aryl group (—O-aryl).

The term "fluoroalkyl" represents a straight or branched saturated hydrocarbon chain having the designated number of carbon atoms, substituted with one or more fluorine atoms. Where the number of carbon atoms is not specified, 1 to 20 carbons are intended.

"Aryl" refers to a mono- or bicyclic ring system having one or two aromatic rings including, but not limited to, phenyl, naphthyl, indenyl, tetrahydronaphthyl, indanyl, anthracenyl, fluorenyl and the like. The aryl group can be unsubstituted or substituted with one, two, or three substituents independently selected from lower alkyl, halo, cyano, nitro, haloalkyl, hydroxy, alkoxy, carboxy, carboxyalkyl, carboxamide, mercapto, sulfhydryl, amino, alkylamino, dialkylamino, sulfonyl, sulfonamido, aryl and heteroaryl.

The term "arylakyl" refers to an aryl group bonded directly to a subject structure through an alkyl group.

The term "heteroatom," as used herein, means a nitrogen, sulfur, or oxygen atom. Multiple heteroatoms in the same group may be the same or different.

The term "heteroalkyl" refers to an alkyl group which has at least one heteroatom.

The term "heterocycle" or "heterocyclic ring" is defined by all non-aromatic, heterocyclic rings of 3–7 atoms containing 1–3 heteroatoms selected from N, O and S, such as oxirane, oxetane, tetrahydrofuran, tetrahydropyran, pyrrolidine, piperidine, piperazine, tetrahydropyridine, tetrahydropyrimidine, tetrahydrothiophene, tetrahydrothiopyran, morpholine, hydantoin, valerolactam, pyrrolidinone, and the like.

The term "heterocyclic acidic functional group" is intended to include groups such as, pyrrole, imidazole, triazole, tetrazole, and the like.

"Heteroaryl" refers to 5- or 10-membered single or benzofused aromatic rings consisting of 1 to 3 heteroatoms independently selected from the group consisting of —O—, —S—, and —N═, provided that the rings do not possess adjacent oxygen and/or sulfur atoms. The heteroaryl group can be unsubstituted or substituted with one, two, or three substituents independently selected from lower alkyl, halo, cyano, nitro, haloalkyl, hydroxy, alkoxy, carboxy, carboxyalkyl, carboxamide, mercapto, amino, alkylamino and dialkylamino. Representative heteroaryl groups include thiazoyl, thienyl, pyridyl, benzothienyl and quinolyl.

The term "heteroarylalkyl" refers to a heteroaryl group bonded directly to a subject structure through an alkyl group.

N-oxides can form on a tertiary nitrogen present in an R substituent, or on ═N— in a heteroaryl ring substituent and are included in the compounds of formula 1.

The term "prodrug," as used herein, represents compounds that are drug precursors which, following administration to a patient, release the drug in vivo via a chemical or physiological process (e.g., a prodrug on being brought to a physiological pH or through an enzyme action is converted to the desired drug form). A discussion of prodrugs is provided in T. Higuchi and V. Stella, *Pro-drugs as Novel Delivery Systems*, Vol. 14 of A.C.S. Symposium Series (1987), and in *Bioreversible Carriers in Drug Design*, E. B. Roche, ed., American Pharmaceutical Ass'n and Pergamon Press (1987), each of which is incorporated herein by reference in its entirety.

As used herein, the term "composition" is intended to encompass a product comprising the specified ingredients in the specified amounts, as well as any product which results, directly or indirectly, from combination of the specified ingredients in the specified amounts.

The phrase "effective amount," as used herein, means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically-acceptable excipient(s)/carrier(s) utilized, and like factors within the knowledge and expertise of the attending physician.

As used herein the term "disease" is intended to include any abnormal physical or mental condition, including disorders, as well as any symptoms which are subject evidence of a disease or disorder.

The term "compound having the formula I", and the like as used herein, represents a compound having a chemical structure encompassed by formula I, and includes any and all isomers (e.g., enantiomers, stereoisomers, diastereomers, rotomers, tautomers) and prodrugs of the compound. These compounds can be neutral, acidic or alkaline, and further include their corresponding pharmaceutically-acceptable salts, solvates, esters, and the like.

All isomers of the compounds of the instant invention are contemplated, either in admixture or in pure or substantially pure form. The definition of compounds according to the invention embraces all the possible isomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. Unless noted otherwise, inventive compounds designated with a 1 or 2 above the formula correspond to the first and second isomers, respectively, to elute from a chiral chromatography column during separation from a diastereomeric mixture.

The following are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA): triethylamine ($Et_3N$); diethyl ether ($Et_2O$); ethyl chloroformate ($CICO_2$ Et); 1-(3-dimethylaminopropyl)-3-ethyl carbodiimide hydrochloride (DEC); t-butoxycarbonyl (BOC); phenyl group (Ph); trimethylsilyl isocyanate (TMSNCO); acetyl chloride (AcCl); acetonitrile ($CH_3CN$); n-butyllithium (n-BuLi); triethylamine (TEA); methyl iodide (MeI); dimethyl sulfoxide (DMSO); diethylamine (DEA); isopropanol (IPA); N-methylmorpholine (NMM); acetic acid (AcOH); lithium aluminum hydride (LAH); di-tert-butyl dicarbonate $(BOC)_2O$; diisubutyl aluminum hydride (DIBAL-H); methyl magnesium bromide (MeMgBr); and acetic anhydride ($Ac_2O$).

As used herein the following terms have the following meanings unless indicated otherwise:

"At least one" means "one or more" preferably 1 to 12, more preferably 1 to 6, most preferably 1, 2 or 3.

Antineoplastic agent—means a chemotherapeutic agent effective against cancer;

Concurrently—means (1) simultaneously in time; and

Sequentially—means (1) administration of one component of the method ((a) compound of the invention, or (b) antineoplastic agent and/or radiation therapy) followed by administration of the other component; after administration of one component, the second component can be administered substantially immediately after the first component, or the second component can be administered after an effective time period after the administration of the first component; the effective time period is the amount of time given for realization of maximum benefit from the administration of the first component.

Chemotherapeutic Agents

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxycoformycin, Mitomycin-C, L-Asparaginase, Interferons-α and β (especially IFN-α), Etoposide, and Teniposide.

Hormonal agents and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin and Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, Navelbene, CPT-11, Anastrazole, Letrazole, Capecitabine, Ralozifine, Droloxifine and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

Examples of biological agents useful in the methods of this invention include, but are not limited to, interferon-α, interferon-β and gene therapy.

Microtubule Affecting Agents

As used herein, a microtubule affecting agent is a compound that interferes with cellular mitosis, i.e., having an anti-mitotic effect, by affecting microtubule formation and/or action. Such agents can be, for instance, microtubule stabilizing agents, or agents which disrupt microtubule formation.

Microtubule affecting agents useful in the invention are well known to those of skill in the art and include, but are not limited to allocolchicine (NSC 406042), Hali hondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055–3064; Panda (1997) Proc. Natl. Acad. Sci. USA 94:10560–10564; Muhlradt (1997) Cancer Res.

57:3344–3346; Nicolaou (1997) Nature 387:268–272; Vasquez (1997) Mol. Biol. Cell. 8:973–985; Panda (1996) J. Biol. Chem. 271:29807–29812.

Particularly preferred microtubule affecting agents are compounds with paclitaxel-like activity. These include, but are not limited to, paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17–23, Horwitz (1992) Trends Pharmacol. Sci. 13: 134–146, Rowinsky (1990) J. Natl. Canc. Inst. 82: 1247–1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37–47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus. e.g., disruption of normal spindle formation. Cells in which mitosis is interrupted may be characterized by altered morphology (e.g., microtubule compaction, increased chromosome number, etc.).

In a preferred embodiment, compounds with possible tubulin polymerization activity are screened in vitro. The compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145–150.

Other methods of screening compounds for desired activity are well known to those of skill in the art. Typically, these involve assays for inhibition of microtubule assembly and/or disassembly. Assays for microtubule assembly are described, for example, by Gaskin et al. (1974) J. Molec. Biol., 89: 737–758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA).

The present invention provides a method of treating or preventing androgen-dependent diseases comprising administering to a mammal in need thereof an effective amount of a compound of the invention in combination with at least one anti-androgenic agent (i.e. agents that decrease androgen synthesis or activity).

Examples of such agents include but are not limited to: inhibitors of 5α-reductase type 1 and/or type 2, e.g. finasteride, SKF105,657, LY191,704, LY320,236, dutasteride, Flutamide, nicalutamide, bicalutamide, LHRH agonists e.g. leuprolide and zoladex, LHRH antagonists, e.g. abarelix and cetrorelix, inhibitors of 17α-hydroxylase/C17-20 lyase, e.g. YM116, CB7630 and liarozole; inhibitors of 17β-Hydroxysteroid dehydrogenase type 5 and/or other 17β-Hyroxysteroid dehydrogenase/17β-oxidoreductase isoenzymes, e.g. EM-1404.

Types of androgen or estrogen dependent diseases include, but are not limited to, prostate cancer, benign prostatic hyperplasia, prostatic intraepithelial neoplasia, acne, seborrheas, hirsutism, androgenic alopecia, precocious puberty, adrenal hyperplasia, and polycystic ovarian syndrome, breast cancer, endometriosis and leiomyoma.

This invention also provides a method of treating or preventing benign prostatic hyperplasia comprising administering an effective amount of a compound of the invention in combination with at least one agent useful in the treatment or prevention of benign prostatic hyperplasia. Examples of such agents include, but are not limited to, alpha-1 adrenergic antagonists, e.g. tamsulosin and terazosin.

This invention also provides a method of treating or preventing hair loss, comprising administering an effective amount of a compound of the invention in combination with at least one potassium channel agonist e.g. minoxidil and KC-516, or 5α-reductase inhibitor, e.g., finasteride and dutasteride.

The present invention also provides a method of treating or preventing proliferative diseases, especially cancers (tumors), comprising administering concurrently or sequentially, (1) an effective amount (e.g., a therapeutically effective amount) of a compound of the invention, described herein, to a mammal (e.g., a human) in need of such treatment in combination with (2) an effective amount of an anti-cancer agent i.e., a chemotherapeutic agent, biological agent, and/or surgery, e.g., prostatectomy and/or radiation therapy.

Examples of cancers (i.e. tumors) which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), renal cancers, myeloid leukemias (for example, acute myelogenous leukemia (AML), thyroid follicular cancer, myelodysplastic syndrome (MDS), bladder carcinoma, epidermal carcinoma, melanoma, breast cancer and prostate cancer.

Preferrably for compounds of the Formula (I),
  $R^1$ and $R^2$ are the same or different and are independently selected from the group consisting of aryl and heteroaryl, each optionally substituted with one to six groups selected from the group consisting of:
  a) halogen;
  b) —$OCF_3$;
  c) —$CF_3$;

d) —CN;

e) $(C_1$–$C_{20})$alkyl or $R^{18}$—$(C_1$–$C_{20})$alkyl;

f) heteroalkyl or $R^{18}$-heteroalkyl;

g) aryl or $R^{18}$-aryl;

h) heteroaryl or $R^{18}$-heteroaryl;

i) arylalkyl or $R^{18}$-arylalkyl;

j) heteroarylalkyl or $R^{18}$-heteroarylalkyl;

k) hydroxy;

l) alkoxy;

m) aryloxy;

n) —$SO_2$-alkyl;

o) —$NR^{11}R^{12}$;

p) —$N(R^{11})C(O)R^{13}$;

q) methylenedioxy;

r) difluoromethylenedioxy;

s) trifluoroalkoxy;

t) —$SCH_3$; and u) —$SO_2CF_3$;

$R^4$, $R^5$, $R^7$ and $R^8$ are the same or different and are independently selected from the group consisting of H, alkyl, heteroalkyl, aryl, cycloalkyl, arylalkyl, heteroaryl, heteroarylalkyl, heterocycloalkyl, —$OR^{14}$, —$NR^{11}R^{12}$,

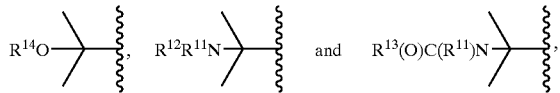

provided that when Z and/or X is N then $R^4$, $R^5$, $R^7$ and $R^8$ are each not —$OR^{14}$ or —$NR^{11}R^{12}$;

$R^{11}$ is selected from the group consisting of H and alkyl.

More preferably for compounds of the Formula (I), $R^1$ and $R^2$ are the same or different and are independently selected from the group consisting of aryl and heteroaryl, each optionally substituted with one to six groups selected from the group consisting of:

a) halogen;

b) —$OCF_3$;

c) —$CF_3$;

d). trifluoroalkoxy;

e) (C1–C6)alky or $R^{18}$-(C1–C6)alkyl;

f) heteroalkyl or $R^{18}$-heteroalkyl;

g) aryl or $R^{18}$-aryl;

h) arylalkyl or $R^{18}$-arylalkyl;

i) heteroarylalkyl or $R^{18}$-heteroarylalkyl;

j) alkoxy;

k) —$SO_2$-alkyl; and l) —$SO_2CF_3$;

$R^4$, $R^5$, $R^7$ and $R^8$ are the same or different and are independently selected from the group consisting of H, alkyl, heteroalkyl, aryl, cycloalkyl, arylalkyl, heteroaryl, heteroarylalkyl, heterocycloalkyl, —$R^{14}$, —$NR^{11}R^{12}$,

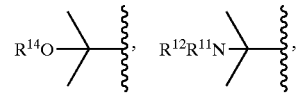

and

provided that when Z and/or X is N then $R^4$, $R^5$, $R^7$ and $R^8$ are each not —$OR^{14}$ or —$NR^{11}R^{12}$;

$R^{11}$ is selected from the group consisting of H and alkyl; and

Z is C.

Even more preferrably for compounds of the Formula (I), $R^1$ and $R^2$ are the same or different and are independently selected from the group consisting of aryl and heteroaryl, each optionally substituted with one to six groups selected from the group consisting of:

a) halogen;

b) —$OCF_3$;

c) —$CF_3$;

d) alkoxy;

e) trifluoralkoxy;

f) (C1–C6)alkyl;

g) —$SO_2$-alkyl; and h) —$SO_2CF_3$;

$R^3$ is H or —OH, provided that when X is N, $R^3$ is not —OH;

$R^4$ and $R^5$ are the same or different and are each independently selected from the group consisting of H, (C1–C6)alkyl, heteroalkyl and

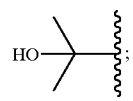

$R^7$ is selected from the group consisting of H, alkyl, —$OR^{14}$ and —$NR^{11}R^{12}$, provided that when X is N, $R^7$ is not —$OR^{14}$ or —$NR^{11}R^{12}$;

$R^8$ is selected from the group consisting of H, alkyl, aryl and heteroaryl;

$R^{11}$ is selected from the group consisting of H and alkyl; and Z is C.

Yet even more preferrably for compounds of the Formula (I), $R^1$ and $R^2$ are the same or different and are independently selected from the group consisting of aryl and heteroaryl, each optionally substituted with one to six groups selected from the group consisting of:

a) halogen;

b) —$OCF_3$;

c) alkoxy;

d) trifluoroalkoxy;

e) —$CF_3$;

f) —$SO_2$-alkyl; and g) —$SO_2CF_3$;

R³ is H;

R⁴ and R⁵ are the same or different and are independently selected from the group consisting of H, (C1–C6)alkyl, heteroalkyl, and

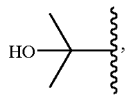

R⁶ is selected from the group consisting of —C(O)R¹⁵ and —SO₂R¹⁵;

R⁷ is selected from the group consisting of H, alkyl, —OR¹⁴ and —NR¹¹R¹², provided that when X is N, R⁷ is not —OR¹⁴ or —NR¹¹R¹²;

R⁸ is selected from the group consisting of H, alkyl, aryl and heteroaryl;

R¹¹ is H or alkyl; and

Z is C.

Still even more preferably for compounds of the Formula (I),

R¹ and R² are the same or different and are independently selected from the group consisting of phenyl and pyridyl, each optionally substituted with one to six groups selected from the group consisting of:

a) Br, F or Cl;

b) —OCF₃;

c) —CF₃;

d) methoxy;

e) ethoxy;

f) cyclopropylmethoxy;

g) —OCH₂CF₃;

h) —SO₂-alkyl; and i) —SO₂CF₃

R³ is H;

R⁴ and R⁵ are the same or different and are independently selected from the group consisting of H, methyl, ethyl, isopropyl, t-butyl and heteroalkyl;

R⁷ is selected from the group consisting of H, —OR¹¹ and alkyl;

R⁸, R⁹, R¹⁰, R¹¹, R¹² and R¹⁴ are each independently selected from the group consisting of H and alkyl;

R¹³ is alkyl;

R¹⁵ is selected from the group consisting of —NR¹⁶R¹⁷, —OR¹⁶ and alkyl;

R¹⁶ and R¹⁷ are the same or different and are independently selected from the group consisting of H and alkyl, provided that when R¹⁵ is —OR¹⁶, R¹⁶ is not H; and Z is C.

Illustrative compounds of Formula (I) are shown below in Table A, where compound numbers S1, S2, etc., are independent of the numbering used in the Example section.

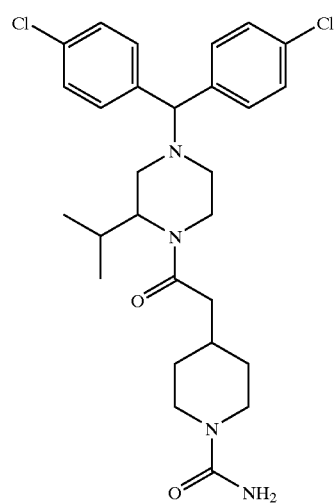

S1

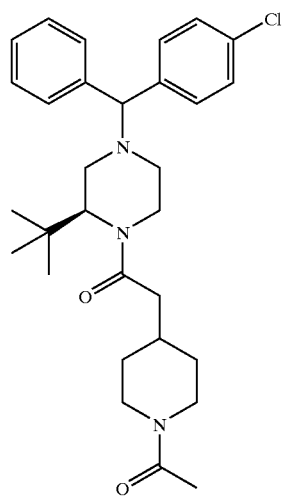

S2

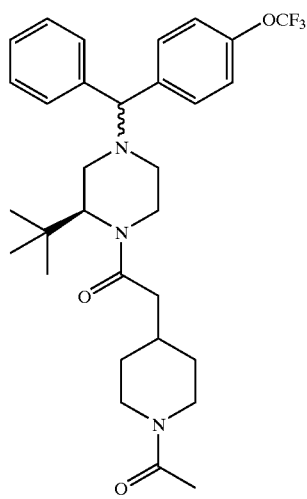

S3

-continued
S4
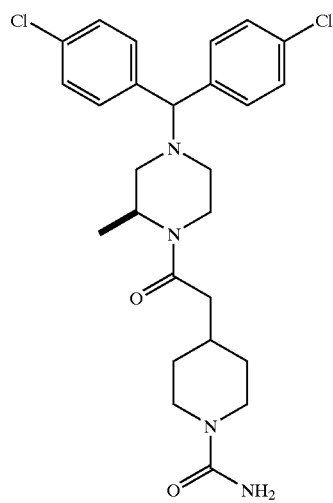
S5
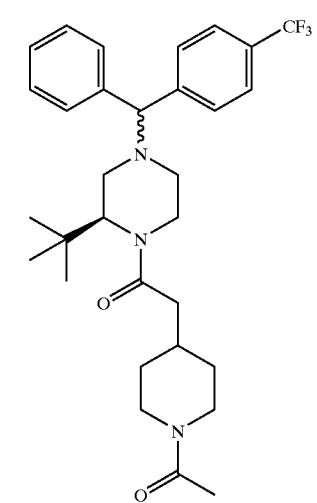
S6
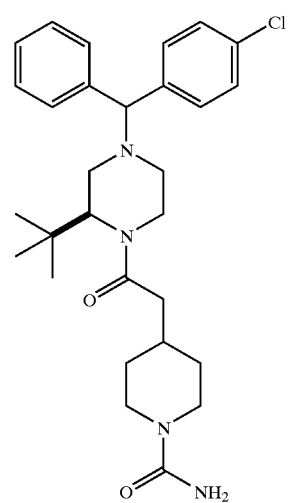
-continued
S7
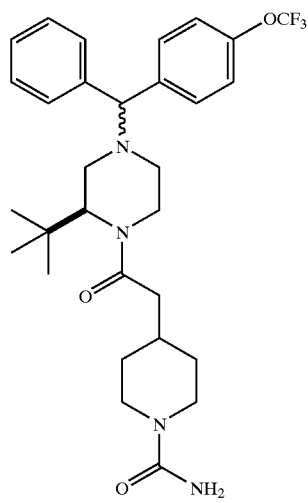
S8
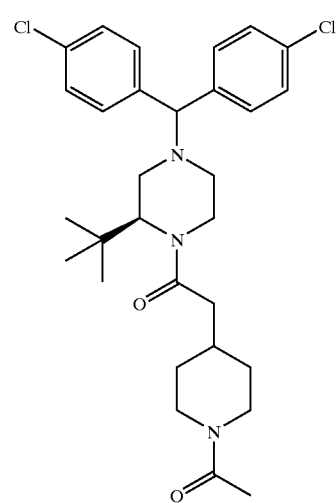
S9
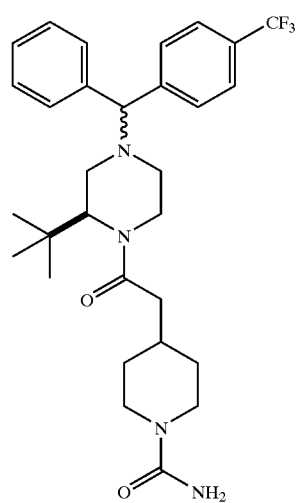

-continued
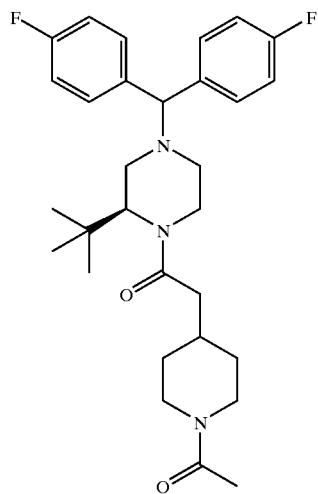
S10
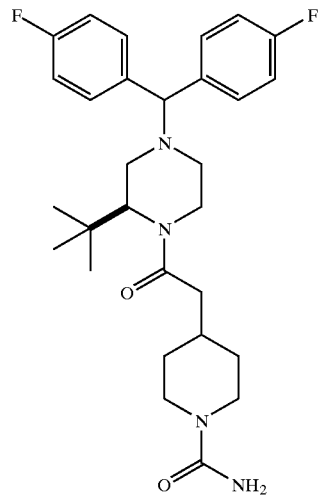
S13
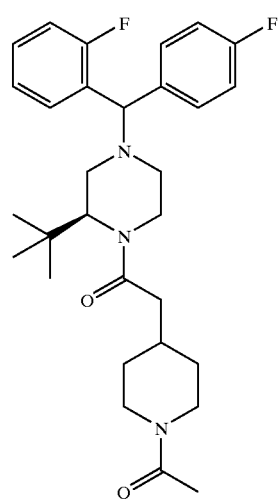
S11
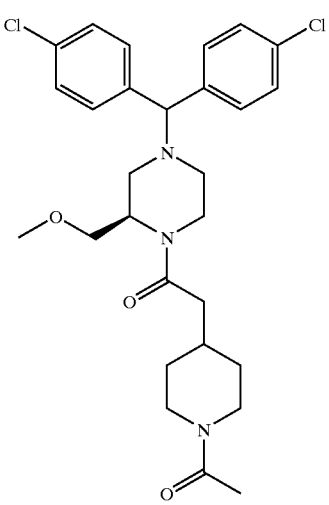
S14
S12
S15

-continued
S16
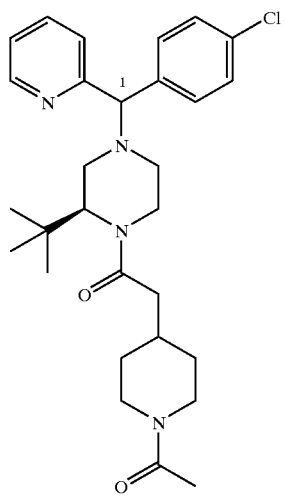
S17
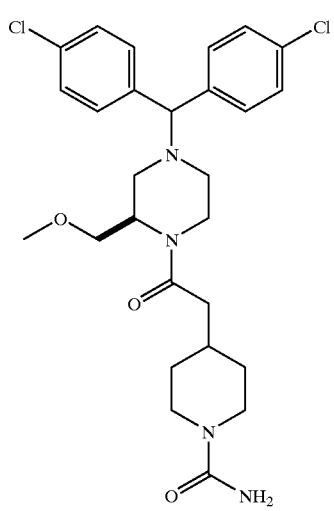
S18
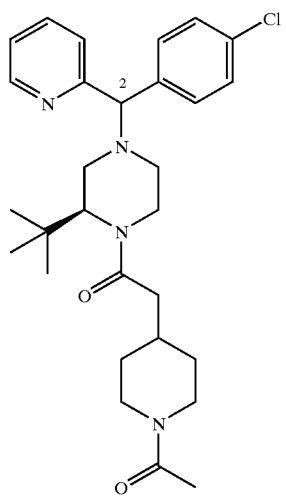
-continued
S19
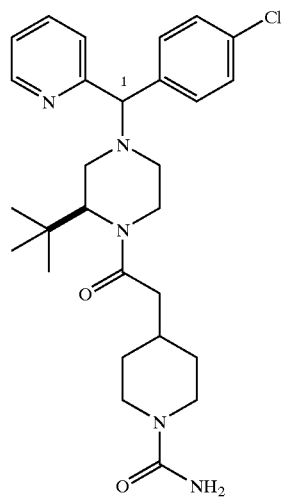
S20
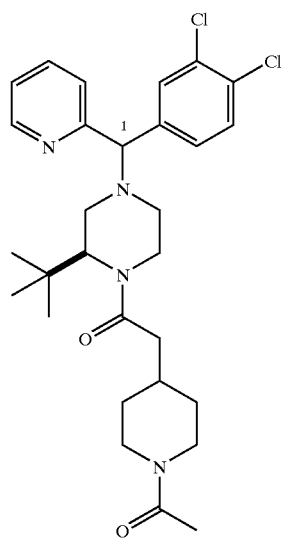
S21
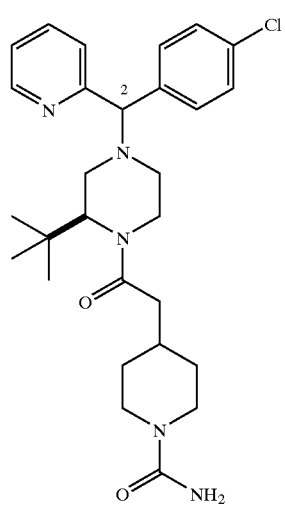

-continued
S22
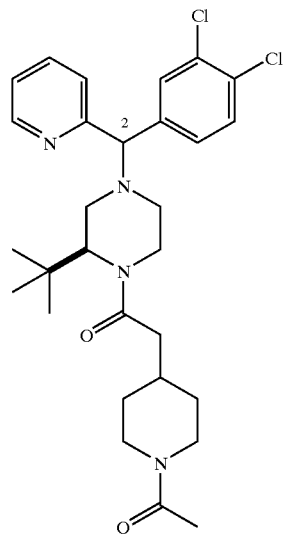
S23
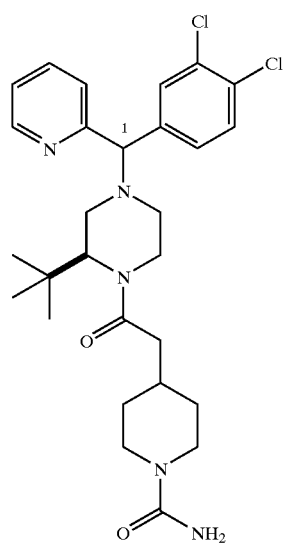
S24
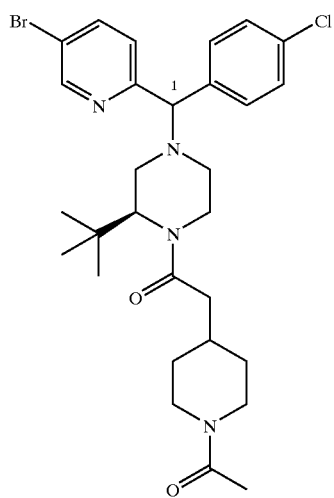
-continued
S25
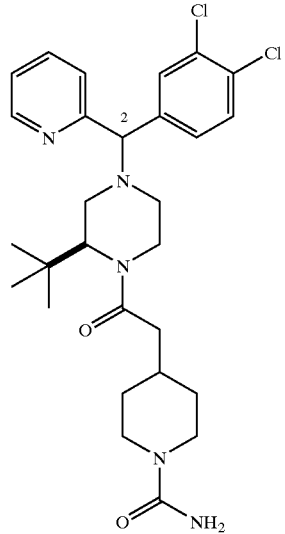
S26
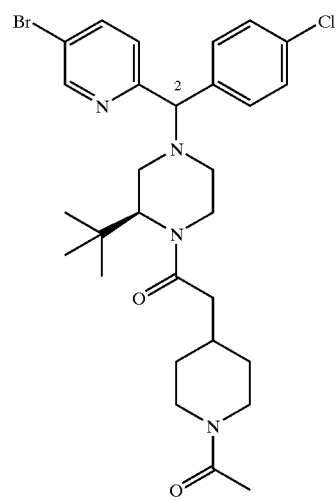
S27
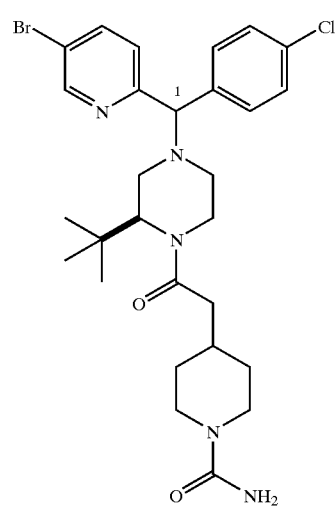

-continued
S28
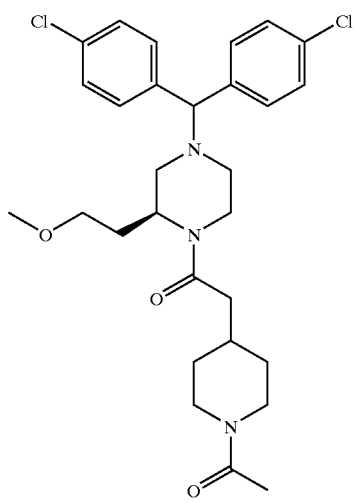
S29
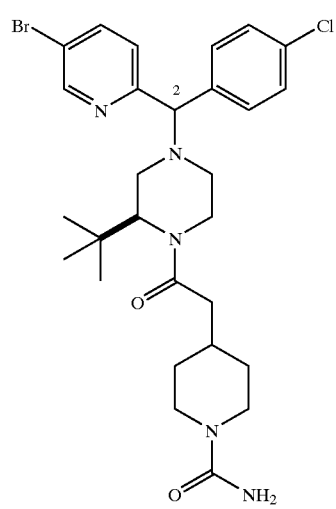
S30
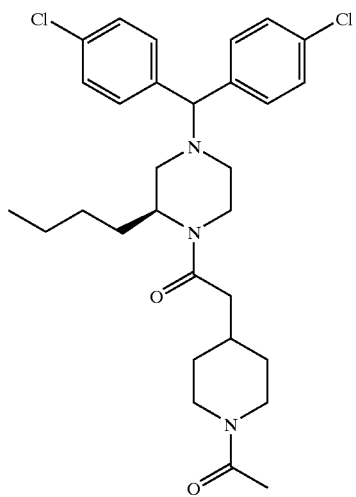
-continued
S31
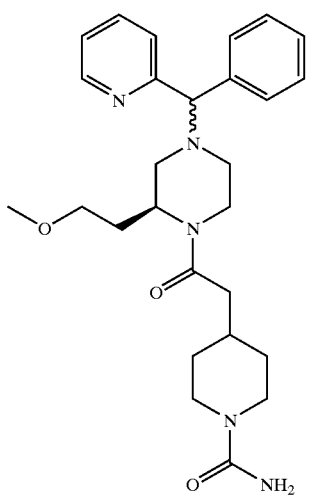
S32
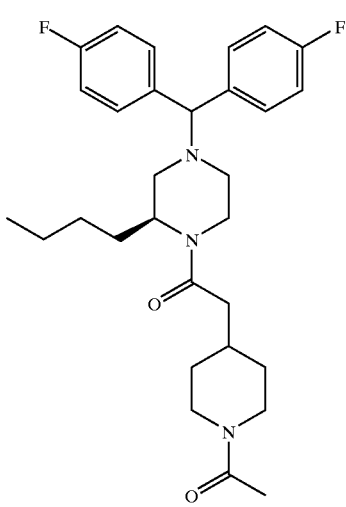
S33
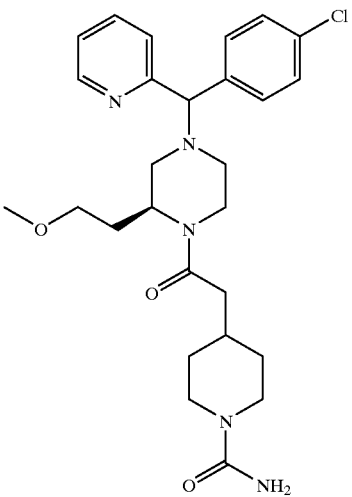

-continued
S34
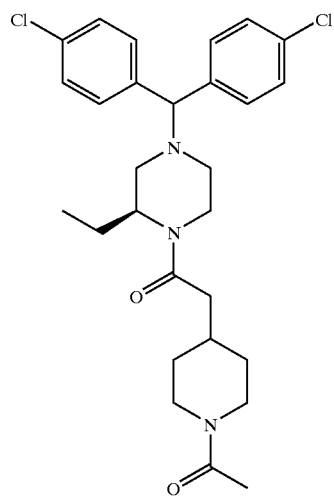
S35
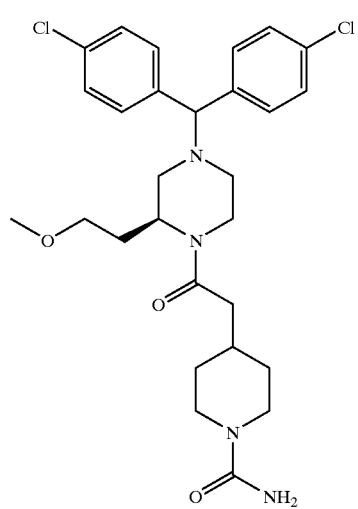
S36
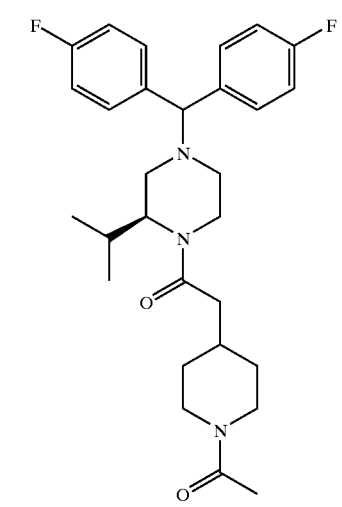
-continued
S37
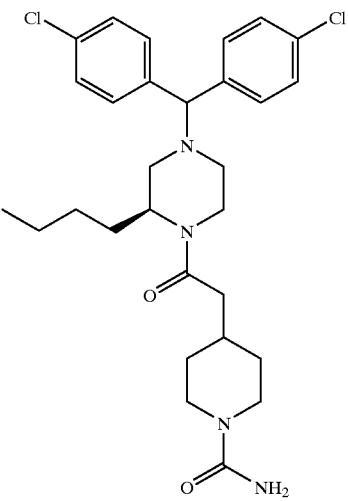
S38
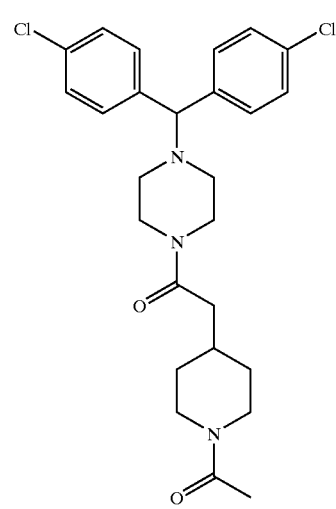
S39
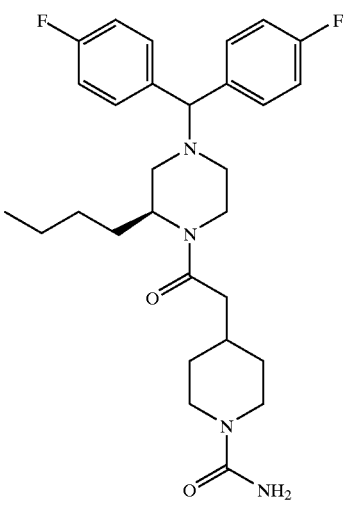

| | |
|---|---|
| -continued | -continued |
| S40 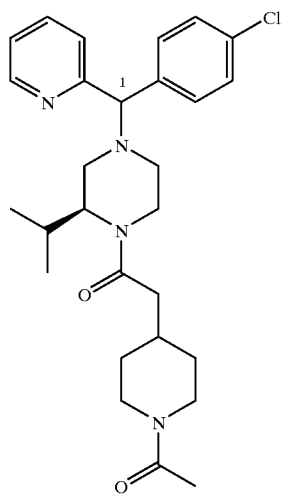 | S43 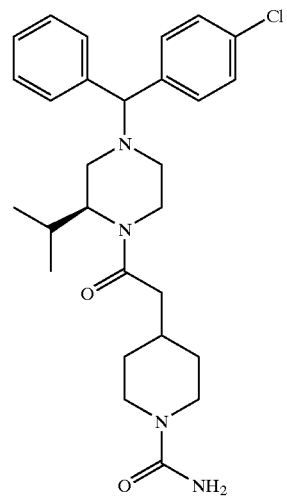 |
| S41 | S44 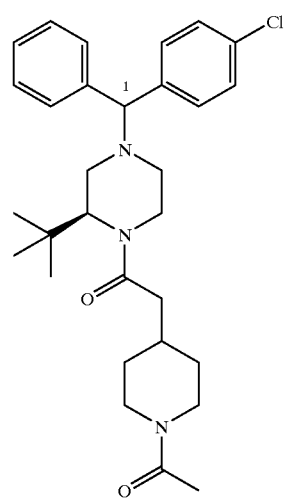 |
| S42 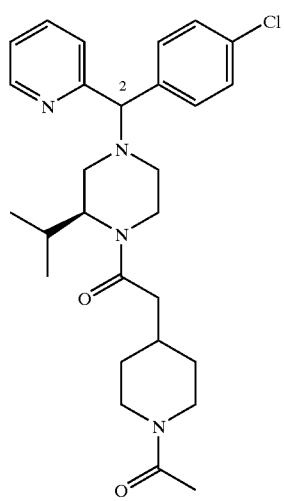 | S45 |

-continued
S46
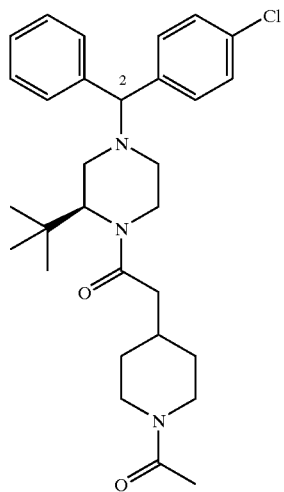
S47
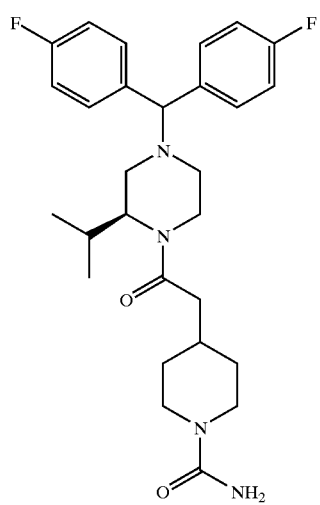
S48
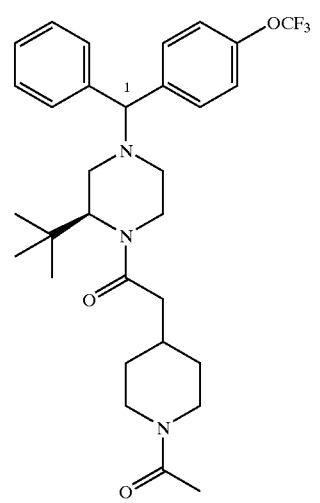
-continued
S49
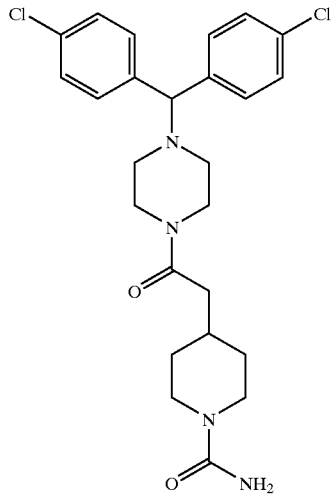
S50
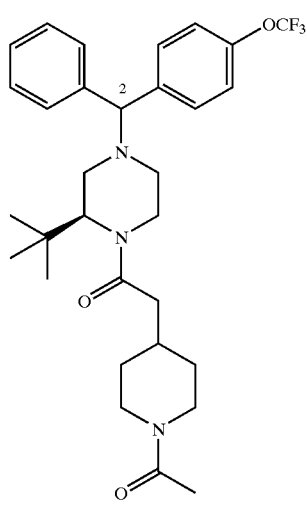
S51

-continued
S52
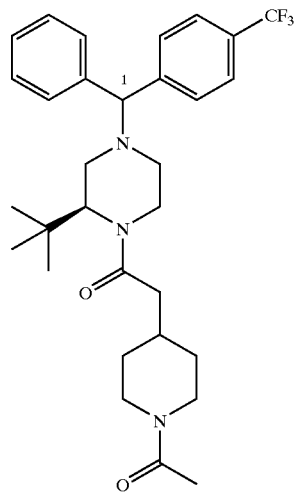
S53
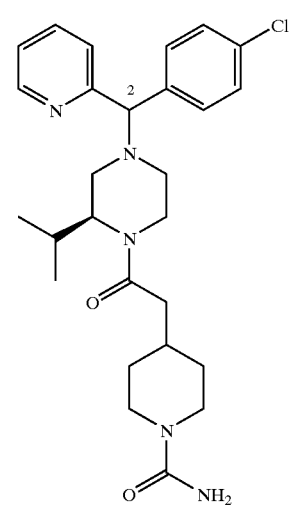
S54
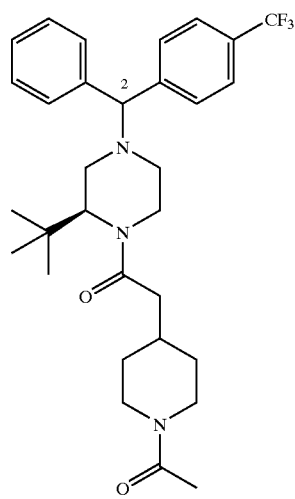
-continued
S55
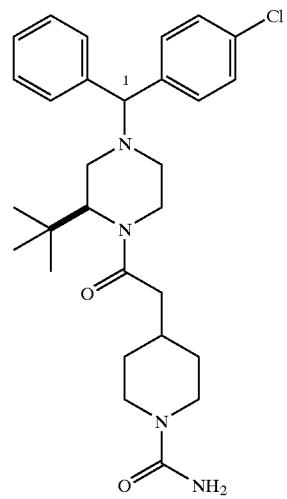
S56
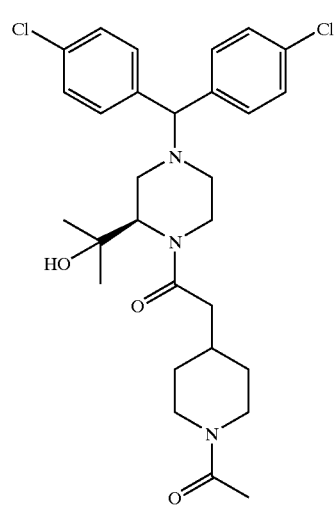
S57
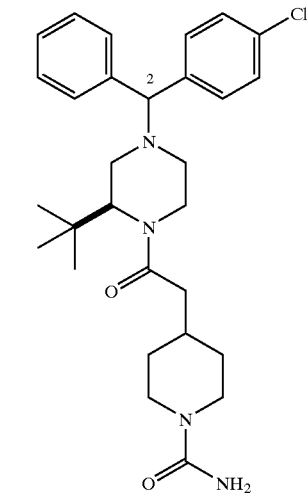

-continued
S58
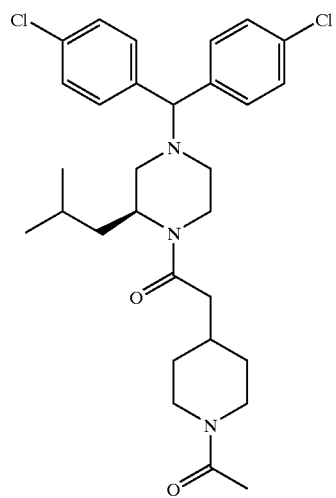
S59
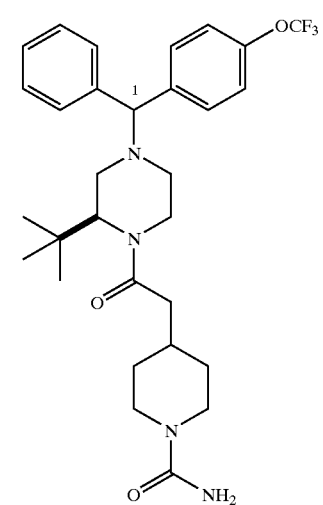
S60
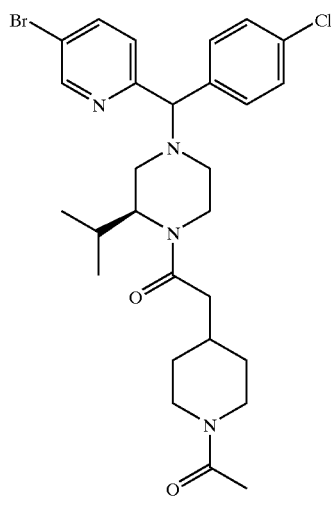
-continued
S61
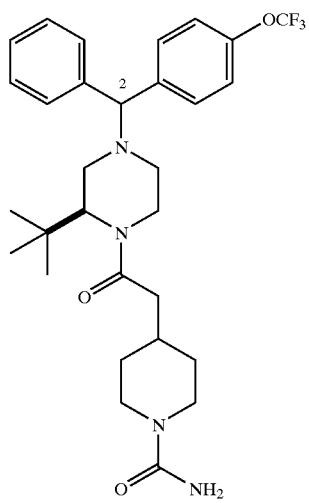
S62
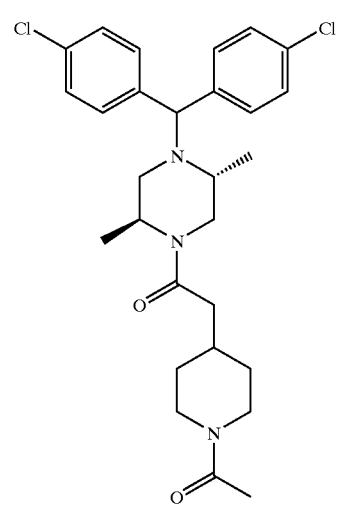
S63
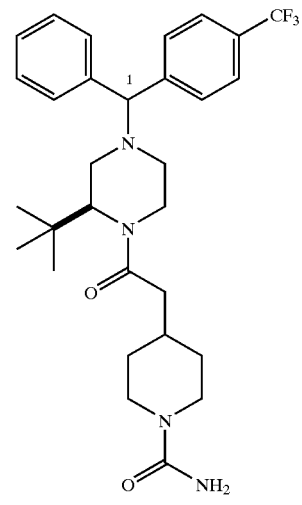

S64
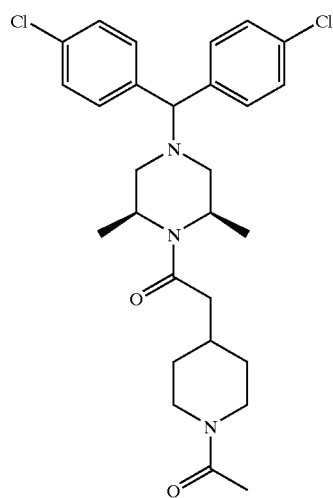
S65
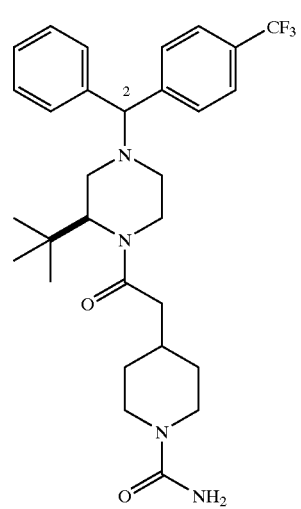
S66
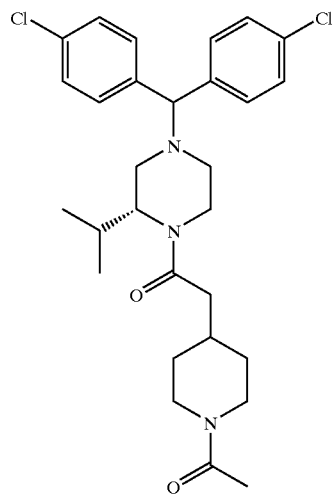
S67
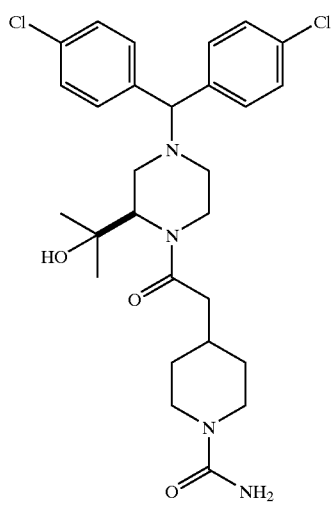
S68
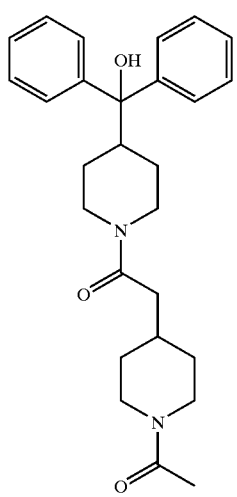
S69
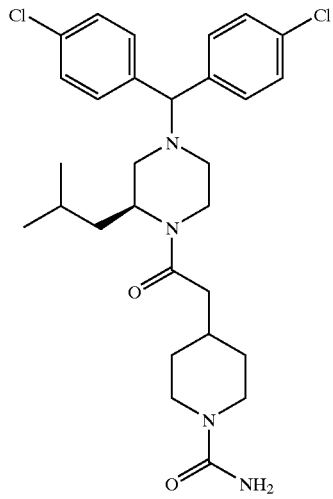

-continued
S70
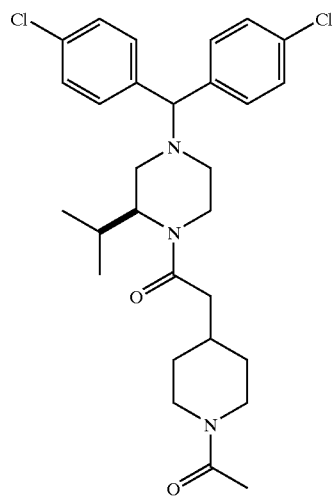
S71
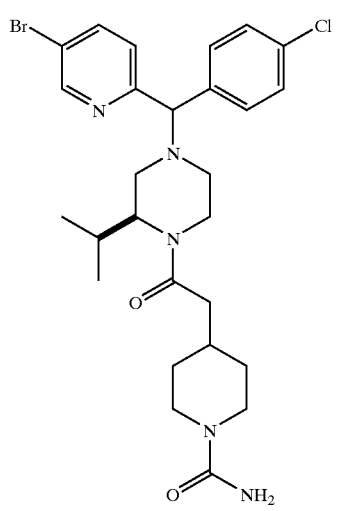
S72
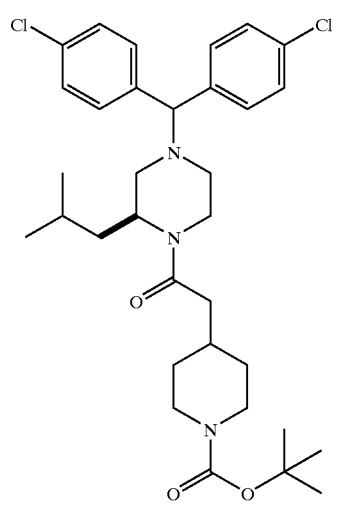
-continued
S73
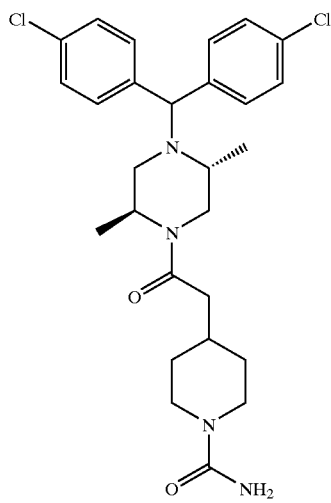
S74
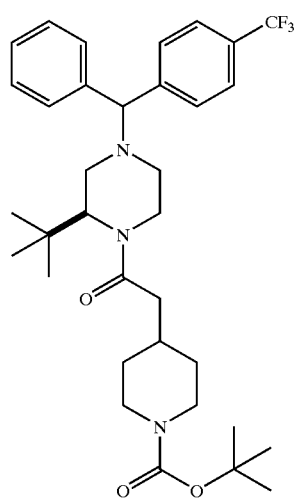
S75
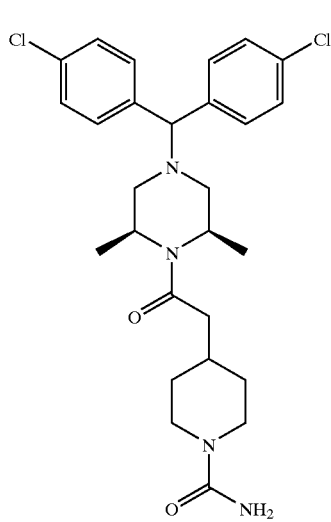

-continued
S76
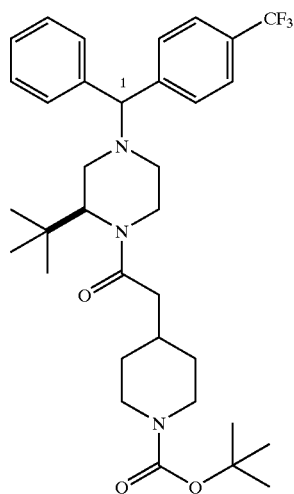
S77
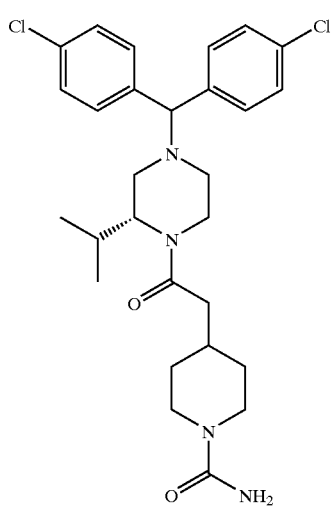
S78
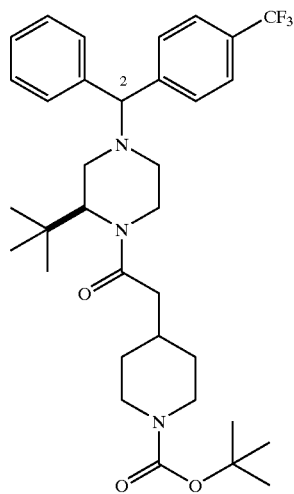
-continued
S79
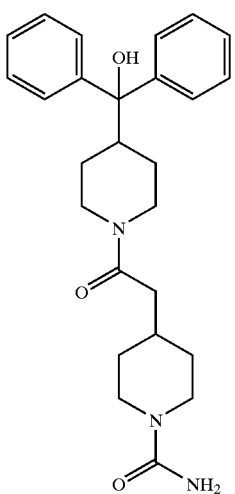
S80
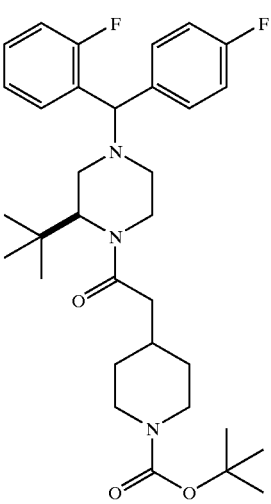
S81
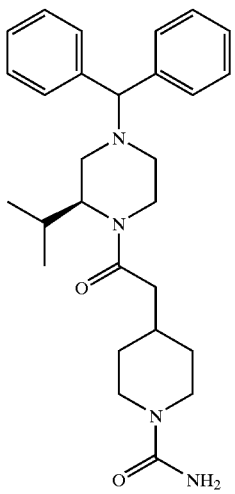

-continued
S82
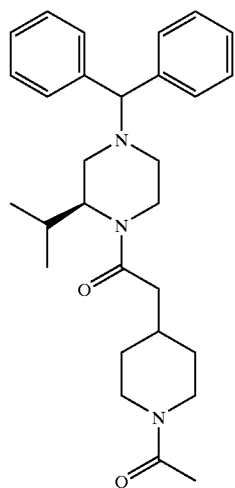
S83
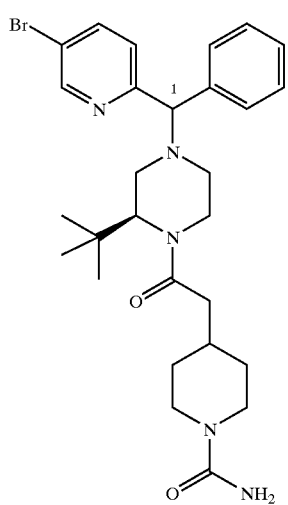
S84
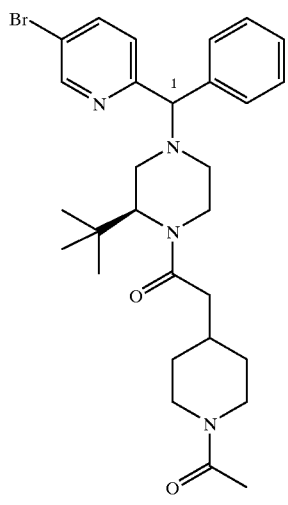
-continued
S85
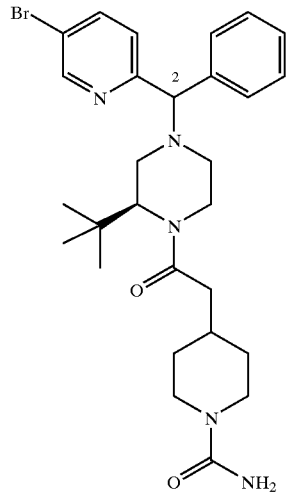
S86
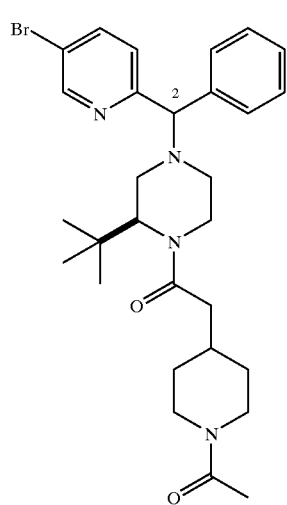
S87
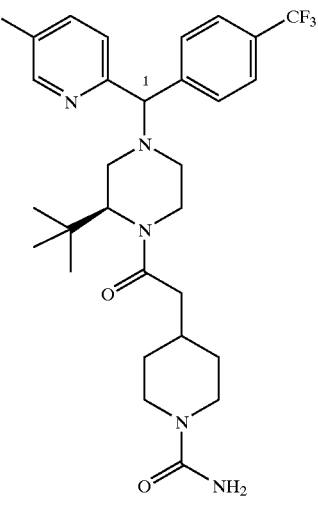

-continued
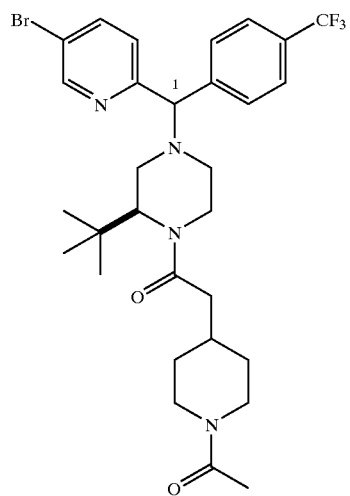
S88
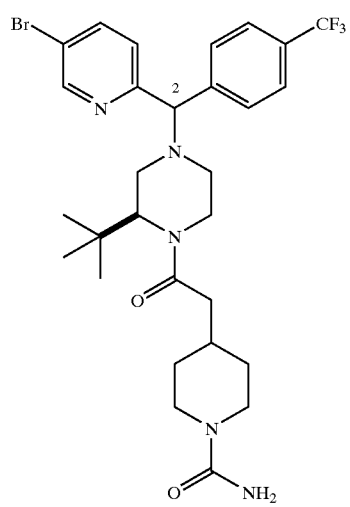
S89
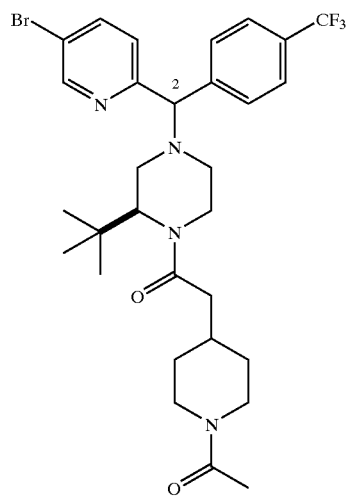
S90
-continued
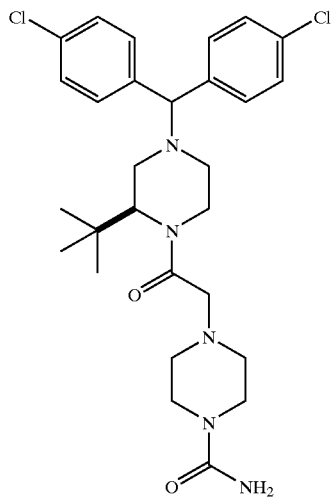
S91
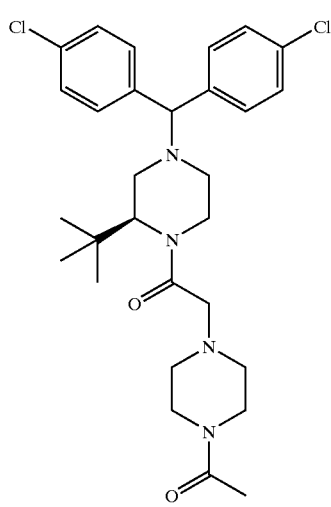
S92
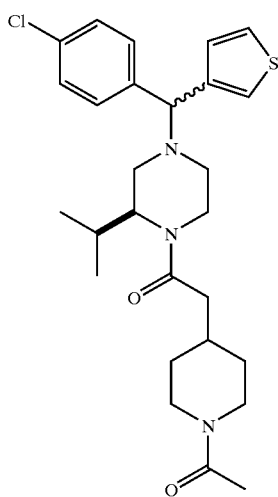
S93

-continued
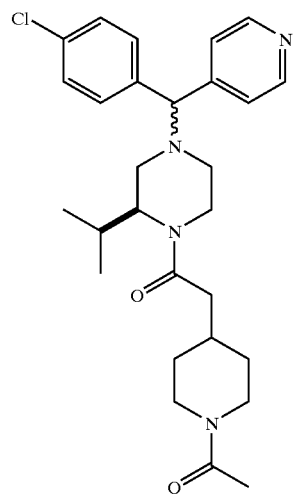
S94
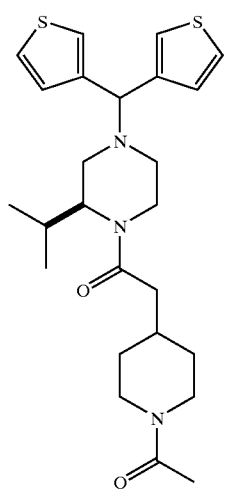
S95
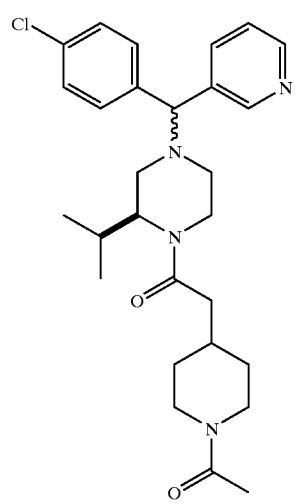
S96
-continued
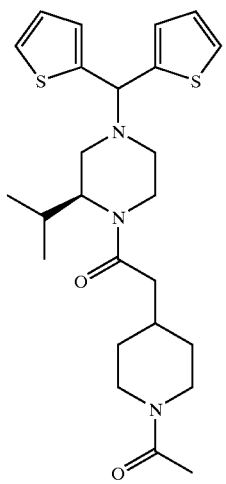
S97
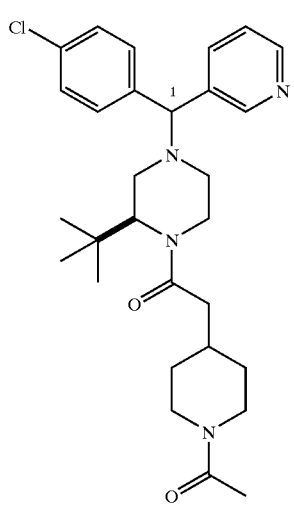
S98
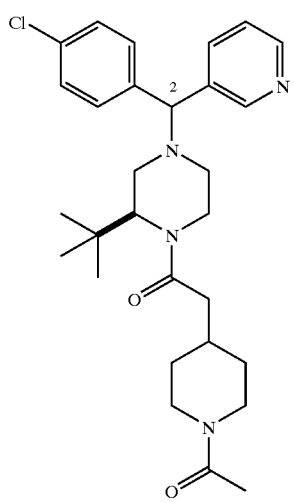
S99

-continued
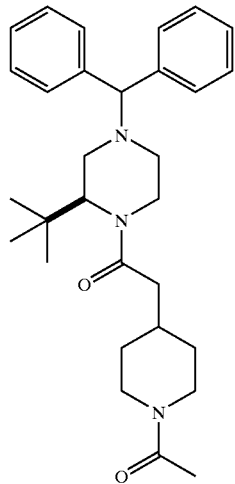
S100
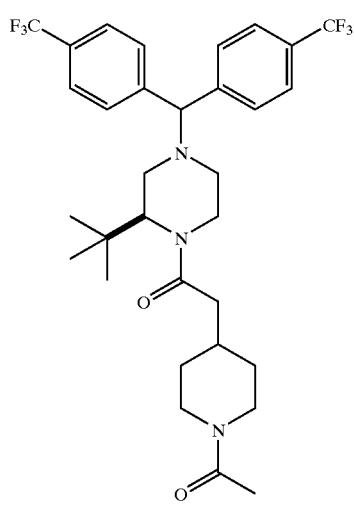
S101
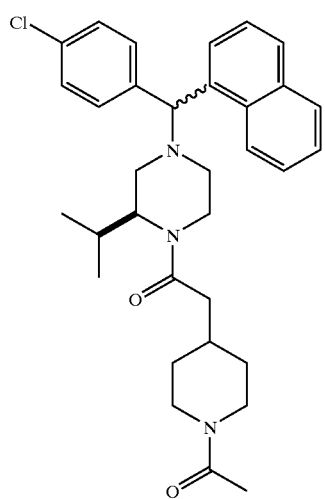
S102
-continued
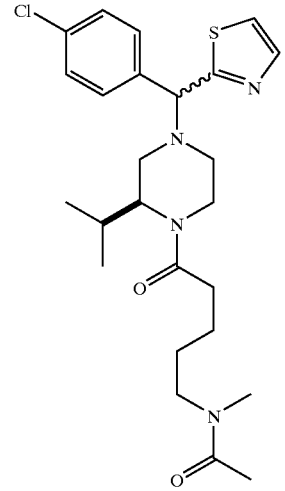
S103
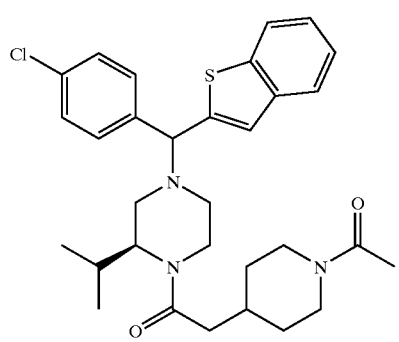
S104
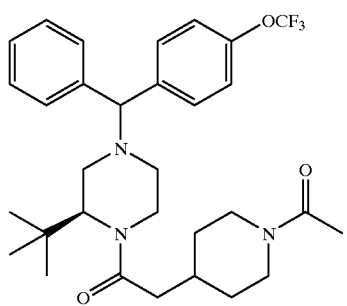
S105
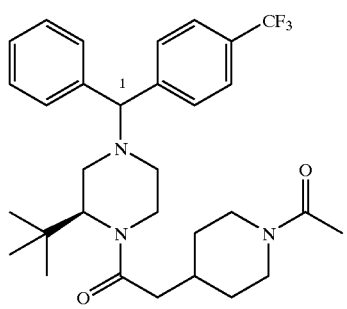
S106

-continued
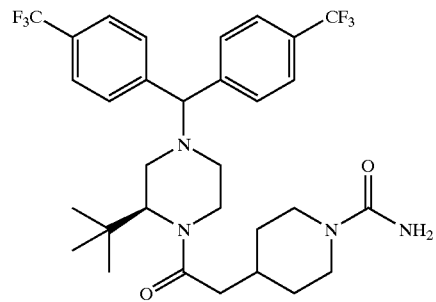 S107
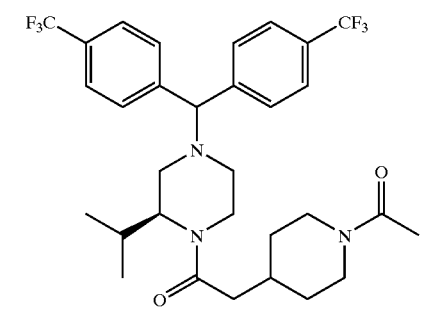 S108
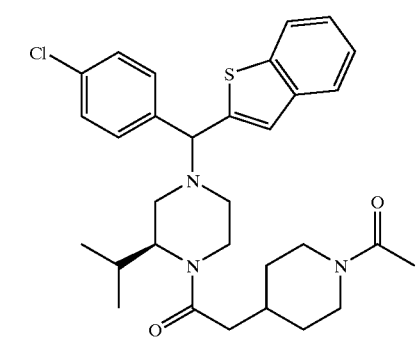 S109
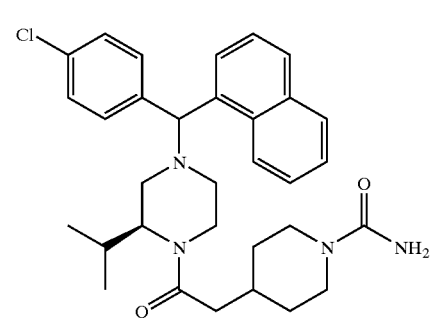 S110
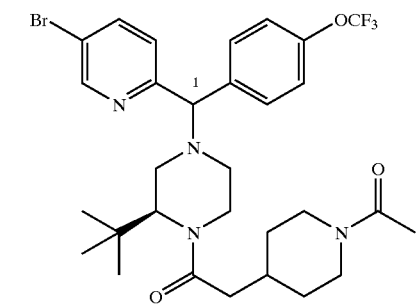 S111
-continued
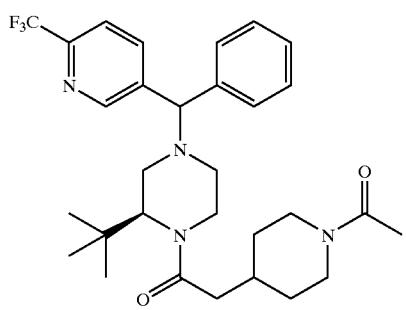 S112
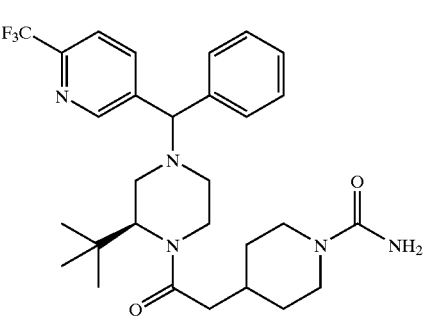 S113
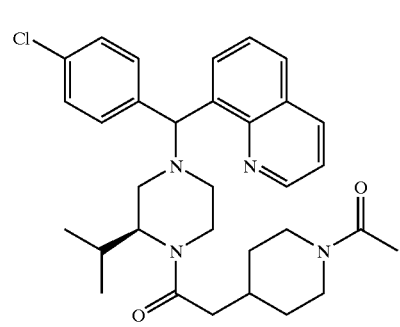 S114
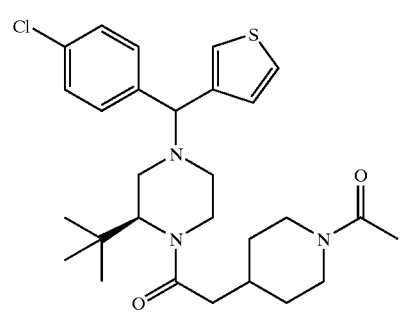 S115
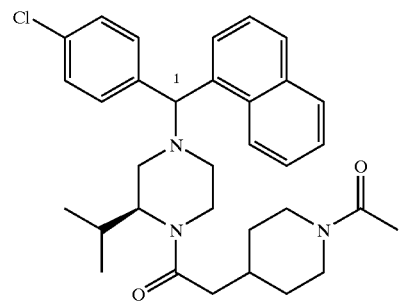 S116

-continued
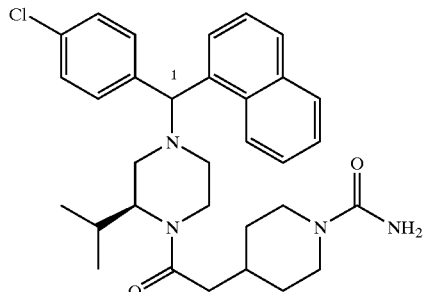
S117
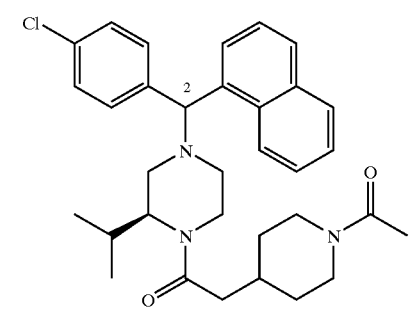
S118
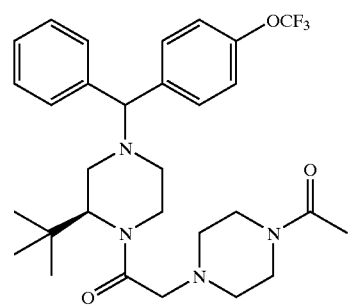
S119
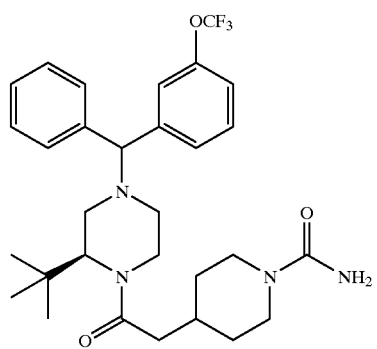
S120
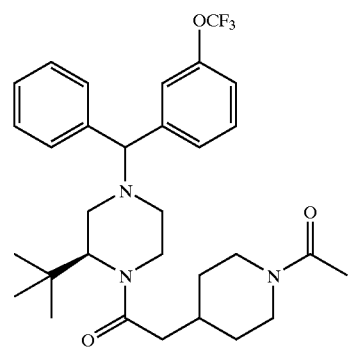
S121
-continued
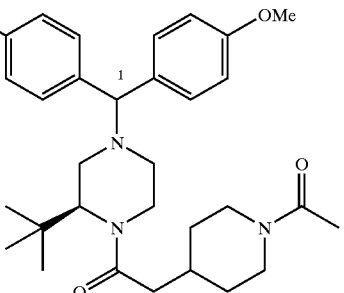
S122
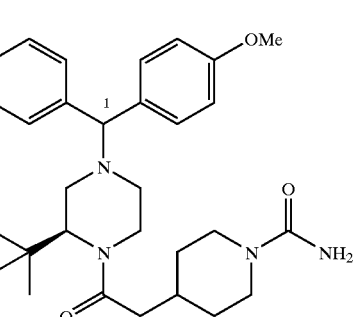
S123
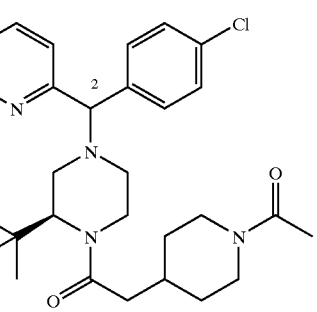
S124
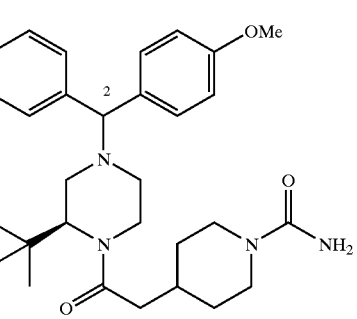
S125
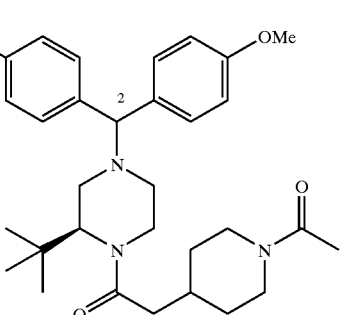
S126

-continued
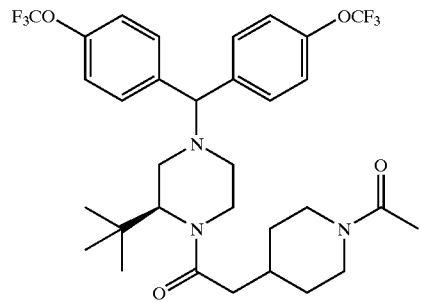 S127
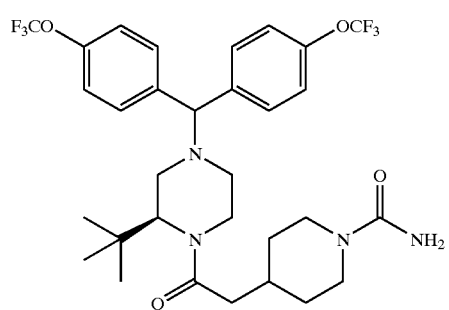 S128
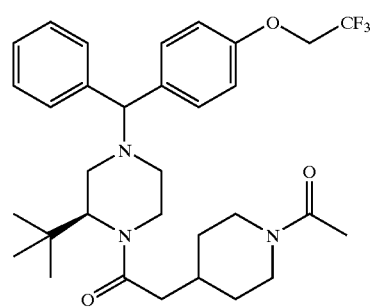 S129
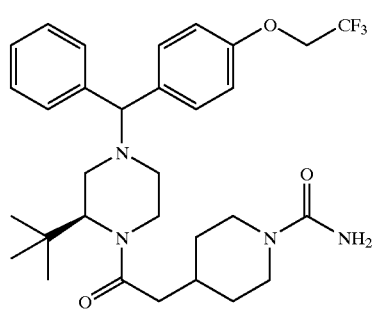 S130
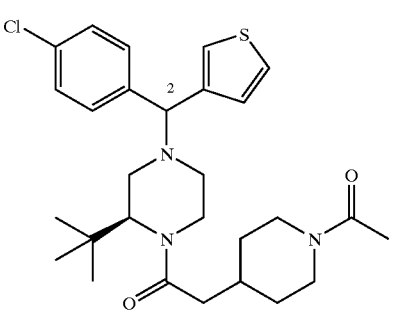 S131
-continued
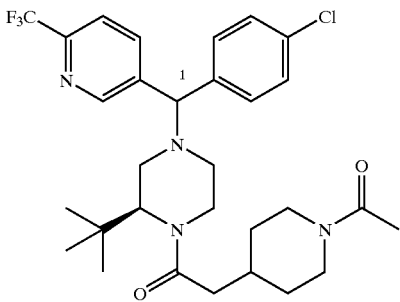 S132
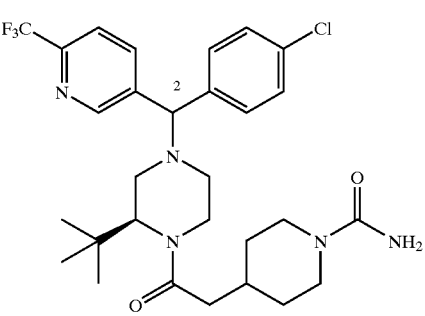 S133
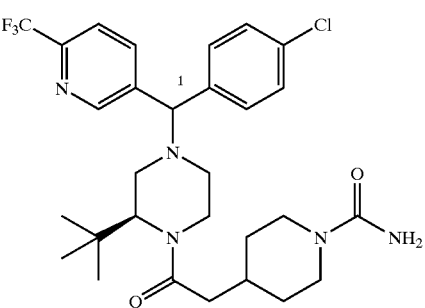 S134
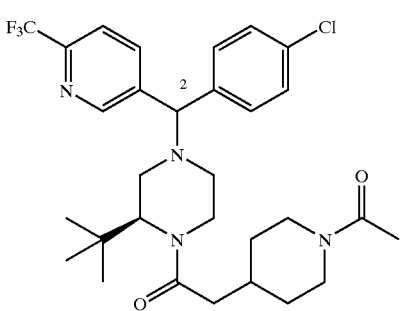 S135
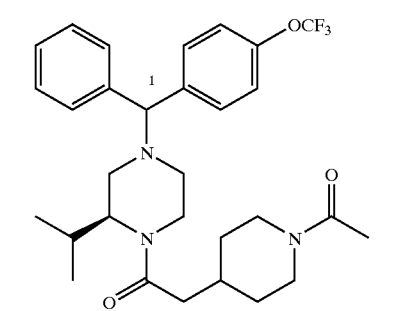 S136

-continued
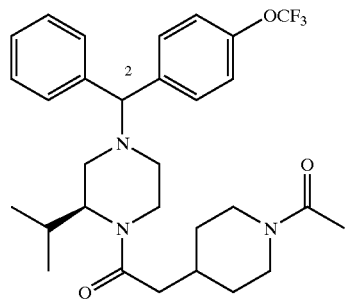
S137
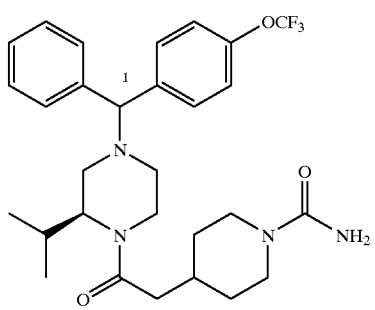
S138
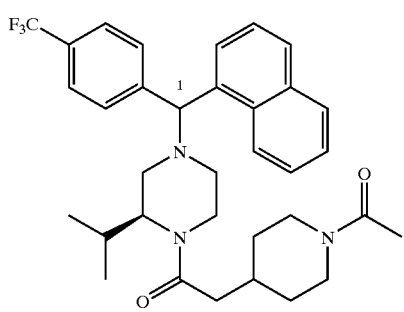
S139
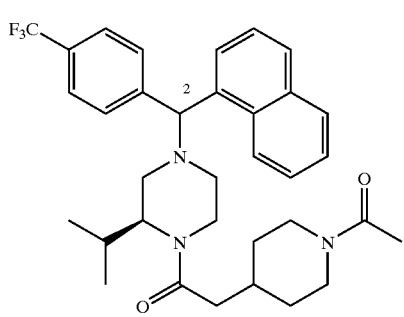
S140
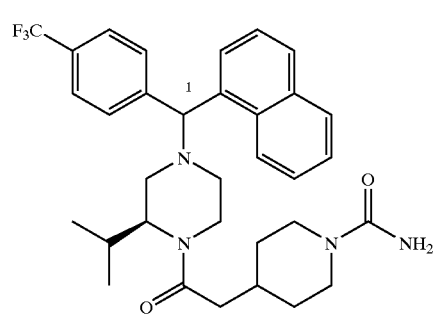
S141
-continued
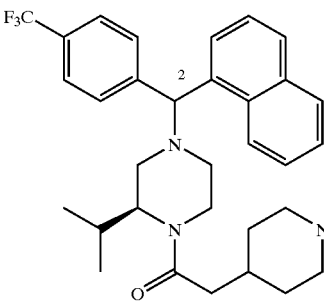
S142
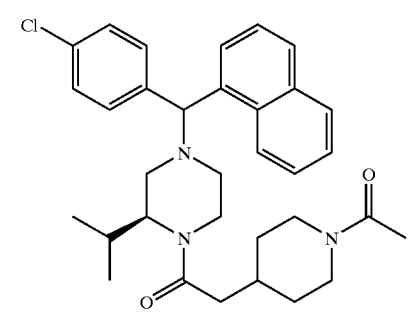
S143
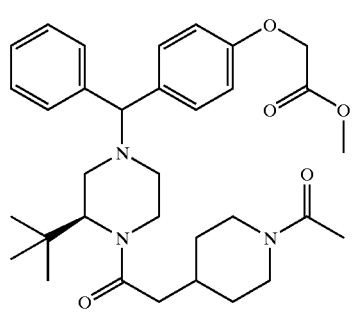
S144
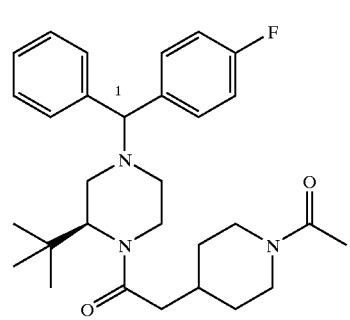
S145
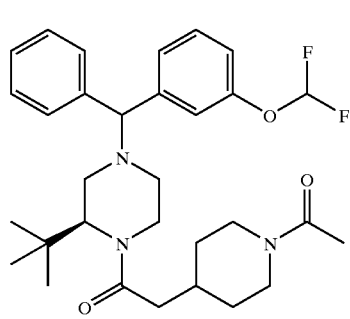
S146

-continued
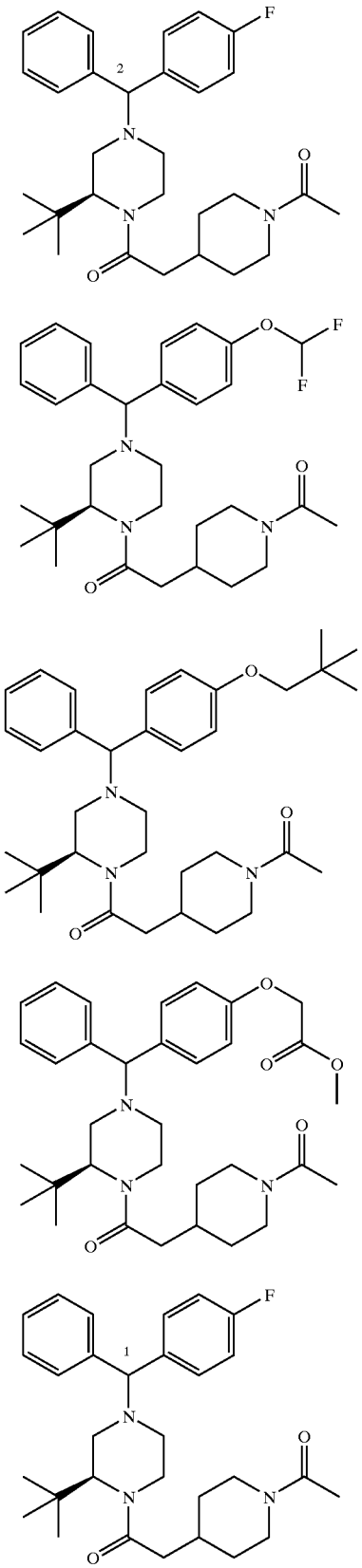
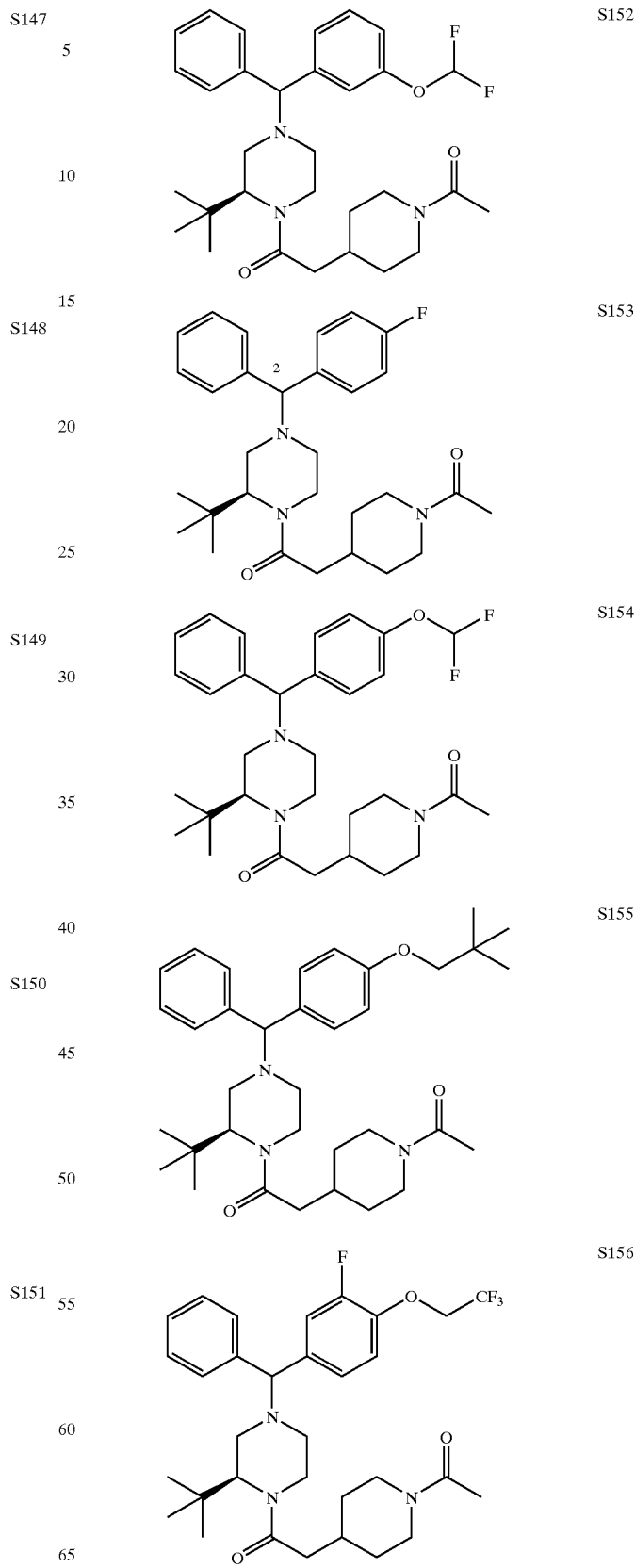

| 61 | 62 |
|---|---|
| -continued | -continued |
S157
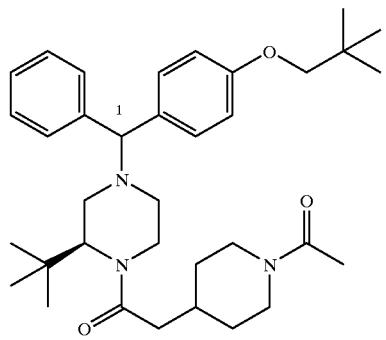
S158
S159
S160
S161
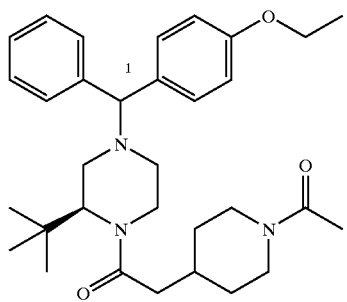
S162
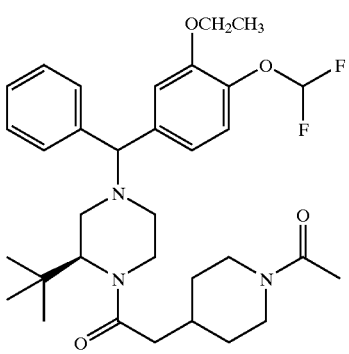
S163
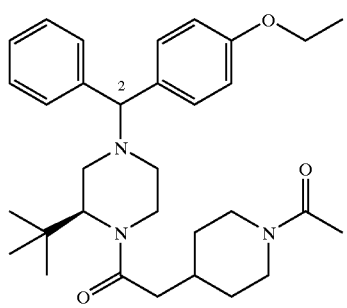
S164
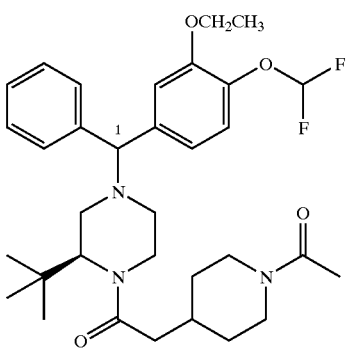

-continued
S165
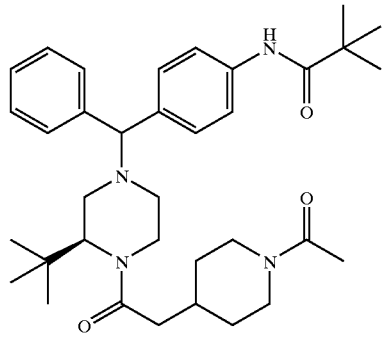
S166
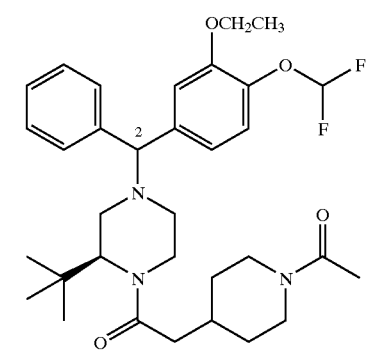
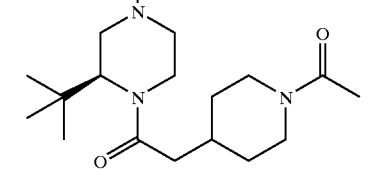
S167
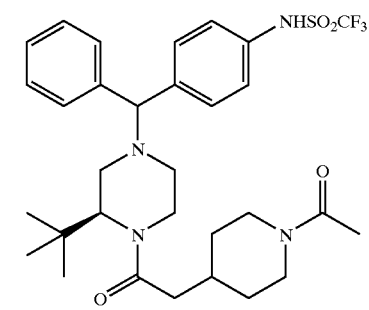
S168
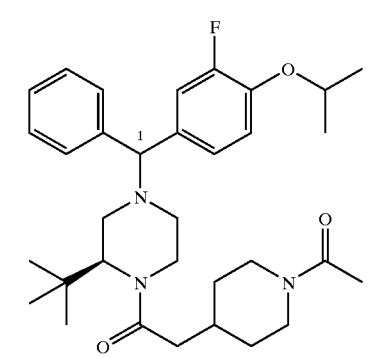
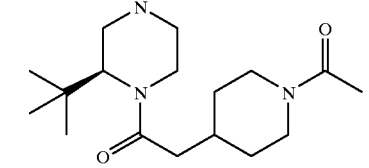
-continued
S169
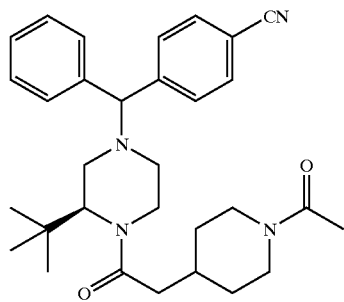
S170
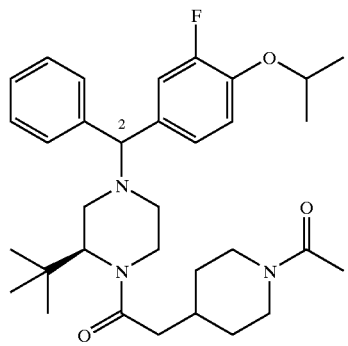
S171
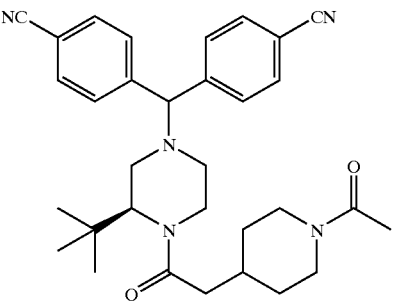
S172
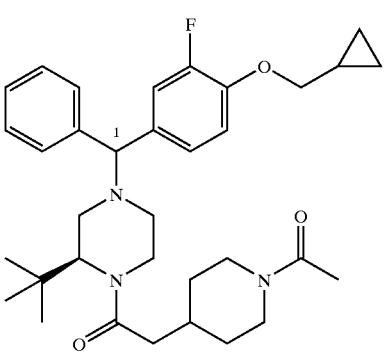

-continued
S173
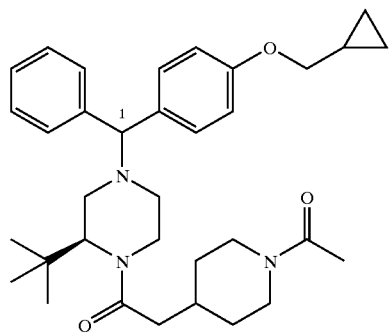
S174
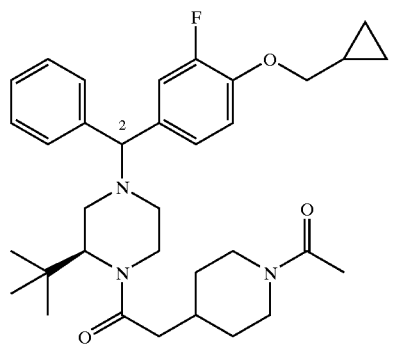
S175
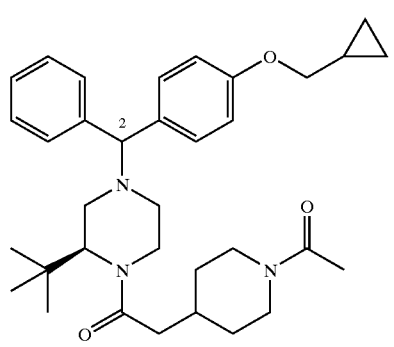
S176
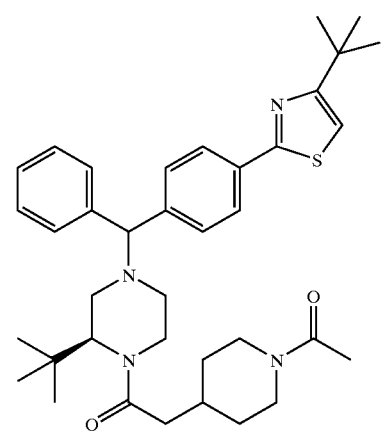
-continued
S177
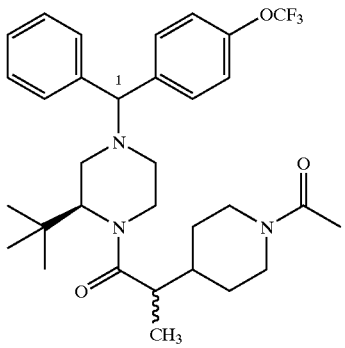
S178
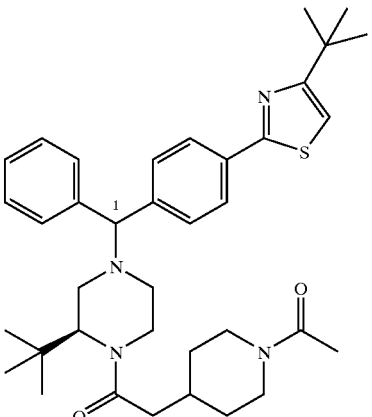
S179
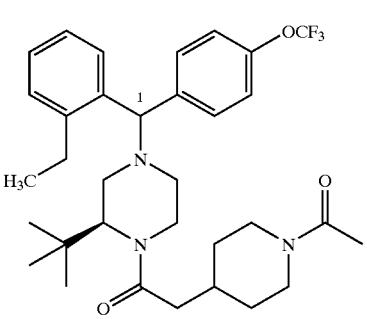
S180
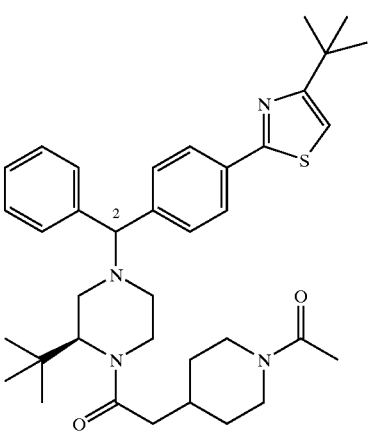

-continued
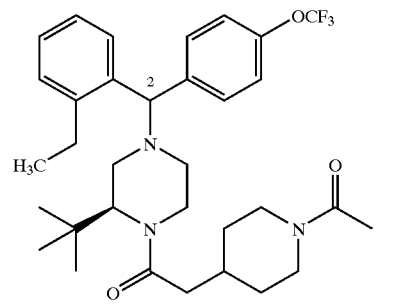 S181
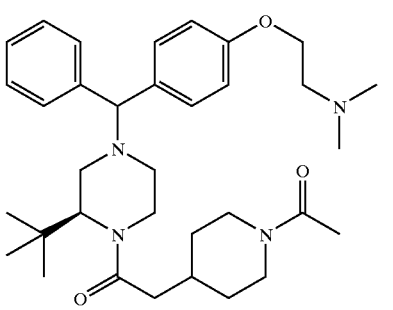 S182
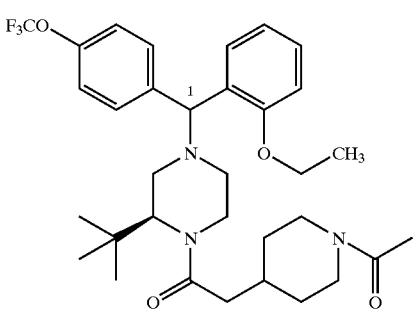 S183
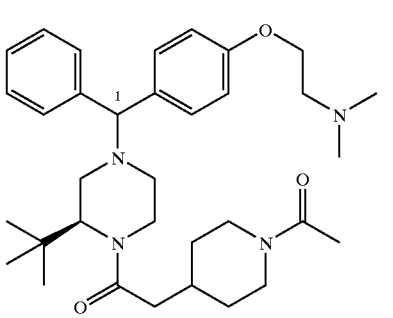 S184
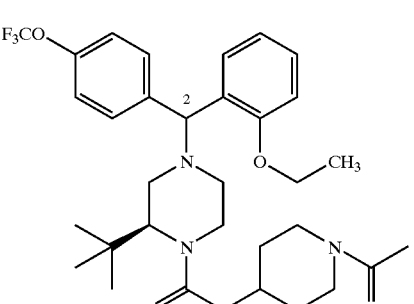 S185
-continued
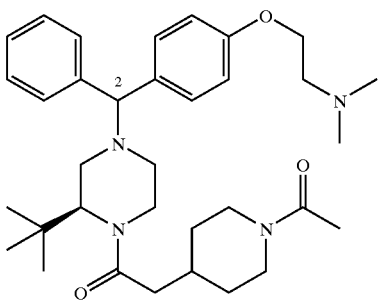 S186
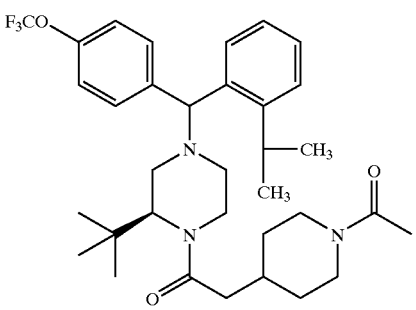 S187
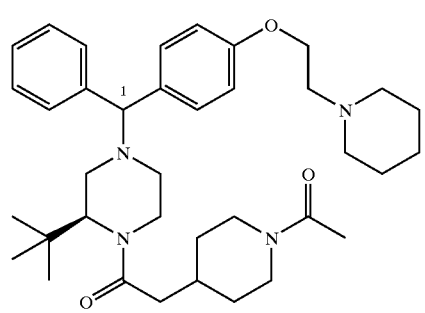 S188
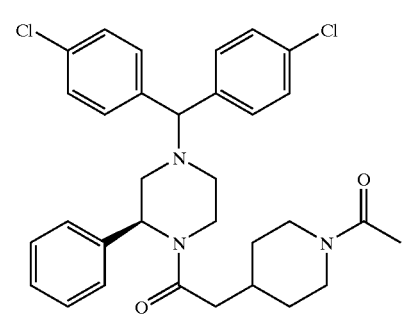 S189
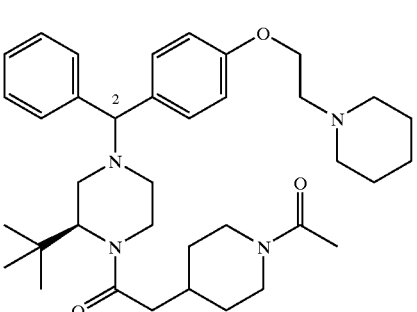 S190

-continued
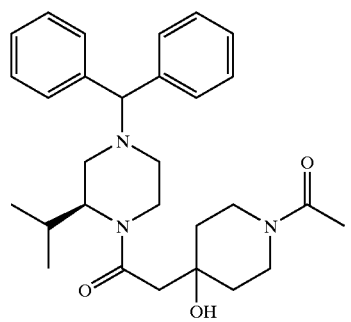 S191
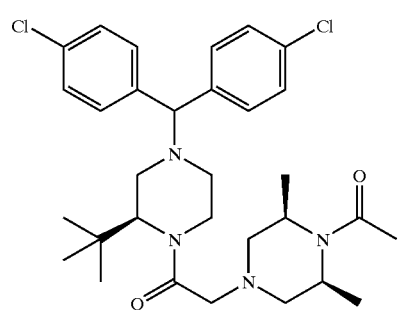 S192
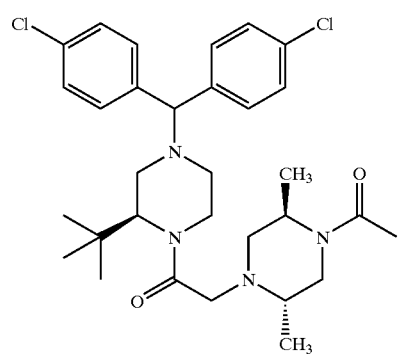 S193
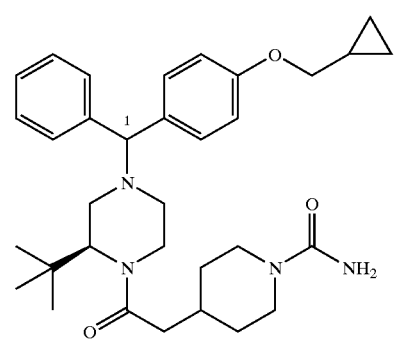 S194
-continued
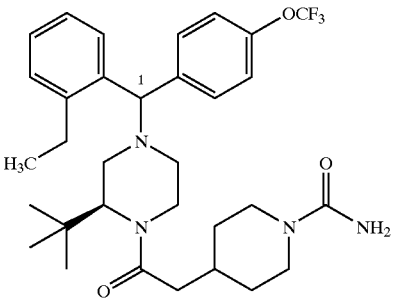 S195
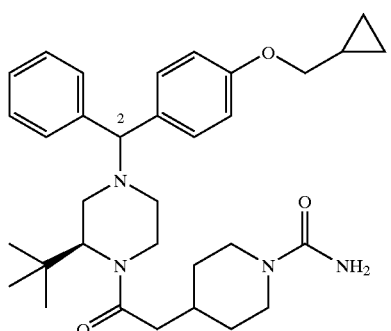 S196
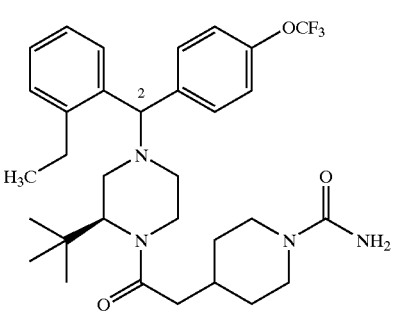 S197
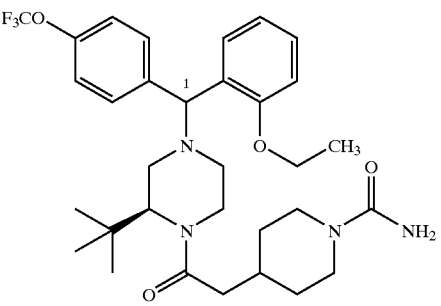 S198
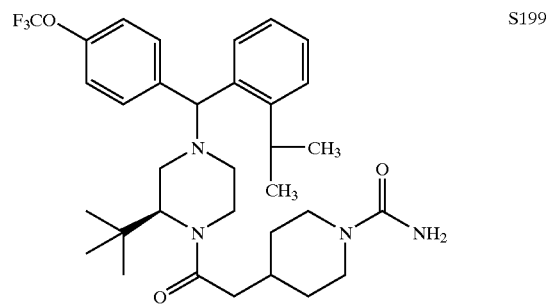 S199

-continued
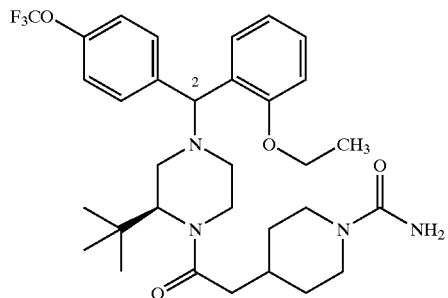 S200
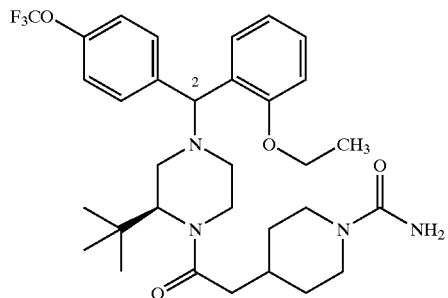 S201
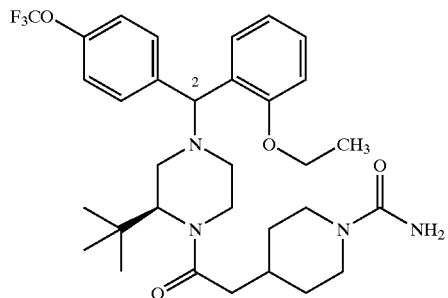 S202
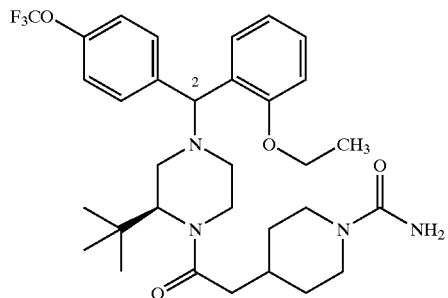 S203
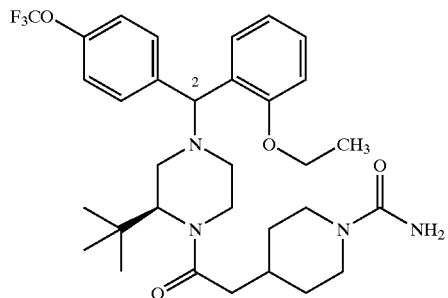 S204
-continued
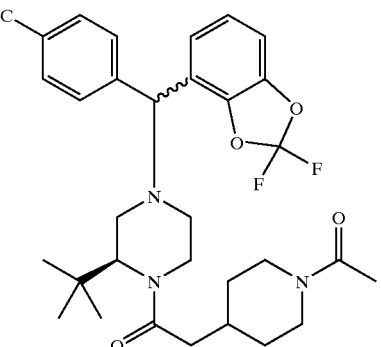 S205
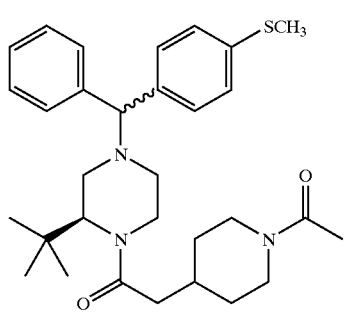 S206
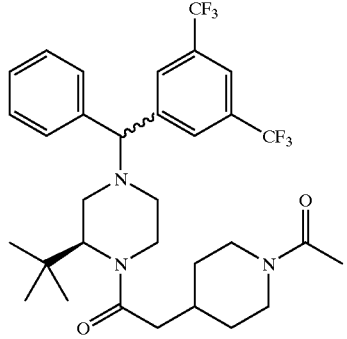 S207
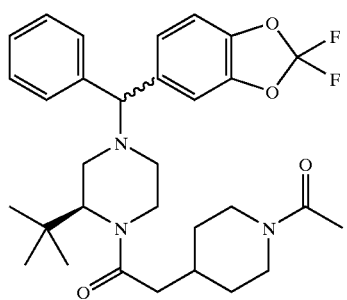 S208
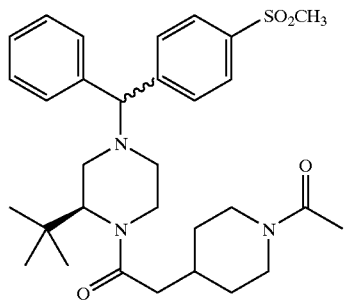 S209

-continued
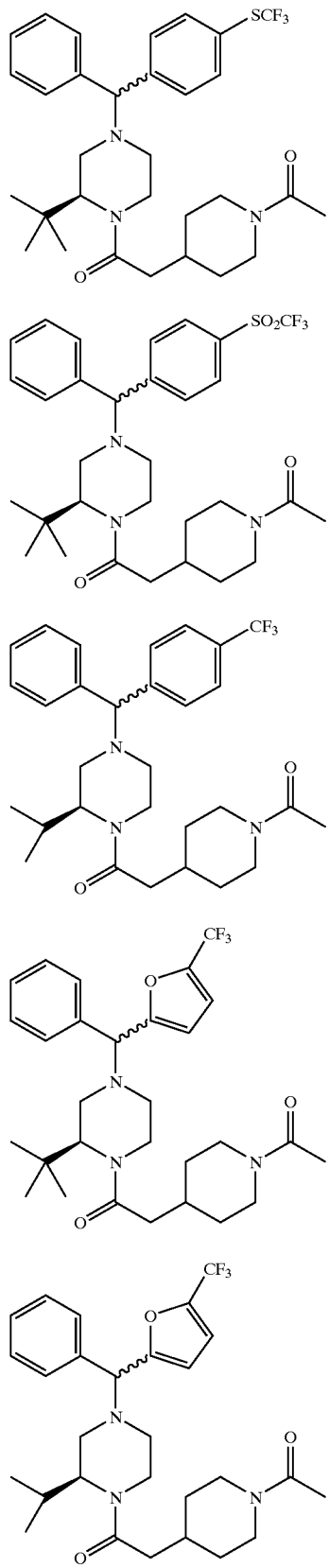
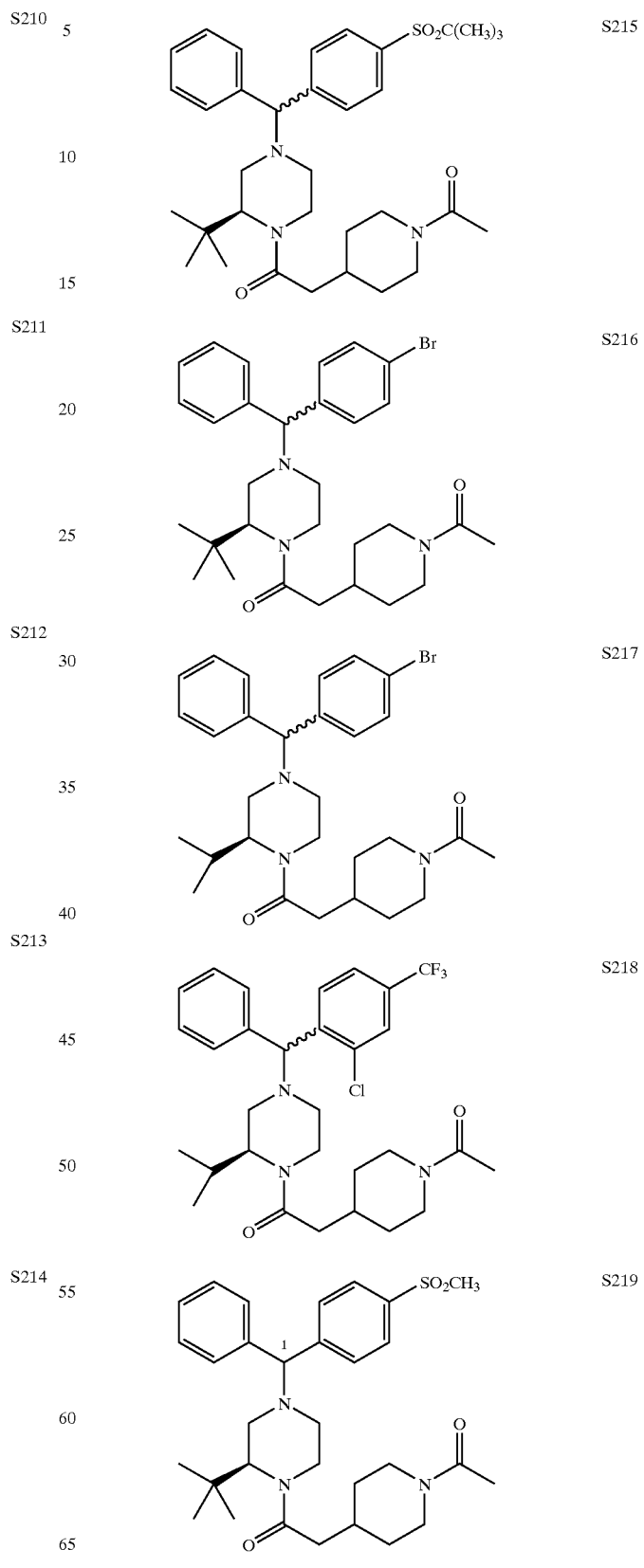

-continued
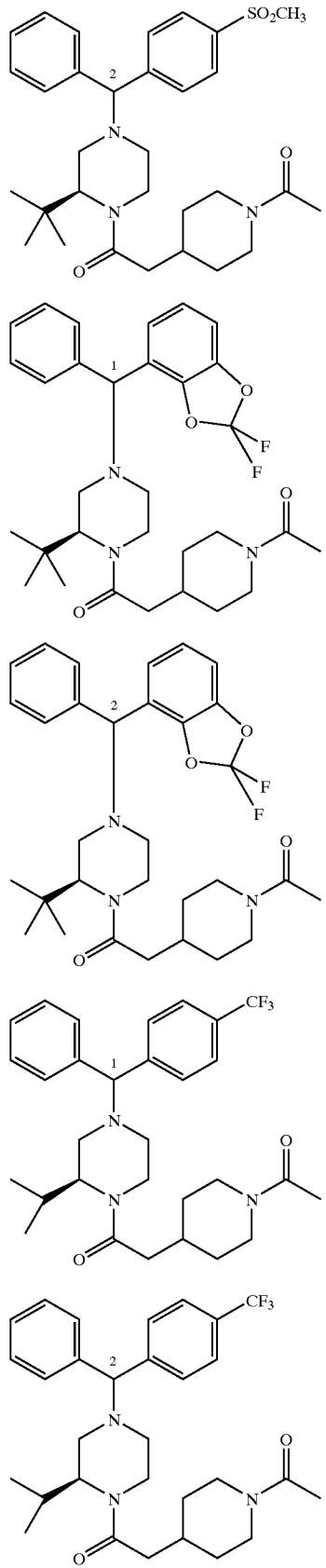
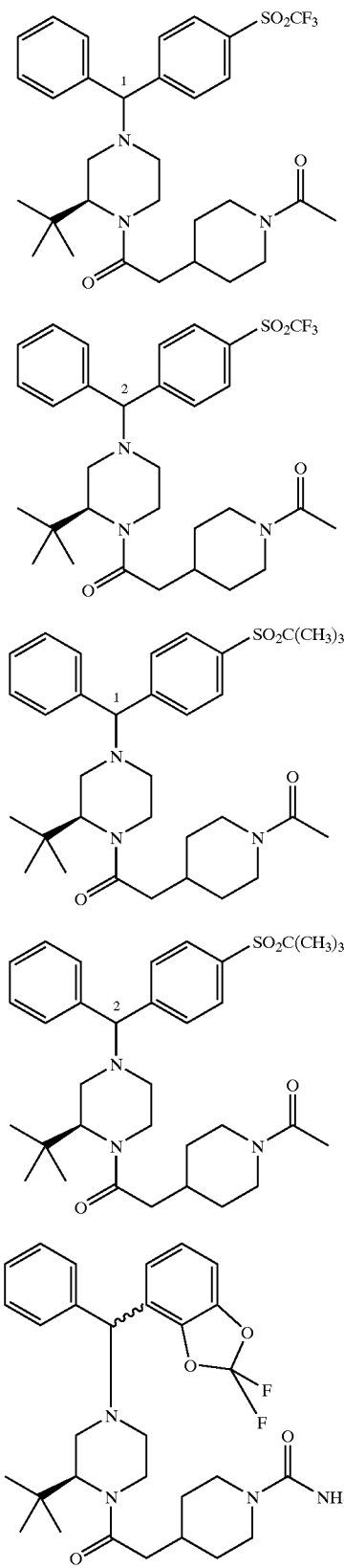

-continued
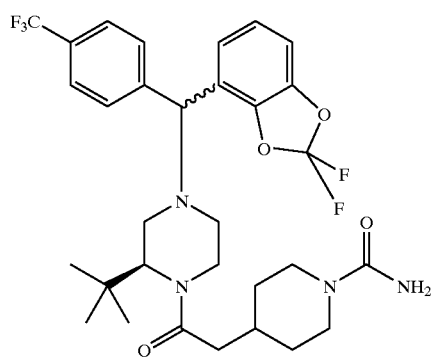 S230
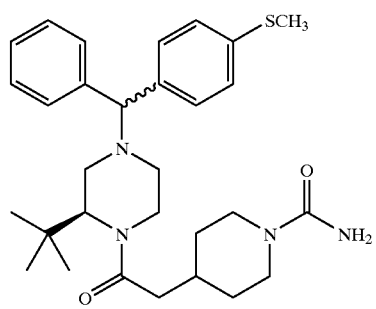 S231
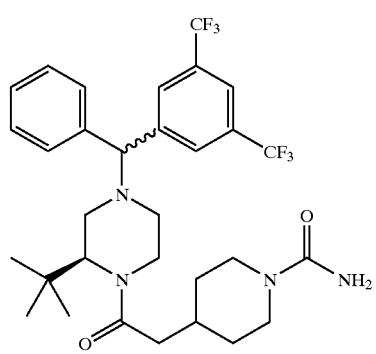 S232
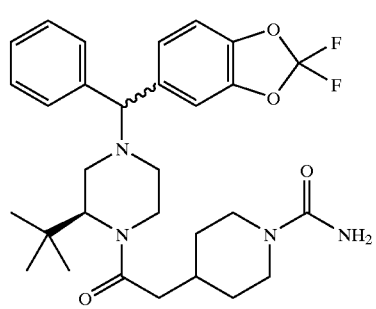 S233
-continued
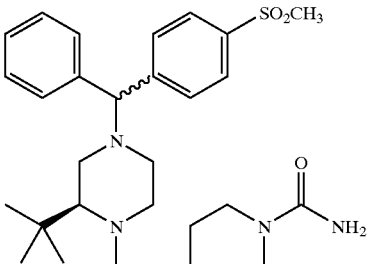 S234
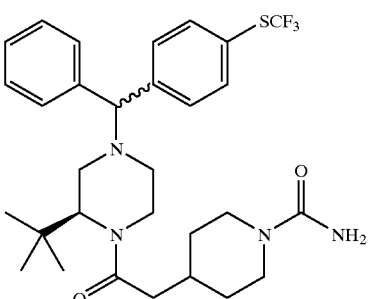 S235
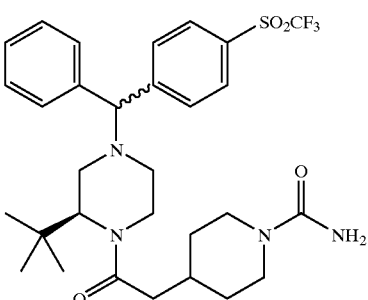 S236
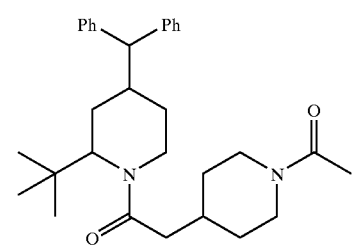 S237
isomer 1
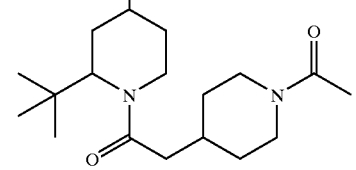 S238
isomer 2

-continued

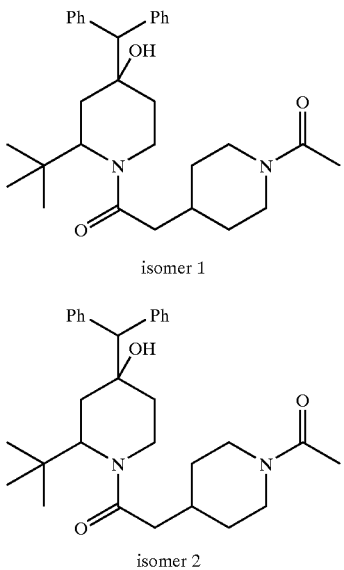

isomer 1 isomer 2

S239

S240

Preferred are compounds represented by the following numbers from Table A above: S1–3, S5, S7–9, S11, S16, S18, S22, S26, S28, S30, S35, S37, S46, S48, S50, S52, S54–55, S57, S59, S61, S63, S65, S70, S85, S90, S92, S100–101, S105, S107–143, S145, S147–149, S156–164, S166, S168, S170, S172–175, S184, S186, and S204–240.

More preferred are compounds represented by the following numbers from Table A above: S1, S8, S11, S26, S30, S37, S44, S46, S48, S50, S52, S54–55, S57, S59, S61, S63, S65, S70, S85, S90, S92, S101, S107–108, S 16–118, S122, S126–131, S139, S141, S145, S147, S157–160, S168, S170, S172–175, and S219–229.

Even more preferred, is a compound represented by the following numbes from Table A above: S1, S8, S11, S26, S30, S37, S48, S50, S54, S61, S65, S70, S85, S101, S107–108, S117, S126–128, S131, S157–160, S174–175, S219–220, and S225–228.

Yet even more preferred compounds are represented by the following numbers in Table A above: S8, S48, S50, S54, S108, S160, S174, and S220.

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, or by separating isomers of a compound of formula I.

Compounds of formula I can exist in unsolvated and solvated forms, including hydrated forms. In general, the solvated forms, with pharmaceutically acceptable solvents such as water, ethanol and the like, are equivalent to the unsolvated forms for purposes of this invention.

A compound of formula I may form pharmaceutically acceptable salts with organic and inorganic acids or bases. Examples of suitable bases for salt formation include, but are not limited to, sodium hydroxide, lithium hydroxide, potassium hydroxide, and calcium hydroxide. Also contemplated are salts formed with pharmaceutically acceptable amines such as ammonia, alkyl amines, hydroxyalkylamines, N-methylglucamine and the like. Certain compounds will be acidic in nature, e.g. those compounds which possess a carboxyl or phenolic hydroxyl group. Salts of phenols can be made by heating acidic compounds with any of the above mentioned bases according to procedures well known to those skilled in the art. For purposes of the invention aluminum, gold and silver salts of the compounds are also contemplated. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, lithium hydroxide, potassium hydroxide, calcium hydroxide, potassium carbonate, ammonia or sodium bicarbonate.

The method of treating proliferative diseases (cancer), according to this invention, includes a method for treating (inhibiting) the abnormal growth of cells, including transformed cells, in a patient in need of such treatment (e.g., a mammal such as a human), by administering, concurrently or sequentially, an effective amount of a compound of this invention and an effective amount of a chemotherapeutic agent, biological agent, surgery (e.g. prostatectomy) and/or radiation (preferably γ-radiation). Abnormal growth of cells means cell growth independent of normal regulatory mechanisms (e.g., contact inhibition or apoptosis), including the abnormal growth of: (1) tumor cells (tumors) expressing an activated ras oncogene; (2) tumor cells in which the ras protein is activated as a result of oncogenic mutation in another gene; and (3) benign and malignant cells of other proliferative diseases.

In preferred embodiments, the methods of the present invention include methods for treating or inhibiting tumor growth in a patient in need of such treatment (e.g., a mammal such as a human) by administering, concurrently or sequentially, (1) an effective amount of a compound of this invention and (2) an effective amount of an antineoplastic/microtubule agent; biological agent, and/or surgery (e.g. prostatectomy) and/or radiation therapy. Examples of tumors which may be treated include, but are not limited to, epithelial cancers, e.g., prostate cancer, lung cancer (e.g., lung adenocarcinoma), pancreatic cancers (e.g., pancreatic carcinoma such as, for example, exocrine pancreatic carcinoma), breast cancers, renal cancers, colon cancers (e.g., colorectal carcinomas, such as, for example, colon adenocarcinoma and colon adenoma), ovarian cancer, and bladder carcinoma. Other cancers that can be treated include melanoma, myeloid leukemias (for example, acute myelogenous leukemia), sarcomas, thyroid follicular cancer, and myelodysplastic syndrome.

Biological Data
17β-Hydroxysteroid Dehydrogenase Inhibition Data
Methods:

To prepare human recombinant type 3 17β-hydroxysteroid dehydrogenase enzyme (17β-HSD3), HEK-293 cells stably transfected with human 17β-HSD type 3 were cultured to confluency and harvested for enzyme. The cells were suspended in isolation buffer (20 mM $KH_2PO_4$, 1 mM EDTA, 0.25 M Sucrose, 1 mM PMSF, 5 µg/ml pepstatin A, 5 µg/ml antipain and 5 µg/ml leupeptin) to a concentration between $5.0\times10^6$ and $1.0\times10^7$ cells/ml. The cells were sonicated on ice using a micro-ultrasonic cell disrupter at an output setting of No. 40 for four 10 second bursts. The broken cells were then centrifuged at 100,000×g for 60 min at 4° C., and the resulting pellet was resuspended, aliquoted into microfuge tubes, and stored at −80° C.

To measure conversion of $^{14}$C-androstenedione to $^{14}$C-testosterone, which occurs primarily through the enzymatic action of 17β-HSD3, reaction buffer (12.5 mM $KH_2PO_4$, 1 mM EDTA), NADPH cofactor (1 mM final), test compound, 17β-HSD3 enzyme (30 μg protein) and $^{14}$C-androstenedione substrate (100 nM; 2.7 nCi/tube) were added to 13×100 borosilicate glass tubes to a total volume of 0.5 mL/tube. The tubes were placed in a prewarmed 37° C. water bath for 30 minutes. The reaction was then stopped by adding 1 ml of ethyl ether. The tubes were centrifuged for 20 minutes at 3000 rpm at 4° C. in a table top centrifuge and then snap frozen in a dry ice-methanol bath. The ether layer was decanted into another glass tube, and then evaporated to dryness using compressed nitrogen gas. The samples were resuspended in chloroform (20 mL) and spotted onto silica G60 thin layer chromatography plates. $^{14}$C-Androstenedione substrate and $^{14}$C-testosterone product were separated by placing the plates in chloroform:ethyl acetate (3:1). The plates were dried, exposed overnight, scanned and quantitated on a FUJI FLA2000 phosphorimager.

The percent inhibition of 17β-HSD3 activity is the difference between the percent of maximum specific binding ("MSB") and 100%. The percent of MSB is defined by the following equation, wherein "dpm" represents "disintegrations per minute":

$$\% \text{ MSB} = \frac{(\text{dpm of unknown}) - (\text{dpm of nonspecific binding})}{(\text{dpm of total binding}) - (\text{dpm of nonspecific binding})} \times 100$$

The concentration at which a compound having formula I produces 50% inhibition of binding is then used to determine an inhibition constant ("Ki") using the Chang-Prusoff equation.

It will be recognized that the compounds having formula I can inhibit 17β-HSD3 to varying degrees The compounds useful for practice of the invention exhibit potent affinities to bind 17β-HSD3 as measured by Ki values (in nM). The activities (potencies) for these compounds are determined by measuring their Ki values. The smaller the Ki value, the more active is a compound for inhibiting a particular NK enzyme.

Compounds of this invention have a range of 17B-Hydroxysteroid dehydrogenase Type 3 binding activity from about 0.005 nM to about >100 nM. Preferably, compounds of this invention have a binding activity in the range of about 0.005 nM to 100 nM, more preferably about 0.005 to 50 nM, and even more preferably about 0.005 nM to 10 nM. Yet even more preferred compounds have a binding activity in the range of about 0.005 nM to 0.050 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal composition can take the form of creams, lotions, aerosols and/or emulsions and can be included in a transdermal patch of the matrix or reservoir type as are conventional in the art for this purpose.

Preferably, the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of formula (I) will be regulated according to the judgment of the attending clinician (physician) considering such factors as age, condition and size of the patient as well as severity of the disease being treated. A dosage regimen of the compound of formula (I) can be oral administration of from 10 mg to 2000 mg/day, preferably 10 to 1000 mg/day, more preferably 50 to 600 mg/day, in two to four (preferably two) divided doses. Intermittant therapy (e.g., one week out of three weeks or three out of four weeks) may also be used.

The chemotherapeutic agent and/or radiation therapy can be administered in association with the compounds of the present invention according to the dosage and administration schedule listed in the product information sheet of the approved agents, in the Physicians Desk Reference (PDR) as well as therapeutic protocols well known in the art. Table 1.0 below gives ranges of dosage and dosage regimens of some exemplary chemotherapeutic agents useful in the methods of the present invention. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered chemotherapeutic agents (i.e., antineoplastic agent or radiation) on the patient, and in view of the observed responses of the disease to the administered therapeutic agents.

TABLE 1.0

Exemplary Chemotherapeutic Agents
Dosage and Dosage Regimens

| | |
|---|---|
| Cisplatin: | 50–100 mg/m² every 4 weeks (IV)* |
| Carboplatin: | 300–360 mg/m² every 4 weeks (IV) |
| Taxotere: | 60–100 mg/m² every 3 weeks (IV) |
| Gemcitabine: | 750–1350 mg/m² every 3 weeks (IV) |
| Taxol: | 65–175 mg/m² every 3 weeks (IV) |

*(IV)—intravenously

Anti-androgenic agents, anti-benign prostatic hyperplasia agents, potassium channel agonists and biological agents can be administered in association with the compounds of the present invention according to the dosage and administration schedule listed in the product information sheet of the approved agents, in the Physicians Desk Reference (PDR), as well as therapeutic protocols well known in the art. It will be apparent to those skilled in the art that the administration of the agents can be varied depending on the disease being treated and the known effects of the agents on that disease. Also, in accordance with the knowledge of the skilled clinician, the therapeutic protocols (e.g., dosage amounts and times of administration) can be varied in view of the observed effects of the administered agents on the patient and in view of the observed responses of the disease to the administered therapeutic agents.

Compounds of formula (I) may be produced by processes known to those skilled in the art in the following reaction schemes and in the preparations and examples below.

The compounds of this invention can be prepared as illustrated by the representative examples below.

Scheme 1

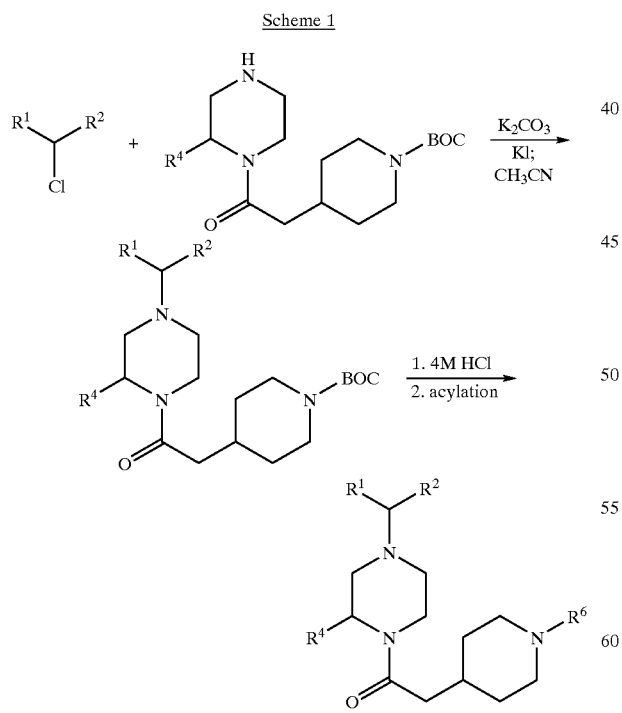

As shown in Scheme 1, the piperazine-piperidine core may be added to an appropriate chloride. Deprotection and acylation gives the desired product.

Scheme 2

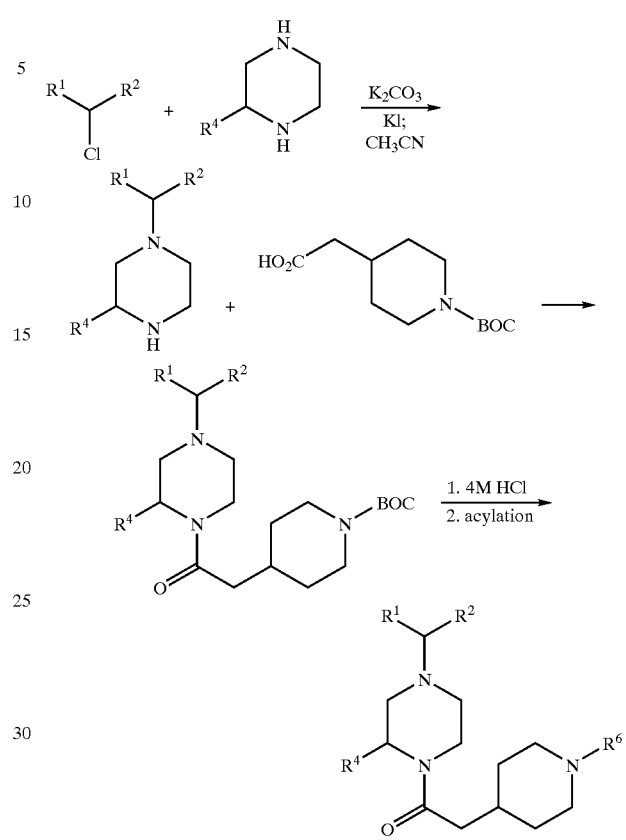

Alternatively, for those more sterically encumbered piperazines, direct coupling is successful in giving the regiochemically desired product, as shown in Scheme 2 above.

Scheme 3

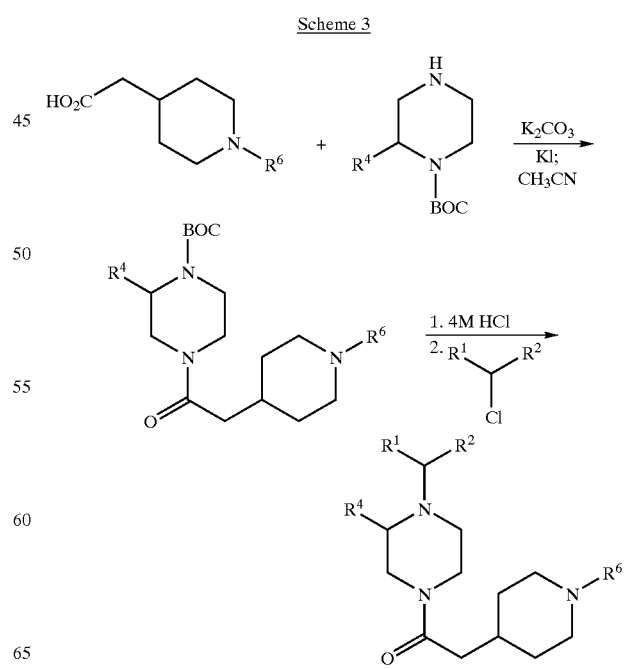

The regiochemical analogs can be prepared through the sequential modification of protecting groups as shown in Scheme 3 above.

Scheme 4

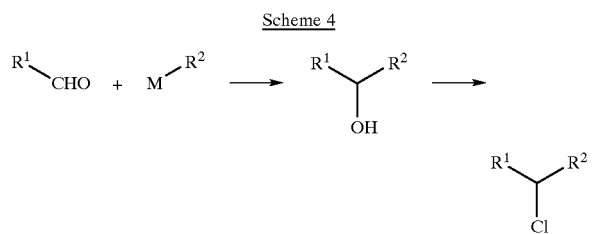

The synthesis of desired chlorides can be accomplished by the addition of an appropriate organometallic to an appropriate aldehyde (see Scheme 4 above). The resulting alcohol is then converted to the requisite chloride under standard conditions.

Scheme 5

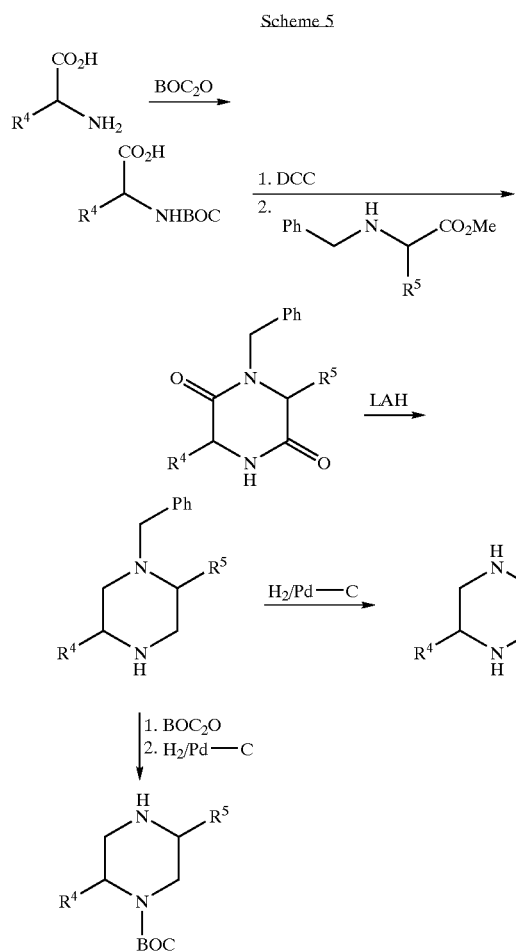

The substituted piperazines can be prepared through the reduction of commercially available diketopiperazines, or alternatively from the desired amino acids, as shown in Scheme 5 above.

Scheme 6

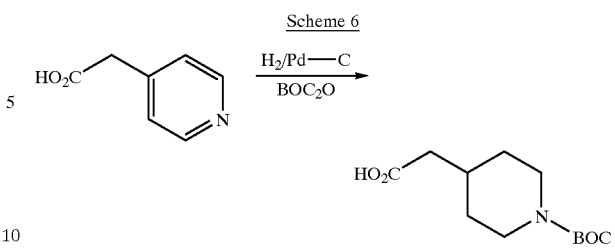

The N-BOC or N-acyl piperidine acetic acid can be prepared as described previously through the reduction of 4-pyridine acetic acid (see Scheme 6 above).

The invention disclosed herein is exemplified by the following preparations and examples, which should not be construed to limit the scope of the disclosure. Alternative mechanistic pathways and analogous structures may be apparent to those skilled in the art.

PREPARATIVE EXAMPLE 1

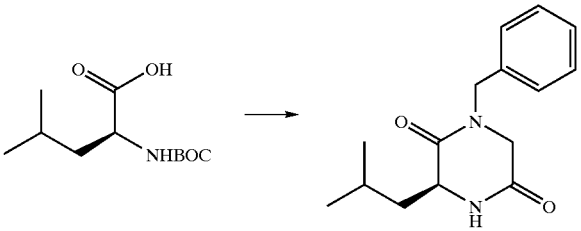

To a solution of DCC (43.2 mL, 1.0 M in $CH_2Cl_2$, 1.0 eq.) in $CH_2Cl_2$ (200 mL) at 0° C. was added N-t-BOC-L-leucine (10 g, 43.2 mmol). To the resulting slurry was added ethyl N-benzylglycinate (8.1 mL, 1.0 eq.) over 15 minutes. The resulting solution was stirred at 0° C. for 2 hours and room temperature 1 hour, filtered and the concentrated to give an oil (20.7 g, LCMS: $MH^+$=407). The intermediate was dissolved in $CH_2Cl_2$ (150 mL) through which HCl (g) was bubbled for 4 hours. The solution was purged with $N_2$ and concentrated under reduced pressure. The residue was neutralized with saturated $NaHCO_3$ and extracted with EtOAc (3×200 mL). The combined organics were washed with water, dried over $Na_2SO_4$, filtered and concentrated to give a solid which was used without further purification (11.3 g, 100% yield). LCMS: $MH^+$=261.

PREPARATIVE EXAMPLE 2–5.10

By essentially the same procedure set forth in Preparative Example 1, using the appropriate amino acids listed in Column 2 of Table 1 below, the compounds listed in Column 3 of Table 1. (CMPD), were prepared.

TABLE 1
| Prep. Ex. | Column 2 | Column 3 | CMPD |
|---|---|---|---|
| 2 | 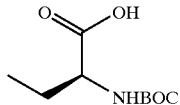 | | LCMS: MH$^+$ = 233 |
| 3 | 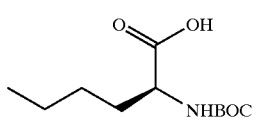 | | LCMS: MH$^+$ = 261 |
| 4 | 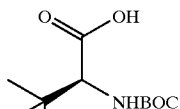 | | LCMS: MH$^+$ = 261 |
| 5 | 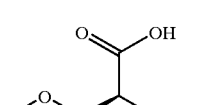 | | LCMS: MH$^+$ = 249 |
| 5.10 | 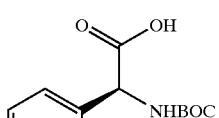 | | LCMS: MH$^+$ = 281 |

PREPARATIVE EXAMPLE 6

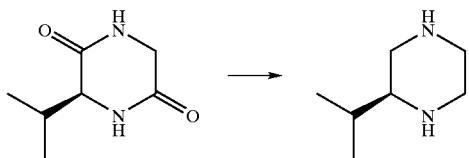

To a solution of (S)-3-isopropyl-2,5-piperazinedione (5.0 g, 32 mmol) in THF (100 mL) at 0° C. was added LAH (137 mL, 1.0 M in THF, 4.3 eq.) dropwise. After the addition was complete, the resulting solution was heated to reflux overnight. The reaction mixture was cooled to room temperature and quenched by the slow, sequential addition of water (5.23 mL), 1N NaOH (5.23 mL), and water (5.23 mL). The resulting slurry was diluted with EtOAc and filtered through a plug of Celite. The residue was washed with EtOAc (4×100 mL) and the combined organics concentrated under reduced pressure. The crude product was purified by flash chromatography using a gradient of 5% MeOH, 10% MeOH, 5% (10% NH$_4$OH) in MeOH, 10% (10% NH$_4$OH) in MeOH, and 20% (10% NH$_4$OH) in MeOH in CH$_2$Cl$_2$ to give a solid (3.03 g, 74% yield). LCMS: MH$^+$=129.

PREPARATIVE EXAMPLE 7–13.1

By essentially the same procedure set forth in Preparative Example 6, using the appropriate piperazinediones listed in Column 2 of Table 2 below, the compounds listed in Column 3 of Table 2 (CMPD) were prepared.

TABLE 2

| Prep. Ex. | Column 2 | Column 3 | CMPD |
|---|---|---|---|
| 7 | 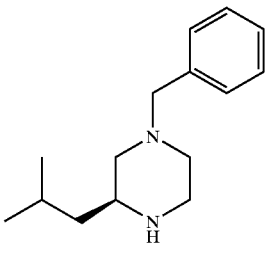 | 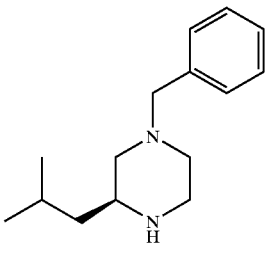 | LCMS: MH$^+$ = 233 |
| 8 | 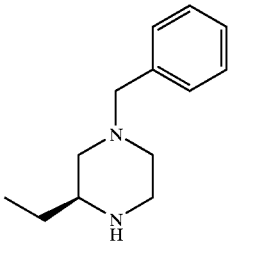 | 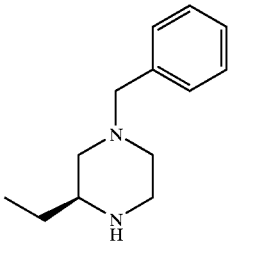 | LCMS: MH$^+$ = 205 |
| 9 | 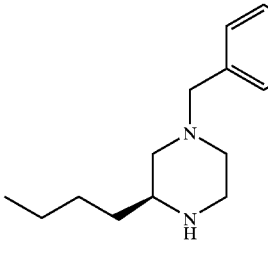 | 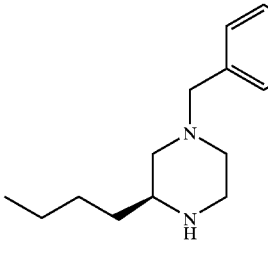 | LCMS: MH$^+$ = 233 |

TABLE 2-continued

| Prep. Ex. | Column 2 | Column 3 | CMPD |
|---|---|---|---|
| 10 | | | LCMS: MH⁺ = 233 |
| 11 | | | LCMS: MH⁺ = 221 |
| 12 | | | FABMS: MH⁺ = 235 |
| 13 | | | LCMS: MH⁺ = 143 |
| 13.1 | | | LCMS: MH⁺ = 253 |

PREPARATIVE EXAMPLE 14

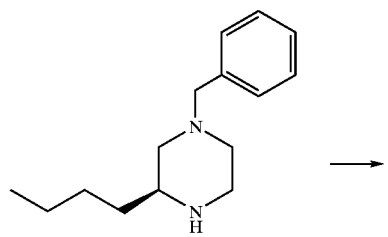

To a solution of the product from Preparative Example 9 (8.2 g, 31.5 mmol) in $CH_2Cl_2$ (300 mL) was added $(BOC)_2O$ (7.5 g, 1.02 eq.). The resulting solution was stirred at room temperature overnight. The reaction was quenched by the addition of saturated $NaHCO_3$ and separated. The organic layer was washed with brine, dried over $Na_2SO_4$, filtered, and concentrated under reduced pressure. The crude product was purified by flash chromatography using a 10% EtOAc in hexanes solution as eluent (10.6 g, 99% yield). LCMS: $MH^+$=333.

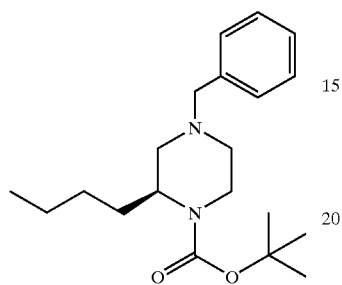

PREPARATIVE EXAMPLES 15 AND 16

By essentially the same procedure set forth in Preparative Example 14, using the appropriate compound from Preparative Example 8 and Preparative Example 12 listed in Column 2 of Table 3 below, the compounds listed in Column 3 of Table 3 were prepared:

TABLE 3

| Prep. Ex. | Column 2 | Column 3 | CMPD |
|---|---|---|---|
| 15 | (structure) | (structure) | LCMS: $MH^+$ = 305 |
| 16 | (structure) | (structure) | LCMS: $MH^+$ = 335 |

PREPARATIVE EXAMPLE 17

Step A:

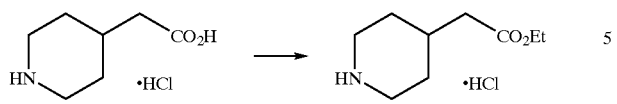

To a solution of piperidine-4-acetic acid (10.0 g, 70.0 mmol) in EtOH (100 mL) was added concentrated HCl (2.68 mL, 2.2 eq.). The resulting solution was heated at reflux for 12 hours. The reaction mixture was concentrated under reduced pressure and used without further purification (10 g, 84% yield).

Step B:

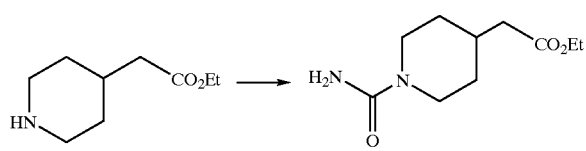

To a solution of the product from Preparative Example 17, Step A (2.0 g, 9.6 mmol) in $CH_2Cl_2$ (30 mL) at 0° C. was added TMSNCO (6.3 mL, 5.0 eq.) followed by TEA (2.0 mL, 1.5 eq.). The resulting solution was stirred at 0° C. for 3 hours and quenched by the addition water and diluted with saturated $NaHCO_3$. The mixture was extracted with $CH_2Cl_2$ and the combined organics dried over $Na_2SO_4$, filtered, and concentrated. The crude product was purified by flash chromatography using an 8:92 (10%) $NH_4OH$ in $MeOH:CH_2Cl_2$ solution as eluent (1.2 g, 60% yield). FABMS: $MH^+=215$.

Step C:

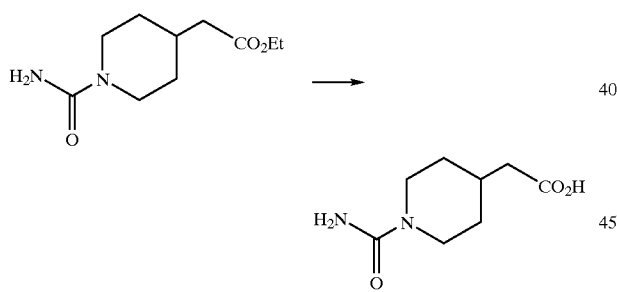

A solution of the product from Preparative Example 17, Step B (1.23 g, 5.7 mmol) and LiOH (0.33 g, 2.4 eq.) in $CH_2Cl_2$ (29 mL), EtOH (29 mL) and water (14 mL) was heated at reflux 3 hours. The resulting solution was cooled to room temperature, neutralized by the addition of 1N HCl (16.1 mL, 2.98 eq.) and concentrated under reduced pressure. The reaction product was further dried by the azeotropic removal of water with toluene to yield a gum (1.1 g, quantitative yield). FABMS: $MH^+=187$.

PREPARATIVE EXAMPLE 18

Step A:

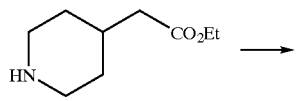

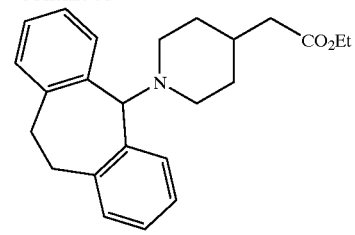

To a solution of the product from Preparative Example 17, Step A (2.5 g, 12.0 mmol) and 5-chlorodibenzosuberane (3.4 g, 1.2 eq.) in $CH_2Cl_2$ (50 mL) was added TEA (8.4 mL, 5.0 eq.) and the resulting solution stirred overnight. The reaction mixture was quenched by the addition of 1N NaOH and extracted with $CH_2Cl_2$. The combined organics were dried over Na2SO4, filtered and concentrated. The crude product was purified by flash chromatography using a 50:50 EtOAc:hexanes mix as eluent (3.45 μg, 79% yield).

Step B:

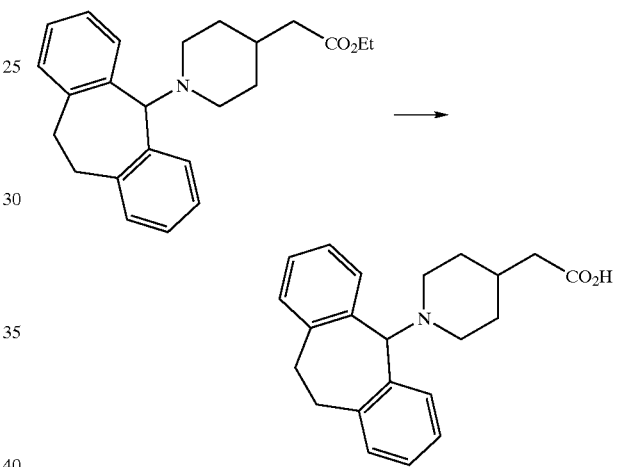

A solution of the product from Preparative Example 18, Step A (3.45 g, 9.5 mL) was heated to reflux in MeOH (100 mL) and 1N NaOH (30 mL, 3 eq.) for 4 hours. The reaction mixture was cooled to room temperature, concentrated under reduced pressure and extracted with $Et_2O$. The aqueous layer was cooled at −4° C. to effect crystallization. The resulting slurry was filtered and dried in vacuo to yield colorless crystals (1.9 g, 59% yield). FABMS: $MH^+=336$.

PREPARATIVE EXAMPLE 18.10

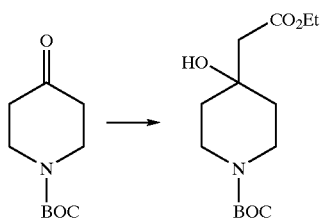

EtOAc (5.68 mmol, 1.0 eq) was added to LDA (3.97 mL, 1.4 eq, 2.0 M in THF/heptane) at −78° C. The resulting solution was stirred 20 minutes before adding N-BOC-4-piperidone (1.13 g, 1.0 eq) in THF (10 mL). The reaction mixture was warmed slowly to room temperature, stirred 2 hours and quenched by the addition of saturated NH₄Cl. The resulting solution was diluted with H₂O and extracted with EtOAC. The combined organics were washed with H₂O and saturated NaCl, dried over Na₂SO₄, filtered, and concentrated under reduced pressure. The crude product was purified by flash chromatography using a 50:50 EtOAc mix as eluent (1.0 g, 61% yield). LCMS: MH⁺=288.

PREPARATIVE EXAMPLE 18.11

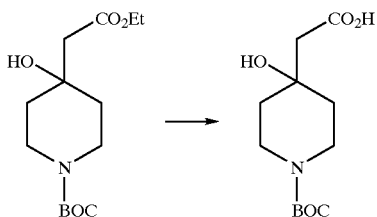

The compound prepared in Preparative Example 18.10 (0.24 g, 0.84 mmol) was stirred at room temperature in MeOH (3 mL) and NaOH (3 mL) overnight. The reaction mixture was concentrated under reduced pressure, diliuted with H₂O, and extracted with EtOAc. The aqueous layer was neutralized with 5% citric acid and extracted with EtOAc. The combined organics were washed with H₂O, saturated NaCl, dried over Na₂SO4, filtered and concentrated. The crude compound was used without further purification (0.17 g, 77% yield).

PREPARATIVE EXAMPLE 19

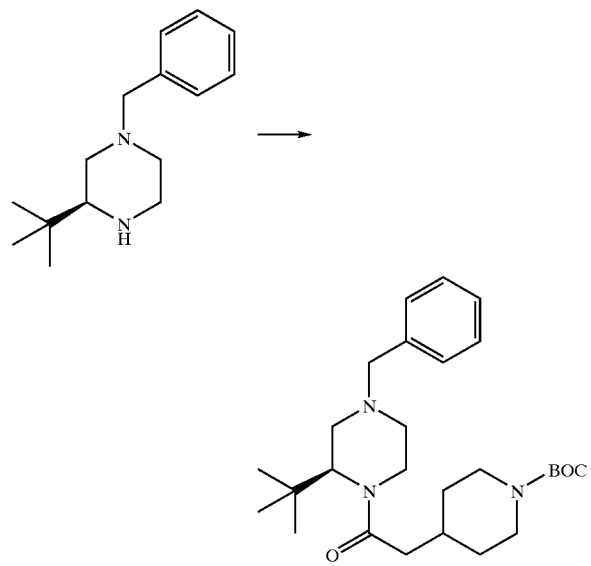

To a solution of N-Boc-4-piperidine acetic acid (described in U.S. Pat. No. 5,874,442) (10.0 g, 41.1 mmol) and TEA (5.7 mL, 1.0 eq.) in toluene (50 mL) at 0° C. was added trimethylacetyl chloride (5.1 mL, 1.0 eq.). The resulting slurry was stirred at 0° C. for 1.5 hours before adding the product from Preparative Example 10 (10.0 g, 43 mmol, 1.05 eq.) in toluene (20 mL) and the resulting solution was warmed to room temperature and stirred overnight. The reaction mixture was neutralized by the addition of 1N NaOH and extracted with EtOAc. The combined organics were dried over Na₂SO₄, filtered, and concentrated. The crude product was purified by flash chromatography using a 50:50 EtOAc:hexanes solution as eluent (11.1 g, 59% yield). LCMS: MH⁺=458.

PREPARATIVE EXAMPLE 19.1

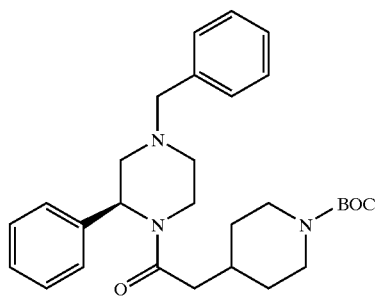

By essentially the same procedure set forth in Preparative Example 19, the above compound was prepared.

PREPARATIVE EXAMPLE 20

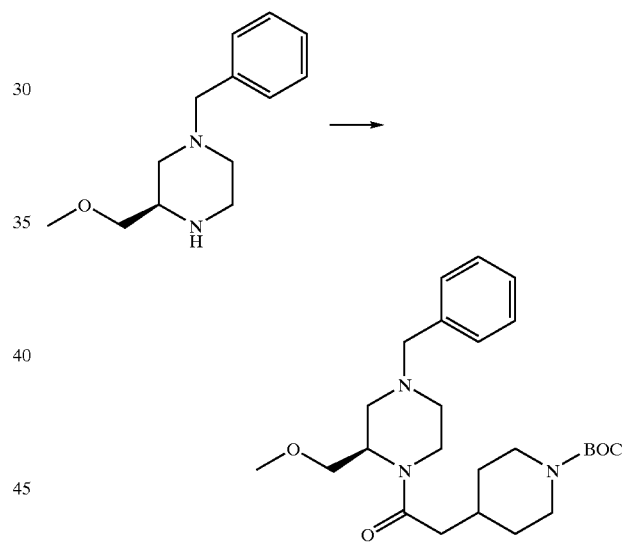

By essentially the same procedure set forth in Preparative Example 19, using the product from Preparative Example 11 (0.49 g, 2.0 mmol), the above compound was prepared (0.85 g, 46% yield). LCMS: MH⁺=446.

PREPARATIVE EXAMPLE 21

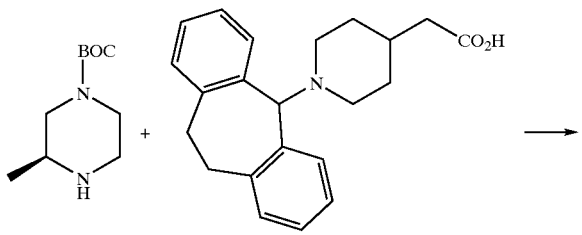

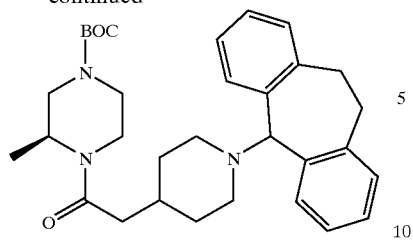

To a solution of 2(S)-methyl-4-t-butoxycarbonylpiperazine (0.22 g, 1.1 mmol) and the product from Preparative Example 18, Step B (0.44 g, 1.2 eq.) in CH₂Cl₂ (10 mL) was added HOBt (0.19 g, 1.3 eq.), NMM (0.30 mL, 2.5 eq.) and DEC (0.27 g, 1.3 eq.) and the resulting solution stirred at room temperature overnight. The reaction mixture was quenched by the addition of saturated NaHCO₃ and extracted with CH₂Cl₂, dried over Na₂SO₄, filtered, and concentrated under reduced pressure. The crude product was purified by flash chromatography using a 2% MeOH in CH₂Cl₂ solution as eluent (0.54 g, 95% yield). FABMS: MH⁺=518.

PREPARATIVE EXAMPLE 22

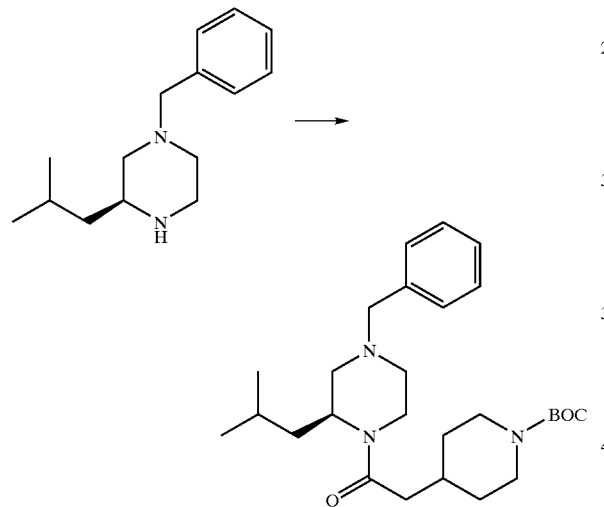

By essentially the same procedure set forth in Preparative Example 21, using the product from Preparative Example 7 and N-Boc-piperidine acetic acid, the above compound was prepared. LCMS: MH⁺=458.

PREPARATIVE EXAMPLE 23

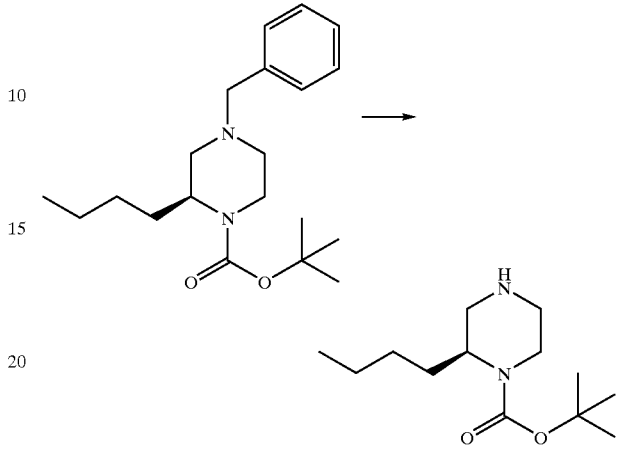

A solution of the product from Preparative Example 14 (10.4 g, 31.3 mmol) and 10% Pd/C (1.95 g) in EtOH (130 mL) was hydrogenated on a Parr apparatus at 50 psi overnight. The reaction mixture was filtered through Celite and the filtrate concentrated in vacuo to give the product as an oil (6.93 g, 91% yield) which was used without further purification. LCMS: MH⁺=243.

PREPARATIVE EXAMPLES 24–28.10

By essentially the same procedure set forth in Preparative Example 23, using the appropriate compounds from Preparative Examples 15, 16, 19, 19.1, 20, and 22 listed in Column 2 of Table 4, the compounds listed in Column 3 of Table 4 (CMPD) were prepared.

TABLE 4

| Prep. Ex. | Column 2 | Column 3 | CMPD |
|---|---|---|---|
| 24 | 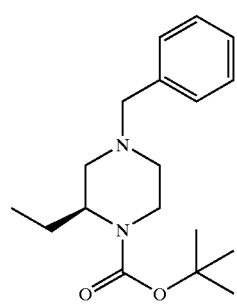 | | LCMS: MH⁺ = 305 |

TABLE 4-continued

| Prep. Ex. | Column 2 | Column 3 | CMPD |
|---|---|---|---|
| 25 | | | LCMS: MH⁺ = 245 |
| 26 | | | LCMS: MH⁺ = 368 |
| 27 | | | LCMS: MH⁺ = 356 |
| 28 | | | LCMS: MH⁺ = 368 |
| 28.10 | | | LCMS: MH+ = |

PREPARATIVE EXAMPLE 29

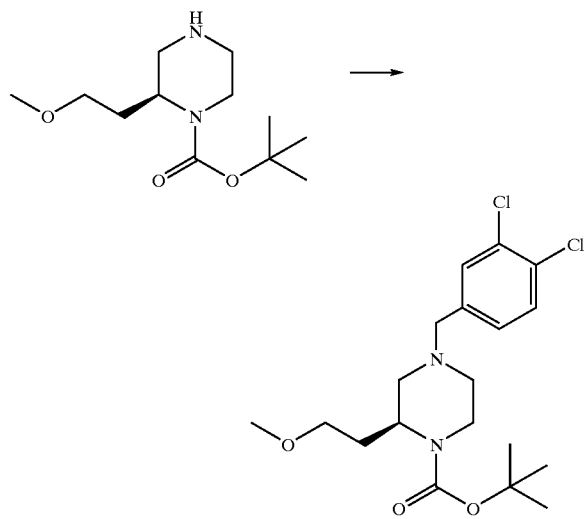

To a solution of the product from Preparative Example 25 (0.25 g, 1.0 mmol) and 3,4-dichlorobenzaldehyde (0.23 g, 1.3 eq.) in CH$_2$Cl$_2$ (5 mL) was added NaHB(OAc)$_3$ (0.32 g, 1.5 eq.) and AcOH (0.14 mL, 2.4 eq.) and the resulting solution was stirred at room temperature 96 hours. The reaction mixture was quenched by the addition of saturated NaHCO$_3$ and extracted with CH$_2$Cl$_2$. The combined organics were dried over Na$_2$SO$_4$, filtered and concentrated under reduced pressure. The crude product was purified by flash chromatography using a 10% EtOAc in CH$_2$Cl$_2$ solution as eluent (0.27 g, 66% yield). FABMS: MH$^+$=403.

PREPARATIVE EXAMPLE 30

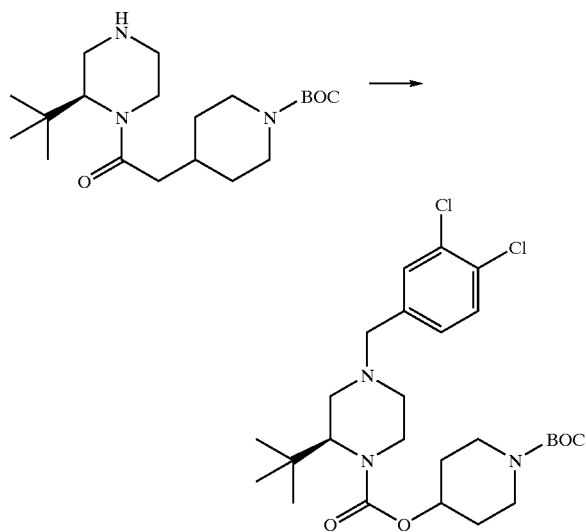

By essentially the same procedure set forth in Preparative Example 29, using the product from Preparative Example 26, the above compound was prepared (0.33 g, 92% yield). LCMS: MH$^+$=526.

PREPARATIVE EXAMPLE 31

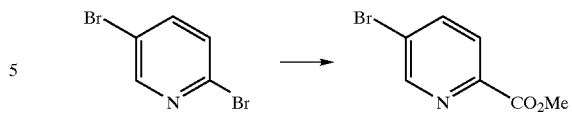

A solution of 2,5-dibromopyridine (10 g, 42.2 mmol), TEA (11.6 mL, 2.0 eq.), 1,1-bis(diphenylphosphino)ferrocene (1.4 g, 6 mol %), and Pd(OAc)$_2$ (0.28 g, 3 mol %) in MeOH (40 mL) and DMF (40 mL) was stirred under CO (40 psi) at 50° C. for 6 hours. The reaction mixture was cooled to room temperature, diluted with water, and extracted with EtOAc. The combined organics were dried over Na$_2$SO$_4$, filtered, and concentrated under reduced pressure. The crude product was purified by flash chromatography using a 50:50 EtOAc:hexanes mix as eluent to give the desired product (5.6 g, 61% yield) and the bis-carbonylated product (1.0 g). LCMS: MH$^+$=216.

PREPARATIVE EXAMPLE 32

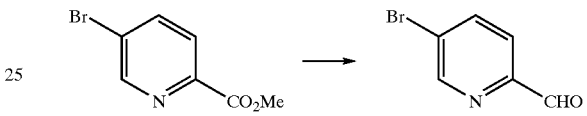

To a solution of the product from Preparative Example 31 (1.0 g, 4.6 mmol) in CH$_2$Cl$_2$ (15 mL) was added DIBAL-H (10.2 mL, 1M in toluene, 2.2 eq.) at −5° C. The resulting solution was stirred 15 minutes before quenching with saturated Na$_2$SO$_4$. The residue was extracted with CH$_2$Cl$_2$ and the combined organics dried over Na$_2$SO$_4$, filtered, and concentrated under reduced pressure. The crude product was purified by flash chromatography using a 50:50 EtOAc:hexanes solution as eluent (0.55 g, 64% yield). LCMS: MH$^+$= 186.

PREPARATIVE EXAMPLE 33

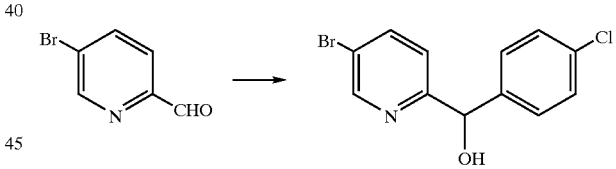

To a solution of 1-chloro-4-iodobenzene (1.07 g, 1.4 eq.) in THF (10 mL) at −40° C. was added isopropylmagnesium chloride (2.3 mL, 2.0 M in THF, 1.4 eq.) dropwise. The resulting solution was stirred at −40° C. for 2 hours before adding the product from Preparative Example 32 (0.56 g, 3.2 mmol) in THF (10 mL). The reaction mixture was warmed to room temperature and stirred 3 hours. The resulting solution was quenched by the addition of saturated NH$_4$Cl an extracted with EtOAc. The combined organics were washed with water, brine, dried over Na$_2$SO$_4$, filtered, and concentrated under reduced pressure. The crude product was purified by flash chromatography using a 20% EtOAc in hexanes solution as eluent to give an oil (0.3 g, 34% yield). LCMS: MH$^+$=299.

PREPARATIVE EXAMPLE 33.1 AND 33.2

By essentially the same procedure set forth in Preparative Example 33, using the aryl halides in Column 3 and the arylaldehydes in Column 2, the products given in Column 4 of Table 4.1 below were prepared:

TABLE 4.1

| Prep. Ex. | Column 2 | Column 3 | Column 4 |
|---|---|---|---|
| 33.1 | 2,2-difluoro-benzo[1,3]dioxole-4-carbaldehyde | 1-iodo-4-(trifluoromethyl)benzene | (2,2-difluoro-benzo[1,3]dioxol-4-yl)(4-(trifluoromethyl)phenyl)methanol |
| 33.2 | benzaldehyde | 2-chloro-1-iodo-4-(trifluoromethyl)benzene | (2-chloro-4-(trifluoromethyl)phenyl)(phenyl)methanol |

PREPARATIVE EXAMPLE 34–40

By essentially the same procedure set forth in Preparative Example 33, using the aryl halides in Table 4.1, Column 2 and the arylaldehydes in Table 4.2, Column 3, the products in Table 4.1, Column 4 were prepared:

TABLE 4.2

| Prep. Ex. | Column 2 | Column 3 | Column 4 |
|---|---|---|---|
| 34 | 5-bromo-pyridine-2-carbaldehyde | 1-bromo-4-(trifluoromethoxy)benzene | (5-bromopyridin-2-yl)(4-(trifluoromethoxy)phenyl)methanol |
| 35 | 5-bromo-pyridine-2-carbaldehyde | 1-bromo-4-(trifluoromethyl)benzene | (5-bromopyridin-2-yl)(4-(trifluoromethyl)phenyl)methanol |
| 36 | pyridine-2-carbaldehyde | 1-bromo-4-chlorobenzene | (4-chlorophenyl)(pyridin-2-yl)methanol |
| 37 | 4-chlorobenzaldehyde | 3-bromopyridine | (4-chlorophenyl)(pyridin-3-yl)methanol |
| 38 | quinoline-3-carbaldehyde | 1-chloro-4-iodobenzene | (4-chlorophenyl)(quinolin-3-yl)methanol |

TABLE 4.2-continued

| Prep. Ex. | Column 2 | Column 3 | Column 4 |
|---|---|---|---|
| 39 | quinoline-4-CHO | 4-chloro-iodobenzene | isoquinolin-4-yl(4-chlorophenyl)methanol |
| 40 | 4-(trifluoromethyl)benzaldehyde | 4-(trifluoromethyl)iodobenzene | bis(4-(trifluoromethyl)phenyl)methanol |

PREPARATIVE EXAMPLE 40.1

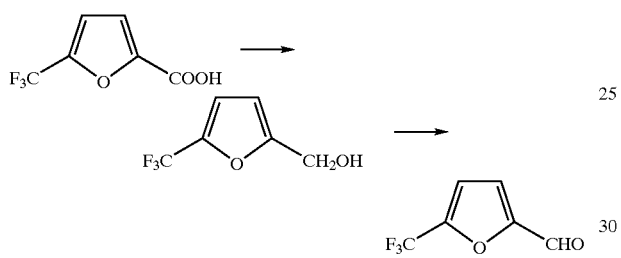

5-trifluoromethyl-2-furanecarboxylic acid ((500 mg, 2.78 mmol) was dissolved in anhydrous Et$_2$O (3 mL) and LiAlH$_4$ (1.0 M in Et$_2$O, 2.2 mL, 2.2 mmol) was added slowly. The mixture was refluxed for 2 hr, then stirred at rt 20 hr. 5% aqueous KOH (0.15 mL) was added, the mixture was filtered, and the solvent was evaporated. 340 mg (74%) of colorless oil was obtained.

The oil (330 mg, 1.99 mmol) was dissolved in anhydrous 1,2-dichloroethane (10 mL), BaMnO$_4$ (2.05 g, 8.0 mmol) was added, and the mixture was stirred and refluxed under N$_2$ 3 hr. CH$_2$Cl$_2$ (20 mL) was added, the mixture was filtered through Celite, and the solvent was evaporated. Crude product (110 mg) was directly used for the preparation of Preparative Example 41.6 below.

PREPARATIVE EXAMPLE 40.2

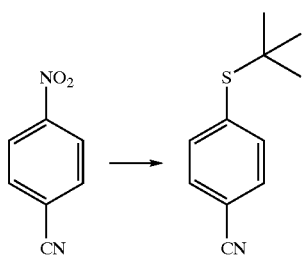

4-nitrobenzonitrile (2.96 g, 20 mmol) was mixed with (CH$_3$)$_3$CSNa (3.36 g, 30 mmol), anhydrous DMSO (40 mL) was added, and the mixture was stirred at rt for 20 hr. The mixture was poured into H$_2$O (1 L) and extracted with Et$_2$O (2×200 mL). The combined extracts were washed with H$_2$O (3×300 mL), dried over Na$_2$SO$_4$, and filtered. The solvent was evaporated and the residue was purified by column chromatography on silicagel with CH$_2$Cl$_2$:hexane (1:1). White solid (2.38 g, 62%) was obtained.

PREPARATIVE EXAMPLE 40.3

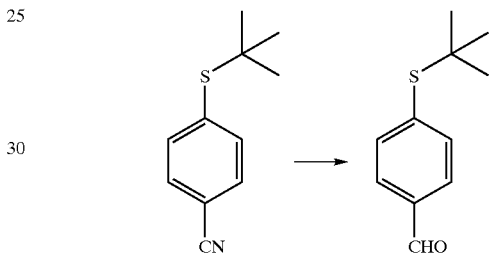

4-tert-butylthiobenzonitrile (960 mg, 5.0 mmol) was dissolved in anhydrous toluene (10 mL), the solution was cooled to 0° C., and DIBAL-H (20% in toluene, 7.1 mL, 10 mmol) was added under N$_2$. The mixture was stirred at 0° C. for 2 hr, washed with 1 M HCl (2×100 mL), brine (100 mL), and dried over Na$_2$SO$_4$. After the solvent had been evaporated, 850 mg of crude aldehyde (which was used directly for the preparation of Preparative Example 41.7) was obtained.

PREPARATIVE EXAMPLE 41

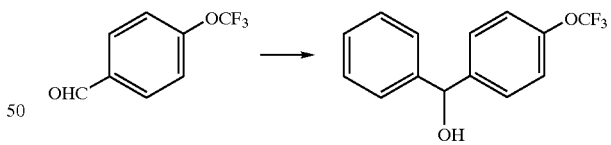

To a solution of 4-trifluoromethoxybenzaldehyde (0.3 g, 1.6 mmol) in THF (3.0 mL) at −78° C. was added phenylmagnesium bromide (3.16 mL, 1M in THF, 2.0 eq.) dropwise. The resulting solution was stirred at −78° C. for 1 hour and stored at −4° C. overnight. The reaction was quenched by the addition of saturated NH$_4$Cl and extracted with CH$_2$Cl$_2$. The combined organics were dried over Na$_2$SO$_4$, filtered, and concentrated under reduced pressure. The crude product was purified by flash chromatography using a 10% EtOAc in hexanes solution as eluent (0.39 g, 93% yield).

PREPARATIVE EXAMPLES 41.1–41.8

By essentially the same procedure set forth in Preparative Example 41, using the arylaldehydes in Column 2 of Table 4.3 and phenylmagnesium bromide, the products given in Column 3 of Table 4.3 were prepared:

| Prep. Ex. | Column 2 | Column 3 |
|---|---|---|
| 41.1 | 2,2-difluoro-1,3-benzodioxole-4-carbaldehyde | phenyl(2,2-difluoro-1,3-benzodioxol-4-yl)methanol |
| 41.2 | 4-(methylthio)benzaldehyde | phenyl(4-(methylthio)phenyl)methanol |
| 41.3 | 3,5-bis(trifluoromethyl)benzaldehyde | phenyl(3,5-bis(trifluoromethyl)phenyl)methanol |
| 41.4 | 2,2-difluoro-1,3-benzodioxole-5-carbaldehyde | phenyl(2,2-difluoro-1,3-benzodioxol-5-yl)methanol |
| 41.5 | 4-(trifluoromethylthio)benzaldehyde | phenyl(4-(trifluoromethylthio)phenyl)methanol |
| 41.6 | 5-(trifluoromethyl)furan-2-carbaldehyde | phenyl(5-(trifluoromethyl)furan-2-yl)methanol |
| 41.7 | 4-(tert-butylthio)benzaldehyde | phenyl(4-(tert-butylthio)phenyl)methanol |
| 41.8 | 4-bromobenzaldehyde | phenyl(4-bromophenyl)methanol |

PREPARATIVE EXAMPLES 41.10–41.16

By essentially the same procedure set forth in Preparative Example 41 only substituting the appropriate compound in column 2 of Table 4.4, the compounds found in column 3 of Table 4.4 were prepared:

TABLE 4.4

| Prep. Ex. | Column 2 | Column 3 |
|---|---|---|
| 41.10 | F₃C–CH₂–O-(3-fluoro-4-substituted phenyl)–CHO | F₃C–CH₂–O-(3-fluoro-4-substituted phenyl)–CH(OH)–Ph |
| 41.12 | F₂HC–O-(3-ethoxy-4-substituted phenyl)–CHO | F₂HC–O-(3-ethoxy-4-substituted phenyl)–CH(OH)–Ph |
| 41.13 | iPr–O-(3-fluoro-4-substituted phenyl)–CHO | iPr–O-(3-fluoro-4-substituted phenyl)–CH(OH)–Ph |
| 41.14 | cyclopropyl–CH₂–O-(3-fluoro-4-substituted phenyl)–CHO | cyclopropyl–CH₂–O-(3-fluoro-4-substituted phenyl)–CH(OH)–Ph |
| 41.15 | 4-tert-butyl-2-(4-formylphenyl)thiazole | 4-tert-butyl-2-[4-(hydroxy(phenyl)methyl)phenyl]thiazole |
| 41.16 | 3-(trifluoromethoxy)benzaldehyde | (3-(trifluoromethoxy)phenyl)(phenyl)methanol |

PREPARATIVE EXAMPLE 42

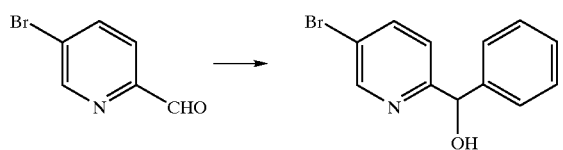

By essentially the same procedure set forth in Preparative Example 41, using the 3-bromopyridine-2-carboxaldehyde prepared in Preparative Example 32, the above compound was prepared. LCMS: MH$^+$=264.

PREPARATIVE EXAMPLE 43

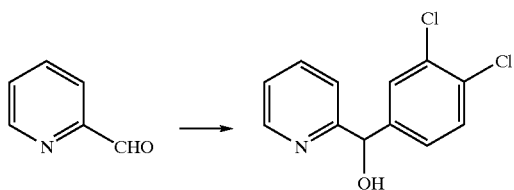

n-BuLi (4.25 mL, 2.5 M in hexanes, 1,2 eq.) was added dropwise to 1-bromo-3,4-dichlorobenzene (2.0 g, 8.9 mmol) in THF (20 mL) at −78° C. The resulting orange solution was stirred 40 minutes before adding pyridine-2-carboxaldehyde (1.1. mL, 1.3 eq.) dropwise. The reaction mixture was stirred 2 hours at −78° C. and quenched by the addition of water. The resulting solution was extracted with CH$_2$Cl$_2$, dried over Na$_2$SO$_4$, filtered, and concentrated. The crude product was purified by flash chromatography using a 40% EtOAc solution in hexanes as eluent. This partially purified residue was repurified using a 3% MeOH in CH$_2$Cl$_2$ solution as eluent to give an oil (0.37 g, 16% yield).

PREPARATIVE EXAMPLE 44–54.14

By essentially the same procedure set forth in Preparative Example 43, using the aryl halides in Table 5, Column 2 and the arylaldehydes in Table 5, Column 3, the compounds in Table 5, Column 4 were prepared:

TABLE 5

| Prep. Ex. | Column 2 | Column 3 | Column 4<br>RR'CHOH |
|---|---|---|---|
| 44 | 2-bromothiophene | thiophene-2-carboxaldehyde | di(thiophen-2-yl)methanol |
| 45 | 3-bromothiophene | thiophene-3-carboxaldehyde | di(thiophen-3-yl)methanol |
| 46 | 2-bromothiophene | 4-chlorobenzaldehyde | (4-chlorophenyl)(thiophen-2-yl)methanol |
| 47 | 2-bromothiazole | 4-chlorobenzaldehyde | (4-chlorophenyl)(thiazol-2-yl)methanol |
| 48 | 1-bromonaphthalene | 4-chlorobenzaldehyde | (4-chlorophenyl)(naphthalen-1-yl)methanol |

TABLE 5-continued

| Prep. Ex. | Column 2 | Column 3 | Column 4 RR'CHOH |
|---|---|---|---|
| 49 | 2-bromonaphthalene | 4-chlorobenzaldehyde | naphthalen-2-yl(4-chlorophenyl)methanol |
| 50 | 4-bromo-1H-pyrazole | 4-chlorobenzaldehyde | (4-chlorophenyl)(1H-pyrazol-4-yl)methanol |
| 51 | 5-bromoisoquinoline | 4-chlorobenzaldehyde | (4-chlorophenyl)(isoquinolin-5-yl)methanol |
| 52 | 8-bromoquinoline | 4-chlorobenzaldehyde | (4-chlorophenyl)(quinolin-8-yl)methanol |
| 53 | 5-bromoquinoline | 4-chlorobenzaldehyde | (4-chlorophenyl)(quinolin-5-yl)methanol |
| 54 | 1-bromonaphthalene | 4-(trifluoromethoxy)benzaldehyde | naphthalen-1-yl(4-(trifluoromethoxy)phenyl)methanol |
| 54.1 | 1-bromo-4-(trifluoromethoxy)benzene | 4-(trifluoromethoxy)benzaldehyde | bis(4-(trifluoromethoxy)phenyl)methanol |
| 54.12 | 1-bromo-2-ethylbenzene | 4-(trifluoromethoxy)benzaldehyde | (2-ethylphenyl)(4-(trifluoromethoxy)phenyl)methanol |

TABLE 5-continued

| Prep. Ex. | Column 2 | Column 3 | Column 4 RR'CHOH |
|---|---|---|---|
| 54.13 | F₃CO—⟨⟩—I | 2-(ethoxy)-benzaldehyde | (2-ethoxyphenyl)(4-trifluoromethoxyphenyl)methanol |
| 54.14 | 2-(isopropyl)-bromobenzene | 4-(trifluoromethoxy)-benzaldehyde | (2-isopropylphenyl)(4-trifluoromethoxyphenyl)methanol |

PREPARATIVE EXAMPLE 55

Step A:

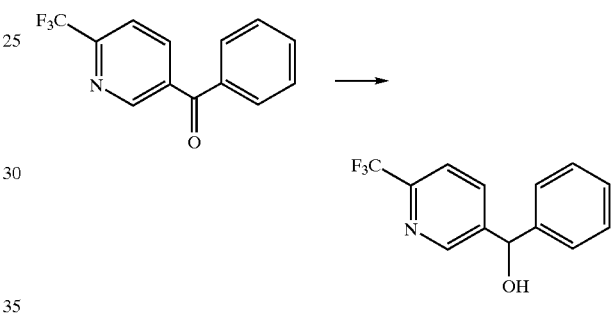

Oxalyl chloride (0.27 mL, 1.2 eq.) was added dropwise to a solution of 2-trifluoromethyl-5-pyridinecarboxylic acid (0.50 g, 2.62 mmol) and DMF (2 drops) in CH₂Cl₂ (20 mL) and the resulting solution was heated to reflux. The reaction mixture was cooled and concentrated under reduced pressure. The residue was redissolved in CH₂Cl₂ (10 mL) and treated with diisopropylethylamine (0.7 mL, 2.3 eq.) and N,O-dimethylhydroxlamine (0.19 g, 1.2 eq.). The resulting solution was stirred at room temperature 3 days, quenched by the addition of water (25 mL) and extracted with CH₂Cl₂. The combined organics were dried over Na₂SO₄, filtered, and concentrated under reduced pressure. The crude reaction was purified by flash chromatography using a 70:30 EtOAc:hexanes mix as eluent to give an oil (0.29 g, 70% yield). LCMS: MH⁺=235.

Step B:

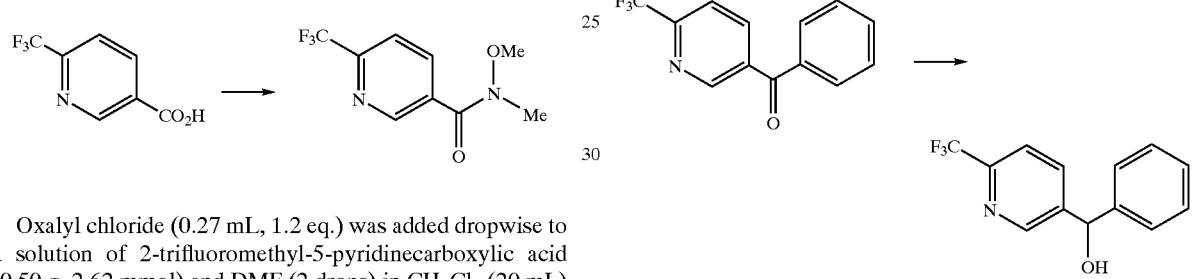

Phenylmagnesium chloride (2.91 mL, 1.0 M in THF, 3.0 eq.) was added to the product from Preparative Example 55, Step A (0.23 g, 0.97 mmol) in THF (10 mL) at 0° C. The resulting solution was warmed slowly to room temperature and stirred 6 hours. The reaction was quenched by the addition of water and extracted with CH₂Cl₂. The combined organics were dried over Na₂SO₄, filtered, and concentrated under reduced pressure. The crude product was purified by flash chromatography using a 50% EtOAc in hexanes solution as eluent (0.24 g, quantitative yield). LCMS; MH⁺=252.

Step C:

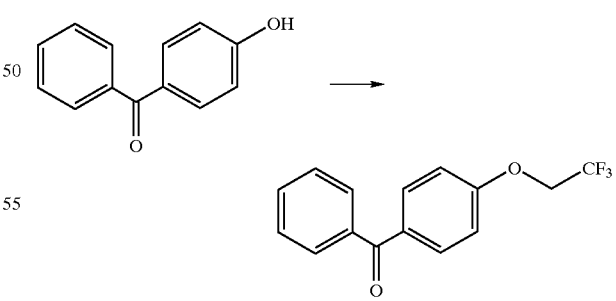

The product from Preparative Example 55, Step B (0.23 g, 0.93 mmol) in EtOH (3.0 mL) and toluene (3.0 mL) was stirred at room temperature with NaBH₄ (0.053 g, 1.5 eq.) 5 hours. The resulting solution was quenched by the addition of water and extracted with EtOAc. The combined organics were dried over Na₂SO₄, filtered, and concentrated under reduced pressure. The crude product was purified by flash chromatography using a 30% EtOAc in hexanes solution as eluent (0.15 g, 66% yield). LCMS: MH⁺=254.

PREPARATIVE EXAMPLE 55.1

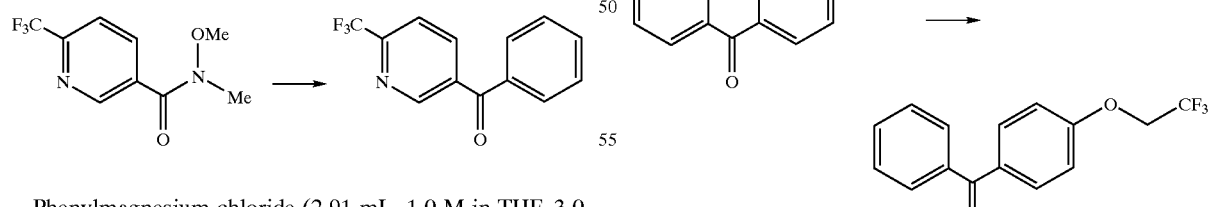

To a solution of 4-hydroxybenzophenone (0.50 g, 2.52 mmol) and K₂CO₃ (0.52 g, 1.5 eq.) in DMF (6 mL) was added trifluromethansulfonic acid 2,2,2-trifluoroethyl ester and the resulting solution was heated to 50° C. for 2 hours. The reaction mixture was cooled to room temperature, diluted with EtOAc and water and extracted. The combined organics were dried over Na₂SO₄, filtered, and concentrated under reduced pressure. The crude product was purified by flash chromatography using an 80:20 hexanes:EtOAc mix as eluent (0.67 g, 94% yield). LCMS: MH$^+$=281.

PREPARATIVE EXAMPLE 55.10

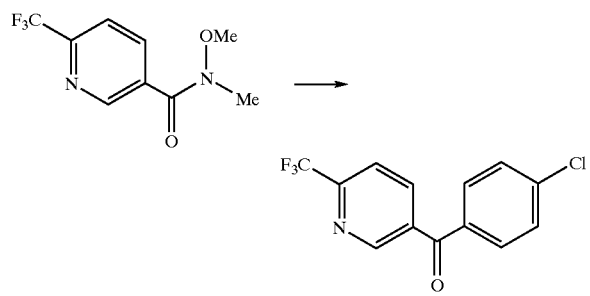

By essentially the same procedure set forth in Preparative Example 55, Step B only substituting 4-chlorophenylmagesium chloride, the above compound was prepared (% yield). LCMS: MH+=.

A solution of 4-hydroxybenzophenone (1.0 g, 5.04 mmol), dimethylaminoethyl chloride hydrochloride (1.09 g, 1.5 eq.), and K$_2$CO$_3$ (3.48 g, 5.0 eq.) was heated at reflux 24 hours in acetone (50 mL). The resulting solution was cooled to room temperature and stirred an additional 32 hours. The reaction mixture was diluted with H$_2$O and extracted with EtOAc. The combined organics were washed with 1N HCl (3×25 mL) and the combined aqueous washings neutralized with 1N NaOH and extracted with CH$_2$Cl$_2$. The combined organics were drie over Na$_2$SO$_4$, filtered and concentrated and used without further purification (1.36 g, 100% yield): LCMS MH$^+$=270.

PREPARATIVE EXAMPLES 55.12–55.14

By essentially the same procedure set forth in Preparative Example 55.11, only substituting the appropriate chloride in column 1 of Table 5.11, the title compounds in column 2 of Table 5.11 were prepared.

TABLE 5.11

| Prep. Ex. | Column 1 | Column 2 |
|---|---|---|
| 55.12 | | |
| 55.13 | | |
| 55.14 | | |

PREPARATIVE EXAMPLE 55.11

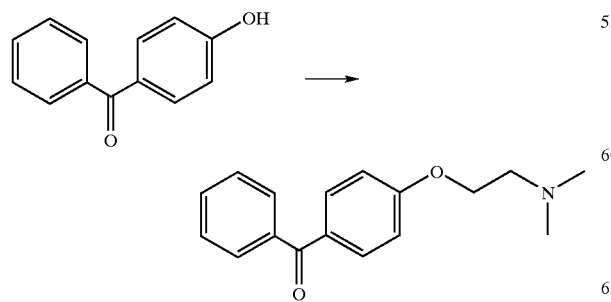

PREPARATIVE EXAMPLE 55.15

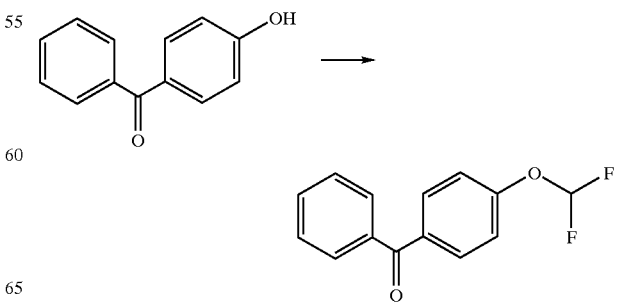

A solution of 4-hydroxybenzophenone (1.0 g, 5.04 mmol), sodium chlorodifluoroacetate (0.77 g, 1.0 eq.), and NaOH (0.20 g, 1.0 eq.) in DMF (10 mL) and H$_2$O (1.4 mL) was heated to 120–125° C. for 2.5 hours. The reaction mixture was cooled to room temperature, diluted with 1N NaOH and extracted with EtOAc. The combined organics were washed with H$_2$O, saturated NaCl, and dried over Na$_2$SO$_4$ and concentrated in vacuo. The crude product was purified by flash chromatography using a 15% EtOAc in hexanes solution as eluent (0.39 g, 31% yield): LCMS MH$^+$=249.

PREPARATIVE EXAMPLES 55.16–55.17

By essentially the same procedure set forth in Preparative Example 15 only substituting the appropriate compounds in column 1 of Table 5.12, the compounds in column 2 of Table 5.12 were prepared.

PREPARATIVE EXAMPLE 55.19

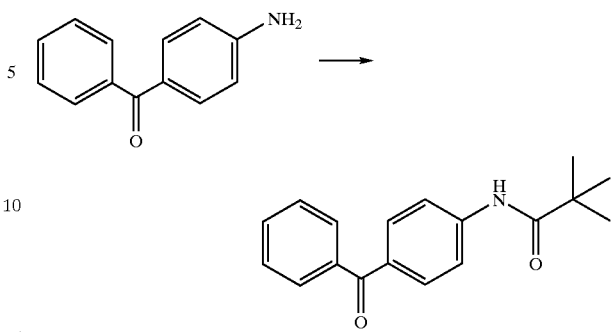

Trimethylacetyl chloride (0.75 mL, 1.2 eq.) was added to a solution of 4-aminobenzophenone (1.0 g, 5.07 mmol) and

TABLE 5.12

| Prep. Ex. | Column 1 | Column 2 | CMPD |
|---|---|---|---|
| 55.16 | (structure: HO, OCH$_2$CH$_3$, CHO) | (structure: F-CHF-O, OCH$_2$CH$_3$, CHO) | — |
| 55.17 | (structure: benzophenone with OH) | (structure: benzophenone with OCHF$_2$) | LCMS: MH$^+$ = 249 |

PREPARATIVE EXAMPLE 55.18

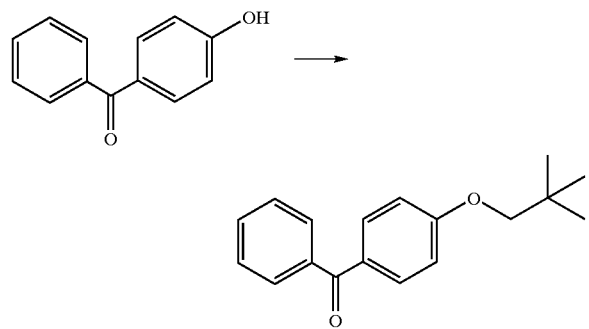

A solution of 4-hydroxybenzophenone (2.0 g, 10.9 mmol), neopentyl bromide (3.05 g, 2 eq.), K$_2$CO$_3$ (2.79 g, 2.0 eq.), KI (2.85 g, 1.7 eq.), and CuI (38 mg, 2 mol %) in DMF (10 mL) was heated to 95° C. for 48 hours. The reaction mixture was cooled to room temperature, diluted with saturated NaHCO$_3$ (50 mL) and extracted with EtOAc (3×100 mL). The combined organics were washed with H$_2$O and brine, dried over Na$_2$SO$_4$, filtered, and concentrated under reduced pressure. The crude product was purified by flash chromatography using a 30% EtOAc in hexanes solution as eluent (0.1 g, 4% yield).

TEA (1.06 mL, 1.5 eq.) in CH$_2$Cl$_2$ (30 mL) at 0° C. The resulting solution was stirred 1.5 hours, warmed to room temperature and quenched by the addition of saturated NaHCO$_3$. The resulting solution was extracted with CH$_2$Cl$_2$, the combined organics dried over Na$_2$SO$_4$, filtered and concentrated. The crude product was purified by flash chromatography using a 30% EtOAC in hexane solution as eluent (1.28 g, 90% yield). LCMS: MH$^+$=282.

PREPARATIVE EXAMPLE 55.191

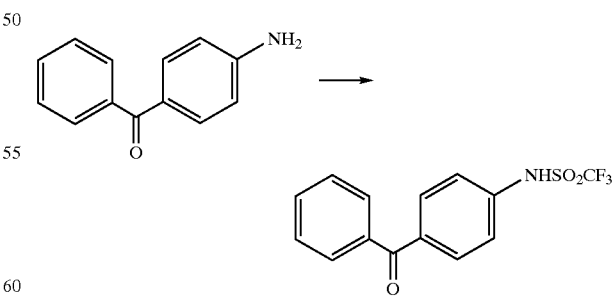

By essentially the same procedure set forth in Preparative Example 55.19, only substituting trifluorosulfonic anhydride, the above compound was prepared.

PREPARATIVE EXAMPLE 55.192

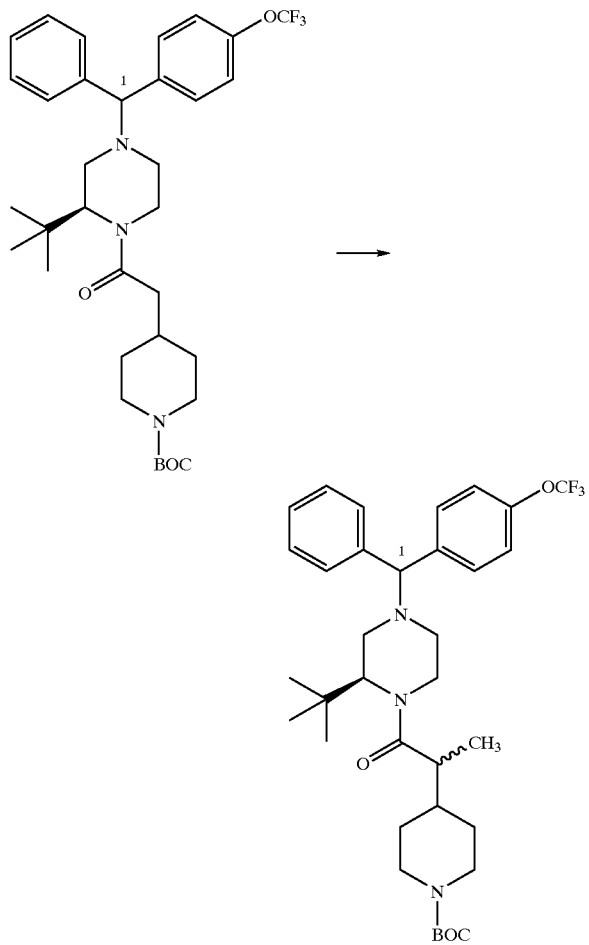

To a solution of the compound from Preparative Example 177 (0.25 g, 0.405 mmol) in THF (5 mL) at −78° C. was added lithium hexamethyldisilazane (0.89 mL, 2.0M in hexanes, 2.2 eq.) dropwise. The resulting solution was stirred 5 minutes and MeI (0.2 mL, 8.0 eq.) was added. The resulting solution was warmed to room temperature and stirred overnight. The reaction mixture was diluted with H$_2$O and extracted with CH$_2$Cl$_2$. The combined organics were dried over Na$_2$SO$_4$, filtered, and concetrated under reduced pressure. The crude product was purified by flash chromatography using a 75:25 hexanes:EtOAc solution as eluent (0.030 g, 12% yield). LCMS: MH$^+$=632.

PREPARATIVE EXAMPLE 55.2

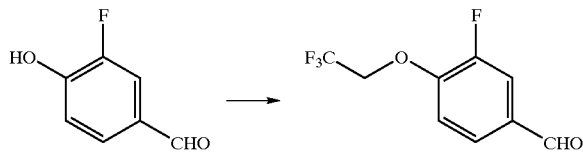

By essentially the same procedure set forth in Preparative Example 55.1, only substituting 3-fluoro-4-hydroxybenzaldehyde, the above compound was prepared (0.70 g, 89% yield): LCMS MH$^+$=223.

PREPARATIVE EXAMPLE 56

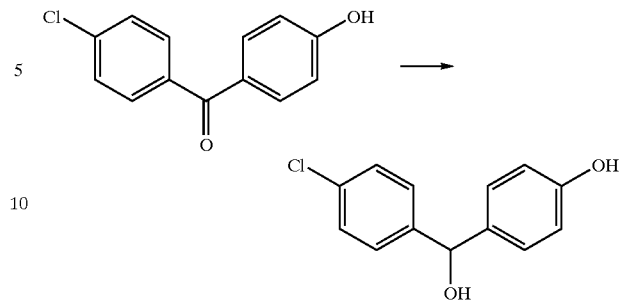

By essentially the same procedure set forth in Preparative Example 55, Step C, using 4-chloro-4'-hydroxybenzophenone (2.0 g, 8.6 mmol) gave the above compound (0.77 g, 34% yield).

PREPARATIVE EXAMPLE 56.1

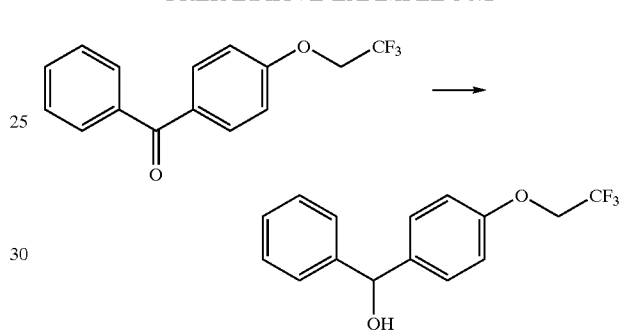

By essentially the same procedure set forth in Preparative Example 55, Step C, using the product from Preparative Example 55.1, the above compound was prepared (0.63 g, 97% yield) and used without further purification.

PREPARATIVE EXAMPLE 56.2

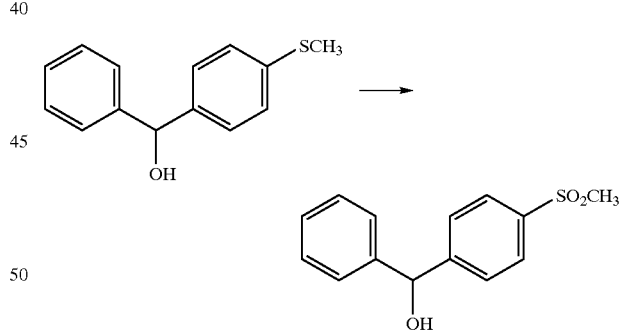

4-methylthiobenzhydrol (1.15 g, 5.0 mmol) was dissolved in acetic acid (25 mL) and H$_2$O$_2$ (35% in H$_2$O, 5.0 mL) was added. The mixture was stirred at 40° C. for 3 days and poured onto NaHCO$_3$ (100 g). Water (800 mL) was added and the mixture was extracted with EtOAc (3×100 mL). The combined extracts were dried over Na$_2$SO$_4$, filtered, and the solvent was evaporated. The residue was purified by column chromatography on silica with CH$_2$Cl$_2$:EtOAc (5:1). White solid (1.21 g, 92%) was obtained.

PREPARATIVE EXAMPLE 56.3 AND 56.4

4-Trifluoromethylsulfonyl benzhydrol and 4-t-butylsulfonylbenzhydrol were prepared using a similar method to that described in Preparative Example 56.2.

PREPARATIVE EXAMPLES 56.10–56.25

By essentially the same procedure set forth in Preparative Example 56, only substituting the appropriate compounds in Column 2 of Table 5.14, the compounds in Column 2 of Table 5.14 were prepared:

TABLE 5.14

| Prep. Ex. | Column 1 | Column 2 |
|---|---|---|
| 56.10 | Phenyl-[4-(2,2,2-trifluoroethoxy)phenyl]methanone | Phenyl-[4-(2,2,2-trifluoroethoxy)phenyl]methanol |
| 56.11 | [4-(difluoromethoxy)phenyl](phenyl)methanone | [4-(difluoromethoxy)phenyl](phenyl)methanol |
| 56.12 | [3-(difluoromethoxy)phenyl](phenyl)methanone | [3-(difluoromethoxy)phenyl](phenyl)methanol |
| 56.13 | {4-[2-(dimethylamino)ethoxy]phenyl}(phenyl)methanone | {4-[2-(dimethylamino)ethoxy]phenyl}(phenyl)methanol |
| 56.14 | phenyl{4-[2-(piperidin-1-yl)ethoxy]phenyl}methanone | phenyl{4-[2-(piperidin-1-yl)ethoxy]phenyl}methanol |
| 56.15 | ethyl [4-(phenylcarbonyl)phenoxy]acetate | ethyl {4-[hydroxy(phenyl)methyl]phenoxy}acetate |
| 56.16 | (4-fluorophenyl)(phenyl)methanone | (4-fluorophenyl)(phenyl)methanol |
| 56.17 | [4-(neopentyloxy)phenyl](phenyl)methanone | [4-(neopentyloxy)phenyl](phenyl)methanol |

TABLE 5.14-continued
| Prep. Ex. | Column 1 | Column 2 |
|---|---|---|
| 56.18 | 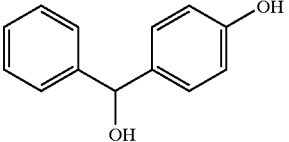 | 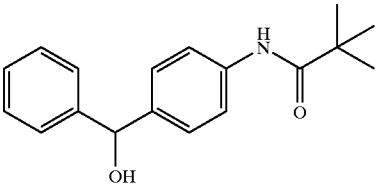 |
| 56.19 | 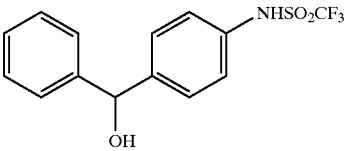 | |
| 56.20 | 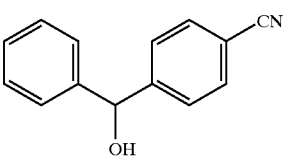 | |
| 56.21 | 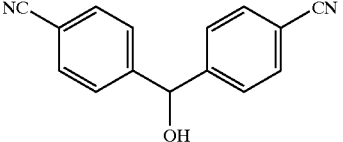 | |
| 56.22 | 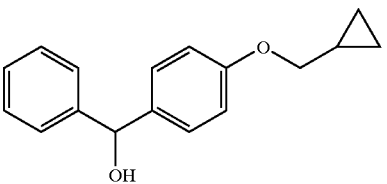 | |
| 56.23 | 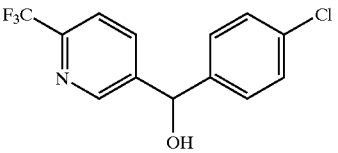 | |
| 56.24 | | |

PREPARATIVE EXAMPLE 57

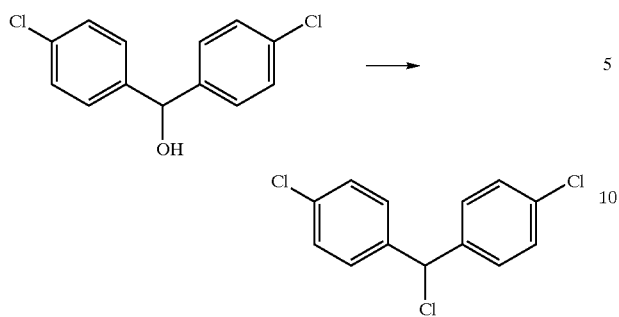

To a solution of 4,4'-dichlorobenzhydrol (1.0 g, 3.95 mmol) in toluene (10 mL) at 0° C. was added SOCl$_2$ (0.52 mL, 1.7 eq.) dropwise. The resulting solution was stirred at 0° C. 1 hour and warmed to room temperature and stirred overnight. The crude reaction mixture was concentrated under reduced pressure to give the above compound which was used without further purification (1.02 g, 95% yield).

PREPARATIVE EXAMPLES 58–82.43

By essentially the same procedure as set forth in Preparative Example 57, the compounds in Table 6, Column 3 were prepared from the corresponding alcohols in Table 6, Column 2:

TABLE 6

| Prep. Ex. | Column 2 | Column 3 |
|---|---|---|
| 58 | Br-pyridine-CH(OH)-C6H4-Cl | Br-pyridine-CH(Cl)-C6H4-Cl |
| 59 | Br-pyridine-CH(OH)-C6H5 | Br-pyridine-CH(Cl)-C6H5 |
| 60 | Br-pyridine-CH(OH)-C6H4-OCF3 | Br-pyridine-CH(Cl)-C6H4-OCF3 |
| 61 | Br-pyridine-CH(OH)-C6H4-CF3 | Br-pyridine-CH(Cl)-C6H4-CF3 |
| 62 | pyridine-CH(OH)-C6H3(Cl)(Cl) | pyridine-CH(Cl)-C6H3(Cl)(Cl) |
| 63 | pyridine-CH(OH)-C6H4-Cl | pyridine-CH(Cl)-C6H4-Cl |

TABLE 6-continued

| Prep. Ex. | Column 2 | Column 3 |
|---|---|---|
| 64 | phenyl-(4-trifluoromethoxyphenyl)methanol | phenyl-(4-trifluoromethoxyphenyl)methyl chloride |
| 65 | phenyl-(4-trifluoromethylphenyl)methanol | phenyl-(4-trifluoromethylphenyl)methyl chloride |
| 66 | 4-(hydroxy(phenyl)methyl)benzonitrile | 4-(chloro(phenyl)methyl)benzonitrile |
| 67 | phenyl(pyridin-2-yl)methanol | phenyl(pyridin-2-yl)methyl chloride |
| 68 | phenyl(6-(trifluoromethyl)pyridin-3-yl)methanol | phenyl(6-(trifluoromethyl)pyridin-3-yl)methyl chloride |
| 69 | (4-chlorophenyl)(4-hydroxyphenyl)methanol | (4-chlorophenyl)(4-hydroxyphenyl)methyl chloride |
| 70 | (4-chlorophenyl)(pyridin-3-yl)methanol | (4-chlorophenyl)(pyridin-3-yl)methyl chloride |
| 71 | (4-chlorophenyl)(quinolin-3-yl)methanol | (4-chlorophenyl)(quinolin-3-yl)methyl chloride |
| 72 | (4-chlorophenyl)(isoquinolin-4-yl)methanol | (4-chlorophenyl)(isoquinolin-4-yl)methyl chloride |

TABLE 6-continued

| Prep. Ex. | Column 2 | Column 3 |
|---|---|---|
| 73 | (4-CF3-phenyl)(4-CF3-phenyl)methanol | (4-CF3-phenyl)(4-CF3-phenyl)methyl chloride |
| 74 | (thiophen-2-yl)(4-chlorophenyl)methanol | (thiophen-2-yl)(4-chlorophenyl)methyl chloride |
| 75 | (thiazol-5-yl)(4-chlorophenyl)methanol | (thiazol-5-yl)(4-chlorophenyl)methyl chloride |
| 76 | (naphthalen-1-yl)(4-chlorophenyl)methanol | (naphthalen-1-yl)(4-chlorophenyl)methyl chloride |
| 77 | (naphthalen-2-yl)(4-chlorophenyl)methanol | (naphthalen-2-yl)(4-chlorophenyl)methyl chloride |
| 78 | (1H-pyrazol-4-yl)(4-chlorophenyl)methanol | (1H-pyrazol-4-yl)(4-chlorophenyl)methyl chloride |
| 79 | (isoquinolin-5-yl)(4-chlorophenyl)methanol | (isoquinolin-5-yl)(4-chlorophenyl)methyl chloride |
| 80 | (quinolin-8-yl)(4-chlorophenyl)methanol | (quinolin-8-yl)(4-chlorophenyl)methyl chloride |
| 81 | (quinolin-5-yl)(4-chlorophenyl)methanol | (quinolin-5-yl)(4-chlorophenyl)methyl chloride |

TABLE 6-continued

| Prep. Ex. | Column 2 | Column 3 |
| --- | --- | --- |
| 82 | 1-naphthyl-CH(OH)-(4-OCF$_3$-C$_6$H$_4$) | 1-naphthyl-CH(Cl)-(4-OCF$_3$-C$_6$H$_4$) |
| 82.1 | (4-F$_3$CO-C$_6$H$_4$)-CH(OH)-(4-OCF$_3$-C$_6$H$_4$) | (4-F$_3$CO-C$_6$H$_4$)-CH(Cl)-(4-OCF$_3$-C$_6$H$_4$) |
| 82.2 | C$_6$H$_5$-CH(OH)-(4-OCH$_2$CF$_3$-C$_6$H$_4$) | C$_6$H$_5$-CH(Cl)-(4-OCH$_2$CF$_3$-C$_6$H$_4$) |
| 82.3 | C$_6$H$_5$-CH(OH)-(2,2-difluoro-benzo[1,3]dioxol-4-yl) | C$_6$H$_5$-CH(Cl)-(2,2-difluoro-benzo[1,3]dioxol-4-yl) |
| 82.4 | (4-F$_3$C-C$_6$H$_4$)-CH(OH)-(2,2-difluoro-benzo[1,3]dioxol-4-yl) | (4-F$_3$C-C$_6$H$_4$)-CH(Cl)-(2,2-difluoro-benzo[1,3]dioxol-4-yl) |
| 82.5 | C$_6$H$_5$-CH(OH)-(4-SCH$_3$-C$_6$H$_4$) | C$_6$H$_5$-CH(Cl)-(4-SCH$_3$-C$_6$H$_4$) |
| 82.6 | C$_6$H$_5$-CH(OH)-(3,5-bis(CF$_3$)-C$_6$H$_3$) | C$_6$H$_5$-CH(Cl)-(3,5-bis(CF$_3$)-C$_6$H$_3$) |
| 82.7 | C$_6$H$_5$-CH(OH)-(2,2-difluoro-benzo[1,3]dioxol-5-yl) | C$_6$H$_5$-CH(Cl)-(2,2-difluoro-benzo[1,3]dioxol-5-yl) |

TABLE 6-continued
| Prep. Ex. | Column 2 | Column 3 |
|---|---|---|
| 82.8 | 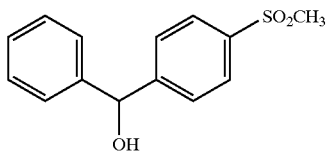 | |
| 82.9 | 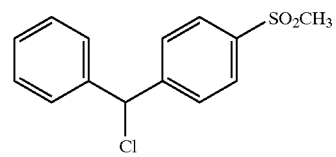 | |
| 82.10 | 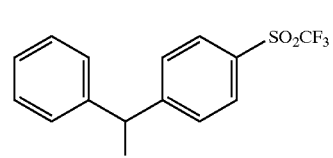 | |
| 82.11 | 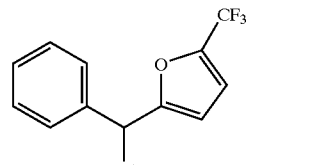 | |
| 82.12 | 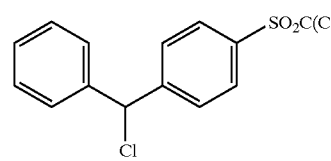 | |
| 82.30 | 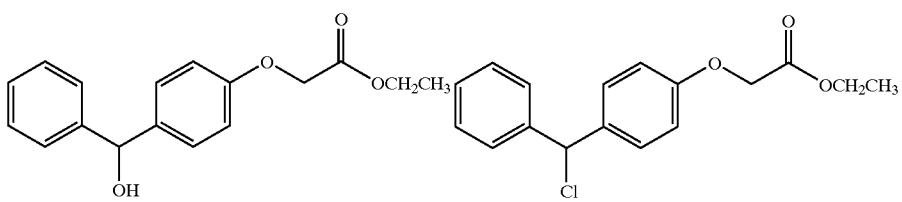 | |
| 82.31 | 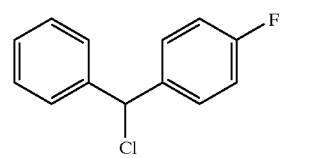 | |
| 82.32 | 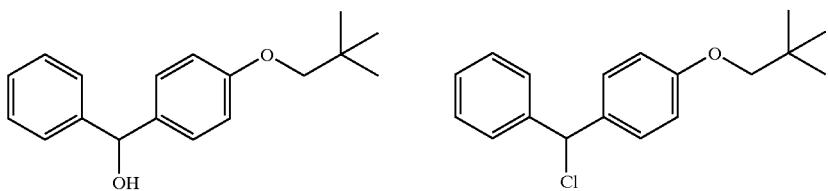 | |

TABLE 6-continued
| Prep. Ex. | Column 2 | Column 3 |
|---|---|---|
| 82.33 | 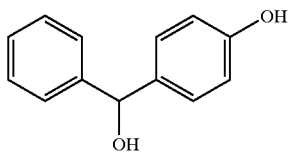 | 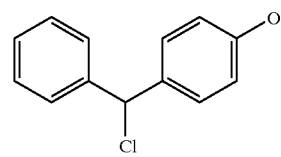 |
| 82.34 | 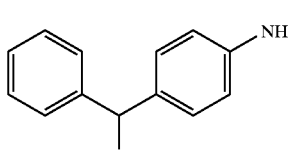 | 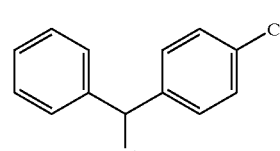 |
| 82.35 | 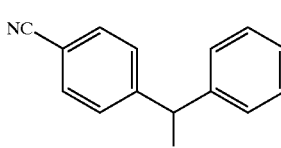 | 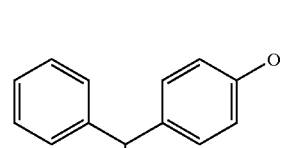 |
| 82.36 | 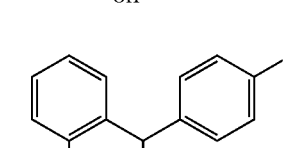 | 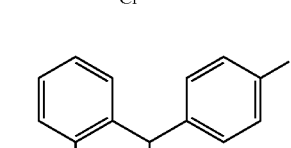 |
| 82.37 | | |
| 82.38 | | |
| 82.39 | | |
| 82.40 | | |

TABLE 6-continued

| Prep. Ex. | Column 2 | Column 3 |
|---|---|---|
| 82.41 | | |
| 82.42 | | |
| 82.43 | | |

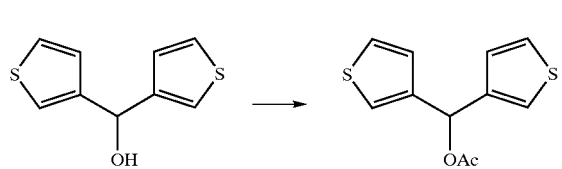

PREPARATIVE EXAMPLE 83

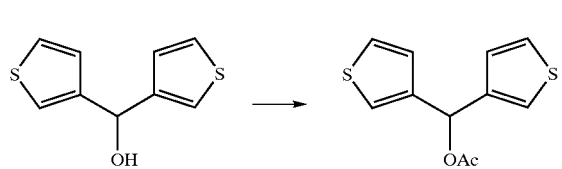

Ac$_2$O (102 mg, 1.0 mmol) and TEA (303 mg, 3.0 mmol) were added under N$_2$ to a stirred solution of bis(3-thienyl)methanol in anhydrous CH$_2$Cl$_2$ (5 mL). The mixture was stirred for 16 hrs, poured into saturated aqueous NaHCO$_3$, and extracted with CH$_2$Cl$_2$ (3×10 mL). The extracts were dried over Na$_2$SO$_4$, filtered, and the solvent was evaporated. The residue was purified by flash chromatography using CH$_2$Cl$_2$ to give 70 mg (58%) of a solid.

PREPARATIVE EXAMPLE 84

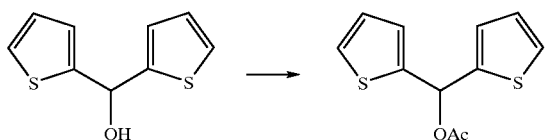

By essentially the same procedure set forth in Preparative Example 83, using the bis(2-thienyl)methanol, the above compound was prepared.

PREPARATIVE EXAMPLE 85

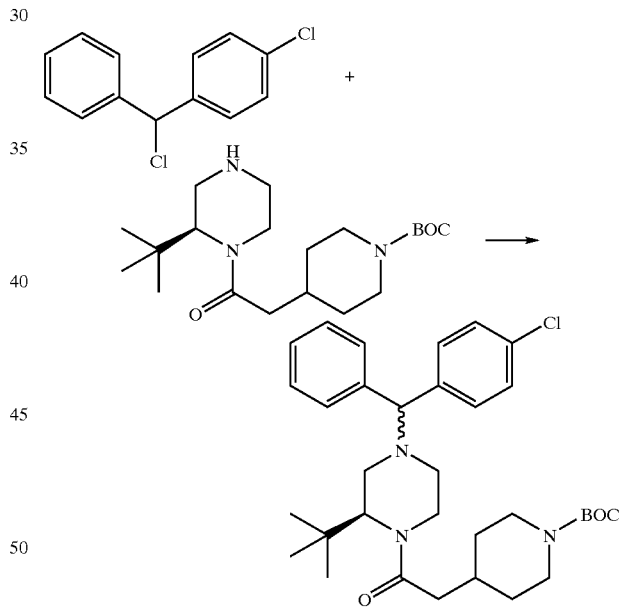

A solution of the product from Preparative Example 26 (0.35 g, 0.95 mmol), 4-chlorobenzhydryl chloride (0.27 mL, 1.2 eq.), K$_2$CO$_3$ (0.33 g, 2.5 eq.), and KI (0.063 g, 40 mol %) in CH$_3$CN (25 mL) was heated to reflux for 22 hours. The reaction mixture was cooled, diluted with water, and extracted with CH$_2$Cl$_2$. The combined organics were dried over Na$_2$SO$_4$, filtered, and concentrated. The crude product was purified by flash chromatography using a 60:40 hexanes:EtOAc mix as eluent (0.32 g, 59% yield). LCMS: MH$^+$=568.

PREPARATIVE EXAMPLES 86–106.28L

By essentially the same procedure set forth in Preparative Example 85, using the amines listed in Column 2 and the chlorides listed in Column 3, of Table 7 below, the compounds in Table 7, Column 4 (CMPD) were prepared:

TABLE 7

| Prep. Ex. | Column 2 | Column 3 | Column 4 | CMPD |
|---|---|---|---|---|
| 86 | | | | LCMS: MH⁺ = 312 |
| 87 | | | | |
| 88 | | | | |
| 89 | | | | FABMS: MH⁺ = 445 |

TABLE 7-continued

| Prep. Ex. | Column 2 | Column 3 | Column 4 | CMPD |
|---|---|---|---|---|
| 90 | | | | LCMS: MH+ = 449 |
| 91 | | | | FABMS: MH+ = 479 |
| 92 | | | | LCMS: MH+ = 569 |

TABLE 7-continued
| Prep. Ex. | Column 2 | Column 3 | Column 4 | CMPD |
|---|---|---|---|---|
| 93 | 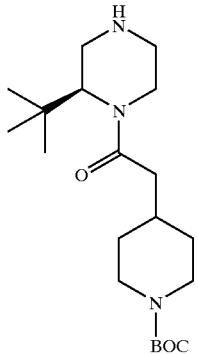 | 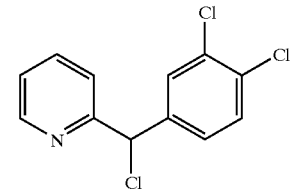 | 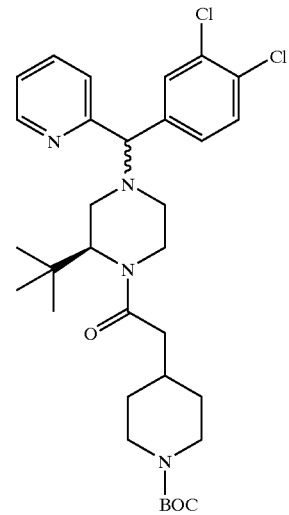 | — |
| 94 | 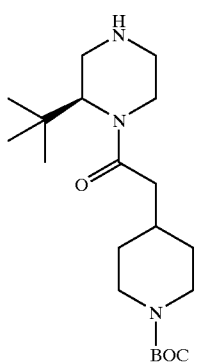 | 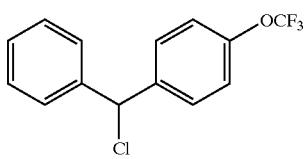 | 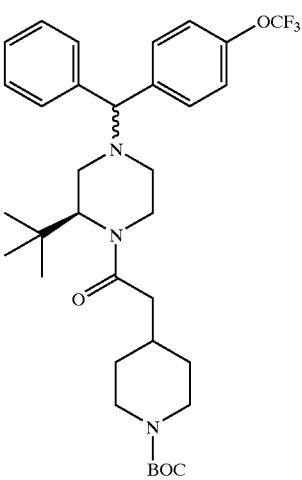 | LCMS: MH$^+$ = 618 |
| 95 | 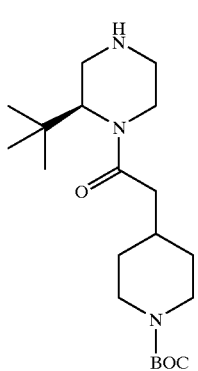 | 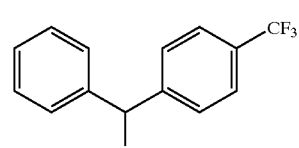 | 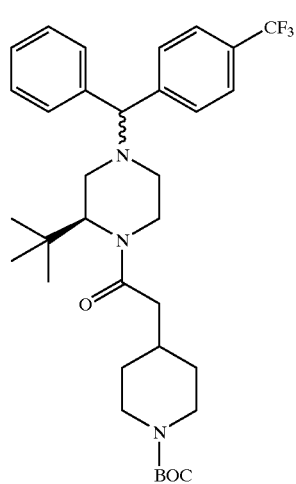 | LCMS: MH$^+$ = 602 |

TABLE 7-continued
| Prep. Ex. | Column 2 | Column 3 | Column 4 | CMPD |
|---|---|---|---|---|
| 96 | 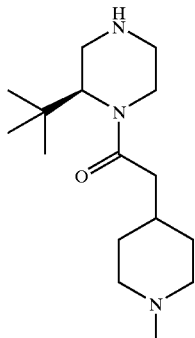 | 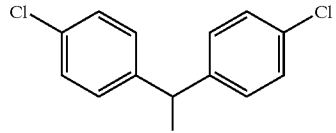 | 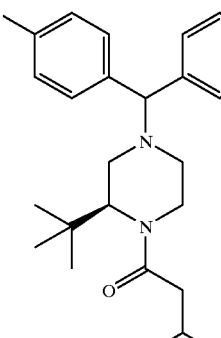 | LCMS: MH$^+$ = 602 |
| 97 | 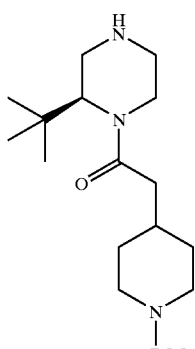 | 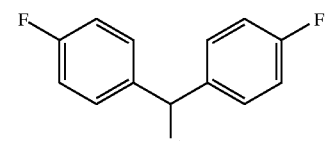 | 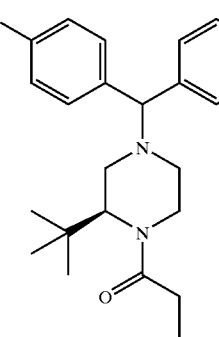 | LCMS: MH$^+$ = 570 |
| 98 | 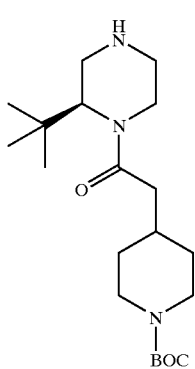 | 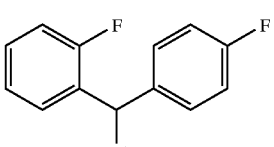 | 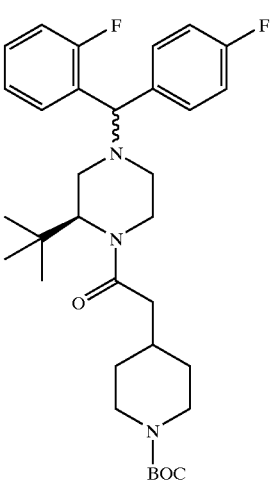 | LCMS: MH$^+$ = 570 |

TABLE 7-continued

| Prep. Ex. | Column 2 | Column 3 | Column 4 | CMPD |
|---|---|---|---|---|
| 99 | | | | LCMS: MH⁺ = 590 |
| 100 | | | | LCMS: MH⁺ = 602 |
| 101 | | | | LCMS: MH⁺ = 647 |

US 6,903,102 B2
153    154
TABLE 7-continued
| Prep. Ex. | Column 2 | Column 3 | Column 4 | CMPD |
|---|---|---|---|---|
| 102 | 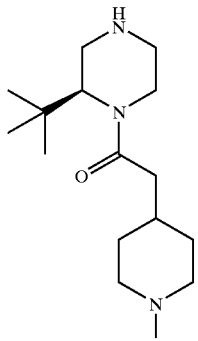 | 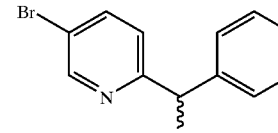 | 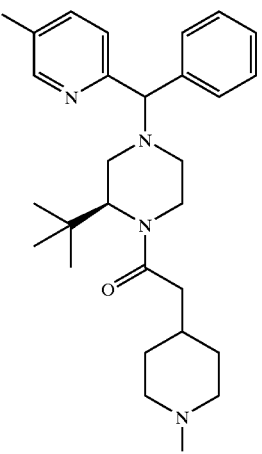 | LCMS: MH$^+$ = 613 |
| 103 | 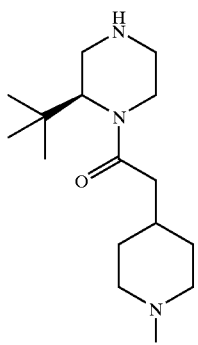 | 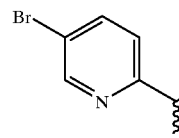 | 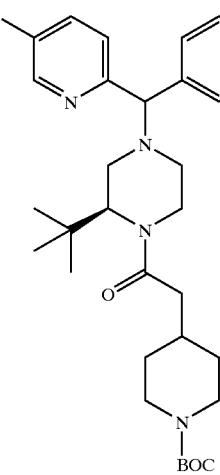 | LCMS: MH$^+$ = 697 |
| 104 | 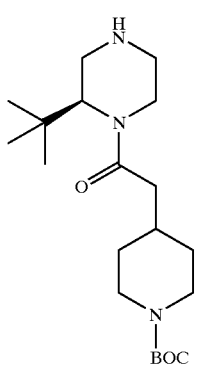 | 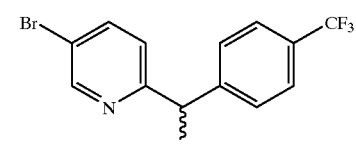 | 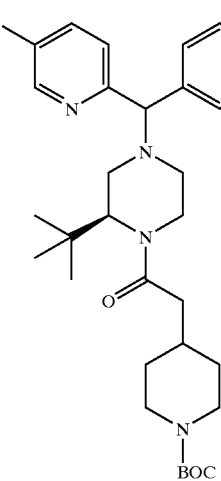 | LCMS: MH$^+$ = 681 |

TABLE 7-continued

| Prep. Ex. | Column 2 | Column 3 | Column 4 | CMPD |
|---|---|---|---|---|
| 105 | | | | — |
| 105.1 | | | | LCMS: MH+ = 702 |
| 105.2 | | | | LCMS: MH+ = 632 |

TABLE 7-continued

| Prep. Ex. | Column 2 | Column 3 | Column 4 | CMPD |
|---|---|---|---|---|
| 106 | | | | LCMS: MH+ = 584 |
| 106.1 | | | | |
| 106.2 | | | | |
| 106.3 | | | | |

TABLE 7-continued

| Prep. Ex. | Column 2 | Column 3 | Column 4 | CMPD |
|---|---|---|---|---|
| 106.4 | | | | |
| 106.5 | | | | |
| 106.6 | | | | |
| 106.7 | | | | |

TABLE 7-continued

| Prep. Ex. | Column 2 | Column 3 | Column 4 | CMPD |
|---|---|---|---|---|
| 106.8 | | | | |
| 106.9 | | | | |
| 106.10 | | | | |
| 106.11 | | | | |

TABLE 7-continued

| Prep. Ex. | Column 2 | Column 3 | Column 4 | CMPD |
|---|---|---|---|---|
| 106.12 | | | | |
| 106.13 | | | | |
| 106.14 | | | | |
| 106.15 | | | | |

TABLE 7-continued

| Prep. Ex. | Column 2 | Column 3 | Column 4 | CMPD |
|---|---|---|---|---|
| 106.16 | | | | LCMS: MH⁺ = 650 |
| 106.17 | | | | LCMS: MH⁺ = 644 |
| 106.18 | | | | LCMS: MH⁺ = 610 |

TABLE 7-continued
| Prep. Ex. | Column 2 | Column 3 | Column 4 | CMPD |
|---|---|---|---|---|
| 106.19 |  | 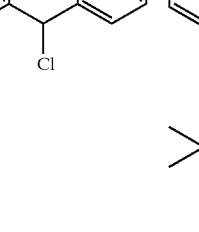 | 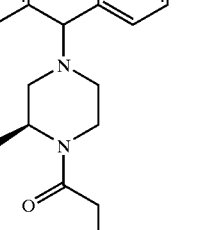 | LCMS: MH+ = 622 |
| 106.20 | 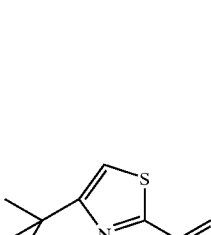 |  | 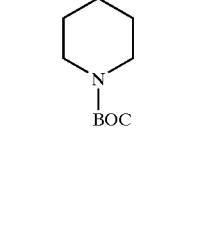 | LCMS: MH+ = 673 |
| 106.21 |  | 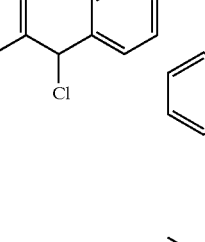 | 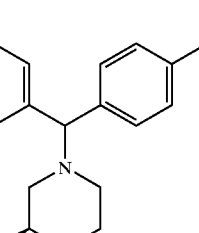 | LCMS: MH+ = 600 |

TABLE 7-continued
| Prep. Ex. | Column 2 | Column 3 | Column 4 | CMPD |
|---|---|---|---|---|
| 106.22 | 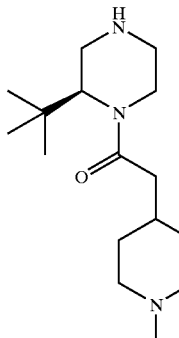 | 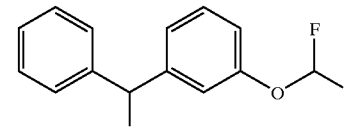 | 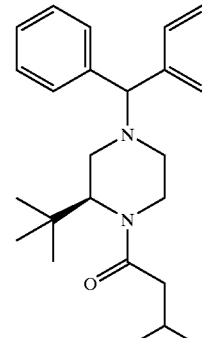 | LCMS: MH+ = 600 |
| 106.23 | 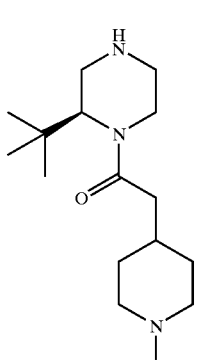 | 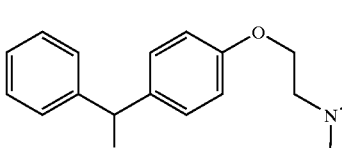 | 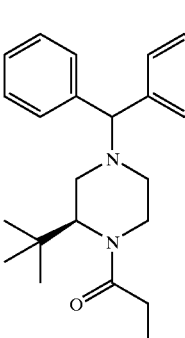 | LCMS: MH+ = 621 |
| 106.24 | 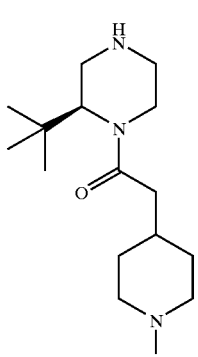 | 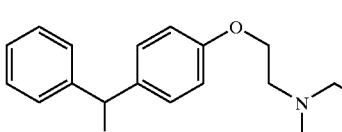 | 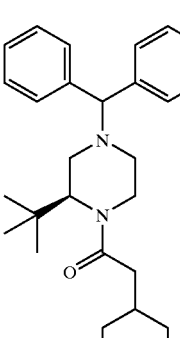 | LCMS: MH+ = 661 |

TABLE 7-continued

| Prep. Ex. | Column 2 | Column 3 | Column 4 | CMPD |
|---|---|---|---|---|
| 106.25 | | | | LCMS: MH+ = 636 |
| 106.26 | | | | LCMS: MH+ = 552 |
| 106.27 | | | | LCMS: MH+ = 620 |

TABLE 7-continued
| Prep. Ex. | Column 2 | Column 3 | Column 4 | CMPD |
|---|---|---|---|---|
| 106.28 | 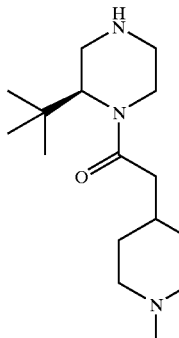 | 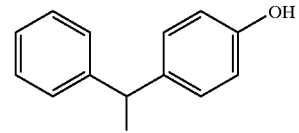 | 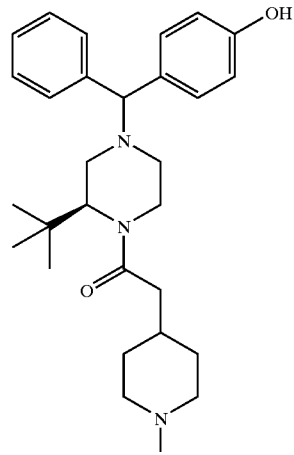 | LCMS: MH$^+$ = 550 |
| 106.28A | 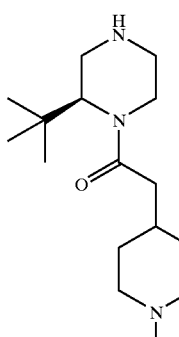 | 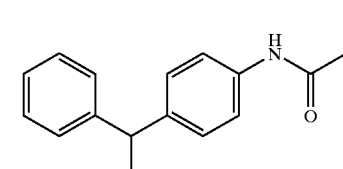 | 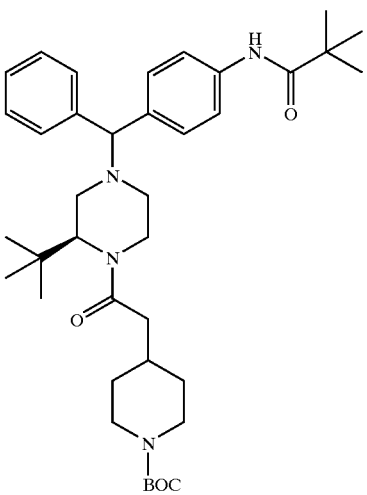 | LCMS: MH$^+$ = 633 |
| 106.28B | 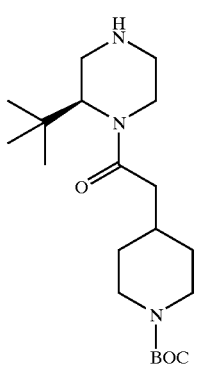 | 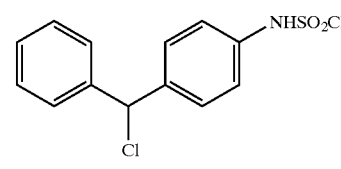 | 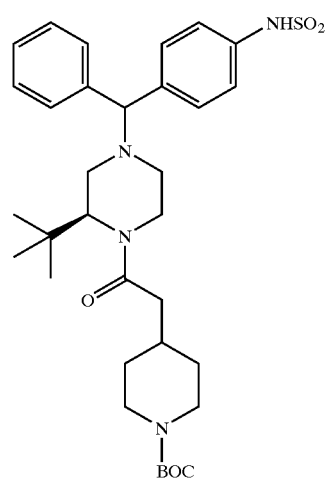 | LCMS: MH$^+$ = 681 |

TABLE 7-continued
| Prep. Ex. | Column 2 | Column 3 | Column 4 | CMPD |
|---|---|---|---|---|
| 106.28C | 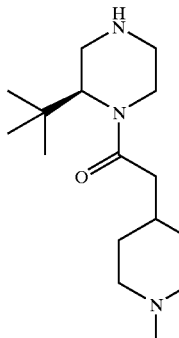 | 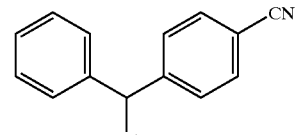 | 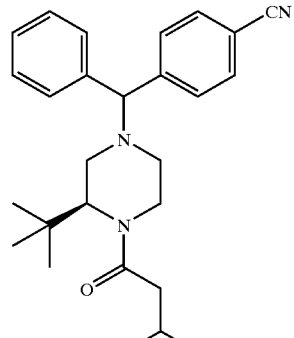 | LCMS: MH+ = 559 |
| 106.28D | 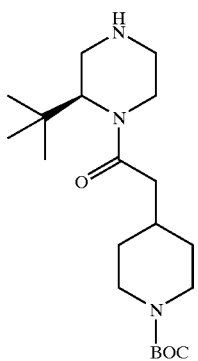 | 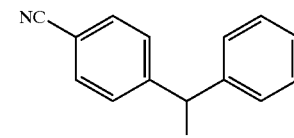 | 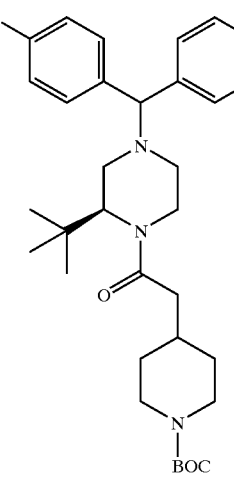 | LCMS: MH+ = 584 |
| 106.28E | 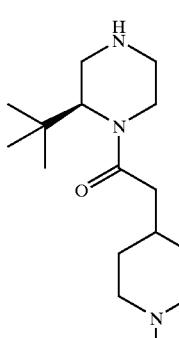 | 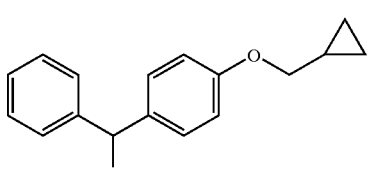 | 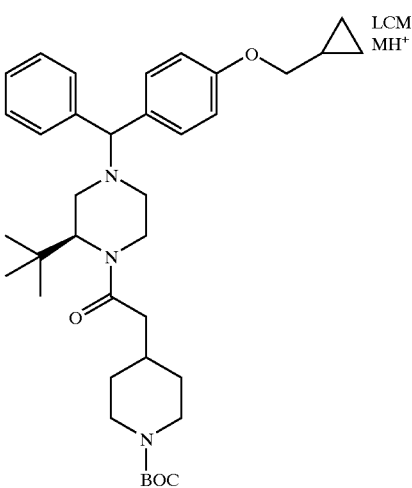 | LCMS: MH+ = 604 |

TABLE 7-continued
| Prep. Ex. | Column 2 | Column 3 | Column 4 | CMPD |
|---|---|---|---|---|
| 106.28F | 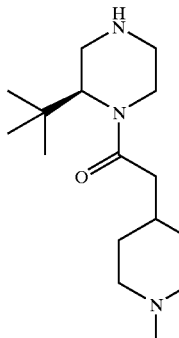 | 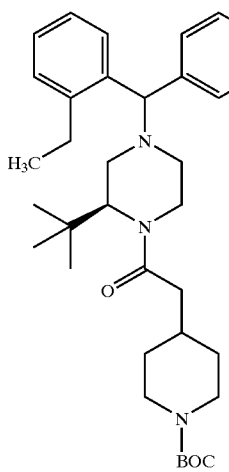 | | LCMS: MH+ = 646 |
| 106.28G | 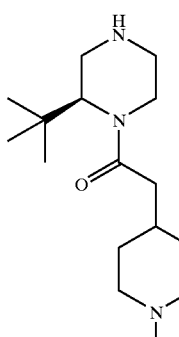 | 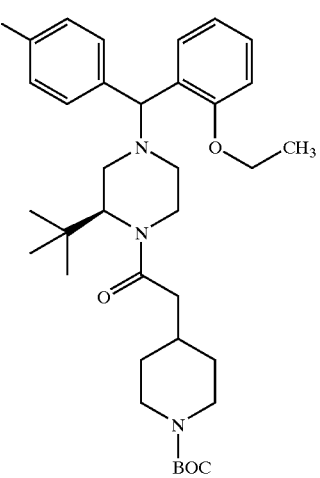 | | LCMS: MH+ = 662 |
| 106.28H | 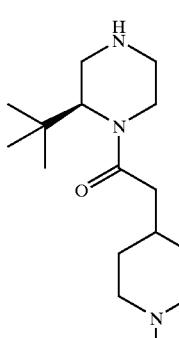 | 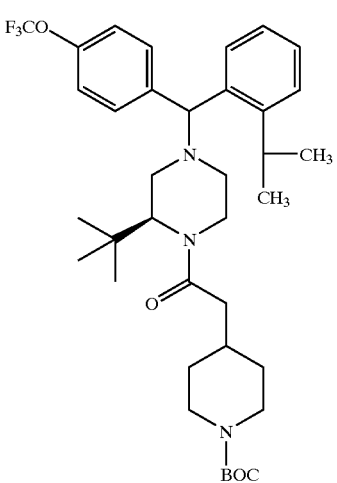 | | LCMS: MH+ = 660 |

TABLE 7-continued
| Prep. Ex. | Column 2 | Column 3 | Column 4 | CMPD |
|---|---|---|---|---|
| 106.28I | 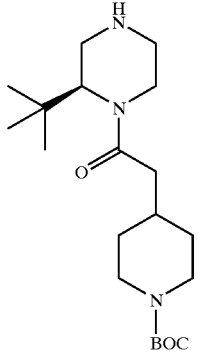 | 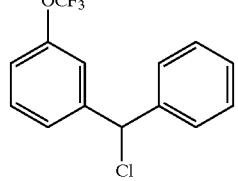 | 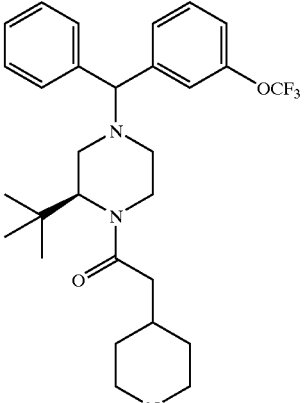 | LCMS: MH$^+$ = 618 |
| 106.28J | 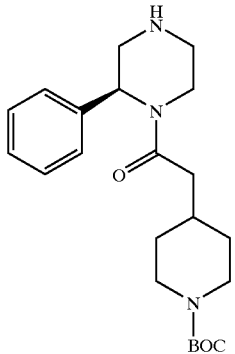 | 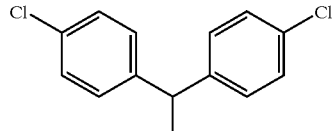 | 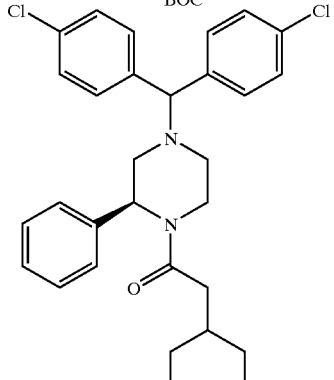 | LCMS: MH$^+$ = 622 |
| 106.28K | 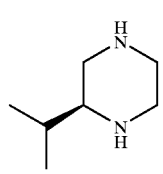 | 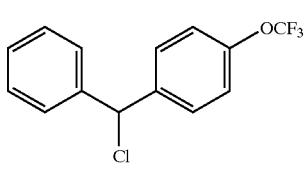 | 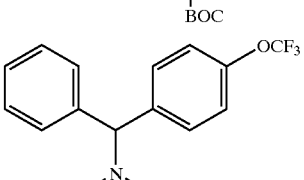 | LCMS: MH$^+$ = 379 |
| 106.28L | 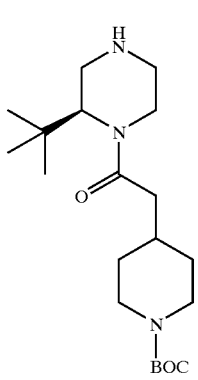 | 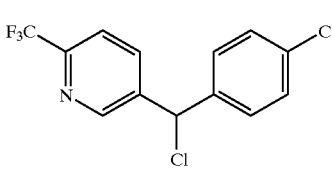 | 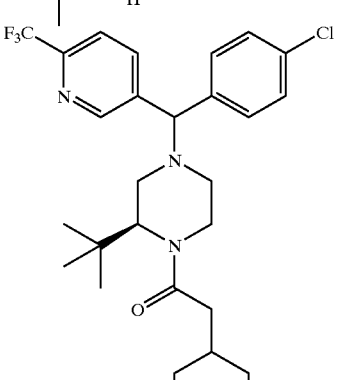 | LCMS: MH$^+$ = 637 |

PREPARATIVE EXAMPLE 106.28M

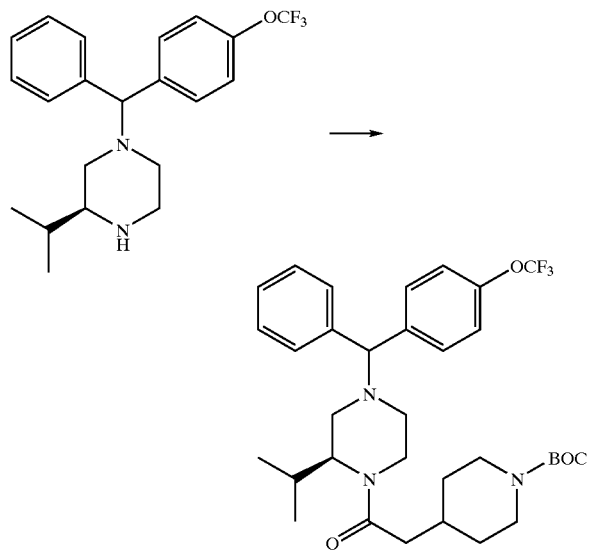

By essentially the same procedure set forth in Preparative Example 21, only substituting the product from Preparative Example 106.28K, the above compound was prepared (54% yield). LCMS: MH$^+$=604.

PREPARATIVE EXAMPLES 106.29 AND 106.30

By essentially the same procedure set forth in Preparative Example 55.11, only substituting compound prepared in Preparative Example 106.28 and the iodide in Column 2 of Table 7.1, the compounds in Column 3 of Table 7.1 (CMPD) were prepared:

TABLE 7.1

| Prep. Ex. | Column 2 | Column 3 | CMPD |
|---|---|---|---|
| 106.29 | Ethyl iodide | (structure) | LCMS: MH$^+$ = 578 |
| 106.30 | Isopropyl iodide | (structure) | LCMS: MH$^+$ = 592 |

PREPARATIVE EXAMPLE 107 AND 108

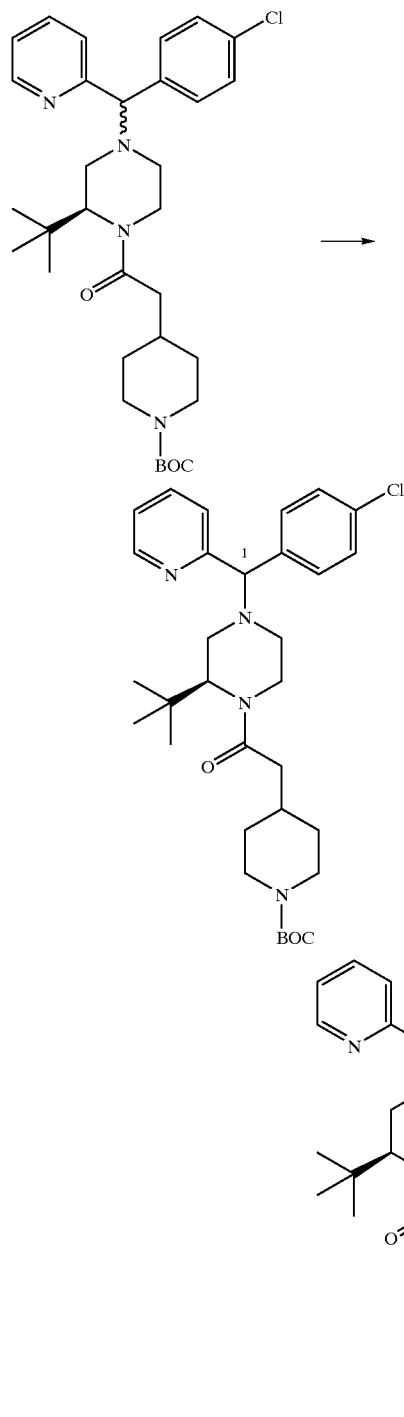

The above compounds were prepared by the separation of the diastereomers of the product from Preparative Example 92:

Preparative Example 107 (first eluting isomer-1): LCMS: MH$^+$=569.

Preparative Example 108 (second eluting isomer-2): LCMS: MH$^+$=569.

PREPARATIVE EXAMPLE 109 AND 110

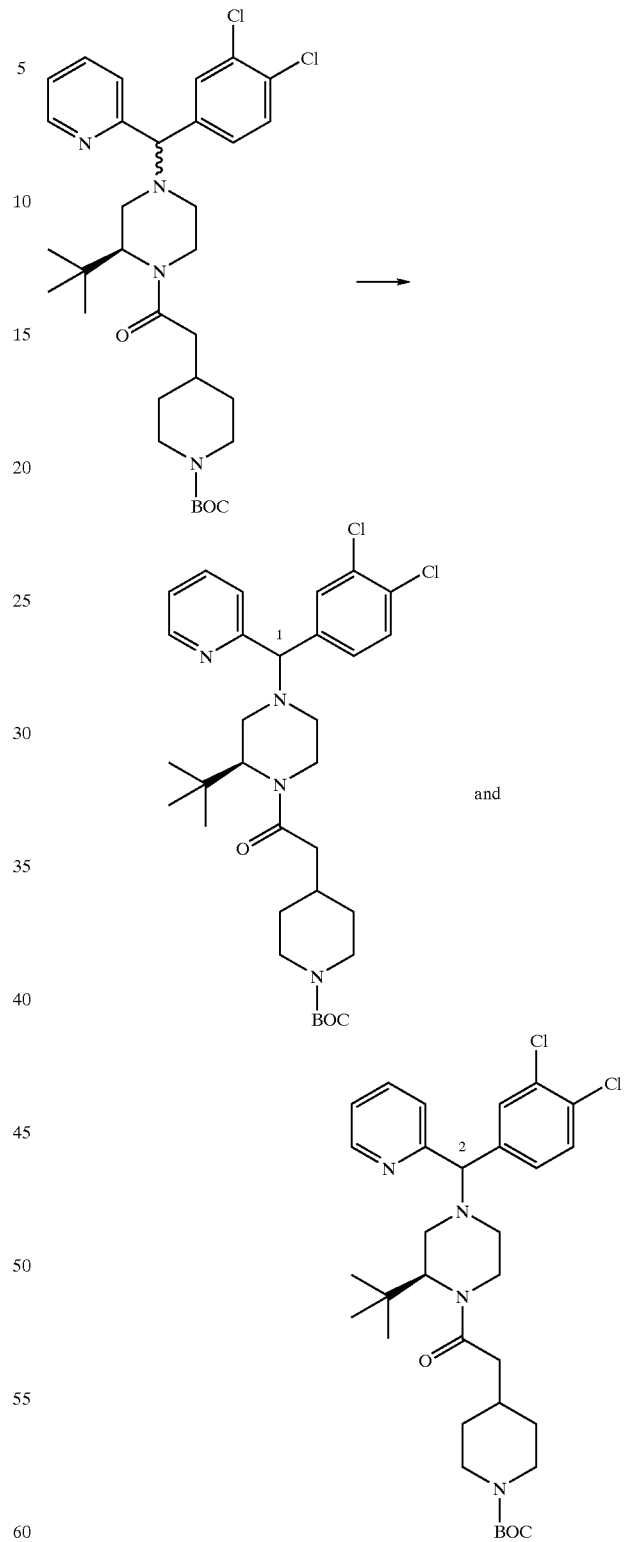

The above compounds were prepared by the separation of the diastereomers of the product from Preparative Example 93 by flash chromatography using a 10% hexanes in EtOAc solution as eluent:

Preparative Example 109 (first eluting isomer-1): LCMS: MH$^+$=603.

Preparative Example 110 (second eluting isomer-2): LCMS: MH+=603.

PREPARATIVE EXAMPLE 111 AND 112

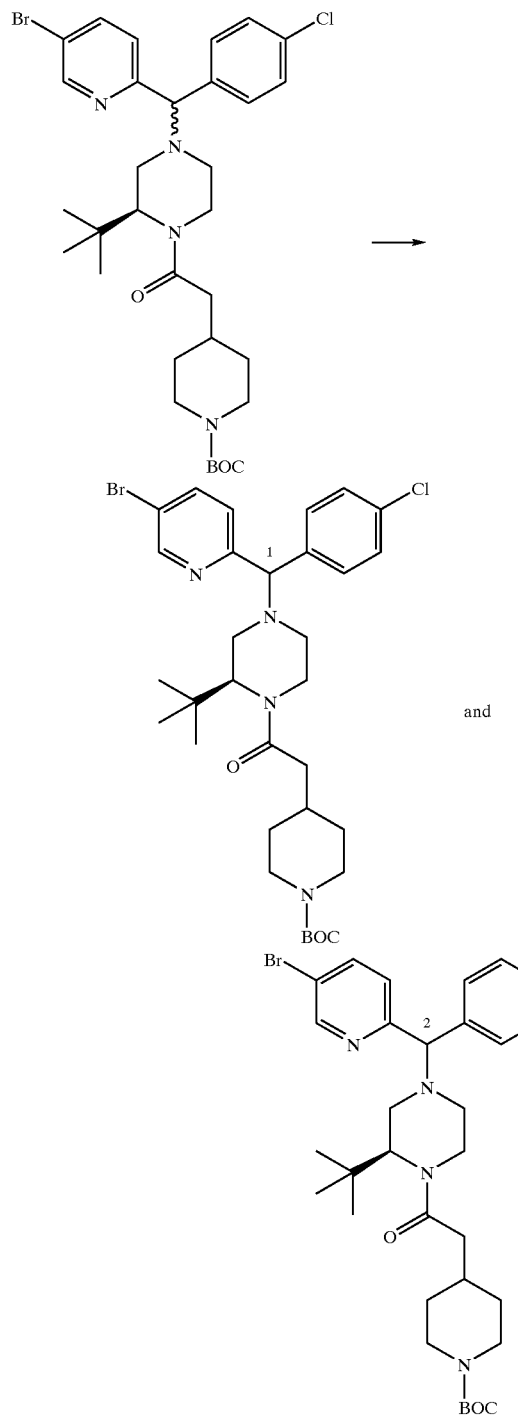

The above compounds were prepared through the separation of diastereomers of the product from Preparative Example 101 using preparative HPLC with a CHIRALPAK AD column using a 95:5 hexanes:IPA with 0.2% DEA as eluent:

Preparative Example 111 (first eluting isomer-1): LCMS: MH+=647.

Preparative Example 112 (second eluting isomer-2): LCMS: MH+=647.

PREPARATIVE EXAMPLE 113 AND 114

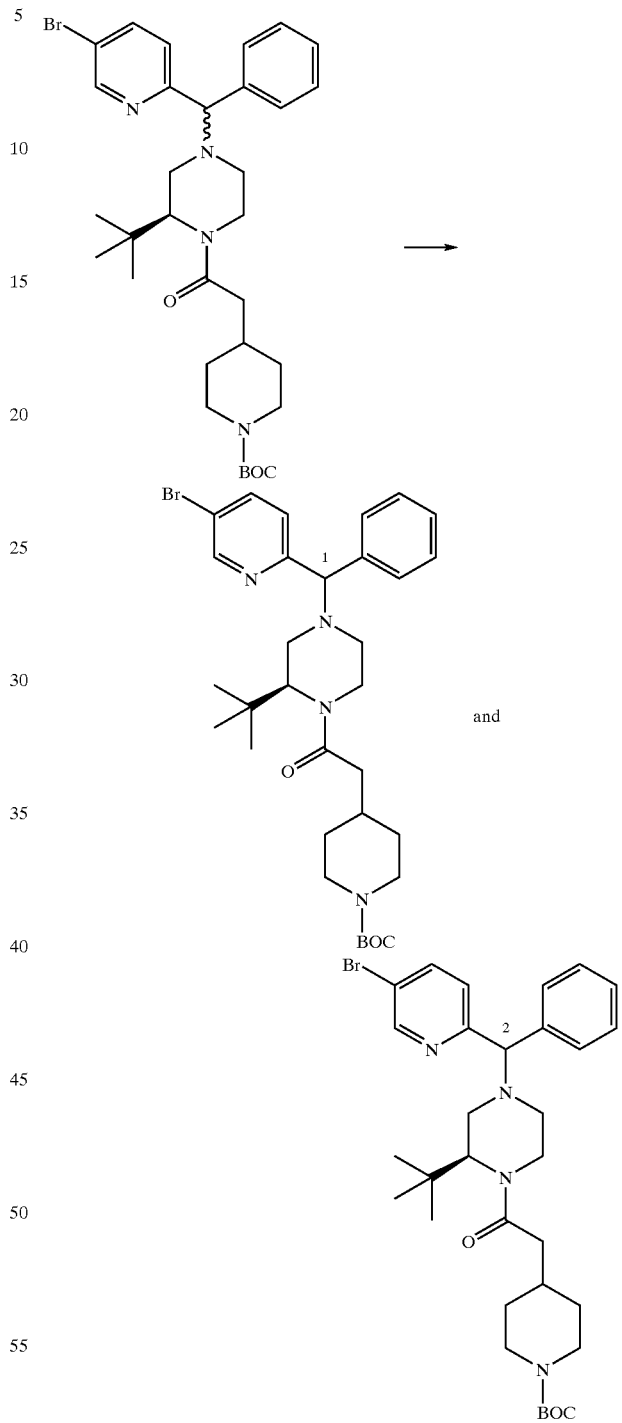

The above compounds were prepared through the separation of diastereomers of the product from Preparative Example 102 by preparative HPLC with a CHIRALPAK AD column using a 95:5 hexanes:IPA with 0.2% DEA as eluent:

Preparative Example 113 (first eluting isomer-1): LCMS: MH+=613.

Preparative Example 114 (second eluting isomer-2): LCMS: MH+=613.

187

PREPARATIVE EXAMPLE 115 AND 116

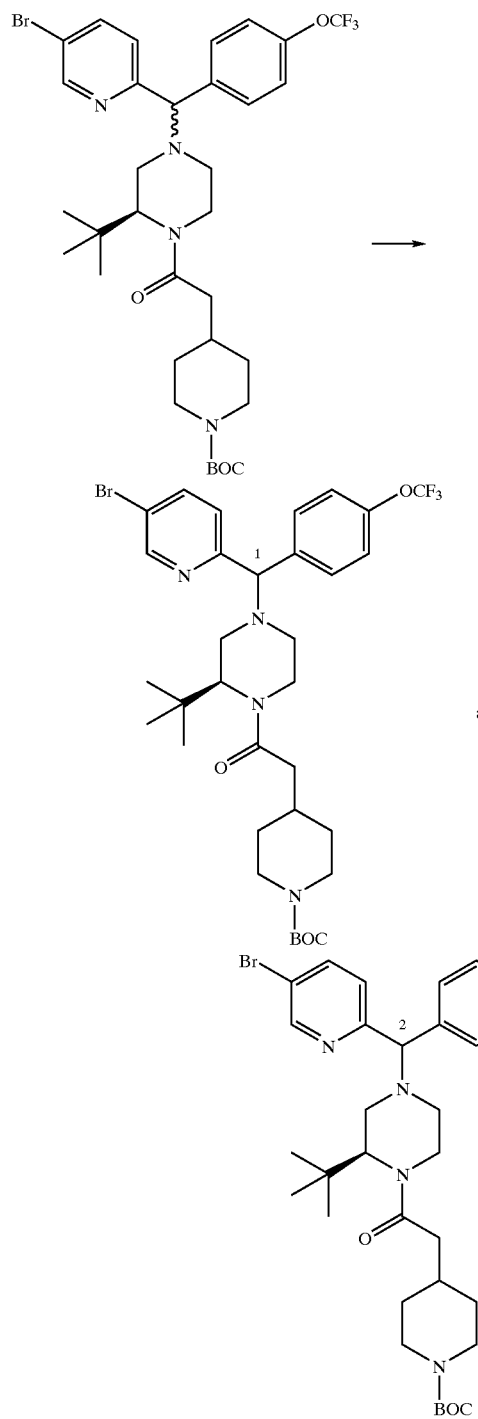

and

188

PREPARATIVE EXAMPLE 117 AND 118

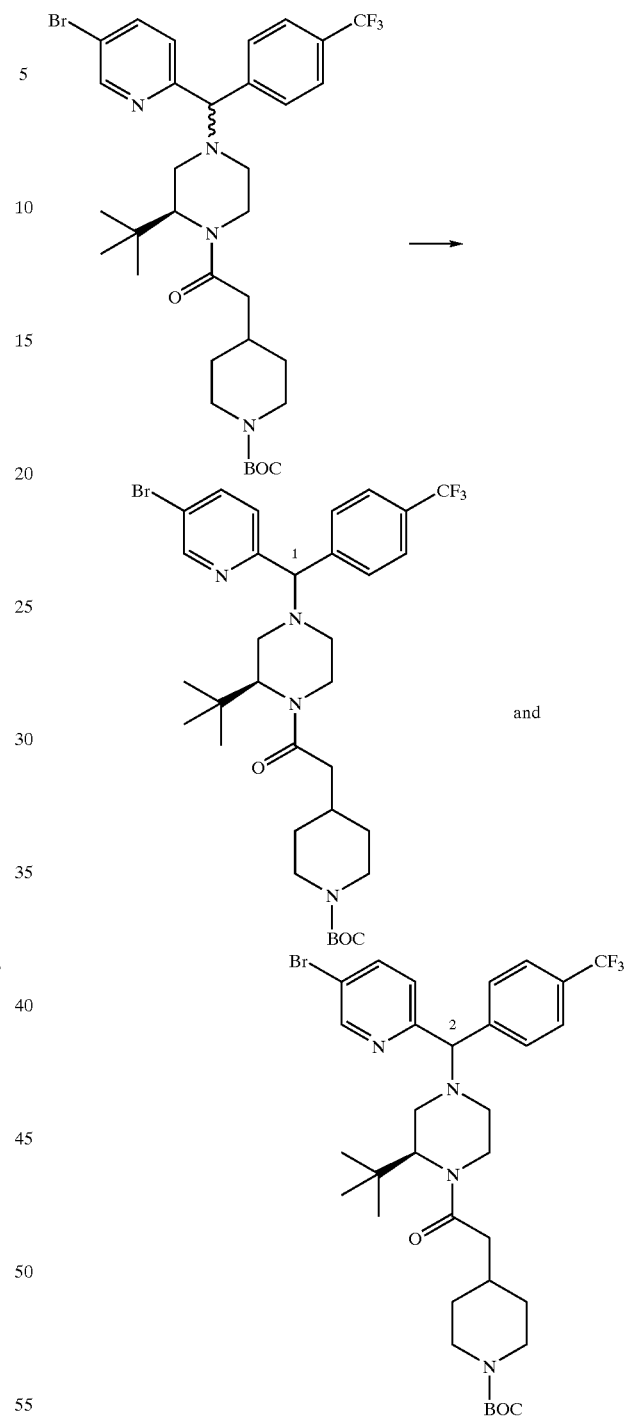

and

The above compounds were prepared through the separation of diastereomers of the product from Preparative Example 103 by preparative HPLC with a CHIRALPAK AD column using a 95:5 hexanes:IPA with 0.2% DEA as eluent:

Preparative Example 115 (first eluting isomer-1): LCMS: MH$^+$=697.

Preparative Example 116 (second eluting isomer-2): LCMS: MH$^+$=697.

The above compounds were prepared through the separation of diastereomers of the product from Preparative Example 104 by preparative HPLC with a CHIRALPAK AD column using a 95:5 hexanes:IPA with 0.2% DEA as eluent:

Preparative Example 117 (first eluting isomer-1): LCMS: MH$^+$=681.

Preparative Example 118 (second eluting isomer-2): LCMS: MH$^+$=681.

PREPARATIVE EXAMPLE 119 AND 120

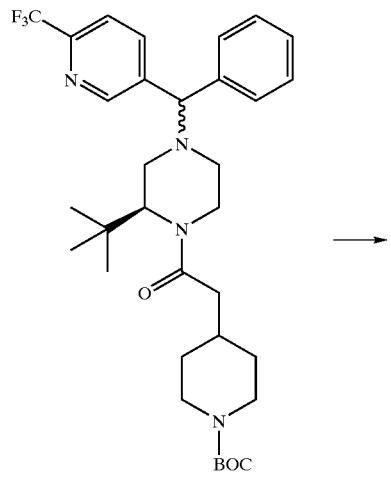

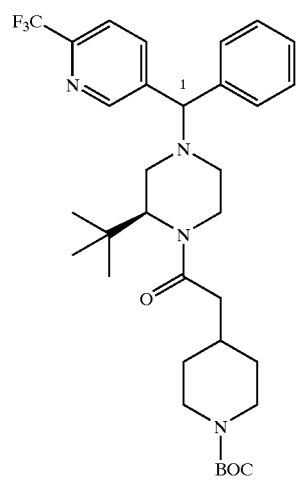

and

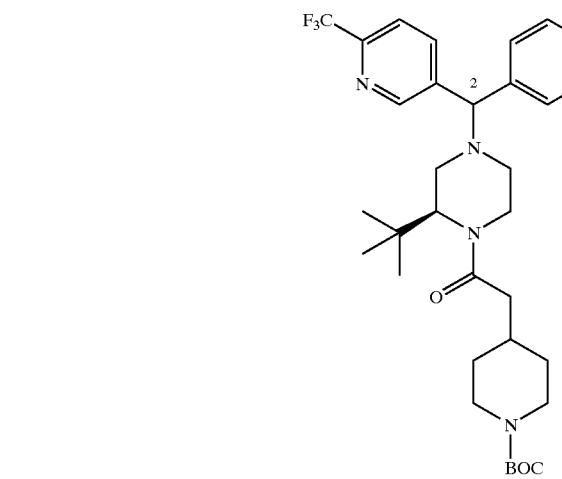

The above compounds were prepared through the separation of diastereomers of the product from Preparative Example 105 by preparative HPLC with a CHIRALPAK AD column using a 95:5 hexanes:IPA with 0.2% DEA as eluent:

Preparative Example 119 (first eluting isomer-1): LCMS: MH$^+$=603.

Preparative Example 120 (second eluting isomer-2): LCMS: MH$^+$=603.

PREPARATIVE EXAMPLE 124

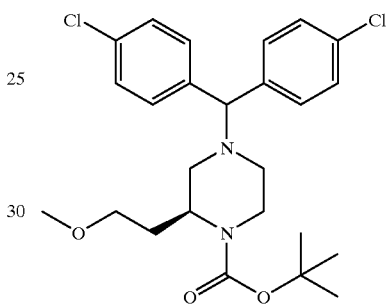

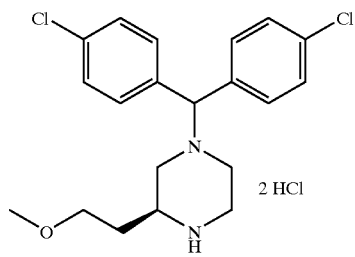

The product from Preparative Example 91 (0.28 g, 0.58 mmol) was stirred at room temperature in 4M HCl in dioxane for 1 hour. The resulting solution was concentrated under reduced pressure and used without further purification.

PREPARATIVE EXAMPLES 125–130

By essentially the same procedure set forth in Preparative Example 124, using the compounds shown in Table 9, Column 2, the compounds in Table 9, Column 3 were prepared:

TABLE 9
| Prep. Ex. | Column 2 | Column 3 |
|---|---|---|
| 125 | 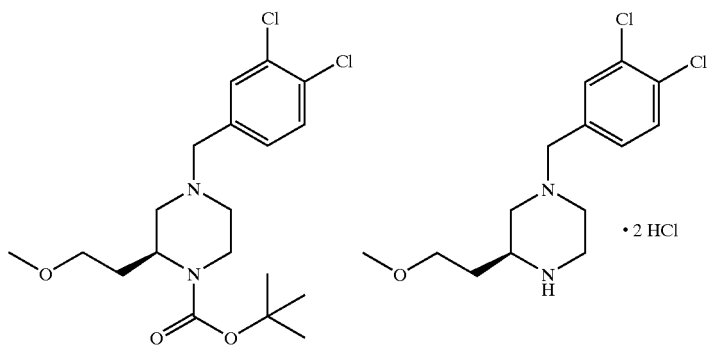 | |
| 126 | 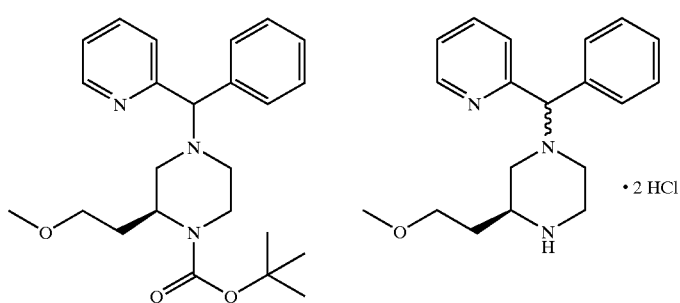 | |
| 127 | 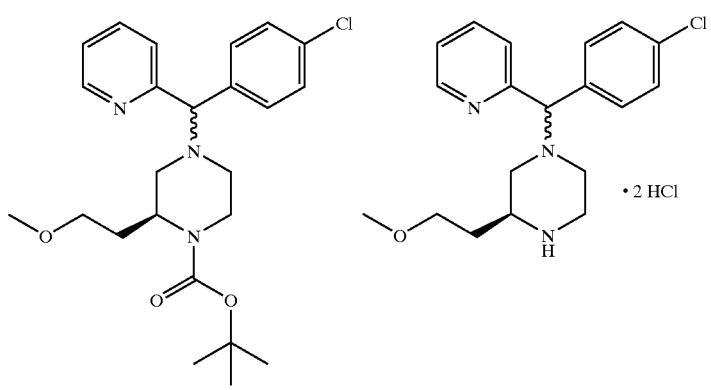 | |
| 128 | 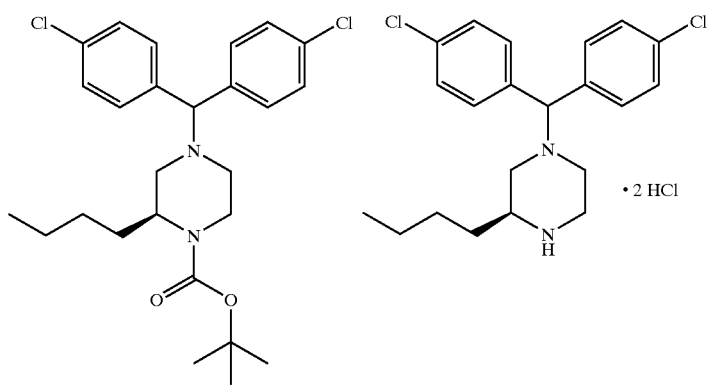 | |

TABLE 9-continued

| Prep. Ex. | Column 2 | Column 3 |
|---|---|---|
| 129 | 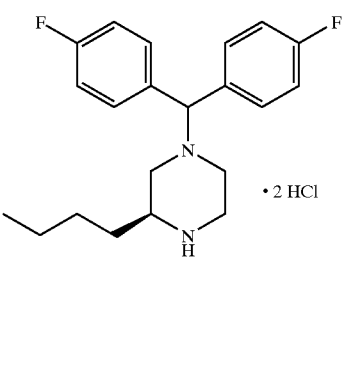 | |
| 130 | 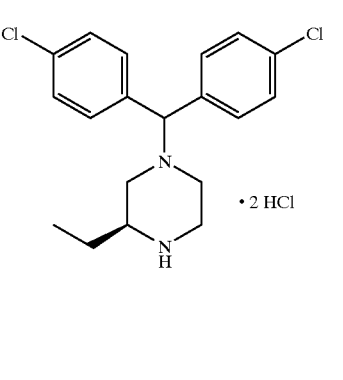 | |

PREPARATIVE EXAMPLE 134

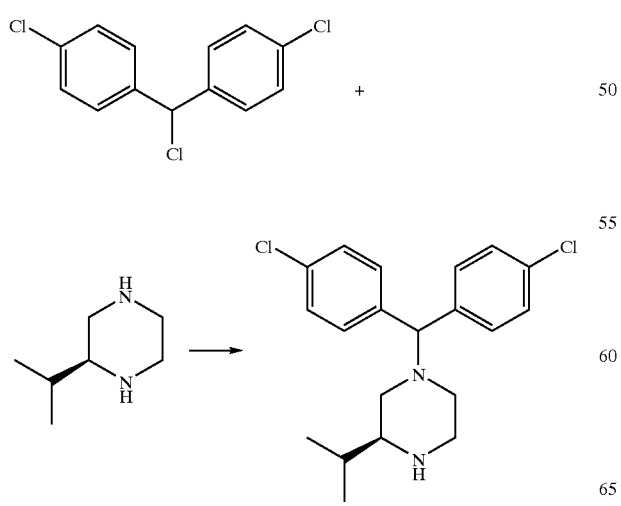

A solution of the product from Preparative Example 57 (2.13 g, 3.52 mmol), the product from Preparative Example 6 (1.0 g, 3.52 mmol) and NaI (0.23 g, 20 mol %) in $CH_3CN$ (50 mL) was heated to reflux overnight. The reaction mixture was cooled to room temperature, quenched by the addition of saturated $NaHCO_3$, and extracted with $CH_2Cl_2$. The combined organics were dried over $Na_2SO_4$, filtered, and concentrated. The crude product was purified by flash chromatography using a 5% (10% $NH_4OH$) in $CH_2Cl_2$ solution as eluent to afford a solid (1.8 g, 64%=yield). LCMS: $MH^+$=363.

PREPARATIVE EXAMPLES 135–144.10

By essentially the same procedure set forth in Preparative Example 134, using the chlorides as shown in Column 2 of Table 10, and the amines as shown in column 3 of Table 10, the products in Column 4 of Table 10 (CMPD), were prepared:

TABLE 10
| Prep. Ex. | Column 2 | Column 3 | Column 4 | CMPD |
|---|---|---|---|---|
| 135 |  | 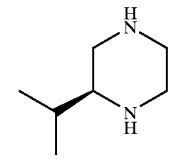 | 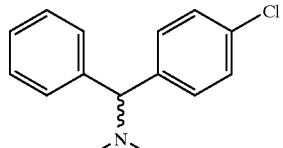 | — |
| 136 | 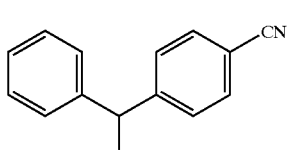 | 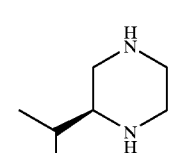 | 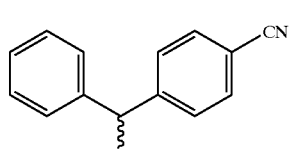 | LCMS: MH+ = 320 |
| 137 | 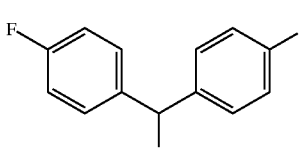 | 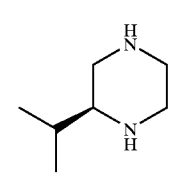 | 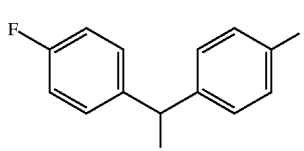 | LCMS: MH+ = 331 |
| 138 | 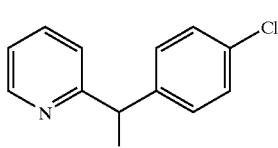 | 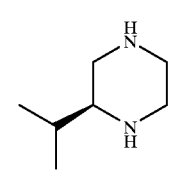 | 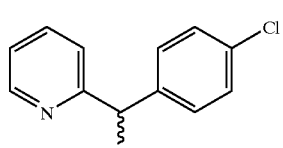 | LCMS: MH+ = 330 |
| 139 | 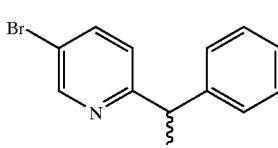 | 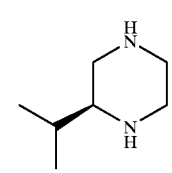 | 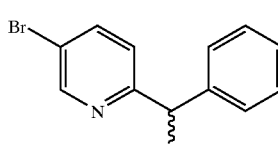 | LCMS: MH+ = 408 |

TABLE 10-continued
| Prep. Ex. | Column 2 | Column 3 | Column 4 | CMPD |
|---|---|---|---|---|
| 140 | 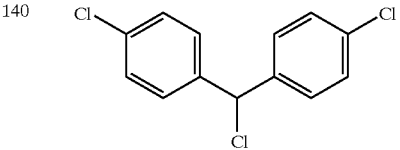 | 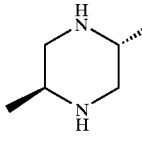 | 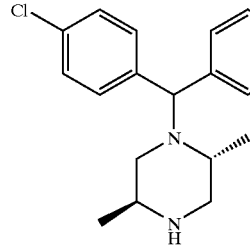 | LCMS: MH$^+$ = 349 |
| 141 | 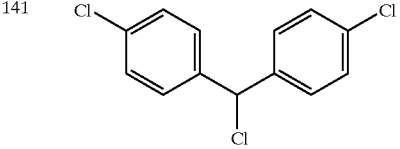 | 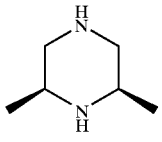 | 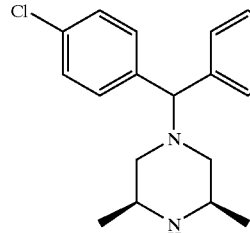 | LCMS: MH$^+$ = 349 |
| 142 | 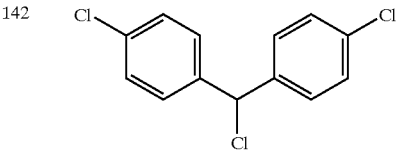 | 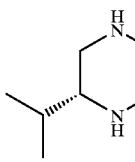 | 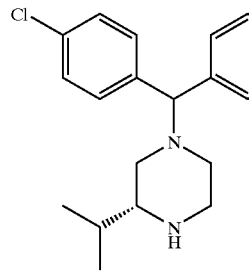 | LCMS: MH$^+$ = 363 |
| 143 | 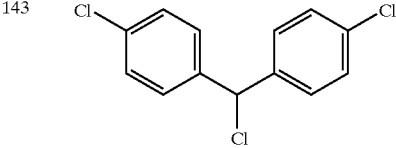 | 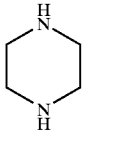 | 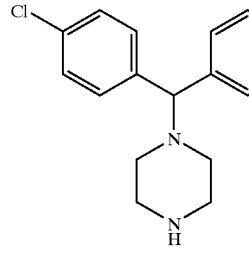 | FABMS: MH$^+$ = 321 |
| 144 | 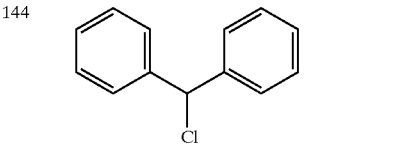 | 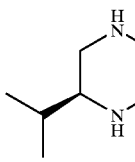 | 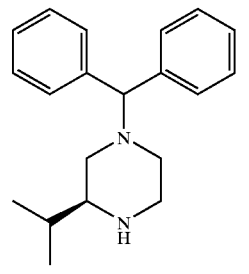 | LCMS: MH$^+$ = 295 |
| 144.10 | 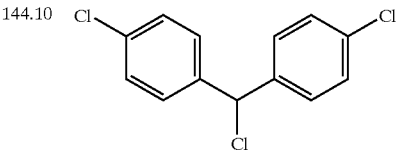 | 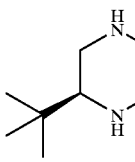 | | LCMS: MH$^+$ = 377 |

PREPARATIVE EXAMPLES 145 AND 146

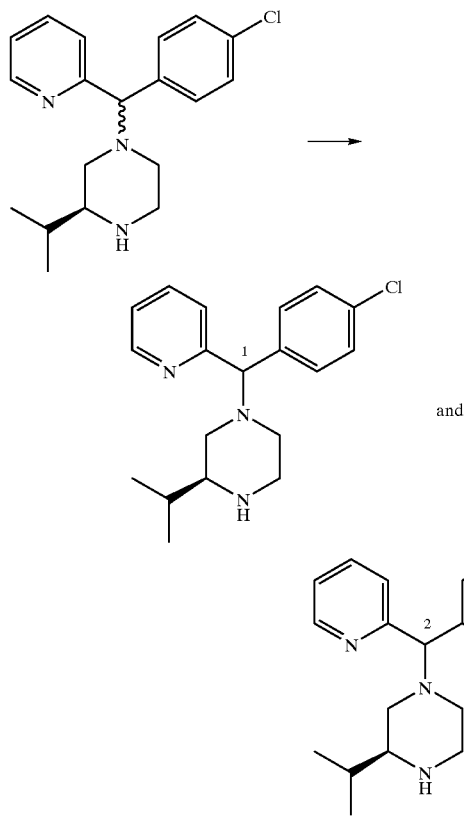

The products were prepared by separation of the mixture of diastereomers of the product from Preparative Example 138 by flash chromatography using a 5% (10% NH₄OH in MeOH) in CH₂Cl₂ as eluent:

Preparative Example 145 (first eluting isomer-1): LCMS: MH⁺=330.

Preparative Example 146 (second eluting isomer-2): LCMS: MH⁺=330.

PREPARATIVE EXAMPLE 149
Step A:

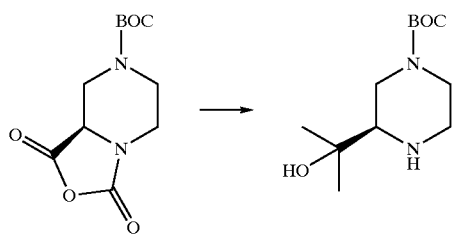

To a solution of anhydride (1.5 g, 5.85 mmol) in THF (10 mL) at −10° C. was added MeMgBr (5.85 mL, 1.0 M in THF, 3.0 eq.). The resulting solution was stirred one hour at −10° C., warmed to room temperature and stirred one hour. The reaction mixture was quenched by the addition of saturated NH₄Cl and extracted with CH₂Cl₂. The combined organics were dried over Na₂SO₄, filtered, and concentrated under reduced pressure. The crude product was purified by flash chromatography using a 10% MeOH in CH₂Cl₂ solution as eluent (0.20 g, 14% yield). LCMS: MH⁺=245.

Step B:

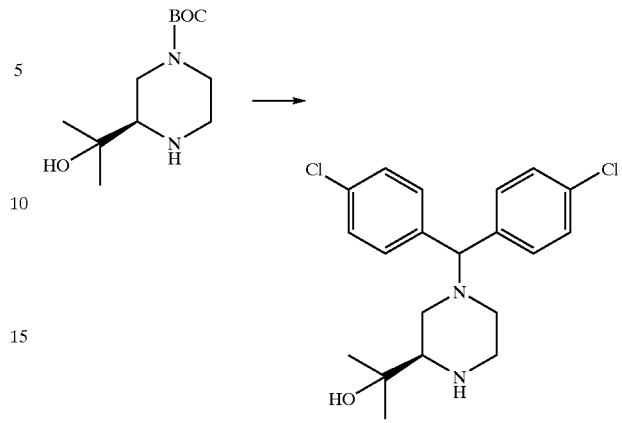

The product from Preparative Example 149, Step A was stirred at room temperature in 4 M HCl in dioxane (4.0 mL) for 10 minutes and the reaction mixture was concentrated under reduced pressure. The residue was dissolved in CH₃CN (10 mL) and the product from Preparative Example 30 (0.24 g, 1.2 eq.), K₂CO₃ (0.91 g, 8 eq.), and KI (0.054 g, 40 mol %) added. The resulting solution was heated to reflux overnight. The reaction mixture was cooled to room temperature, dilute with water and extracted with CH₂Cl₂. The combined organics were dried over Na₂SO₄, filtered, and concentrated under reduced pressure. The crude product was purified by flash chromatography using a 10% (10% NH₄OH in MeOH) in CH₂Cl₂ as eluent (0.20 g, 65% yield). LCMS: MH⁺=379.

PREPARATIVE EXAMPLE 150

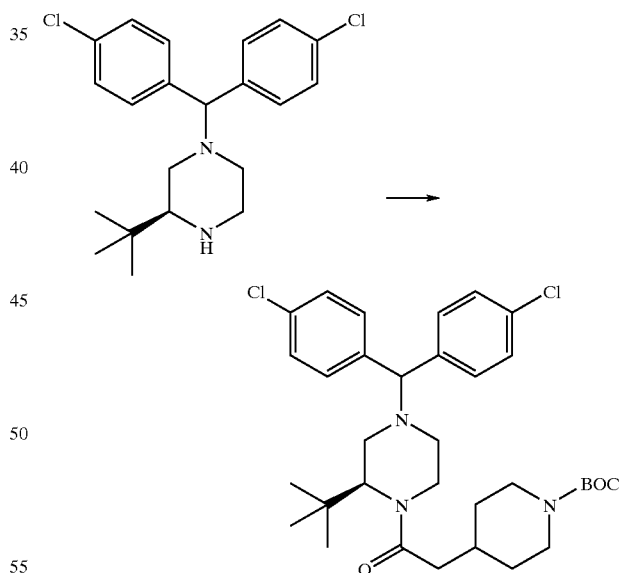

The product from Preparative Example 134 (0.5 g, 1.2 eq.), N-Boc-4-piperadineacetic acid (0.28 g, 1.14 mmol), DEC (0.28 g, 1.3 eq.), HOBt (0.20 g, 1.3 eq.), and NMM (90.31 mL, 2.5 eq.) were stirred at room temperature in CH₂Cl₂ for 3 days. The reaction mixture was poured into saturated NaHCO₃ and extracted with CH₂Cl₂. The combined organics were dried over Na₂SO₄, filtered, and concetrated. The crude product was purified by flash chromatography using a 5% (10% NH₄OH in MeOH) in CH₂Cl₂ as eluent to yield a solid (0.57 g, 85% yield). LCMS: MH⁺= 588.

PREPARATIVE EXAMPLES 151–172
By essentially the same procedure set forth in Preparative Example 150, using the compounds as shown in Column 2 of Table 11, the products in Column 3 of Table 11, were prepared:
TABLE 11
| Prep. Ex. | Column 2 | Column 3 | CMPD |
|---|---|---|---|
| 151 | 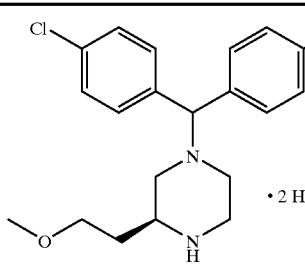 · 2 HCl | 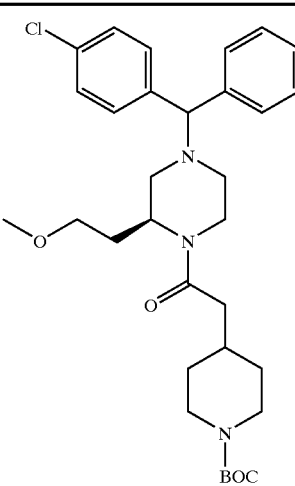 | — |
| 152 | 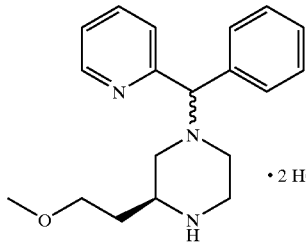 · 2 HCl | 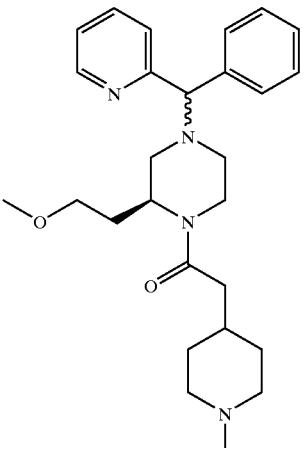 | LCMS: $MH^+ = 537$ |
| 153 | 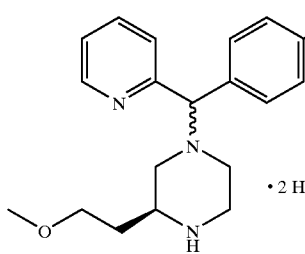 · 2 HCl | 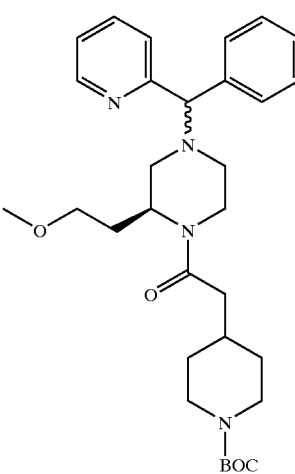 | LCMS: $MH^+ = 571$ |

TABLE 11-continued

| Prep. Ex. | Column 2 | Column 3 | CMPD |
|---|---|---|---|
| 154 | [bis(4-chlorophenyl)methyl-(butyl)piperazine · 2 HCl] | [bis(4-chlorophenyl)methyl-(butyl)piperazine acylated with BOC-piperidinyl-acetyl] | FABMS: MH$^+$ = 602 |
| 155 | [bis(4-fluorophenyl)methyl-(butyl)piperazine · 2 HCl] | [bis(4-fluorophenyl)methyl-(butyl)piperazine acylated with BOC-piperidinyl-acetyl] | FABMS: MH$^+$ = 570 |
| 156 | [bis(4-chlorophenyl)methyl-(ethyl)piperazine · 2 HCl] | [bis(4-chlorophenyl)methyl-(ethyl)piperazine acylated with BOC-piperidinyl-acetyl] | LCMS: MH$^+$ = 574 |

TABLE 11-continued
| Prep. Ex. | Column 2 | Column 3 | CMPD |
|---|---|---|---|
| 157 | 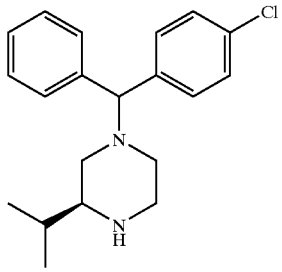 | | LCMS: MH⁺ = 554 |
| 158 | | | LCMS: MH⁺ = 545 |
| 159 | | | LCMS: MH⁺ = 556 |

TABLE 11-continued
| Prep. Ex. | Column 2 | Column 3 | CMPD |
|---|---|---|---|
| 160 | 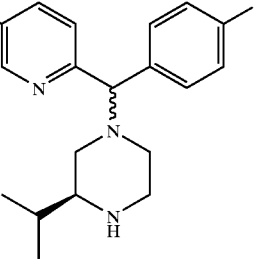 | | LCMS: MH⁺ = 633 |
| 161 | 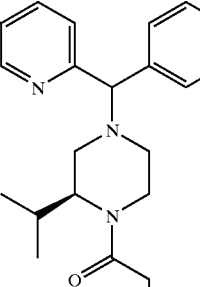 | | LCMS: MH⁺ = 588 |
| 162 | 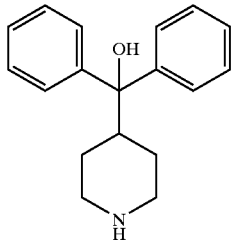 | | FABMS: MH⁺ = 493 |

TABLE 11-continued
| Prep. Ex. | Column 2 | Column 3 | CMPD |
|---|---|---|---|
| 163 | 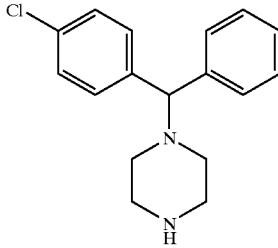 | 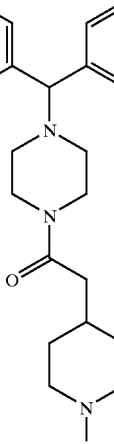 | FABMS: MH+ = 546 |
| 164 | 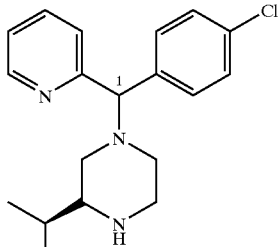 | 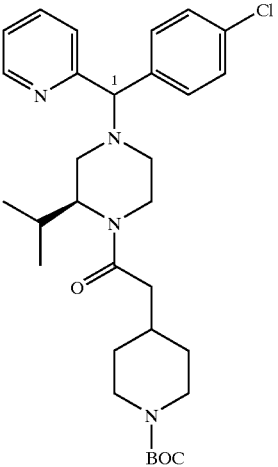 | LCMS: MH+ = 555 |
| 165 | 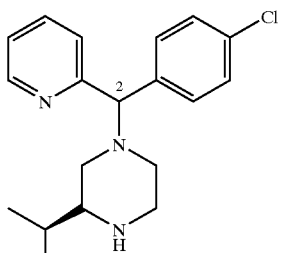 | 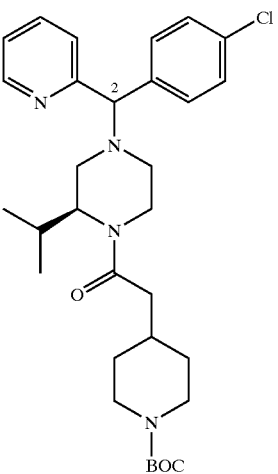 | LCMS: MH+ = 555 |

TABLE 11-continued
| Prep. Ex. | Column 2 | Column 3 | CMPD |
|---|---|---|---|
| 171 | | | LCMS: MH⁺ = 604 |
| 172 | | | LCMS: MH⁺ = 520 |
PREPARATIVE EXAMPLE 172.10
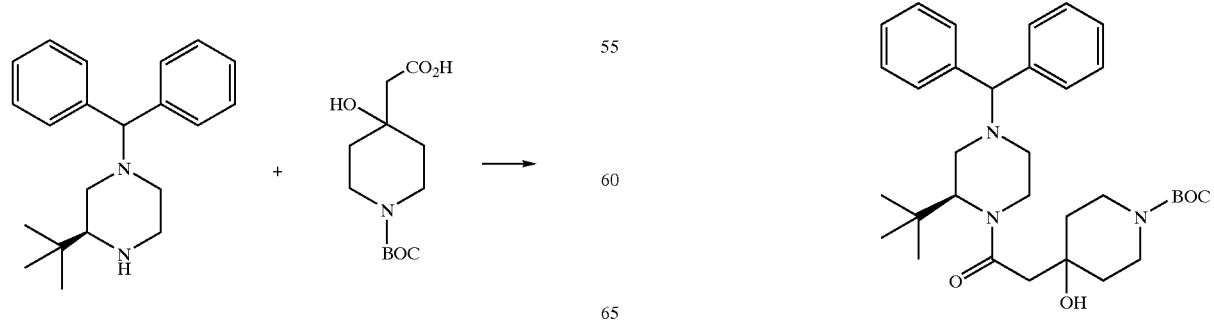

By essentially the same procedure set forth in Preparative Example 150, only substituting the compounds prepared in Preparative Example 144 (0.16 g, 0.55 mmol) and Preparative Example 18.11 (0.17 g, 1.2 eq.), the above compound was prepared (0.11 g, 31% yield). LCMS: MH⁺=536.

PREPARATIVE EXAMPLES 173 AND 174

By essentially the same procedure set forth in Preparative Example 19, using the compounds shown in Table 12, Column 2, the products shown in Table 12, Column 3 (CMPD) were prepared.

TABLE 12

| Prep. Ex. | Column 2 | Column 3 | CMPD |
|---|---|---|---|
| 173 | | | LCMS: MH⁺ = 574 |
| 174 | | | LCMS: MH⁺ = 574 |


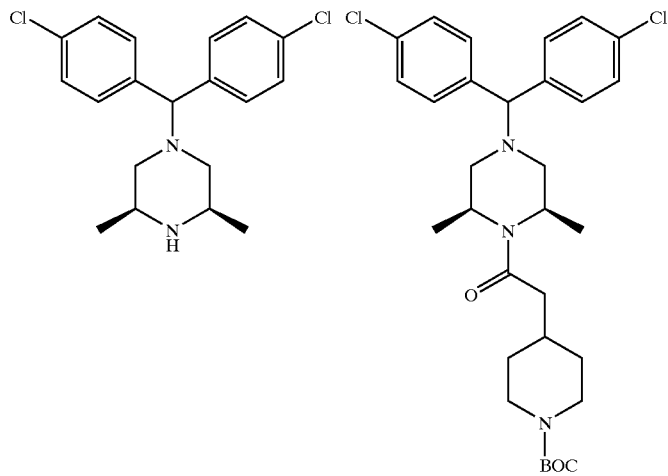

PREPARATIVE EXAMPLE 175 AND 176

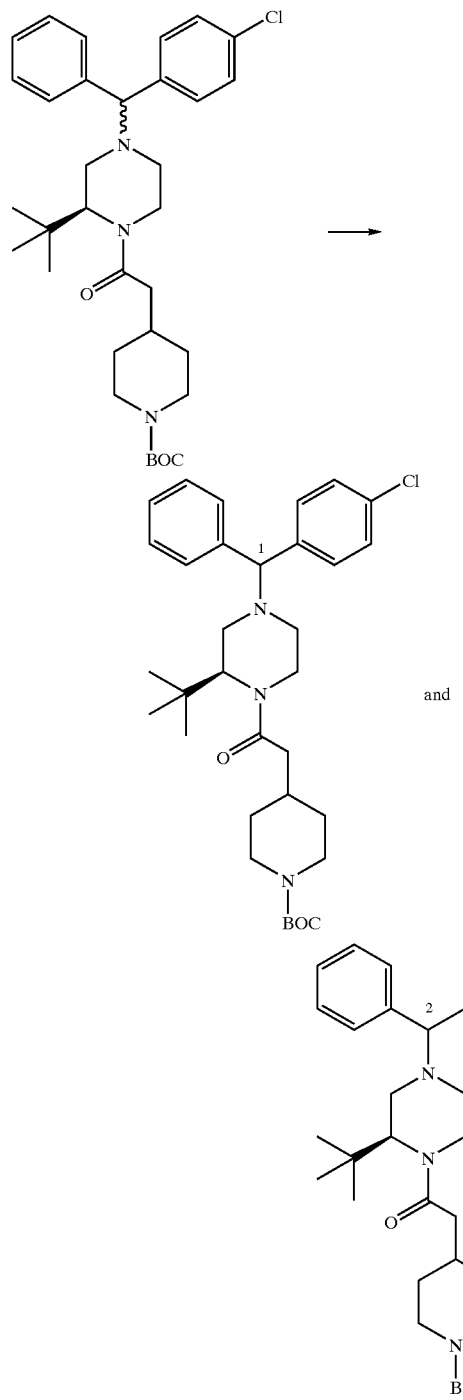

PREPARATIVE EXAMPLE 177 AND 178

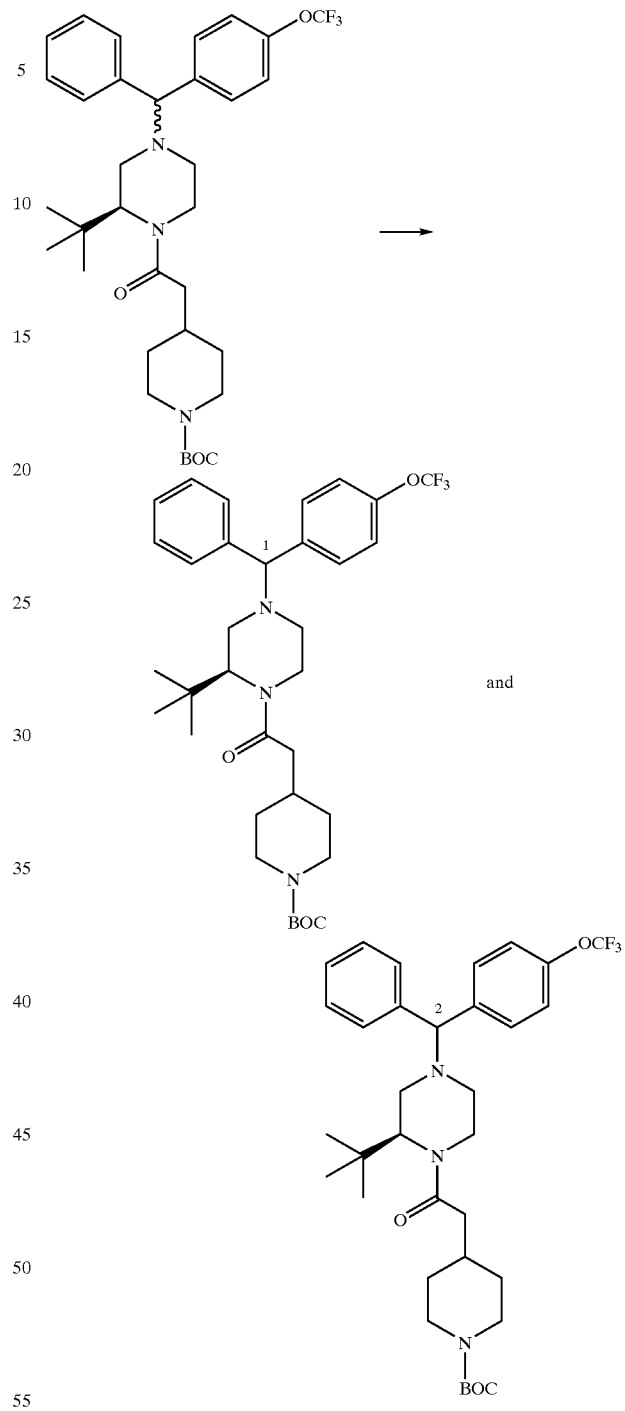

The product from Preparative Example 85 was separated into individual diastereomers by preparative HPLC with a ChiralPak AD column using a 95:5 hexanes:IPA mix with 0.2% DEA as eluent:

Preparative Example 175 (first eluting isomer-1): LCMS: $MH^+=568$.

Preparative Example 176 (second eluting isomer-2): LCMS: $MH^+=568$.

The product from Preparative Example 94 was separated into individual diastereomers using a ChiralPak AD column using a 95:5 hexanes:IPA mix with 0.2% DEA as eluent. Following elution of isomer 1, the eluent was adjusted to a 90:10 hexanes:IPA mix with 0.2% DEA for the elution of isomer 2.

Preparative Example 177 (first eluting isomer-1): LCMS: $MH^+=618$.

Preparative Example 178 (second eluting isomer-2): LCMS: $MH^+=618$.

PREPARATIVE EXAMPLE 179 AND 180

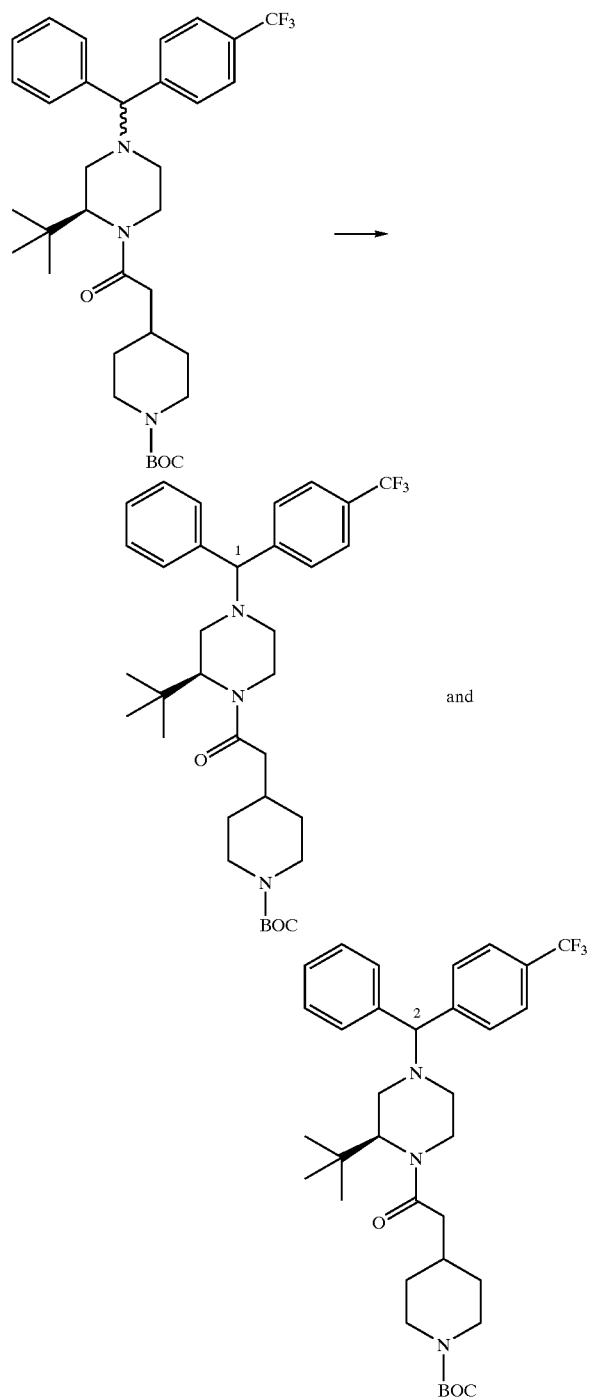

The product from Preparative Example 95 was separated into individual diastereomers using a ChiralPak AD column using a 95:5 hexanes:IPA mix with 0.2% DEA as eluent:

Preparative Example 179 (first eluting isomer): LCMS: MH+=603, mp=69–74° C.

Preparative Example 180 (second eluting isomer): LCMS: MH+=603; mp=74–79° C.

PREPARATIVE EXAMPLES 180.1 AND 180.2

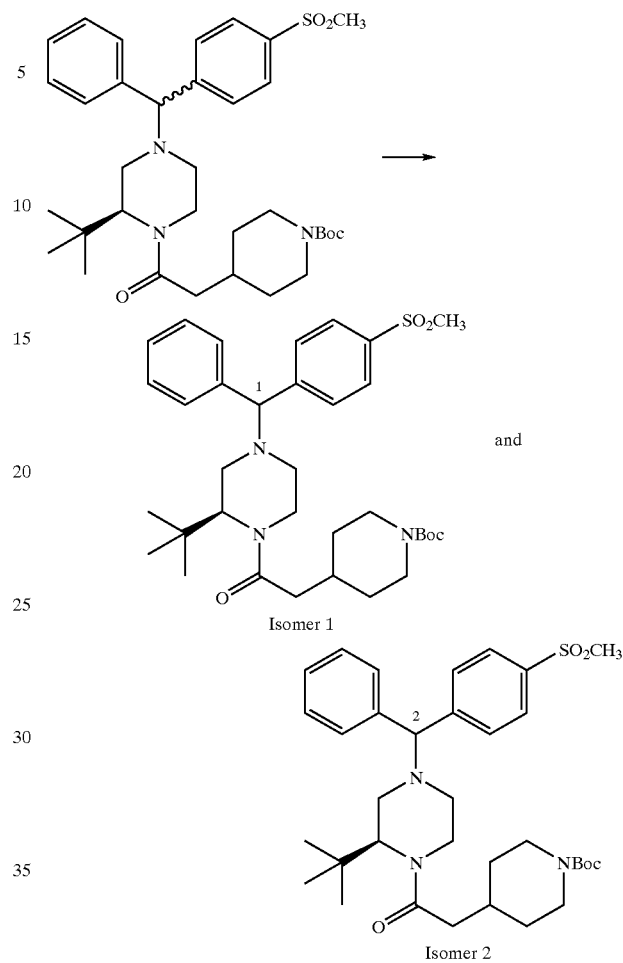

The product from Preparative Example 106.6 was separated into the two individual diastereomers shown here. Chromatography on a Chiralpak AD column using a 95:5 hexanes:IPA mix with 0.2% DEA as eluent afforded Preparative Example 180.1 (first eluting isomer) as a white solid and Preparative Example 180.2 (second eluting isomer) as a white solid.

PREPARATIVE EXAMPLE 180.3 AND 180.4

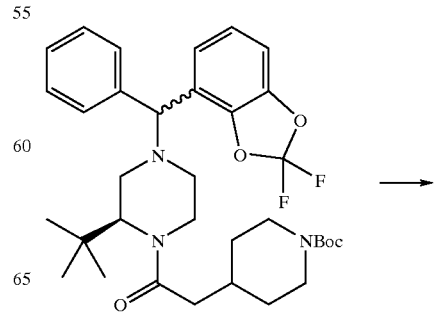

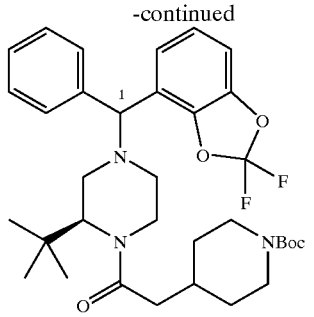

Isomer 1

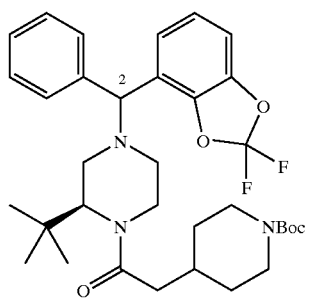

Isomer 2

The product from Preparative Example 106.1 was separated into the two individual diastereomers shown above. Chromatography on a Chiralpak AD column using a 98:2 hexanes:IPA mix with 0.2% DEA as eluent afforded Preparative Example 180.3 (first eluting isomer)=Isomer 1 and Preparative Example 180.4 (second eluting isomer)=Isomer 2.

PREPARATIVE EXAMPLES 180.5 AND 180.6

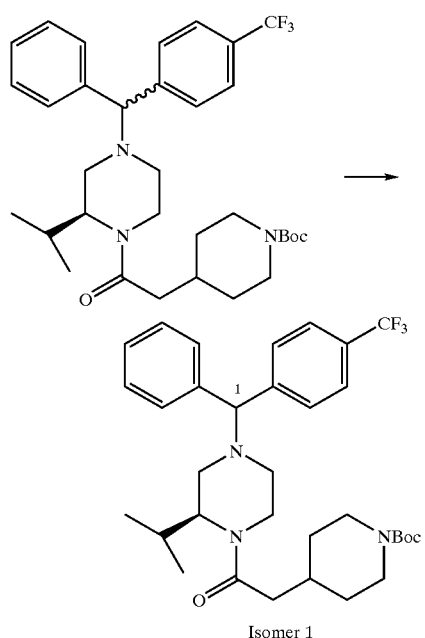

Isomer 1 and

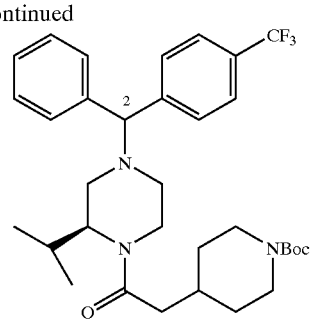

Isomer 2

The product from Preparative Example 106.9 was separated into the two individual diastereomers shown above. Chromatography on a Chiralpak AD column using a 95:5 hexanes:IPA mix with 0.2% DEA as eluent afforded Preparative Example 180.5 (first eluting isomer)=Isomer 1 and Preparative Example 180.6 (second eluting isomer)=Isomer 2.

PREPARATIVE EXAMPLE 180.7 AND 180.8

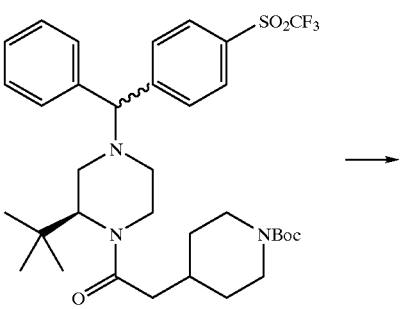

→

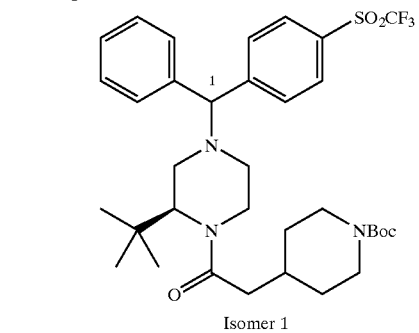

Isomer 1 and

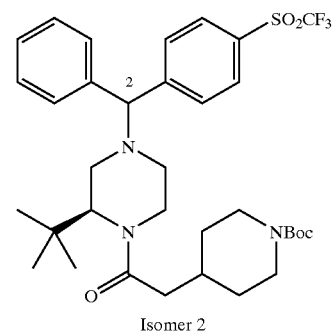

Isomer 2

The product from Preparative Example 106.8 was separated into the two individual diastereomers shown above. Chromotography on a Chiralpak AD column using a 90:10 hexanes:IPA mix with 0.2% DEA as eluent afforded Preparative Example 180.7 (first eluting isomer)=Isomer 1 and Preparative Example 180.8 (second eluting isomer)=Isomer 2.

PREPARATIVE EXAMPLES 180.9 AND 180.10

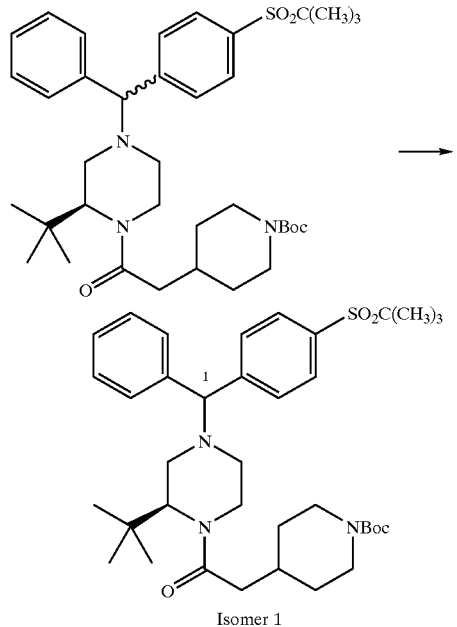

Isomer 1 and

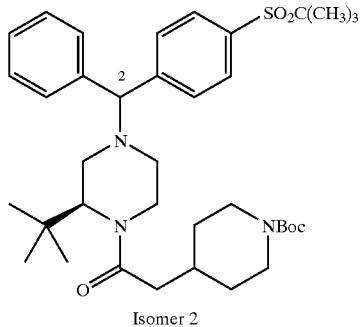

Isomer 2

The product from Preparative Example 106.12 was separated into the two individual diastereomers shown above. Chromatography on a Chiralpak AD column using a 85:15 hexanes:IPA mix with 0.2% DEA as eluent afforded Preparative Example 180.9 (first eluting isomer)=Isomer 1, and Preparative Example 180.10 (second eluting isomer)= Isomer 2.

PREPARATIVE EXAMPLES 180.10A–180.39

By essentially the same procedure set forth in Preparative Example 180, only substituting the diastereomeric mixture from the Preparative Example indicated in Column 2 of Table 12.1 and substituting the eluting solvent in Column 3 of Table 12.1, the compounds in Column 4 of Table 12.1 (CMPD) were prepared:

TABLE 12.1

| Prep. Ex. | Column 2 | Column 3 | Column 4 | CMPD |
|---|---|---|---|---|
| 180.10A | 106.16 | 95:5 hex:<br>IPA with 0.2% DEA | 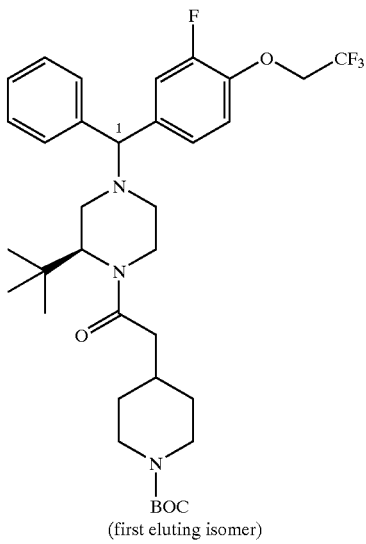<br>(first eluting isomer) | LCMS: MH⁺ = 650 |

TABLE 12.1-continued
| Prep. Ex. | Column 2 | Column 3 | Column 4 | CMPD |
|---|---|---|---|---|
| 180.11 | 106.16 | | 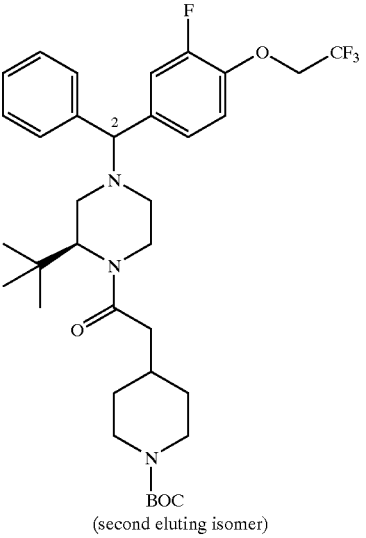<br>(second eluting isomer) | LCMS: MH+ = 650 |
| 180.12 | 106.17 | 97:3 hex:<br>IPA with 0.1% DEA | 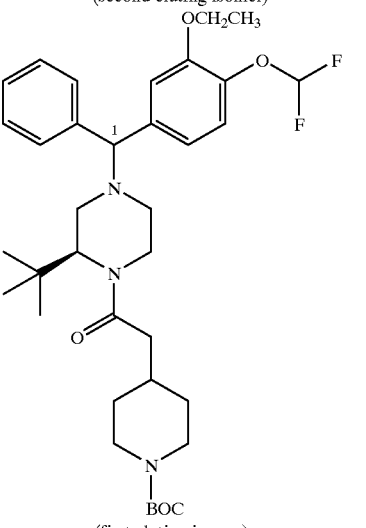<br>(first eluting isomer) | LCMS: MH+ = 644 |
| 180.13 | 106.17 | | 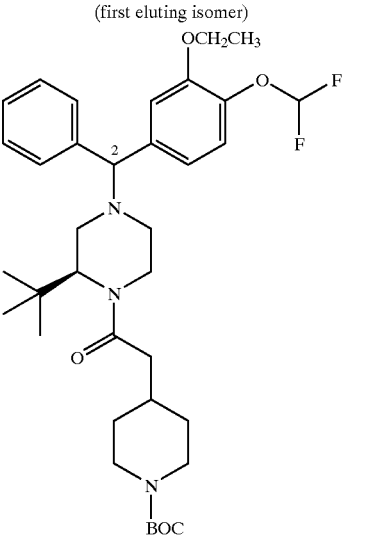<br>(second eluting isomer) | LCMS: MH+ = 644 |

TABLE 12.1-continued
| Prep. Ex. | Column 2 | Column 3 | Column 4 | CMPD |
|---|---|---|---|---|
| 180.14 | 106.18 | 97:3 hex:<br>IPA with 0.1% DEA | 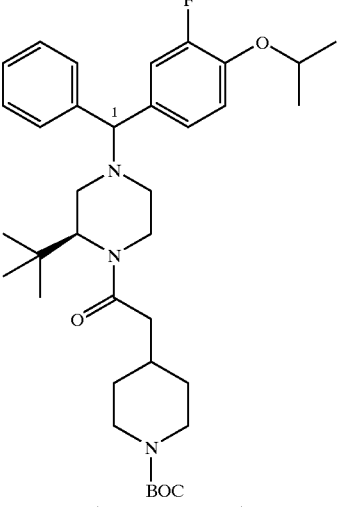<br>(first eluting isomer) | LCMS: MH$^+$ = 610 |
| 180.15 | 106.18 | | 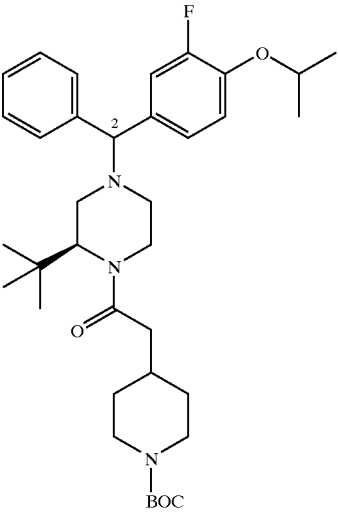<br>(second eluting isomer) | LCMS: MH$^+$ = 610 |
| 180.16 | 106.19 | 97:3 hex:<br>IPA with 0.1% DEA | 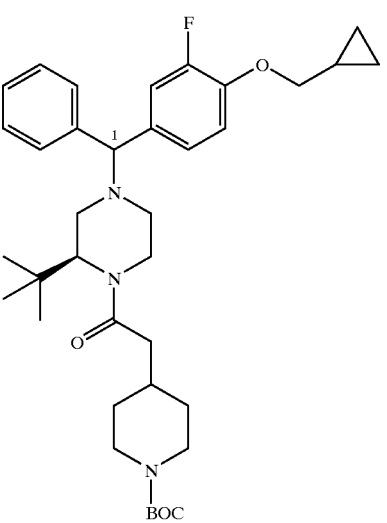<br>(first eluting isomer) | LCMS: MH$^+$ = 622 |

TABLE 12.1-continued
| Prep. Ex. | Column 2 | Column 3 | Column 4 | CMPD |
|---|---|---|---|---|
| 180.17 | 106.19 | | | LCMS: MH⁺ = 622 |
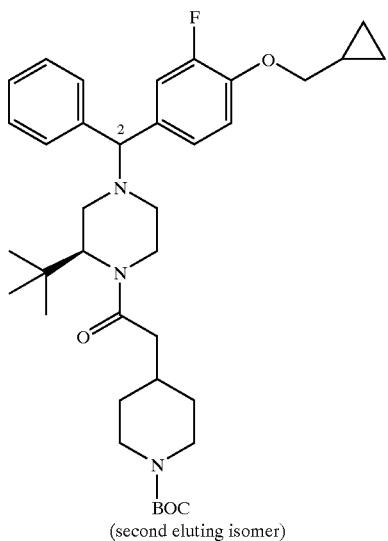
(second eluting isomer)
| 180.18 | 106.20 | 97:3 hex: IPA with 0.2% DEA | | LCMS: MH⁺ = 673 |
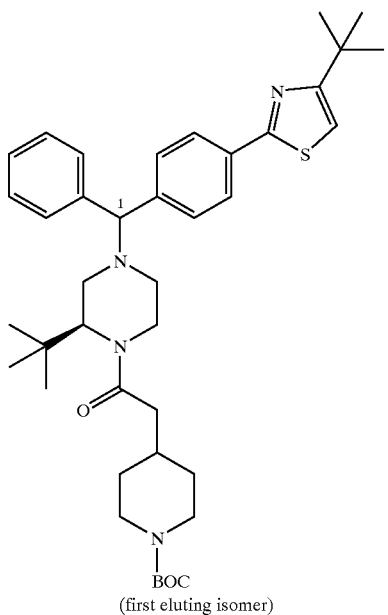
(first eluting isomer)

TABLE 12.1-continued
| Prep. Ex. | Column 2 | Column 3 | Column 4 | CMPD |
|---|---|---|---|---|
| 180.19 | 106.20 | | 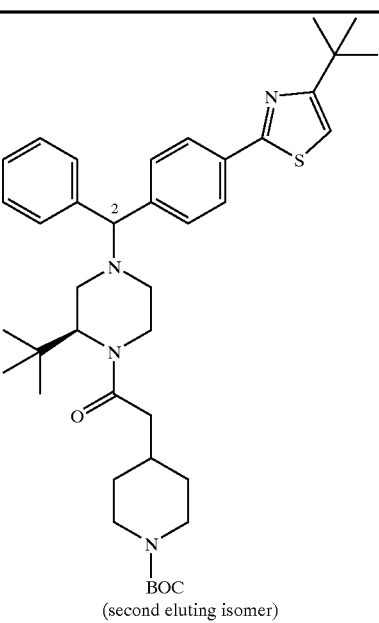<br>(second eluting isomer) | LCMS: MH+ = 673 |
| 180.20 | 106.23 | 93.5:6.5 hex: IPA with 0.2% DEA | 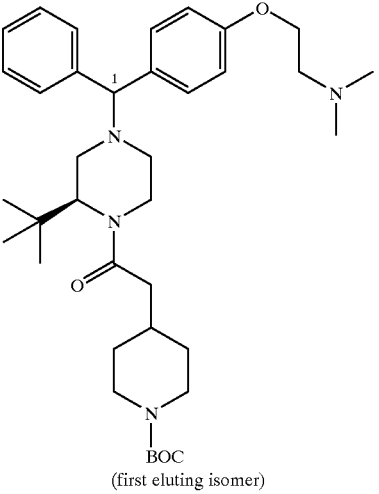<br>(first eluting isomer) | LCMS: MH+ = 621 |
| 180.21 | 106.23 | | 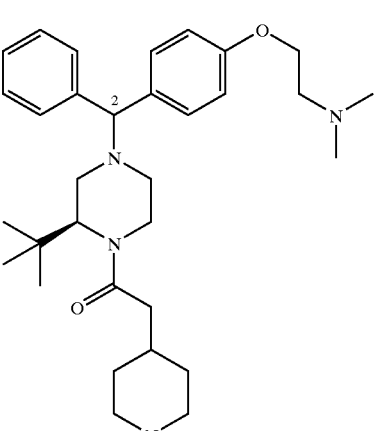<br>(second eluting isomer) | LCMS: MH+ = 621 |

TABLE 12.1-continued
| Prep. Ex. | Column 2 | Column 3 | Column 4 | CMPD |
|---|---|---|---|---|
| 180.22 | 106.24 | 95:5 hex:<br>IPA with 0.1% DEA | 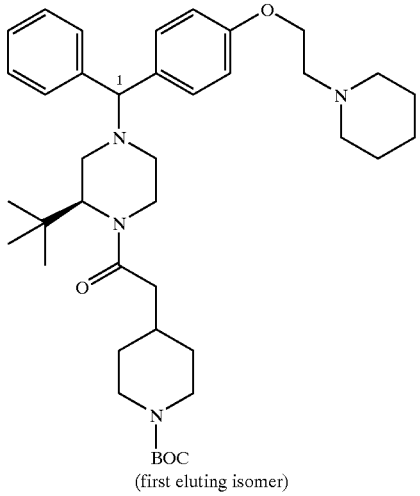<br>(first eluting isomer) | LCMS: MH⁺ = 661 |
| 180.23 | 106.24 | | 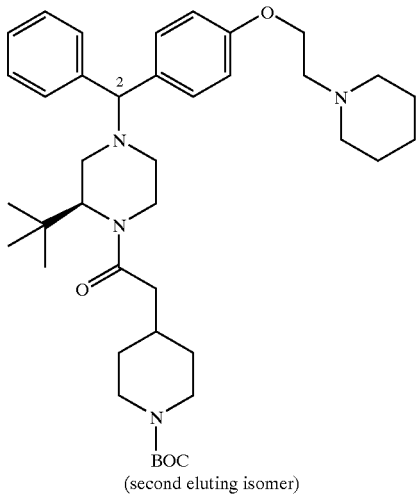<br>(second eluting isomer) | LCMS: MH⁺ = 661 |
| 180.24 | 106.26 | 97:3 hex:<br>IPA with 0.1% DEA | 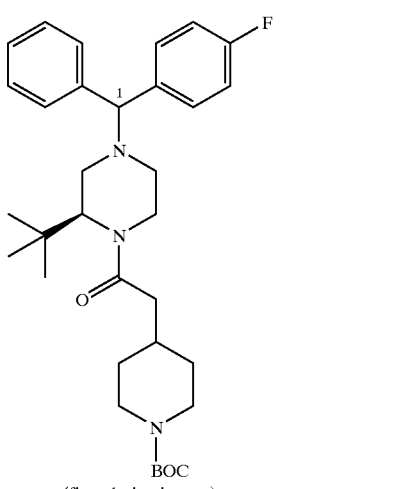<br>(first eluting isomer) | LCMS: MH⁺ = 552 |

TABLE 12.1-continued
| Prep. Ex. | Column 2 | Column 3 | Column 4 | CMPD |
|---|---|---|---|---|
| 180.25 | 106.26 | | 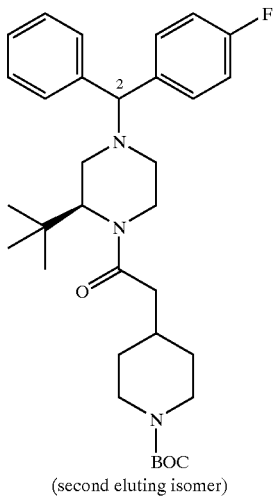 (second eluting isomer) | LCMS: MH⁺ = 552 |
| 180.26 | 106.27 | 98:2 hex: IPA with 0.1% DEA | 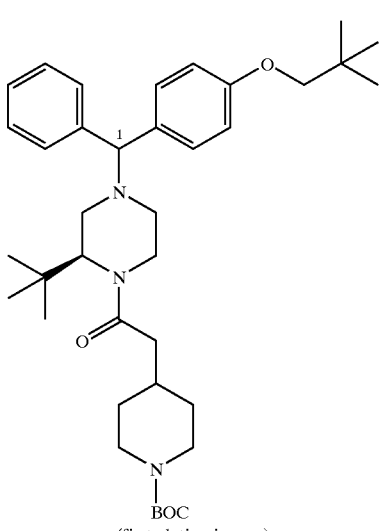 (first eluting isomer) | LCMS: MH⁺ = 620 |
| 180.27 | 106.27 | | 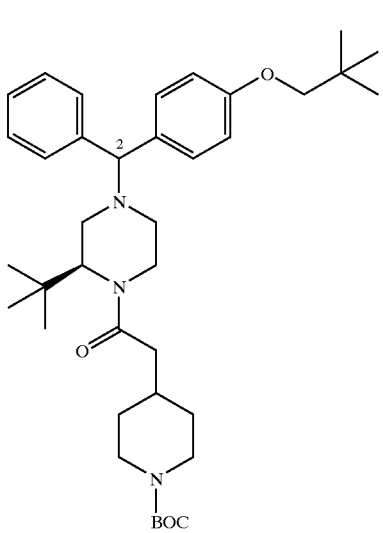 (second eluting isomer) | LCMS: MH⁺ = 620 |

TABLE 12.1-continued
| Prep. Ex. | Column 2 | Column 3 | Column 4 | CMPD |
|---|---|---|---|---|
| 180.28 | 106.29 | 95:5 hex: IPA with 0.1% DEA | 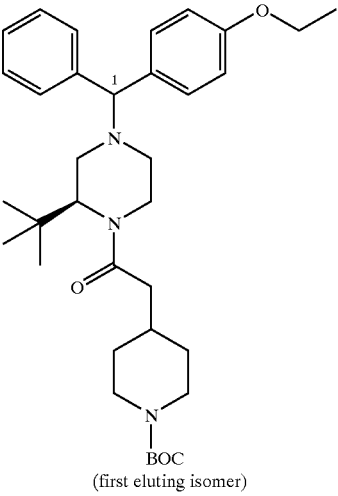<br>(first eluting isomer) | LCMS: MH⁺ = 578 |
| 180.29 | 106.29 | | 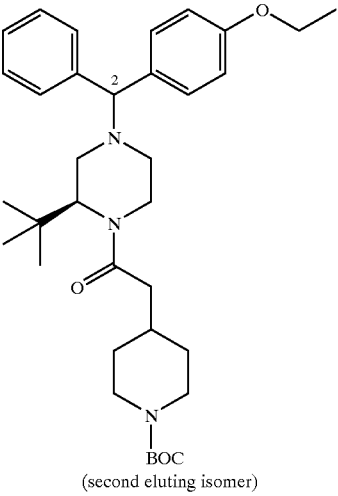<br>(second eluting isomer) | LCMS: MH⁺ = 578 |
| 180.30 | 106.28E | | 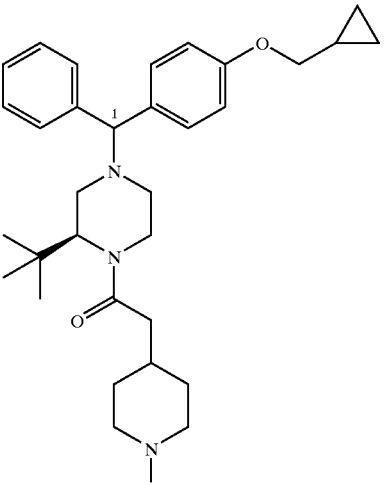<br>(first eluting isomer) | |

TABLE 12.1-continued
| Prep. Ex. | Column 2 | Column 3 | Column 4 | CMPD |
|---|---|---|---|---|
| 180.31 | 106.28E | 95:5 hex:<br>IPA with 0.1% DEA | 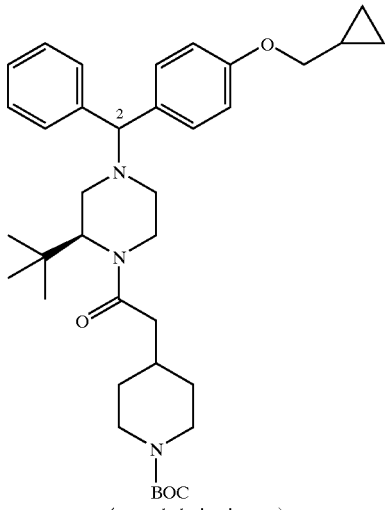<br>(second eluting isomer) | LCMS: MH⁺ = 604 |
| 180.32 | 106.28F | 98:2 hex:<br>IPA with 0.1% DEA | 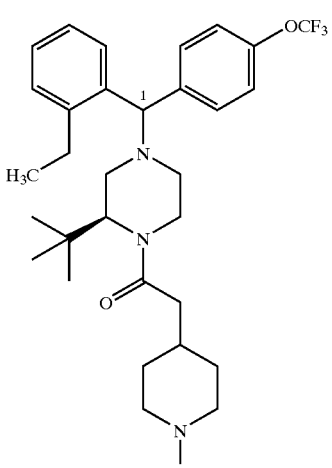<br>(first eluting isomer) | LCMS: MH⁺ = 646 |
| 180.33 | 106.28F | | 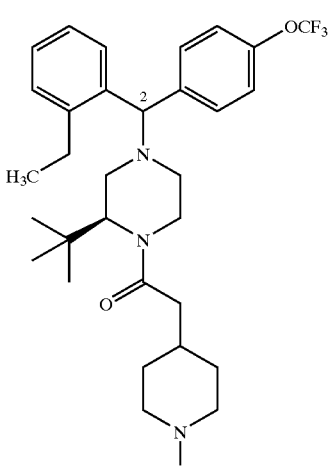<br>(second eluting isomer) | LCMS: MH⁺ = 646 |

TABLE 12.1-continued
| Prep. Ex. | Column 2 | Column 3 | Column 4 | CMPD |
|---|---|---|---|---|
| 180.34 | 106.28G | 99:1 hex: IPA with 0.1% DEA | 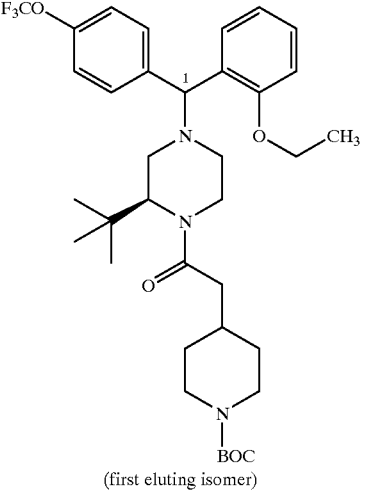<br>(first eluting isomer) | LCMS: MH$^+$ = 662 |
| 180.35 | 106.28G | | 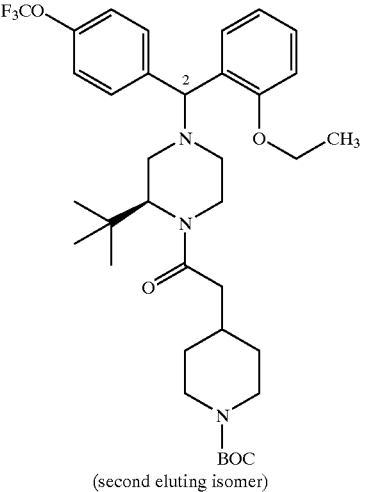<br>(second eluting isomer) | LCMS: MH$^+$ = 662 |
| 180.36 | 106.28L | 93:7 hex: IPA with 0.2% DEA | 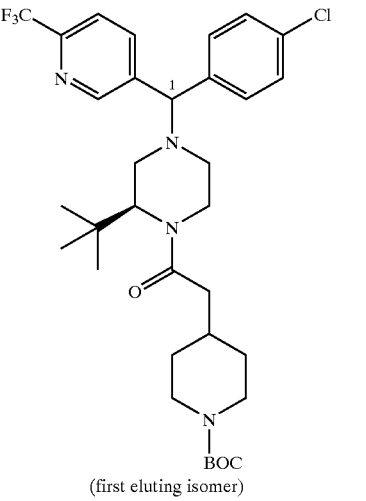<br>(first eluting isomer) | LCMS: MH$^+$ = 637 |

TABLE 12.1-continued
| Prep. Ex. | Column 2 | Column 3 | Column 4 | CMPD |
|---|---|---|---|---|
| 180.37 | 106.28L | | 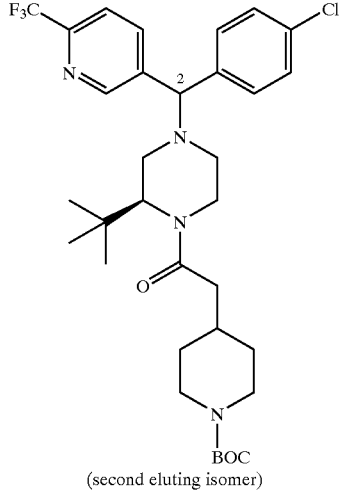<br>(second eluting isomer) | LCMS: MH⁺ = 637 |
| 180.38 | 106.28M | 95:5 hex:<br>IPA with 0.2% DEA | 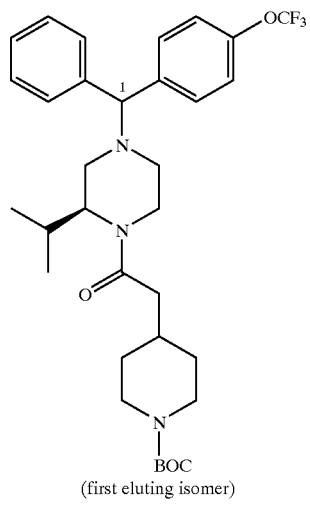<br>(first eluting isomer) | LCMS: MH⁺ = 604 |
| 180.39 | 106.28M | | 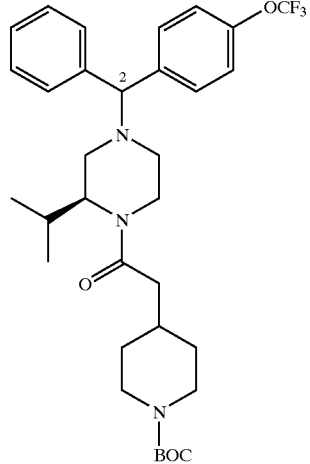<br>(second eluting isomer) | LCMS: MH⁺ = 604 |

PREPARATIVE EXAMPLE 181

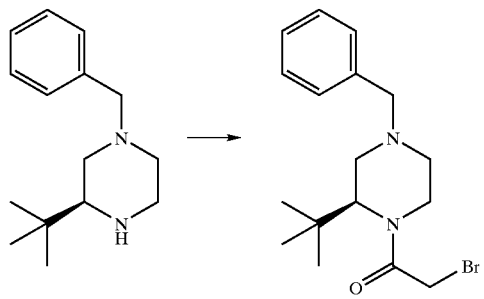

Step A

To the product from Preparative Example 10 (1.64 g, 7.06 mmol) and NaHCO$_3$ (1.19 g, 2 eq.) in CH$_2$Cl$_2$ (30 mL) at 0° C. was added bromoacetyl bromide (0.68 mL, 1.1 eq.) dropwise. The resulting solution was warmed slowly to room temperature and stirred overnight. The reaction mixture was quenched by the addition of water and extracted with CH$_2$Cl$_2$. The combined organics were dried over Na$_2$SO$_4$, filtered, and concentrated under reduced pressure. The crude product (2.2 g, 92% yield) was used without further purification. LCMS: MH$^+$=353.

Step B

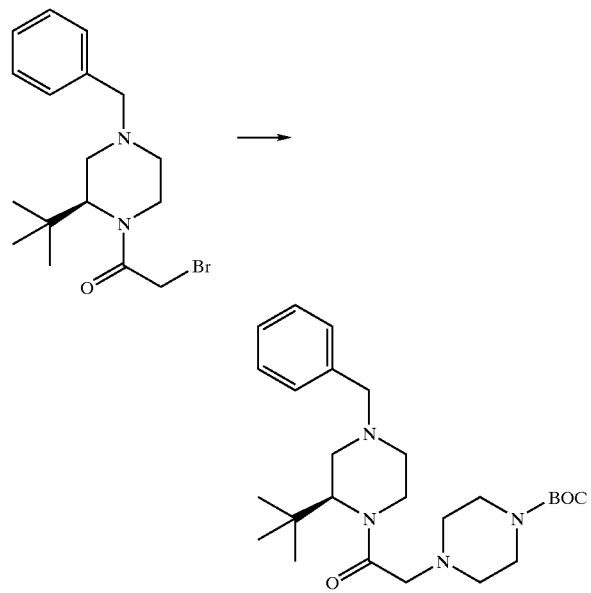

To the product from Preparative Example 181, Step A (2.2 g, 6.23 mmol) and K$_2$CO$_3$ (1.72 g, 2.0 eq.) in CH$_3$CN (50 mL) was added N-BOC-piperazine (1.35 g, 1.2 eq.). The resulting solution was heated to reflux 2 hours, cooled, and diluted with water. The resulting solution was extracted with EtOAc and the combined organics dried over Na$_2$SO$_4$, filtered, and concentrated. The crude product was purified by flash chromatography using a 50:50 EtOAc:hexanes solution as eluent (0.77 g, 27% yield). LCMS: MH$^+$=459.

Step C:

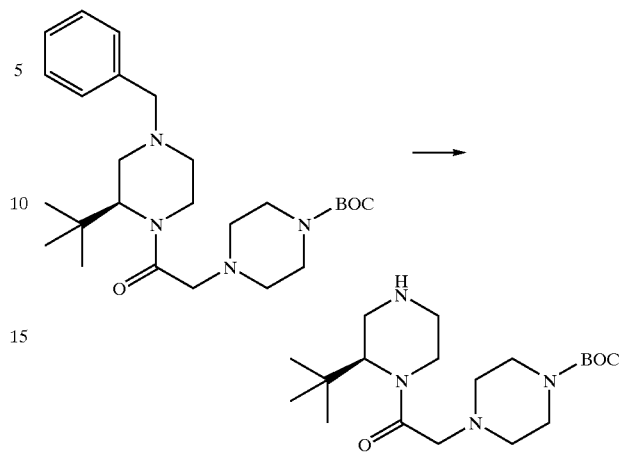

The product from Preparative Example 181, Step B (0.77 g, 1.68 mmol), ammonium formate (2.12 g, 20 eq.) and 10% Pd/C (1.48 g, 50% wet) in EtOH (20 mL) was heated to reflux 4 hours. The resulting solution was cooled, filtered through a plug of Celite and concentrated. The residue was taken up in CH$_2$Cl$_2$ and washed with water. The crude product was purified by flash chromatography using a 7% (10% NH4OH in MeOH in CH$_2$Cl$_2$ solution as eluent (0.57 g, 92% yield). LCMS: MH$^+$=369.

Step D:

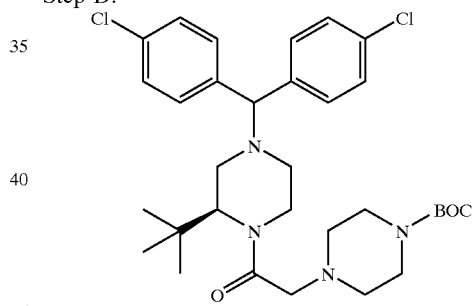

By essentially the same procedure set forth in Preparative Example 85, using the product from Preparative Example 181, Step C, the above compound was prepared (0.14 g, 16% yield). LCMS: MH$^+$=603.

PREPARATIVE EXAMPLE 181.11

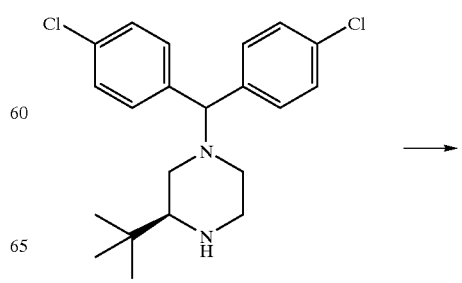

245
-continued

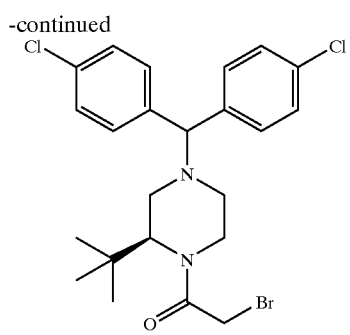

By essentially the same procedure set forth in Preparative Example 181, Step A only substituting the compound prepared in Preparative Example 144.10, the Above compound was prepared. LCMS: MH$^+$=497.

PREPARATIVE EXAMPLE 181.12 AND 181.13

By essentially the same procedure set forth in Preparative Example 181, Step B, only substituting the compounds in Column 2 of Table 12.2, the compounds in Column 3 of Table 12.2 (CMPD) were prepared:

246
PREPARATIVE EXAMPLE 182

Step A:

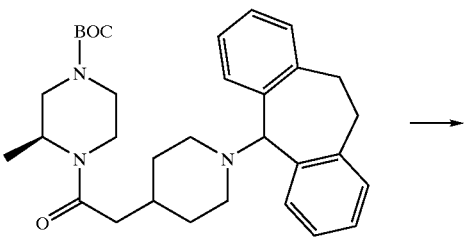

TABLE 12.2

| Prep. Ex. | Column 2 | Column 3 | CMPD |
|---|---|---|---|
| 181.12 | (2R,5S)-2,5-dimethylpiperazine | structure | LCMS: MH$^+$ = 531 |
| 181.13 | (2R,6S)-2,6-dimethylpiperazine | structure | LCMS: MH$^+$ = 531 |

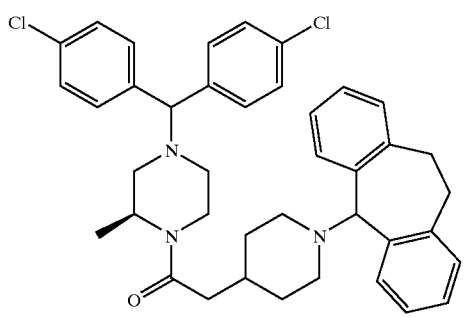

The product from Preparative Example 21 (0.53 g, 1.0 mmol) was stirred in 4M HCl/dioxane (8.0 mL) at room temperature 30 minutes and concentrated under reduced pressure. The crude product was diluted with CH₃CN (10 mL) and by essentially the same procedure set forth in Preparative Example 134 the product was prepared (0.05 g, 25% yield). FaBMS: MH$^+$=652.

Step B:

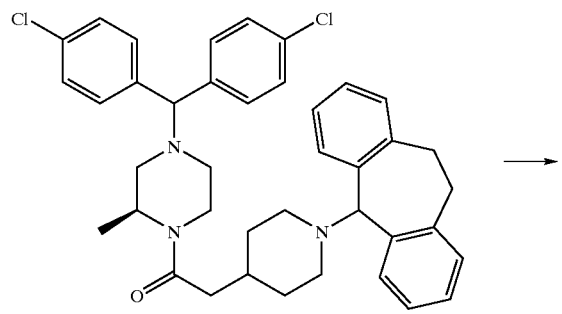

The product from Preparative Example 182, Step A (0.03 g, 0.05 mmol) in 1:1 CH₂Cl₂:HCO₂H was stirred at room temperature 5 hours then at reflux overnight. The reaction mixture was cooled to room temperature and concentrated under reduced pressure. The crude product was purified by flash chromatography using a gradient column from 1% (10% NH₄OH in MeOH) in CH₂Cl₂ to 20% (10% NH₄OH in MeOH) in CH₂Cl₂ (0.01 g, 48% yield). LCMS: MH$^+$=460.

PREPARATIVE EXAMPLE 183

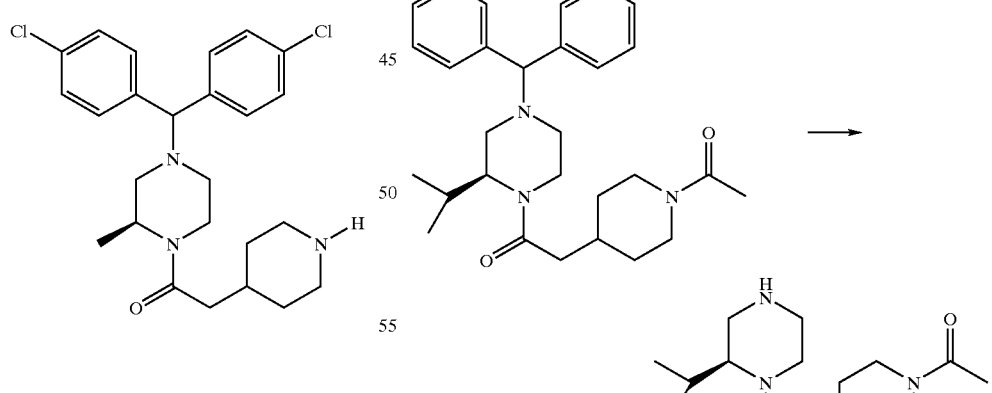

A solution of the product from Preparative Example 150 (0.35 g, 0.59 mmol) was stirred at room temperature in 4 M HCl in dioxane (4 mL) for 30 minutes. The resulting solution was concentrated under reduced pressure. The residue was dissolved in CH₂Cl₂ and neutralized by the addition of 1N NaOH, separated, and the organics dried over Na₂SO₄, filtered and concentrated to give a solid (0.31 g, 94% yield) which was used without further purification. LCMS: MH$^+$=488.

PREPARATIVE EXAMPLE 239

A solution of the product from Example 611 (1.00 g, 2.20 mmol) below, and HCOONH₄ (2.77 g, 44.0 mmol) in anhydrous MeOH (30 mL) was added under N₂ to a suspension of 10% Pd/C (1.17 g) in anhydrous MeOH (20 mL).

The mixture was stirred for 16 hrs under N₂, poured into 250 CH₂Cl₂ (250 mL), and filtered through Celite. The solvent was evaporated and the residue was purified by flash chromatography using 11% MeOH (10% NH₄OH) in CH₂Cl₂ to give 555 mg (87%) of a solid.

PREPARATIVE EXAMPLE 240

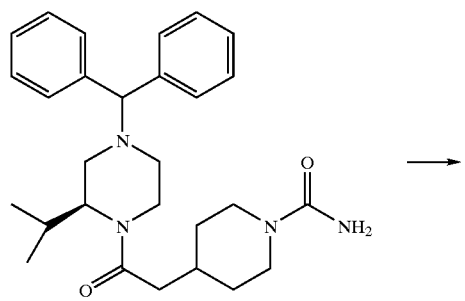

Using essentially the same procedure as described in Preparative Example 239, 1.00 g (2.20 mmol) of the product from Example 612 below, was converted into 520 mg (81%) of a solid.

PREPARATIVE EXAMPLE 241

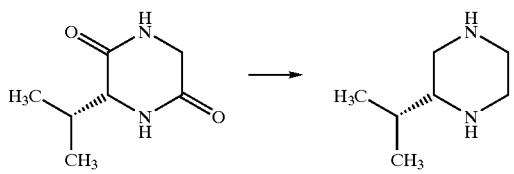

(-)-3-(R)-Isopropyl-2,5-piperazinedione (5 g) (32 mmoles) was dissolved in dry THF (167.5 mL) and the solution was cooled to 0° C. A 1M solution of LiAlH₄ in THF (115.25 mL) (115.25 mmoles) was added dropwise over 20 minutes. The mixture was heated under reflux at 65° C. for 5 h and then stirred at 25° C. for 16 h. Distilled water (37.5 mL) was added dropwise to the stirred reaction mixture, followed by 1N NaOH (21.25 mL) and additional distilled water (37.5 mL). The mixture was extracted with ethyl acetate (1.75 L) and the latter was dried (MgSO₄), filtered and evaporated to dryness. The residue was chromatographed on a silica gel column (40×6.5 cm) using gradient elution with 3%, 4%, 6% and 9% (10% NH₄OH in methanol)-dichloromethane as the eluant to give the product (2.4 g; 58%): $[\alpha]_D^{25° C.}$ +3.7° (c=5.7 mg/2 mL MeOH).

PREPARATIVE EXAMPLE 242

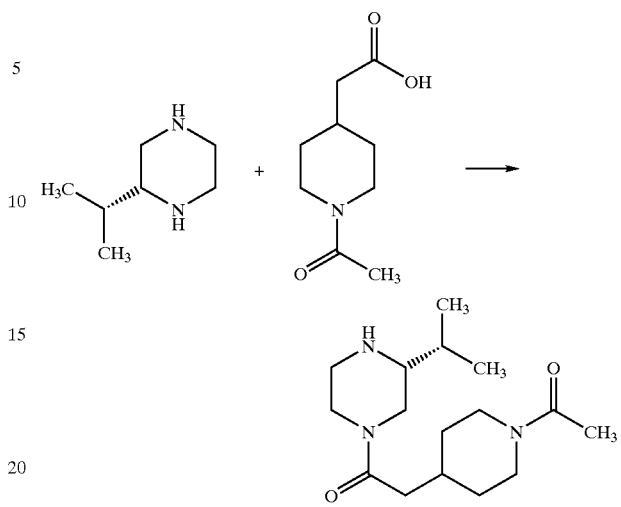

The product from Preparative Example 241 (555.2 mg) (4.33 mmoles) above, was dissolved in anhydrous DMF (16.7 mL). 4-methylmorpholine (0.476 mL) (4.33 mmoles), 1-(3-dimethylaminopropyl)-3-ethylcarbodiimide hydrochloride (830 mg) (4.33 mmoles), 1-hydroxybenzotriazole (585.2 mg) (4.33 mmoles) and N-acetylpiperidine-4-acetic acid (802.3 mg) (4.33 mmoles) was added and the mixture was stirred under argon at 25° C. for 41 h. The mixture was evaporated to dryness and the residue was taken up in dichloromethane and washed with saturated aqueous NaHCO₃.

The dichloromethane layer was dried (MgSO₄), filtered and evaporated to dryness and the residue was chromatographed on a silica gel column (20×5 cm) using 3% (10% NH₄OH in methanol)-dichloromethane as the eluant to give the product (1.25 g; 98%): $[\alpha]_D^{25° C.}$ +16.6° (c=5.6 mg/2 mL MeOH).

EXAMPLE 500

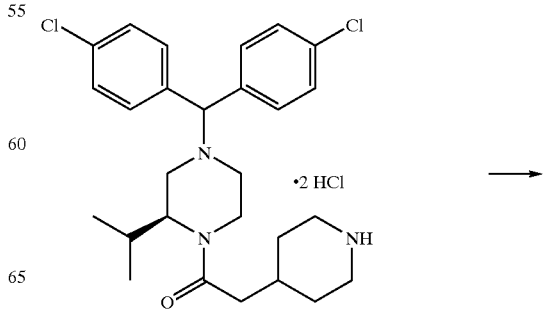

251

-continued

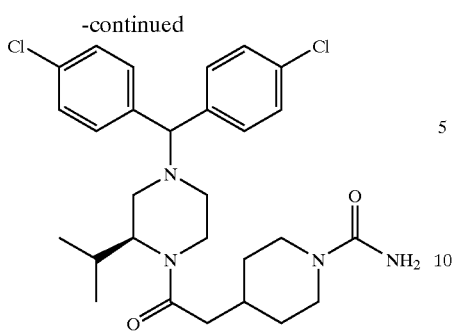

To a solution of the product from Preparative Example 183 (0.15 g, 0.31 mmol) in CH₂Cl₂ (5 mL) at 0° C. was added TEA (0.21 mL, 5 eq.) and TMSNCO (0.41 mL, 10 eq.). The reaction mixture was stirred until TLC showed consumption of starting material (30 minutes). The reaction was quenched by the addition of saturated NaHCO₃ and extracted with CH₂Cl₂. The combined organics were dried over Na₂SO₄, filtered and concentrated. The crude product was purified by flash chromatography using a 5% (10% NH₄OH in MeOH) in CH₂Cl₂ solution as eluent to yield a solid (0.10 g, 61% yield). LCMS: MH$^+$=531: mp=115–128° C.

EXAMPLES 501–558.22

By essentially the same procedure set forth in Example 500, using the compounds shown in column 2 of Table 14, which were prepared in a similar manner to Preparative Example 183 or Example 611 from the corresponding N-BOC-protected amine, the products shown in column 3 of Table 14 (CMPD), were prepared:

TABLE 14

| Ex. | Column 2 | Column 3 | CMPD |
|---|---|---|---|
| 501 | 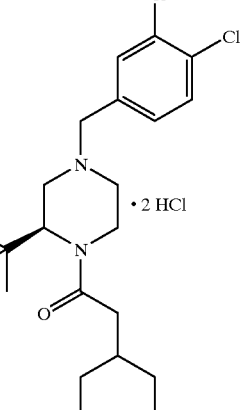 | 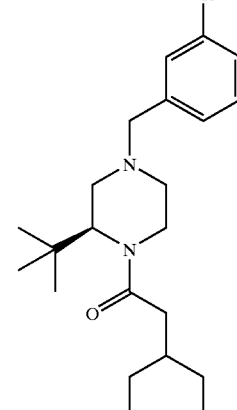 | LCMS: MH$^+$ = 469; Mp = 80–85° C. |
| 502 | 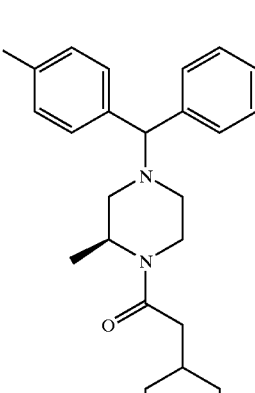 | 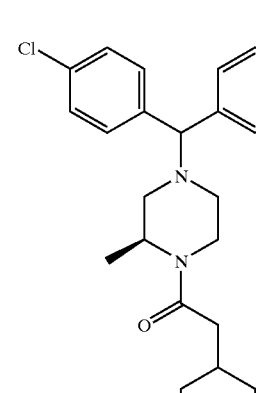 | LCMS: MH$^+$ = 503; mp = 103–109° C. |

TABLE 14-continued
| Ex. | Column 2 | Column 3 | CMPD |
|---|---|---|---|
| 503 | 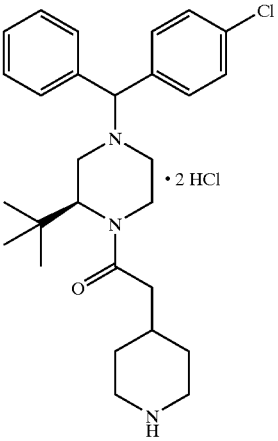 | 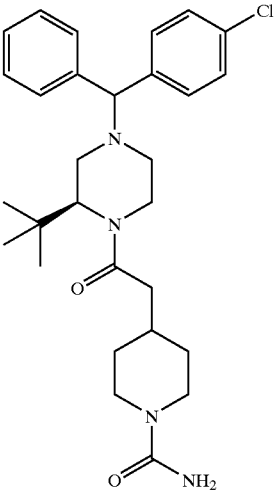 | LCMS: MH+ = 512; mp = 112–117° C. |
| 504 | 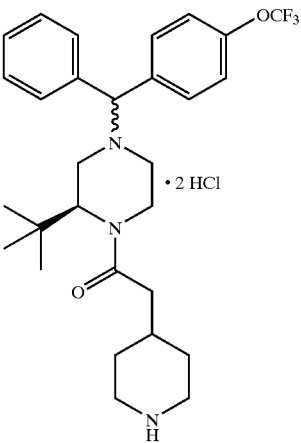 | 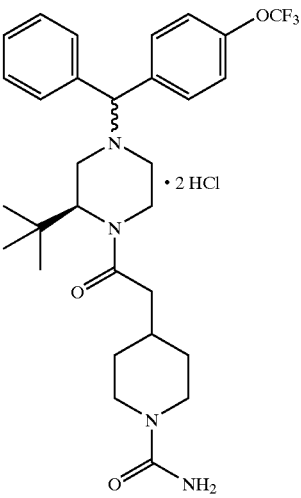 | LCMS: MH+ = 561; mp = 101–105° C. |
| 505 | 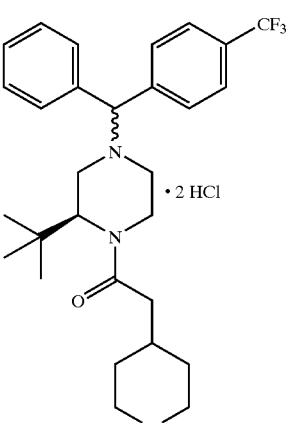 | 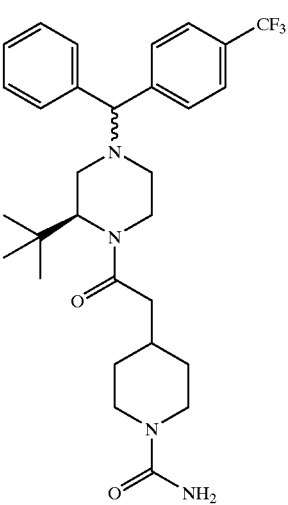 | LCMS: MH+ = 545; mp = 106–111° C. |

TABLE 14-continued
| Ex. | Column 2 | Column 3 | CMPD |
|---|---|---|---|
| 506 | 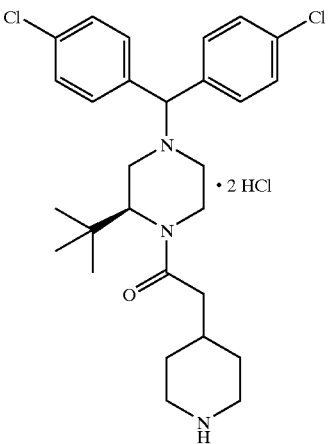 · 2 HCl | 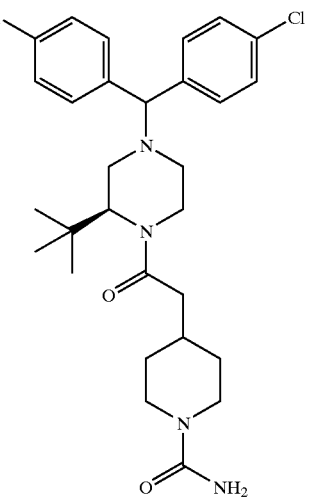 | LCMS:<br>MH$^+$ = 545;<br>mp = 141–160° C. |
| 507 | 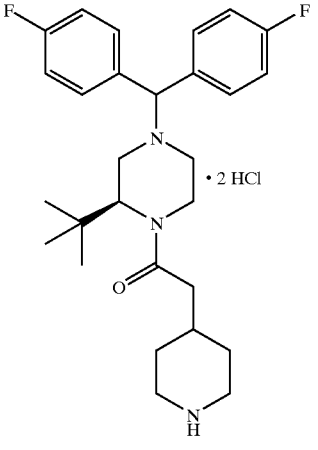 · 2 HCl | 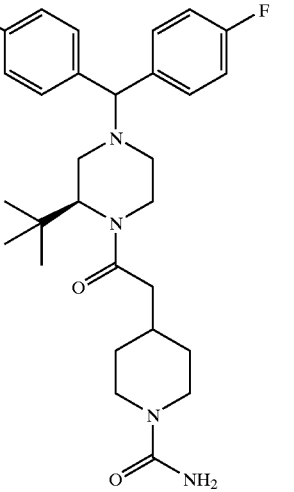 | LCMS:<br>MH$^+$ = 513;<br>mp = 95–101° C. |
| 508 | 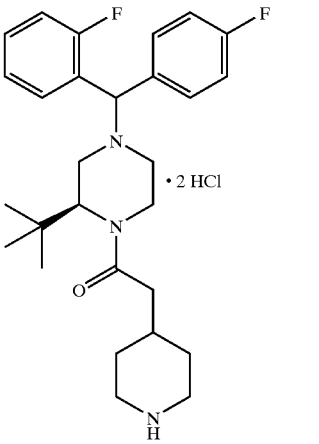 · 2 HCl | 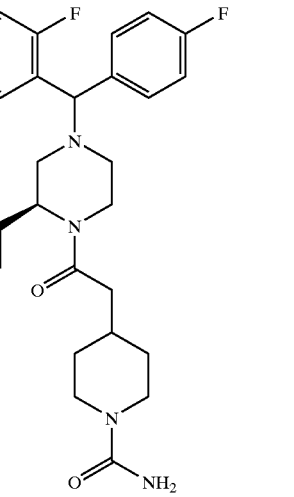 | LCMS:<br>MH$^+$ = 513;<br>mp = 122–127° C. |

TABLE 14-continued
| Ex. | Column 2 | Column 3 | CMPD |
|---|---|---|---|
| 509 | 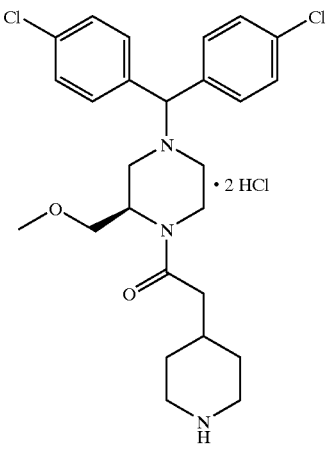 | 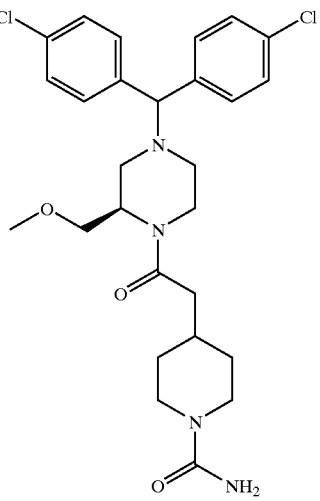 | LCMS: MH+ = 533; mp = 97–101° C. |
| 510 | 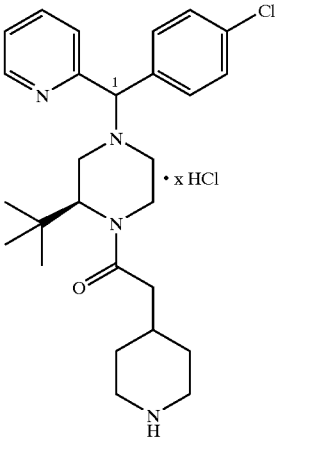 | 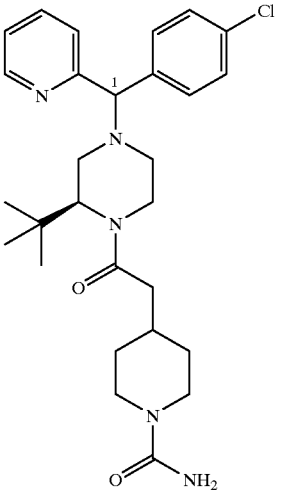 | LCMS: MH+ = 512; mp = 90–117° C. |
| 511 | 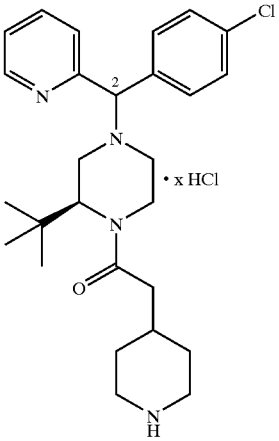 | 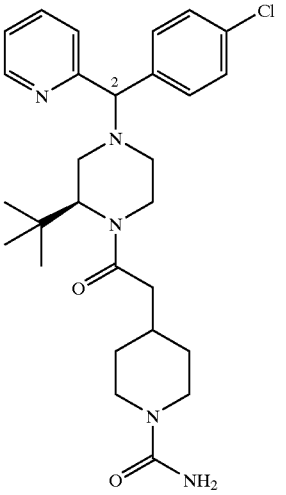 | LCMS: MH+ = 512; mp = 82–93° C. |

TABLE 14-continued
| Ex. | Column 2 | Column 3 | CMPD |
|-----|----------|----------|------|
| 512 | 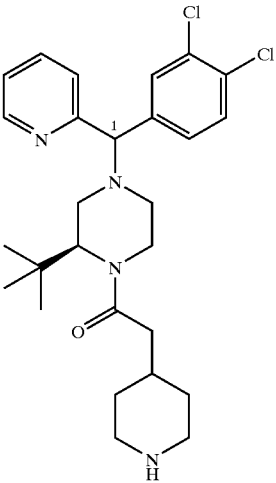 | 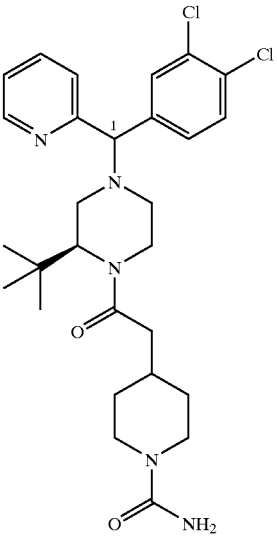 | LCMS:<br>MH⁺ = 546;<br>mp = 113–117° C. |
| 513 | 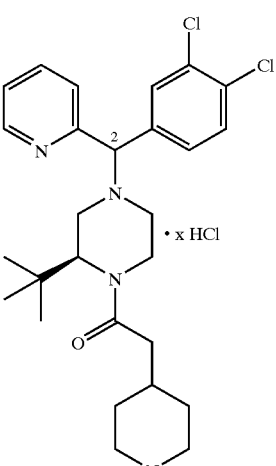 | 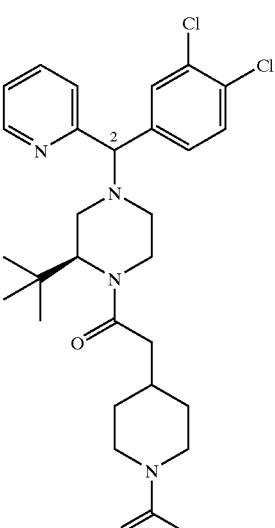 | LCMS:<br>MH⁺ = 546;<br>mp = 107–111° C. |
| 514 | 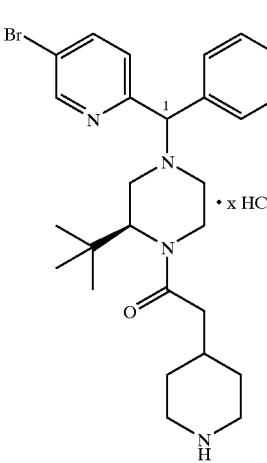 | 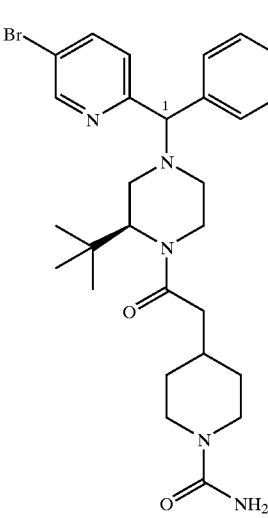 | LCMS:<br>MH⁺ = 590;<br>mp = 92–97° C. |

TABLE 14-continued
| Ex. | Column 2 | Column 3 | CMPD |
|---|---|---|---|
| 515 | 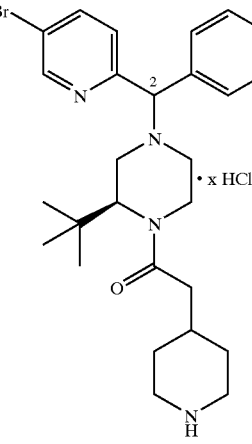 | 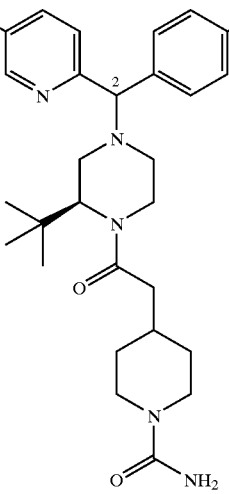 | LCMS:<br>MH+ = 590;<br>mp = 81–87° C. |
| 516 | 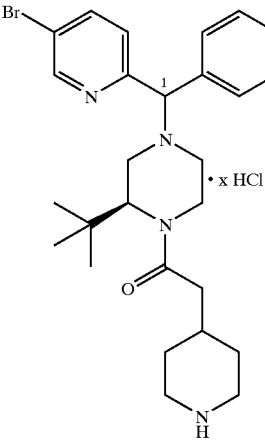 | 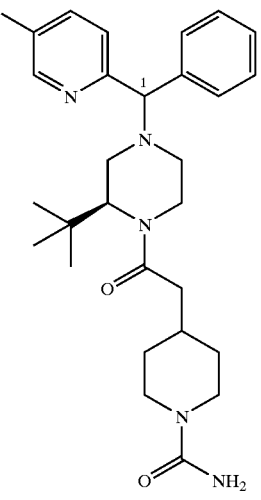 | LCMS:<br>MH+ = 556;<br>mp = 115–120° C. |
| 518 | 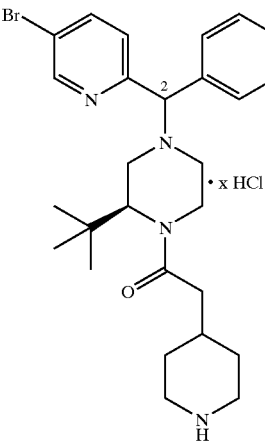 | 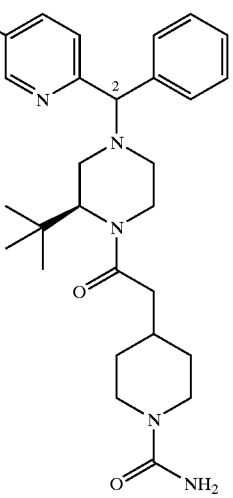 | LCMS:<br>MH+ = 556;<br>mp = 110–115° C. |

TABLE 14-continued
| Ex. | Column 2 | Column 3 | CMPD |
|---|---|---|---|
| 519 | 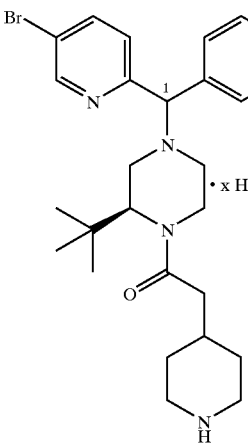 | 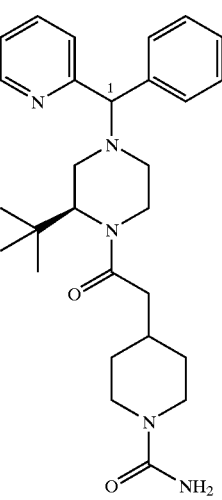 | LCMS:<br>MH+ = 640;<br>mp = 116–121° C. |
| 520 | 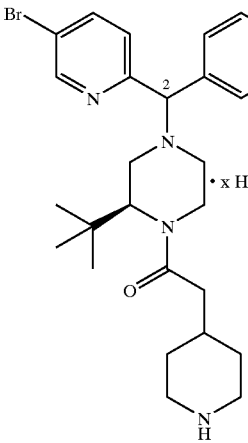 | 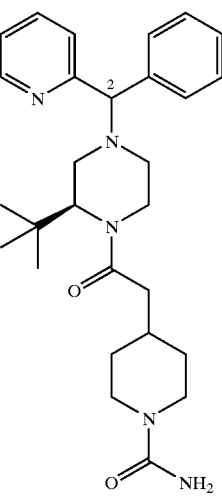 | LCMS:<br>MH+ = 640;<br>mp = 119–125° C. |
| 521 | 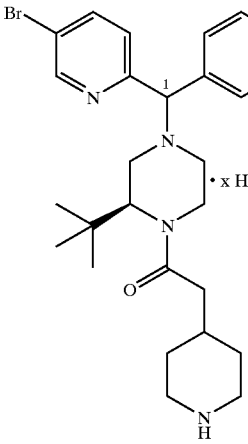 | 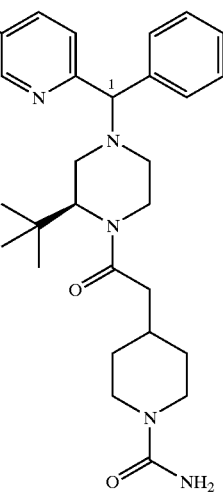 | LCMS:<br>MH+ = 624;<br>mp = 126–132° C. |

TABLE 14-continued
| Ex. | Column 2 | Column 3 | CMPD |
|---|---|---|---|
| 522 | 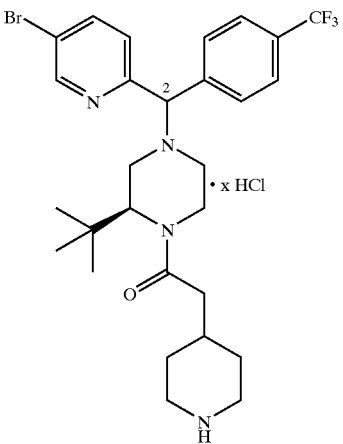 | 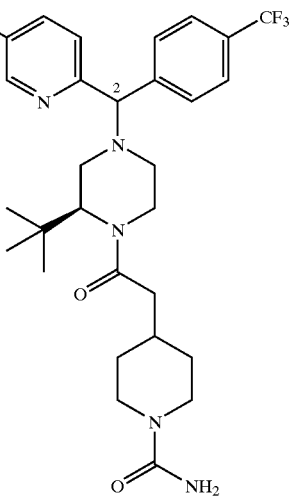 | LCMS:<br>MH+ = 624;<br>mp = 121–130° C. |
| 523 | 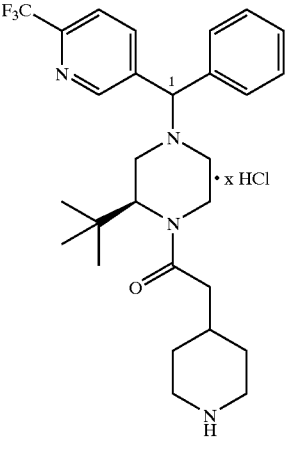 | 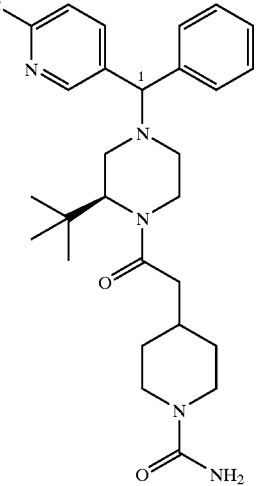 | LCMS:<br>MH+ = 546;<br>mp = 102–106° C. |
| 524 | 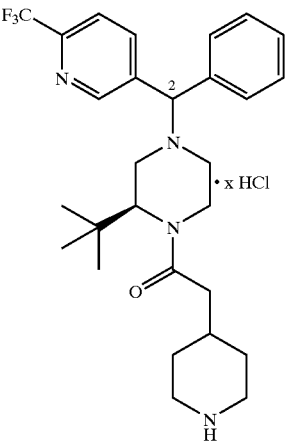 | 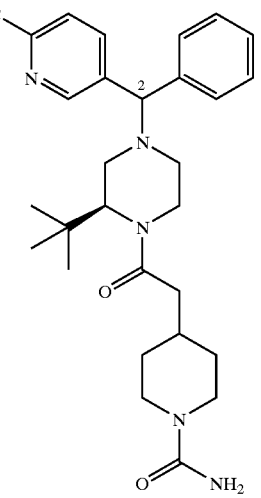 | LCMS:<br>MH+ = 546;<br>mp = 123–127° C. |

US 6,903,102 B2
267                                                                  268
TABLE 14-continued
| Ex. | Column 2 | Column 3 | CMPD |
|---|---|---|---|
| 525 | 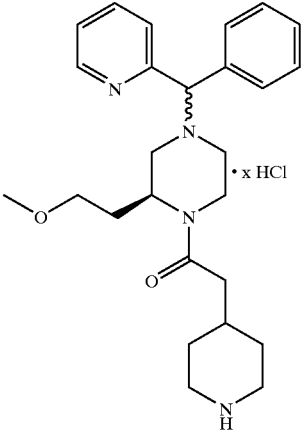 | 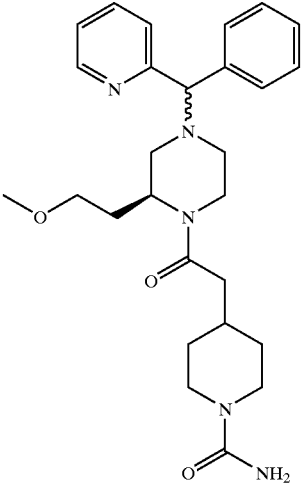 | LCMS:<br>MH+ = 480;<br>mp = 87–119° C. |
| 526 | 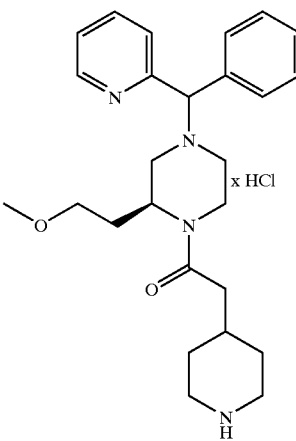 | 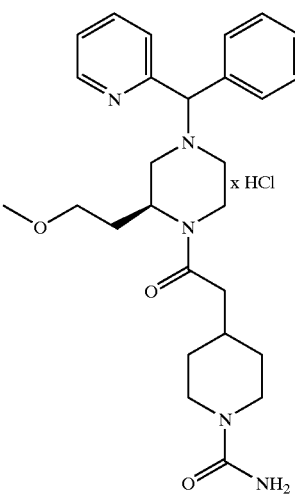 | LCMS:<br>MH+ = 514;<br>mp = 75–79° C. |
| 527 | 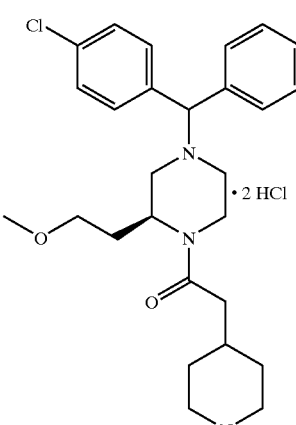 | 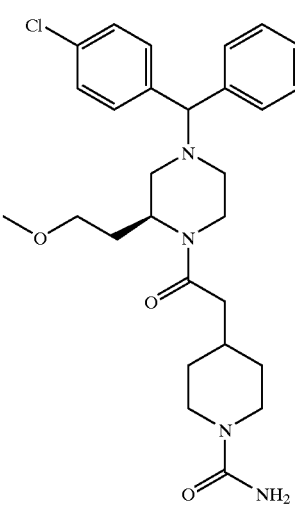 | LCMS:<br>MH+ = 547;<br>mp = 105–109° C. |

TABLE 14-continued
| Ex. | Column 2 | Column 3 | CMPD |
|---|---|---|---|
| 528 | 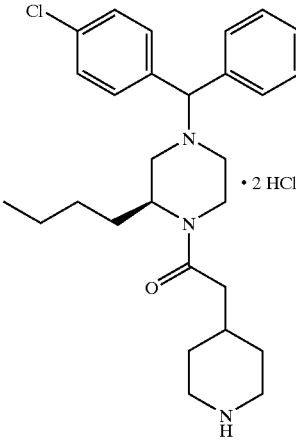 · 2 HCl | 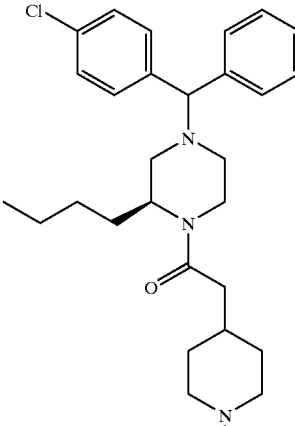 | LCMS:<br>MH⁺ = 545;<br>mp = 103–107° C. |
| 529 | 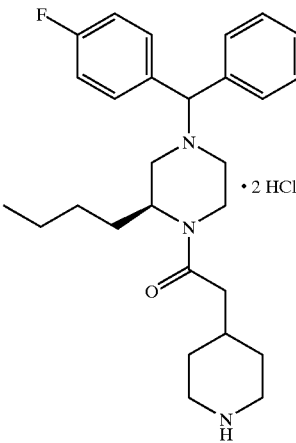 · 2 HCl | 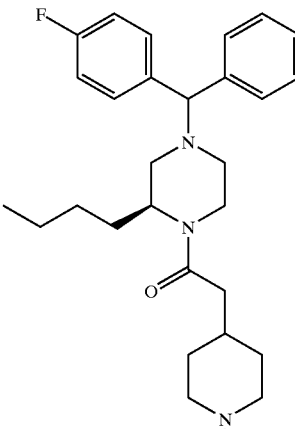 | LCMS:<br>MH⁺ = 513;<br>mp = 91–97° C. |
| 530 | 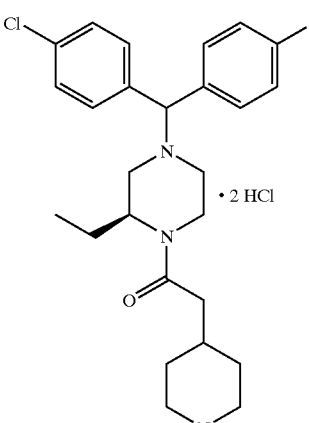 · 2 HCl | 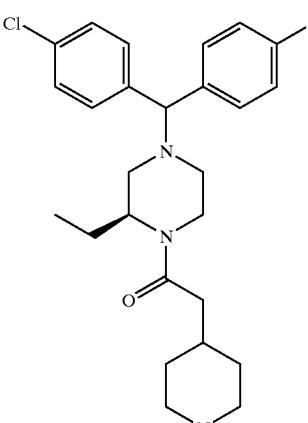 | LCMS:<br>MH⁺ = 517;<br>mp = 93–93° C. |

TABLE 14-continued
| Ex. | Column 2 | Column 3 | CMPD |
|---|---|---|---|
| 531 | 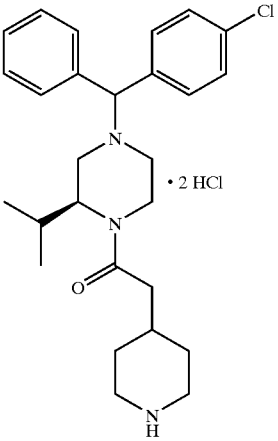 | 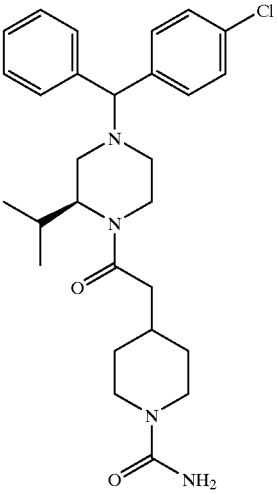 | LCMS:<br>MH+ = 497;<br>mp = 99–102° C. |
| 532 | 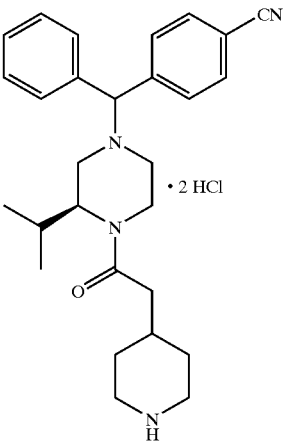 | 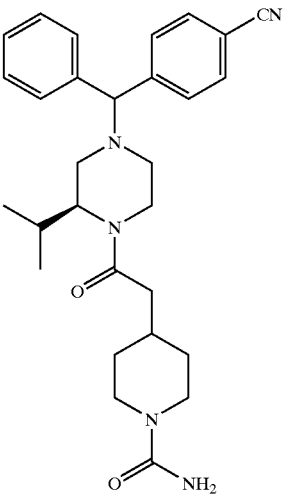 | LCMS:<br>MH+ = 488;<br>mp = 129–133° C. |
| 533 | 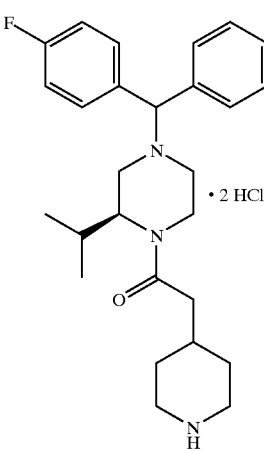 | 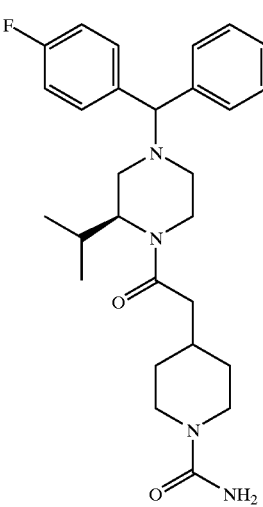 | LCMS:<br>MH+ = 499;<br>mp = 108–111° C. |

TABLE 14-continued
| Ex. | Column 2 | Column 3 | CMPD |
|---|---|---|---|
| 534 | 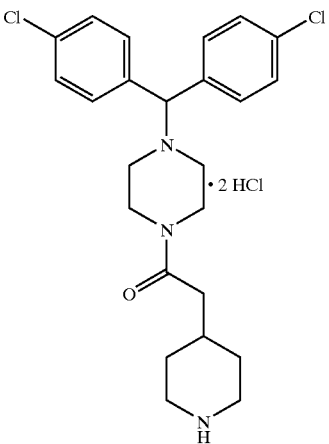 · 2 HCl | 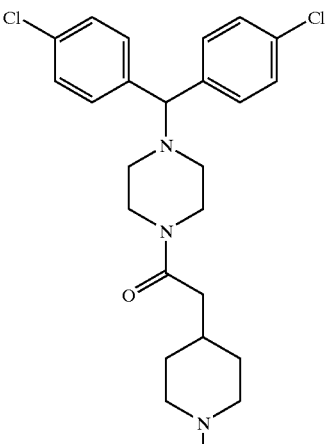 | FABMS:<br>MH⁺ = 489;<br>mp = 126–130° C. |
| 535 | 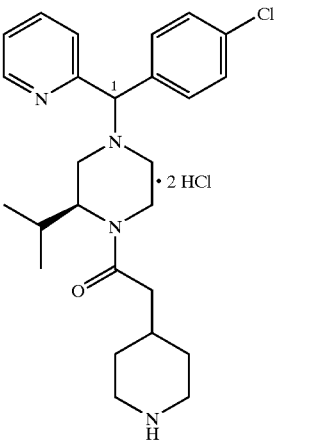 · 2 HCl | 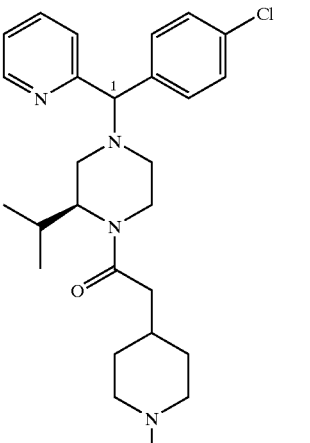 | LCMS:<br>MH⁺ = 497;<br>mp = 75–83° C. |
| 536 | 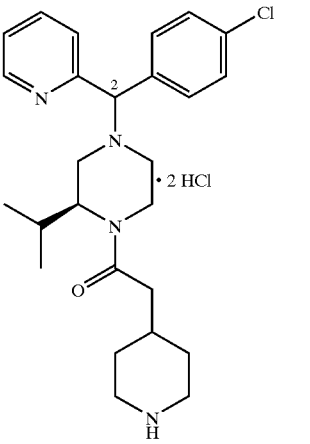 · 2 HCl | 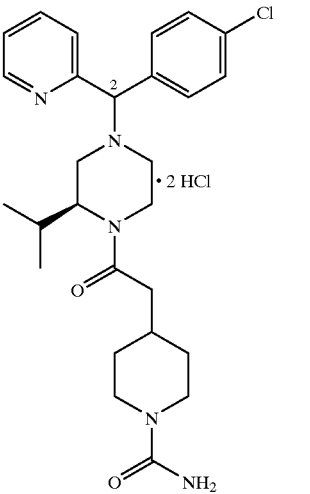 · 2 HCl | LCMS:<br>MH⁺ = 498;<br>mp = 85–89° C. |

TABLE 14-continued
| Ex. | Column 2 | Column 3 | CMPD |
|---|---|---|---|
| 542 | 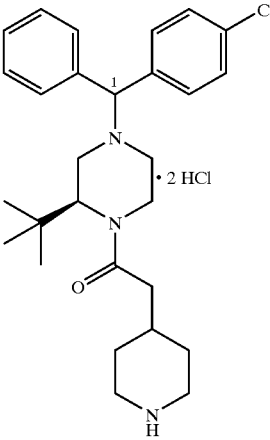 | 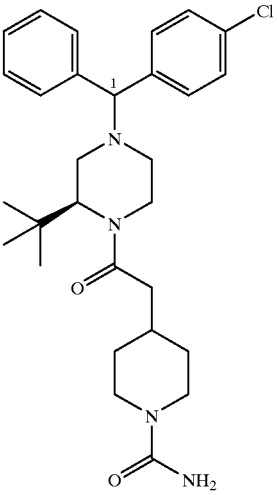 | LCMS:<br>MH⁺ = 511;<br>mp = ° C. |
| 543 | 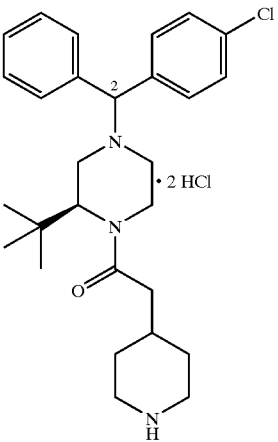 | 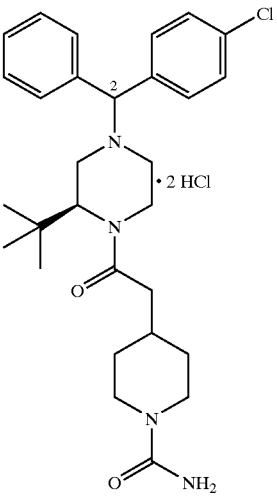 | LCMS:<br>MH⁺ = 511;<br>mp = 79–83° C. |
| 544 | 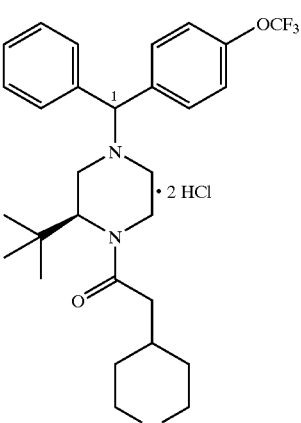 | 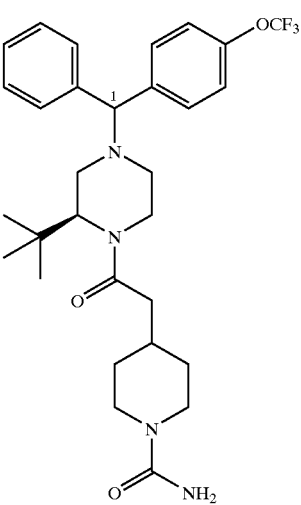 | LCMS:<br>MH⁺ = 561;<br>mp = ° C. |

TABLE 14-continued
| Ex. | Column 2 | Column 3 | CMPD |
|---|---|---|---|
| 545 | 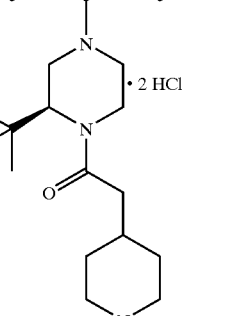 | 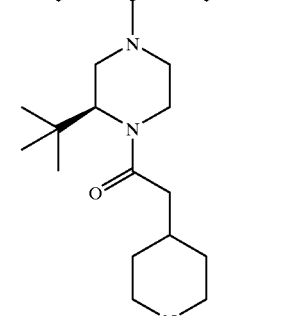 | LCMS:<br>MH+ = 561;<br>mp = 51–65° C. |
| 546 | 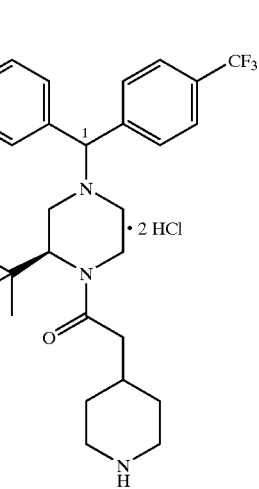 | 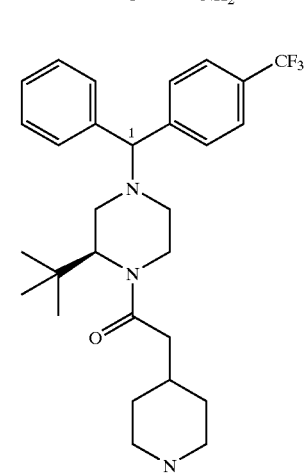 | LCMS:<br>MH+ = 545;<br>mp = 107–109° C. |
| 547 | 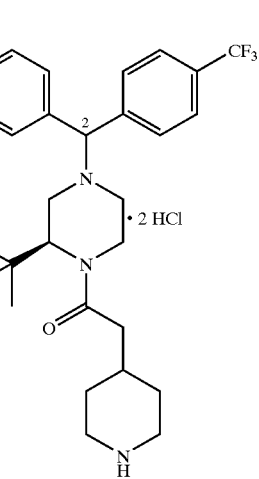 | 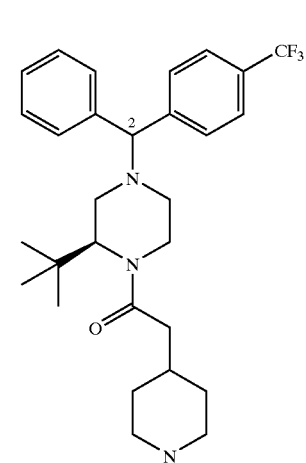 | LCMS:<br>MH+ = 545;<br>mp = 84–88° C. |

TABLE 14-continued
| Ex. | Column 2 | Column 3 | CMPD |
|---|---|---|---|
| 548 | 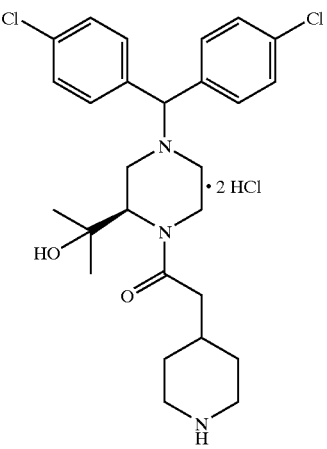 | 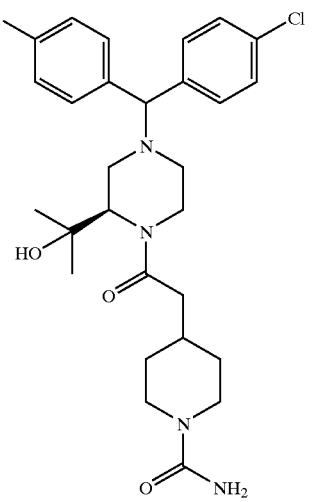 | LCMS:<br>MH+ = 547;<br>mp = 110–114° C. |
| 549 | 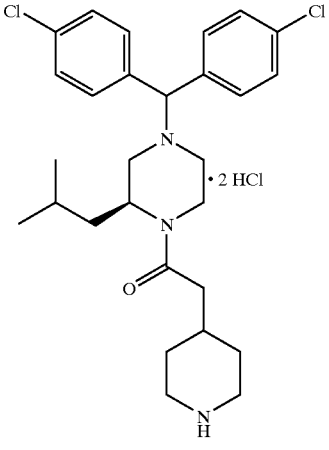 | 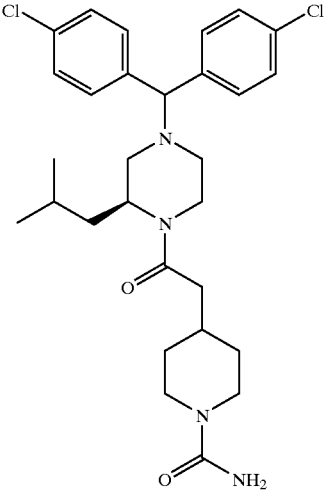 | LCMS:<br>MH+ = 545;<br>mp = 91–93° C. |
| 550 | 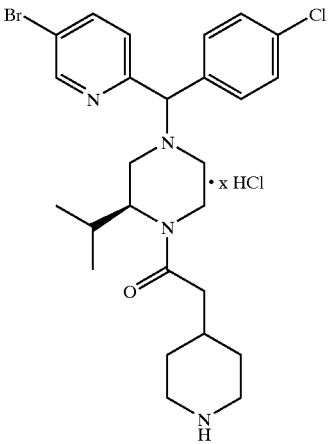 | 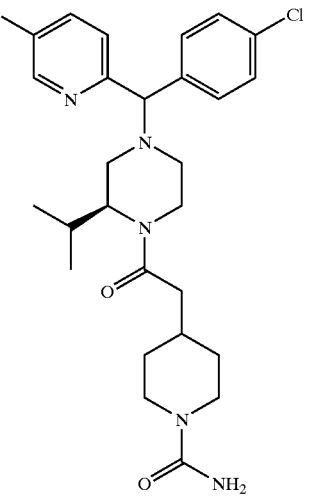 | LCMS:<br>MH+ = 576;<br>mp = 89–109° C. |

TABLE 14-continued
| Ex. | Column 2 | Column 3 | CMPD |
|---|---|---|---|
| 551 | 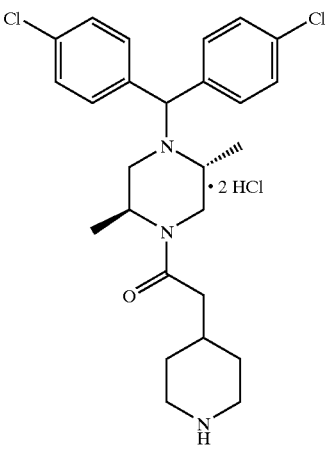 | 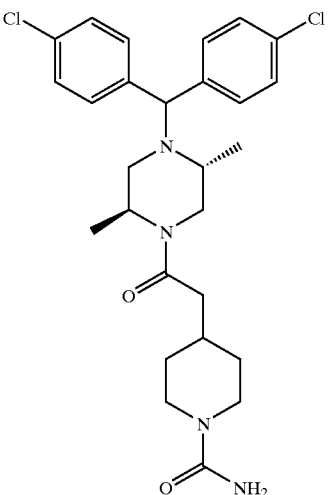 | LCMS:<br>MH⁺ = 517;<br>mp = 105–124° C. |
| 552 | 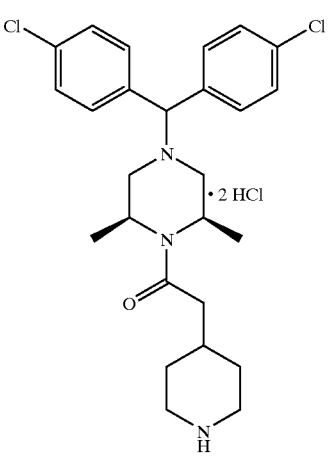 | 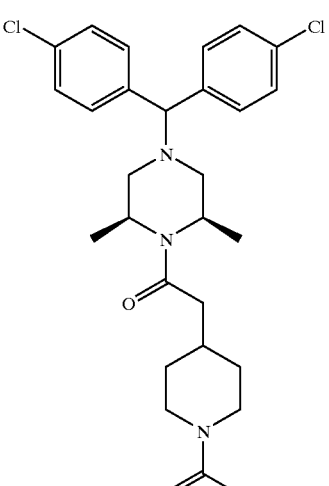 | LCMS:<br>MH⁺ = 517;<br>mp = 100–112° C. |
| 553 | 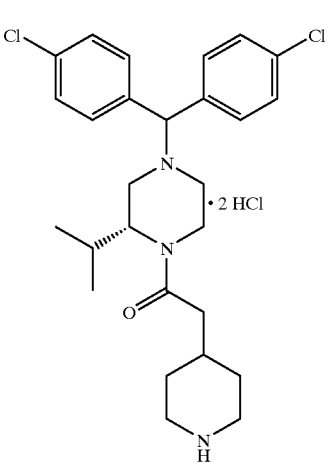 | 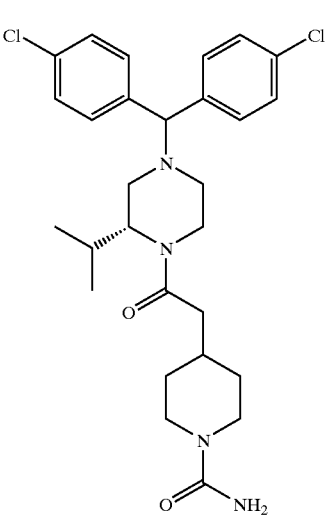 | LCMS:<br>MH⁺ = 531;<br>mp = 99–108° C. |

TABLE 14-continued
| Ex. | Column 2 | Column 3 | CMPD |
|---|---|---|---|
| 554 | 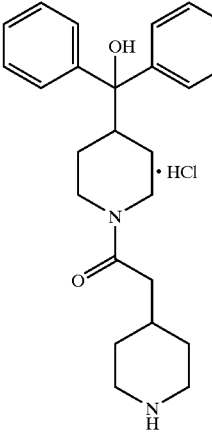 | 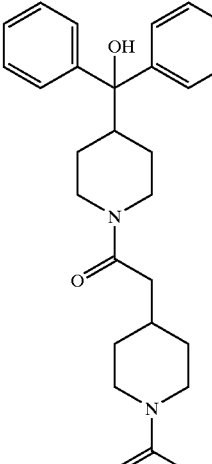 | LCMS:<br>MH+ = 436;<br>mp = 106–112° C. |
| 555 | 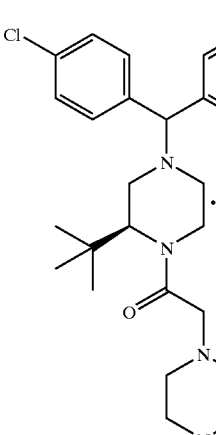 | 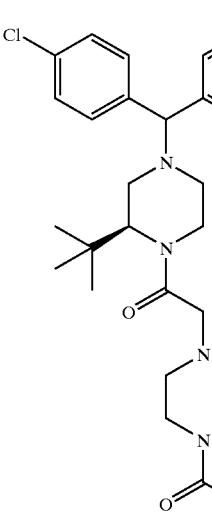 | LCMS:<br>MH+ = 546;<br>mp = 119–127° C. |
| 556 | 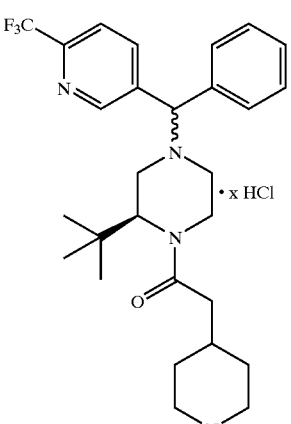 | 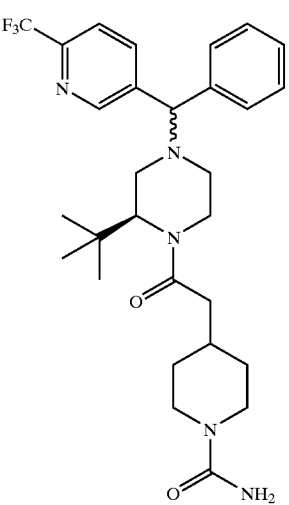 | LCMS:<br>MH+ = 546;<br>mp = 98–101° C. |

TABLE 14-continued
| Ex. | Column 2 | Column 3 | CMPD |
|---|---|---|---|
| 557 | 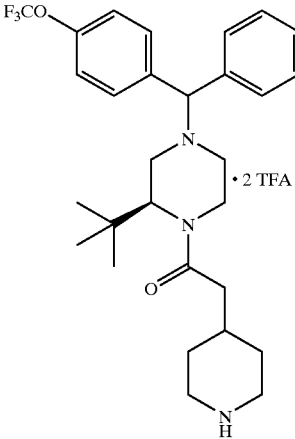 | 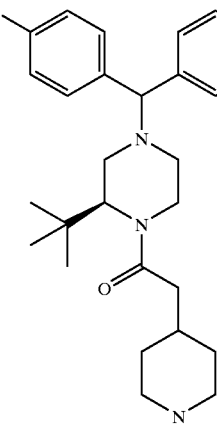 | LCMS: MH⁺ = 645; mp = 85–91° C. |
| 558 | 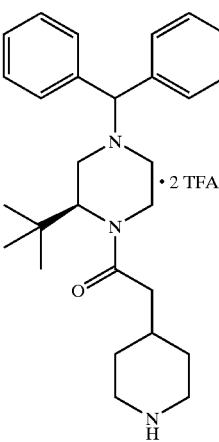 | 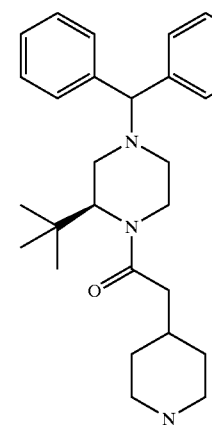 | — |
| 558.10 | 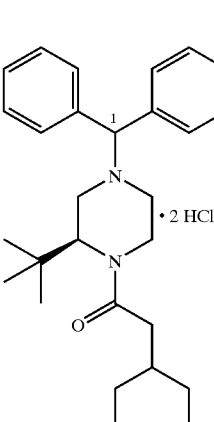 | 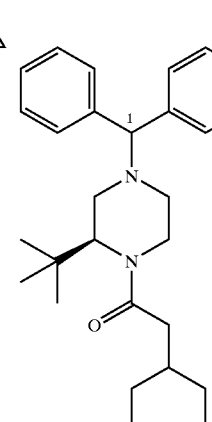 | LCMS: MH⁺ = 547; mp = 100–104° C. |

TABLE 14-continued
| Ex. | Column 2 | Column 3 | CMPD |
|---|---|---|---|
| 558.11 | 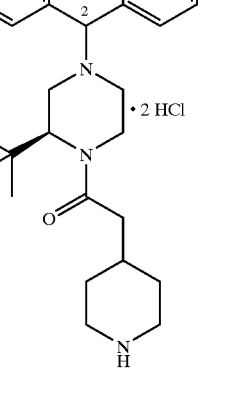 · 2 HCl | 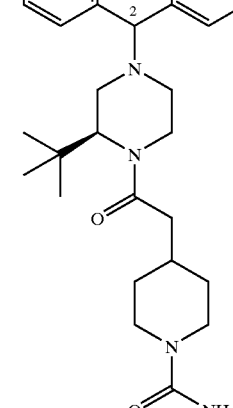 | LCMS: MH+ = 547; mp = 65–68° C. |
| 558.12 | 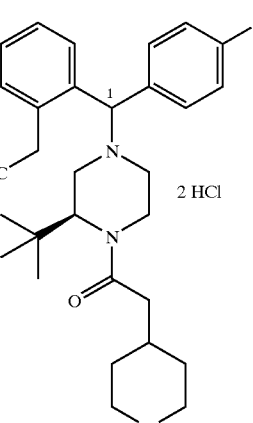 2 HCl | 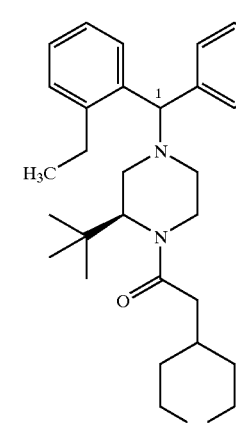 | LCMS: MH+ = 589; mp = 92–103° C. |
| 558.13 | 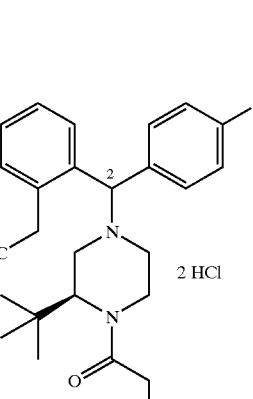 2 HCl | 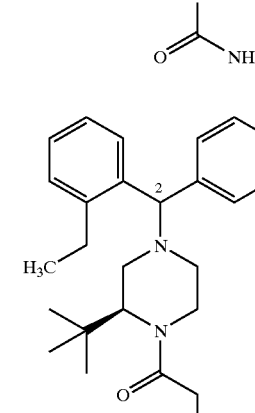 | LCMS: MH+ = 589; mp = 95–190° C. |

TABLE 14-continued
| Ex. | Column 2 | Column 3 | CMPD |
|---|---|---|---|
| 558.14 | 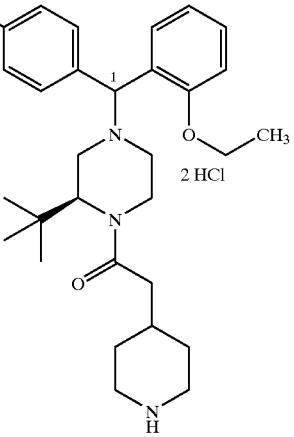 | 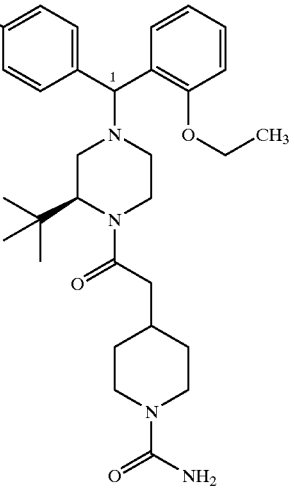 | LCMS: MH+ = 605; mp = 59–83° C. |
| 558.15 | 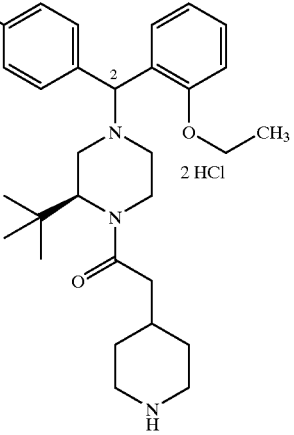 | 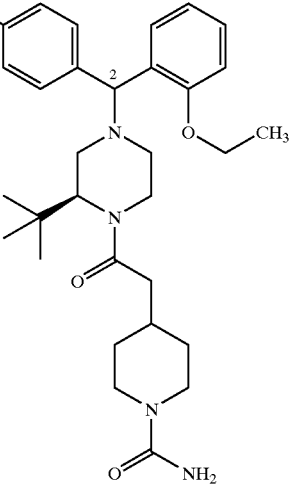 | LCMS: MH+ = 605; mp = 87–99° C. |
| 558.16 | 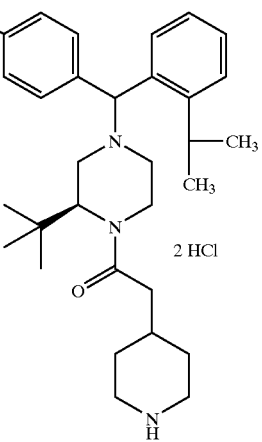 | 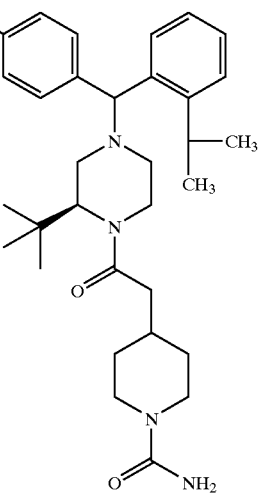 | LCMS: MH+ = 547; mp = 65–68° C. |

TABLE 14-continued
| Ex. | Column 2 | Column 3 | CMPD |
|---|---|---|---|
| 558.17 | 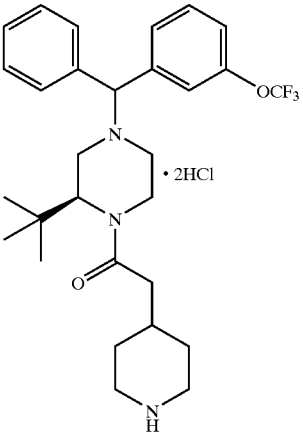 | 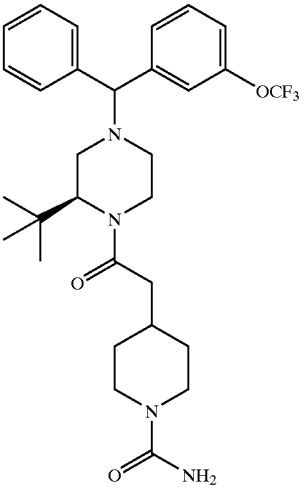 | LCMS:<br>MH+ = 561;<br>mp = 95–101° C. |
| 558.18 | 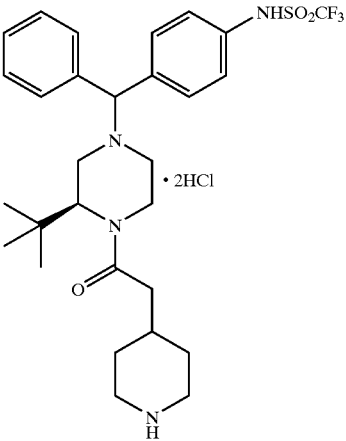 | 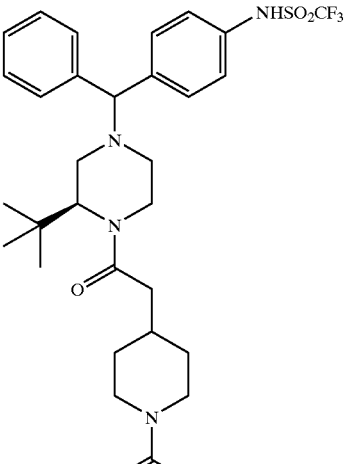 | LCMS:<br>MH+ = 624;<br>mp = 97–101° C. |
| 558.19 | 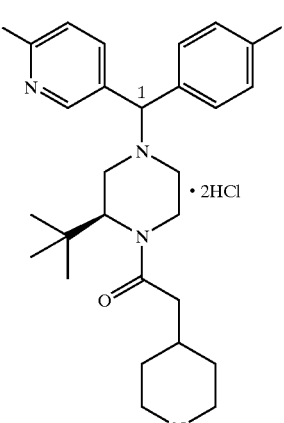 | 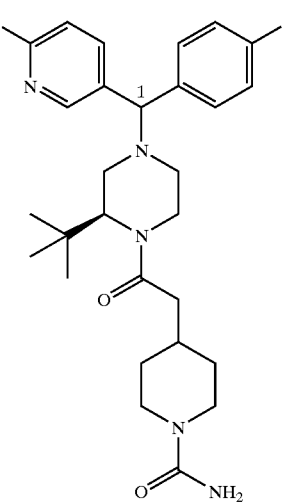 | LCMS:<br>MH+ = 580;<br>mp = 123–127° C. |

TABLE 14-continued
| Ex. | Column 2 | Column 3 | CMPD |
|---|---|---|---|
| 558.20 | 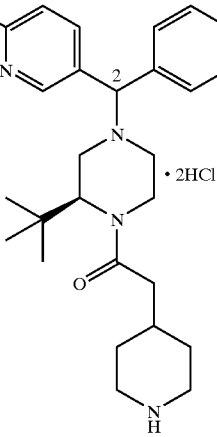 | 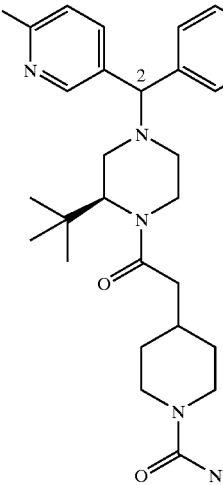 | LCMS:<br>MH+ = 580;<br>mp = 121–124° C. |
| 558.21 | 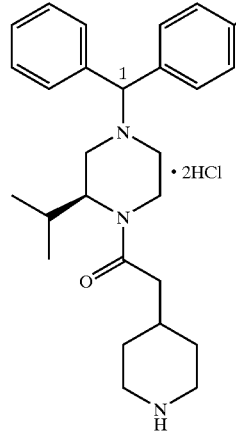 | 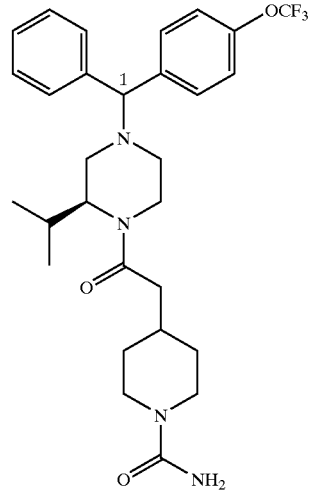 | LCMS:<br>MH+ = 547;<br>mp = 100–103° C. |
| 558.22 | 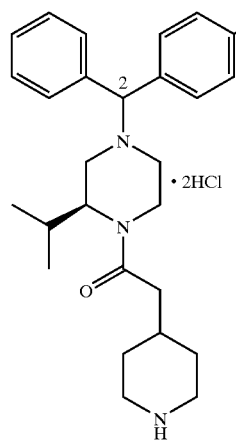 | 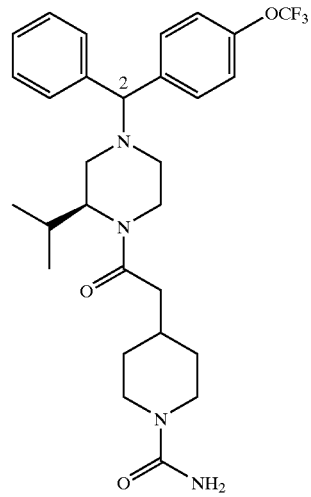 | LCMS:<br>MH+ = 547;<br>mp = 109–114° C. |

EXAMPLES 558.23 AND 558.24
By essentially the same procedure set forth in Example 500, using the compounds shown in Column 2 of Table 14.1, the products shown in Column 3 of Table 14.1 (CMPD) were prepared.
TABLE 14.1
| Ex. | Column 2 | Column 3 | CMPD |
|---|---|---|---|
| 558.23 | | | LCMS: $MH^+$ = 574; mp = 78–103° C. |
| 558.24 | | | LCMS: $MH^+$ = 574; mp = 58–73° C. |
EXAMPLE 559
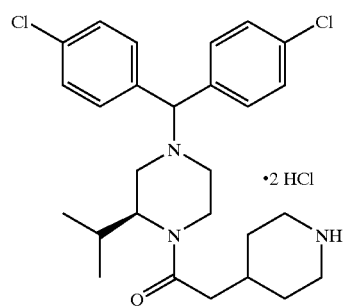
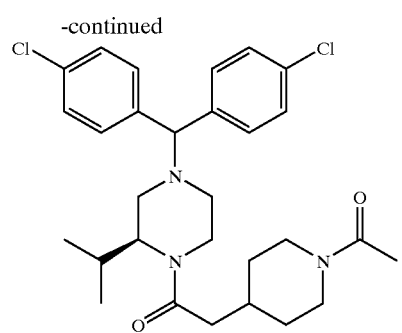
To a solution of the product from Preparative Example 183 (0.15 g, 0.31 mmol) in $CH_2Cl_2$ (5 mL) at 0° C. was added TEA (0.21 mL, 5 eq.) and AcCl (0.03 mL, 1.2 eq.). The reaction mixture was warmed to room temperature and stirred until TLC showed consumption of starting material (20 minutes). The reaction was quenched by the addition of saturated NaHCO$_3$ and extracted with CH$_2$Cl$_2$. The combined organics were dried over Na$_2$SO$_4$, filtered and concentrated. The crude product was purified by flash chromatography using a 5% (10% NH$_4$OH in MeOH) in CH$_2$Cl$_2$ solution as eluent to yield a solid (0.12 g, 75% yield). LCMS: MH$^+$=530; mp=75–1011° C.

EXAMPLES 560–609.68

By essentially the same procedure set forth in Example 558, using the compounds shown in column 2 of Table 15, which were prepared in a similar manner to Preparative Example 183 or Example 611 from the corresponding N-BOC-protected amine, the products shown in column 3 of Table 15 (CMPD) were prepared:

TABLE 15

| Ex. | Column 2 | Column 3 | CMPD |
|---|---|---|---|
| 560 | 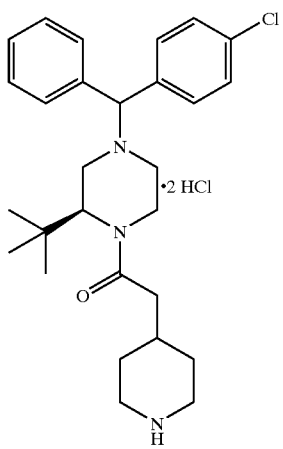 | 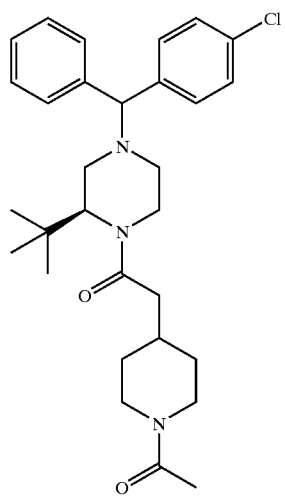 | LCMS:<br>MH$^+$ = 510;<br>mp = 81–85° C. |
| 561 | 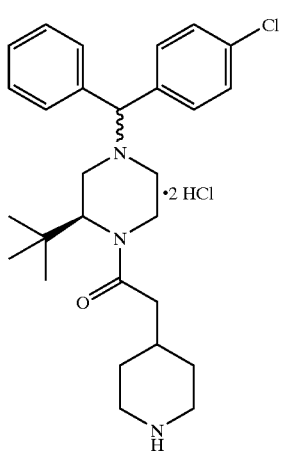 | 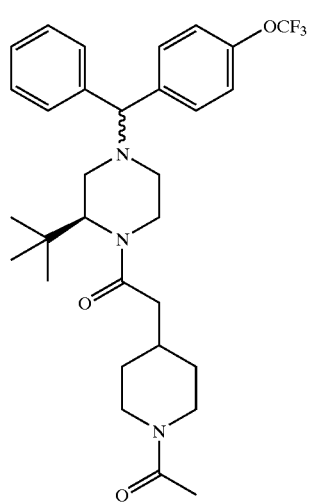 | LCMS:<br>MH$^+$ = 560;<br>mp = 68–71° C. |

TABLE 15-continued
| Ex. | Column 2 | Column 3 | CMPD |
|---|---|---|---|
| 562 | 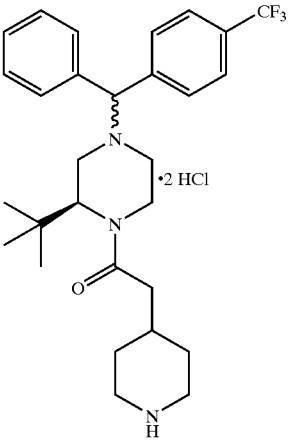 | 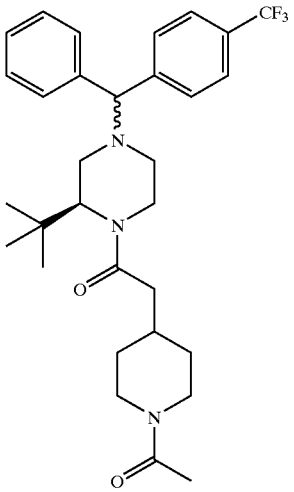 | LCMS: MH$^+$ = 544; mp = 86–88° C. |
| 563 | 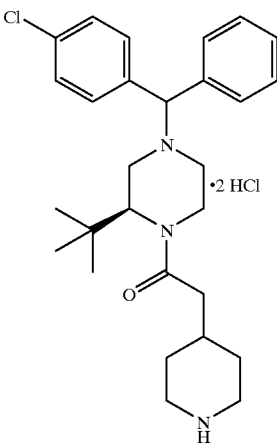 | 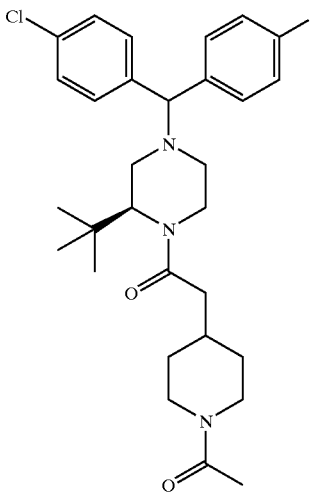 | LCMS: MH$^+$ = 544; mp = 125–145° C. |
| 564 | 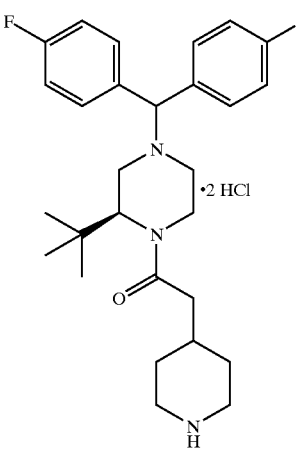 | 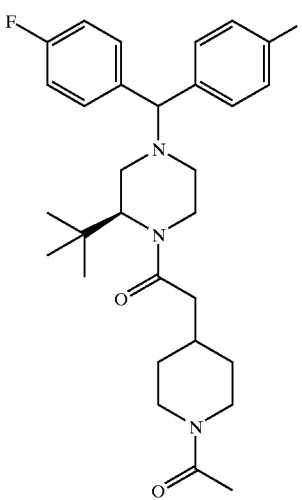 | LCMS: MH$^+$ = 512; mp = 69–75° C. |

US 6,903,102 B2
301 302
TABLE 15-continued
| Ex. | Column 2 | Column 3 | CMPD |
|---|---|---|---|
| 565 | 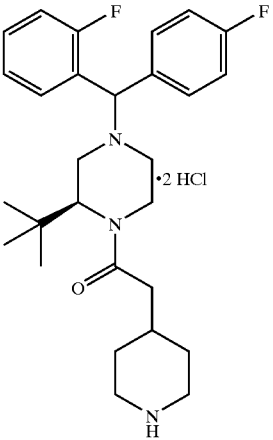 | 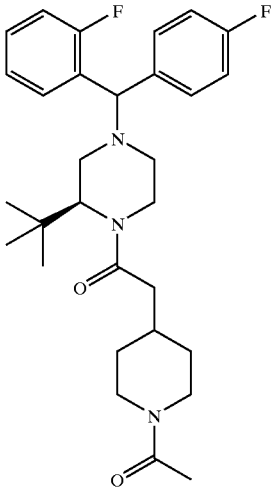 | LCMS: MH+ = 512; mp = 79–92° C. |
| 566 | 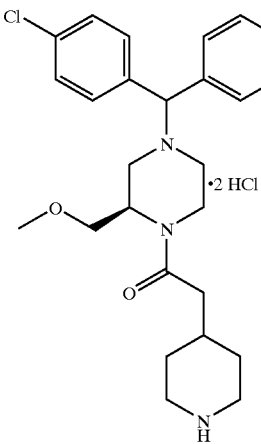 | 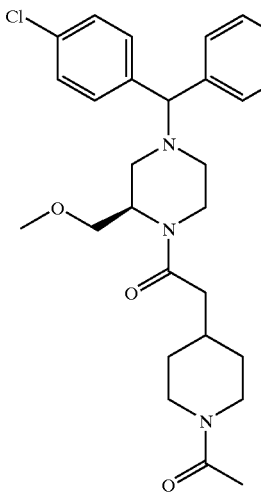 | LCMS: MH+ = 532; mp = 70–73° C. |
| 567 | 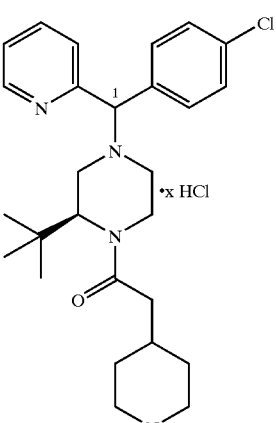 | 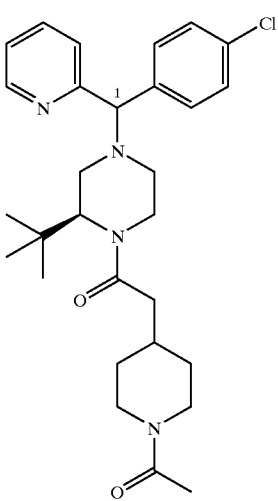 | LCMS: MH+ = 511; mp = 68–79° C. |

TABLE 15-continued
| Ex. | Column 2 | Column 3 | CMPD |
|---|---|---|---|
| 568 | 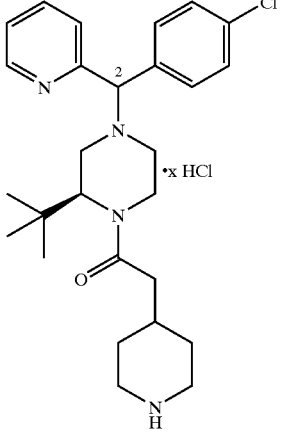 | 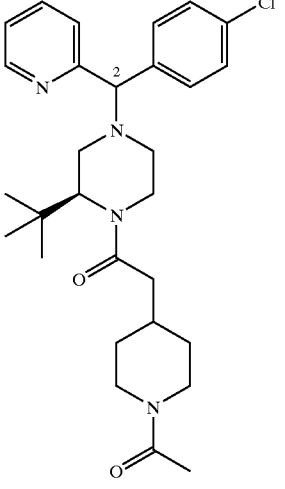 | LCMS:<br>MH⁺ = 511;<br>mp = 74–87° C. |
| 569 | 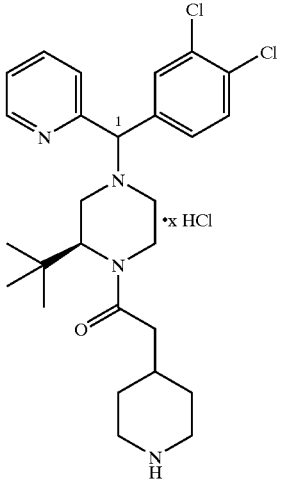 | 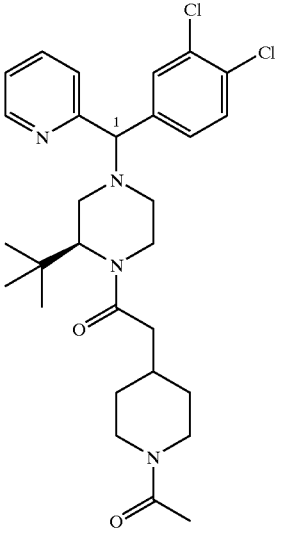 | LCMS:<br>MH⁺ = 545;<br>mp = 93–98° C. |
| 570 | 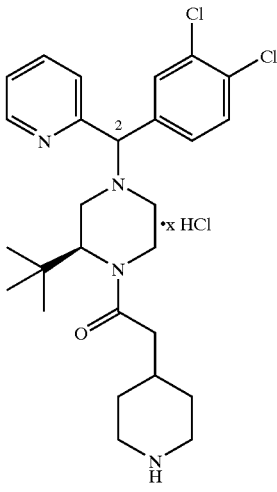 | 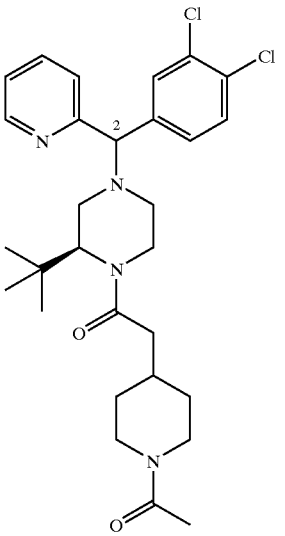 | LCMS:<br>MH⁺ = 545;<br>mp = 95–98° C. |

TABLE 15-continued
| Ex. | Column 2 | Column 3 | CMPD |
|---|---|---|---|
| 571 | 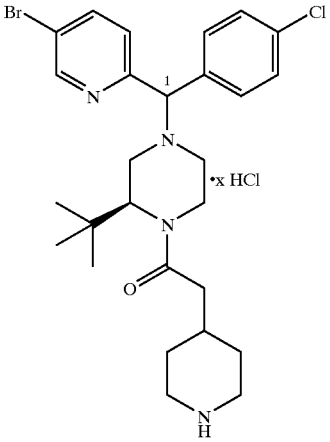 | 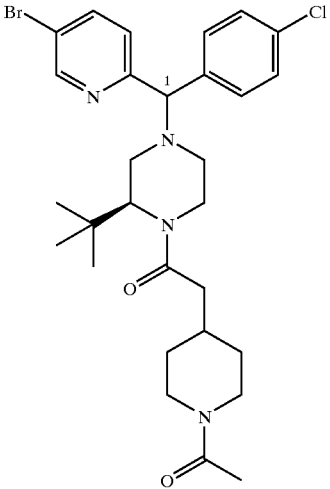 | LCMS: MH⁺ = 589; mp = 81–86° C. |
| 572 | 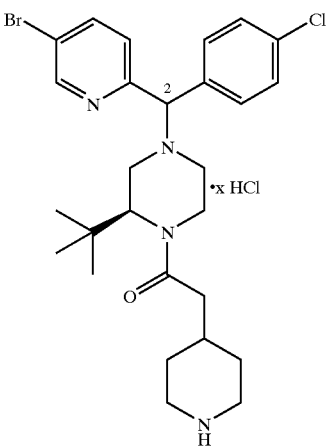 | 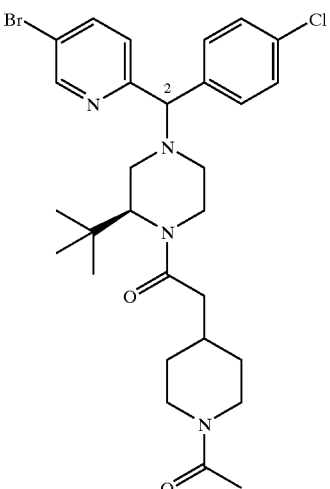 | LCMS: MH⁺ = 589; mp = 69–76° C. |
| 573 | 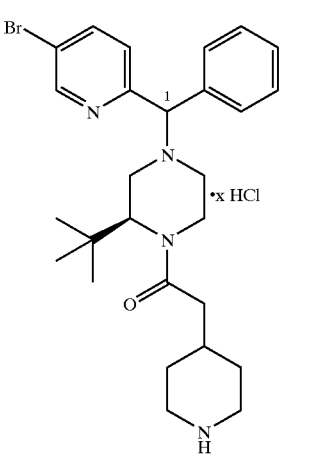 | 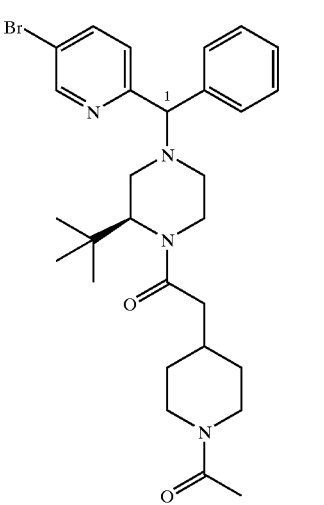 | LCMS: MH⁺ = 555; mp = 68–97° C. |

TABLE 15-continued

| Ex. | Column 2 | Column 3 | CMPD |
|---|---|---|---|
| 574 | | | LCMS: MH+ = 555; mp = 63–81° C. |
| 575 | | | LCMS: MH+ = 639; mp = 80–85° C. |
| 576 | | | LCMS: MH+ = 639; mp = 119–125° C. |

TABLE 15-continued
| Ex. | Column 2 | Column 3 | CMPD |
|---|---|---|---|
| 577 | 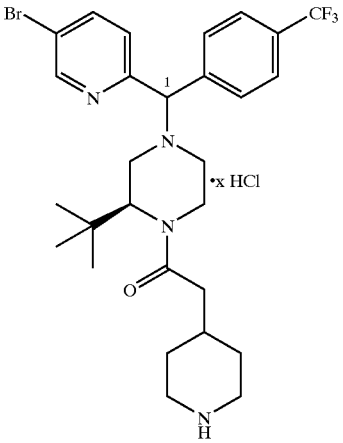 | 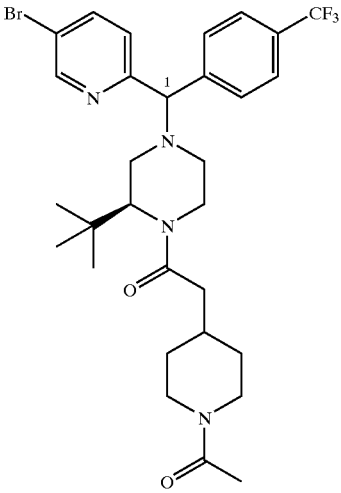 | LCMS: MH+ = 623; mp = 126–132° C. |
| 578 | 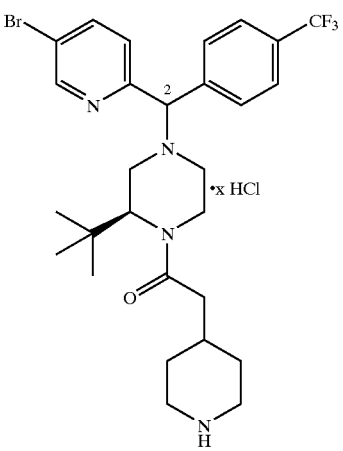 | 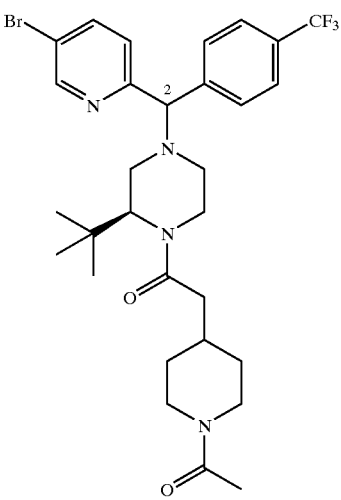 | LCMS: MH+ = 623; mp = 102–105° C. |
| 579 | 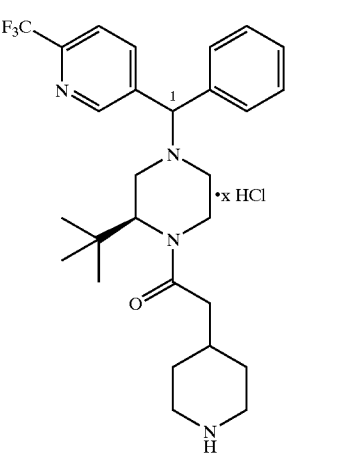 | 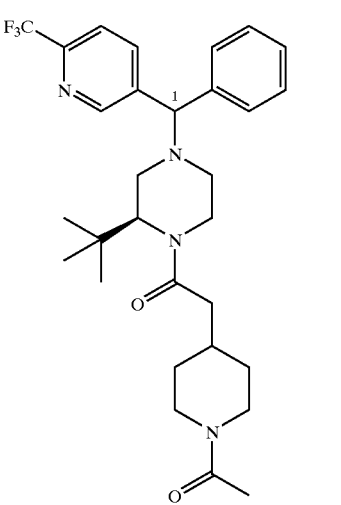 | LCMS: MH+ = 545; mp = 86–89° C. |

TABLE 15-continued
| Ex. | Column 2 | Column 3 | CMPD |
|---|---|---|---|
| 580 | 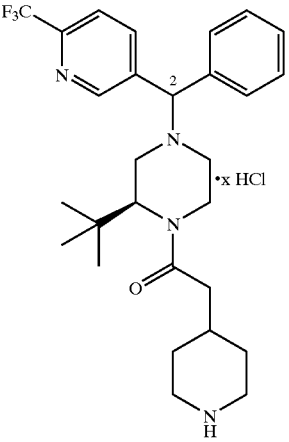 | 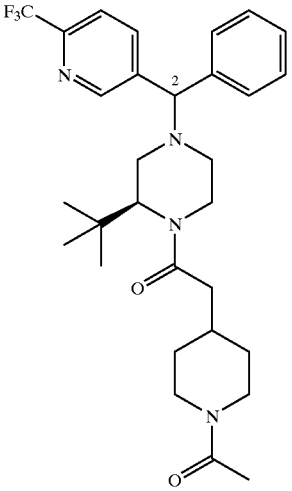 | LCMS: MH⁺ = 545; mp = 71–75° C. |
| 581 | 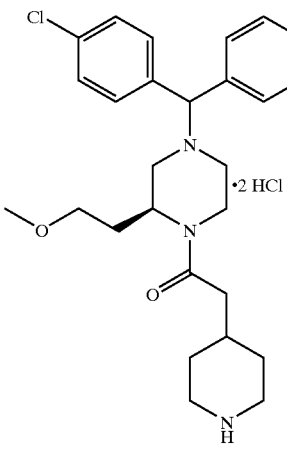 | 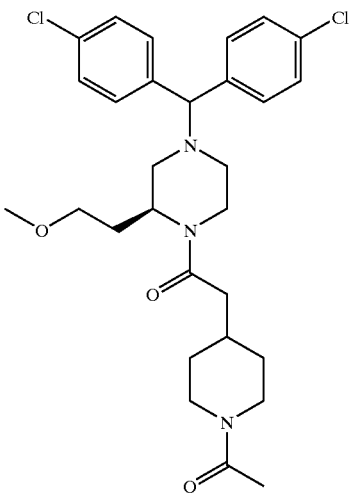 | FABMS: MH⁺ = 546; mp = 81–84° C. |
| 582 | 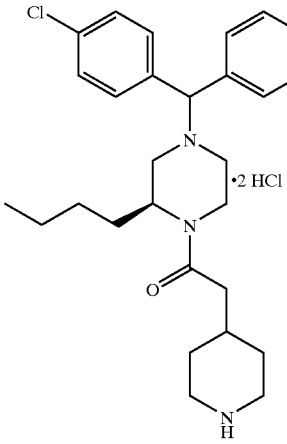 | 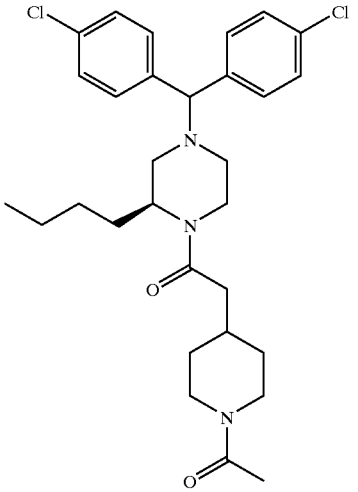 | FABMS: MH⁺ = 544; mp = 75–79° C. |

TABLE 15-continued
| Ex. | Column 2 | Column 3 | CMPD |
|---|---|---|---|
| 583 | 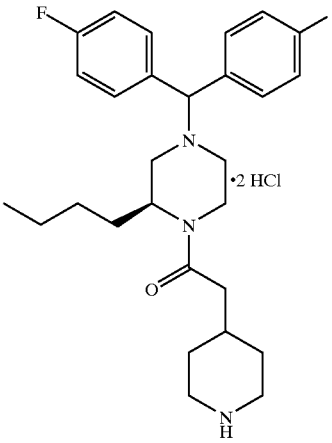 | 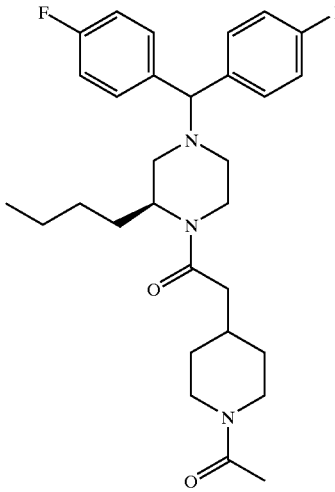 | FABMS:<br>MH+ = 512;<br>mp = 59–62° C. |
| 584 | 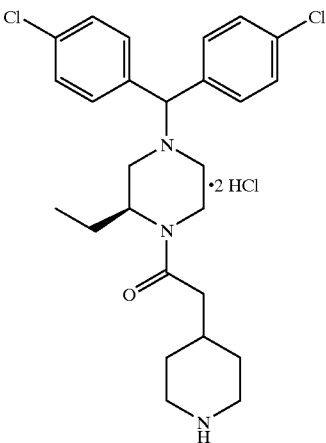 | 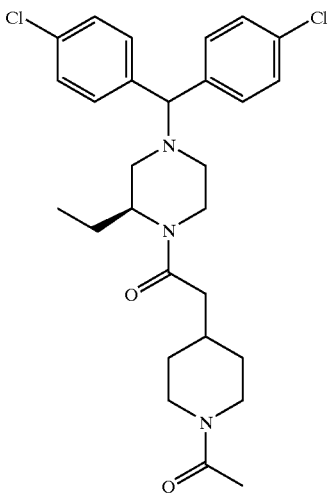 | LCMS:<br>MH+ = 516;<br>mp = 60–66° C. |
| 585 | 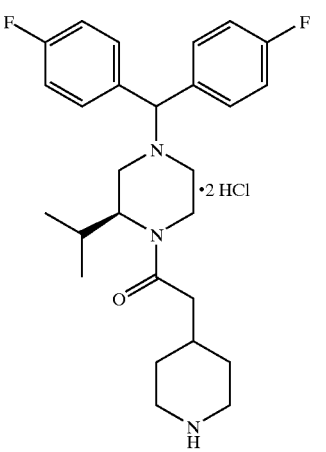 | 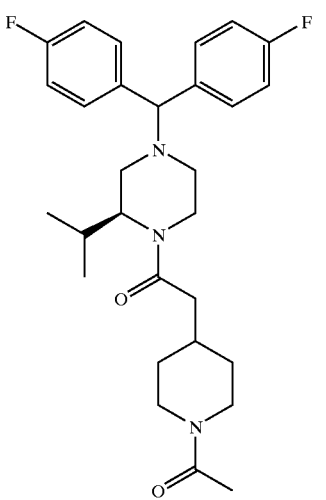 | LCMS:<br>MH+ = 498;<br>mp = 68–71° C. |

TABLE 15-continued
| Ex. | Column 2 | Column 3 | CMPD |
|---|---|---|---|
| 586 | 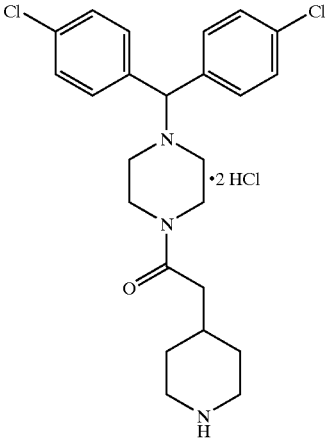 | 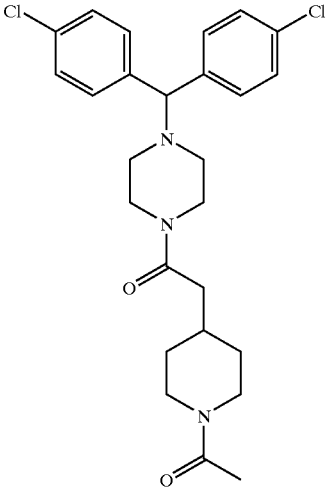 | FABMS: MH+ = 488; mp = 76–81° C. |
| 587 | 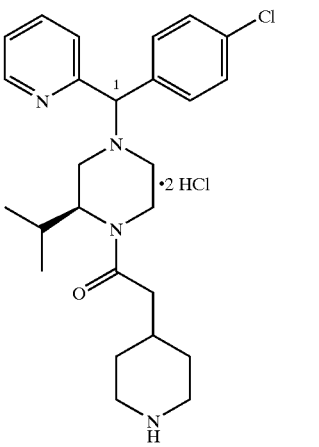 | 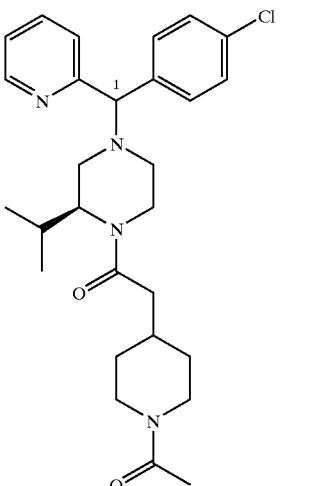 | LCMS: MH+ = 497; mp = 75–83° C. |
| 588 | 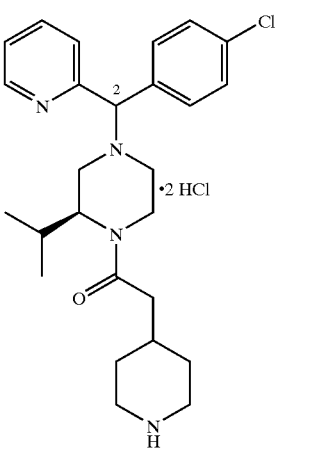 | 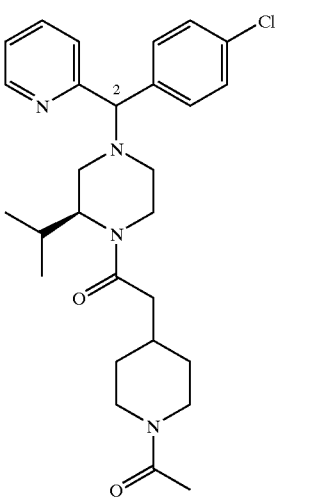 | LCMS: MH+ = 497; mp = 74–79° C. |

US 6,903,102 B2
317 318
TABLE 15-continued
| Ex. | Column 2 | Column 3 | CMPD |
|-----|----------|----------|------|
| 594 | 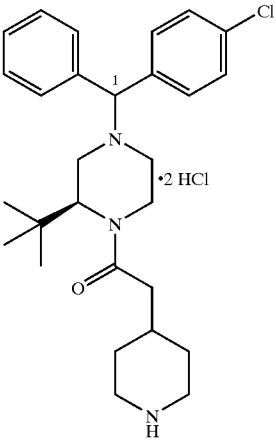 | 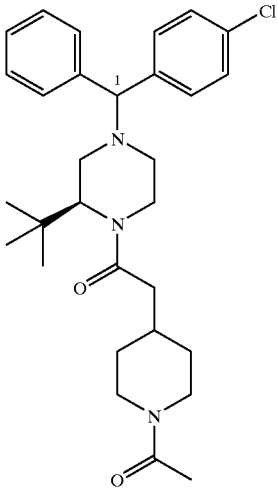 | LCMS: MH$^+$ = 510; mp = 69–72° C. |
| 595 | 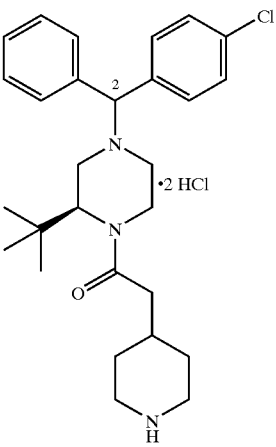 | 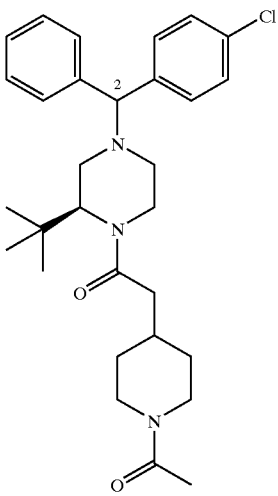 | LCMS: MH$^+$ = 510; mp = 56–62° C. |
| 596 | 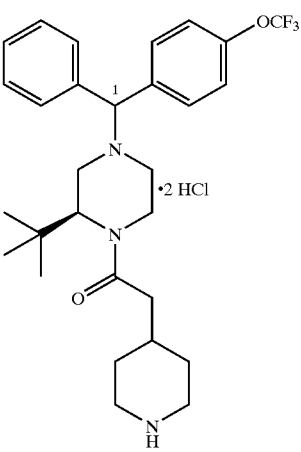 | 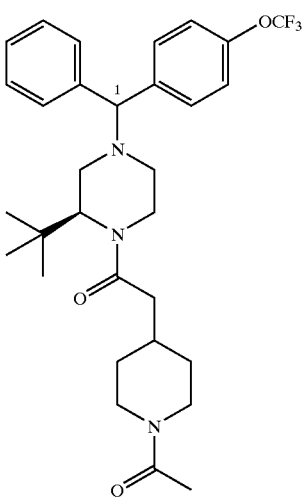 | LCMS: MH$^+$ = 560; mp = 62–75° C. |

TABLE 15-continued
| Ex. | Column 2 | Column 3 | CMPD |
|---|---|---|---|
| 597 | 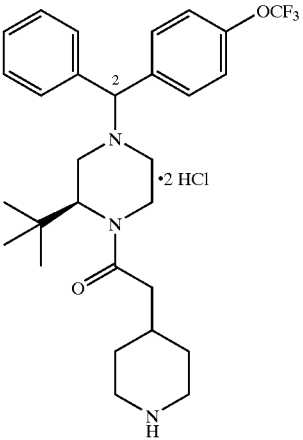 | 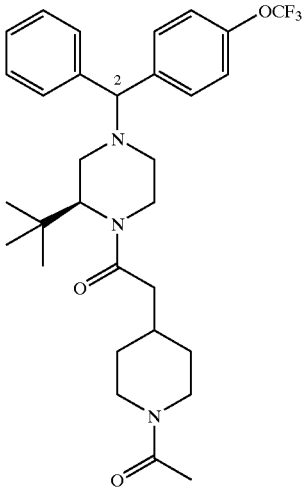 | LCMS: MH+ = 560; mp = 59–71° C. |
| 598 | 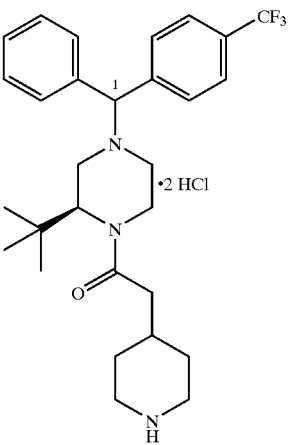 | 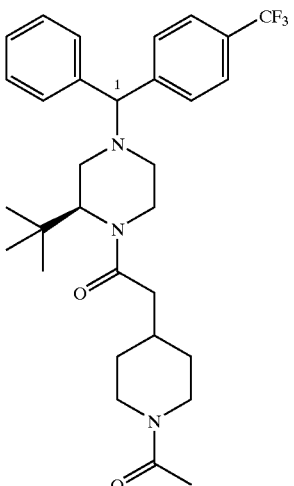 | LCMS: MH+ = 544; mp = 83–88° C. |
| 599 | 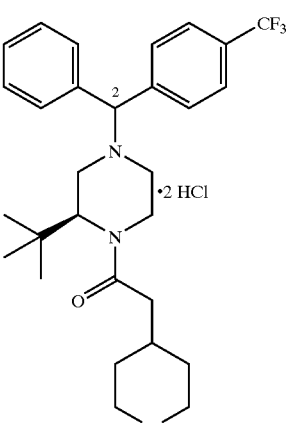 | 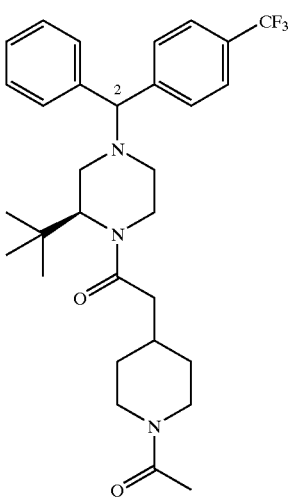 | LCMS: MH+ = 544; mp = 77–80° C. |

TABLE 15-continued

| Ex. | Column 2 | Column 3 | CMPD |
|---|---|---|---|
| 600 | | | LCMS: MH⁺ = 546; mp = 89–95° C. |
| 601 | | | LCMS: MH⁺ = 544; mp = 69–70° C. |
| 602 | | | LCMS: MH⁺ = 575; mp = 73–91° C. |

TABLE 15-continued
| Ex. | Column 2 | Column 3 | CMPD |
|---|---|---|---|
| 603 | 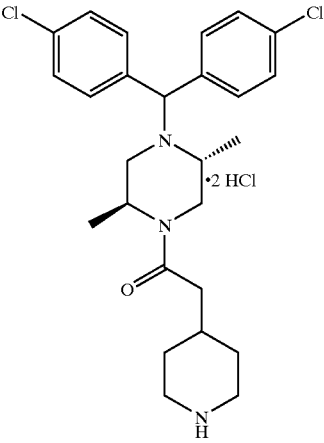 | 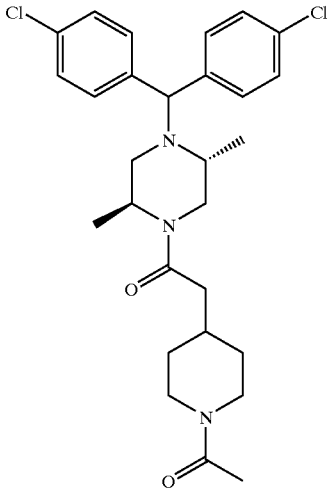 | LCMS: MH+ = 516; mp = 69–84° C. |
| 604 | 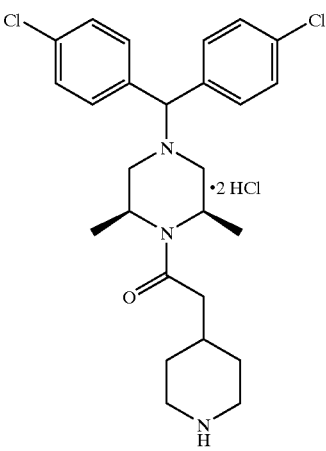 | 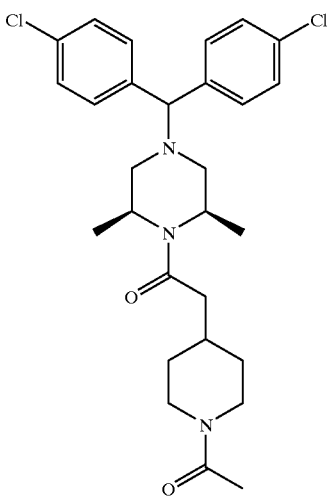 | LCMS: MH+ = 516; mp = 62–81° C. |
| 605 | 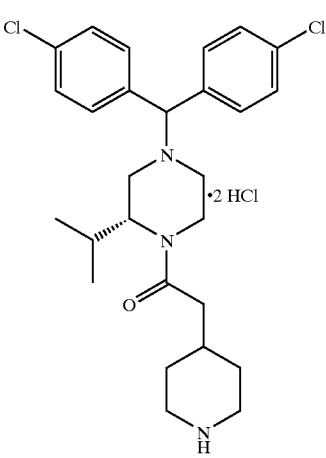 | 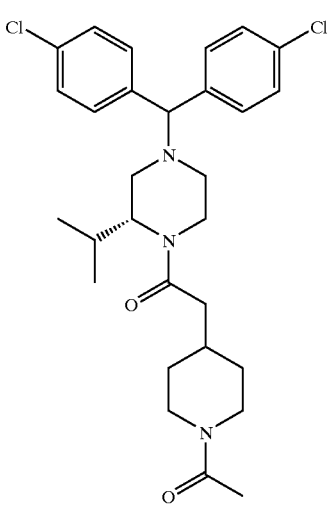 | LCMS: MH+ = 530; mp = 75–82° C. |

TABLE 15-continued
| Ex. | Column 2 | Column 3 | CMPD |
|-----|----------|----------|------|
| 606 | 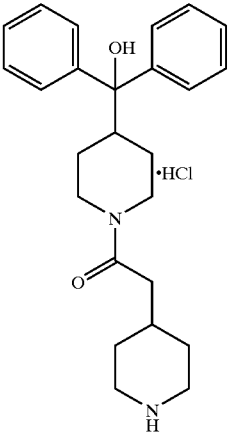 | 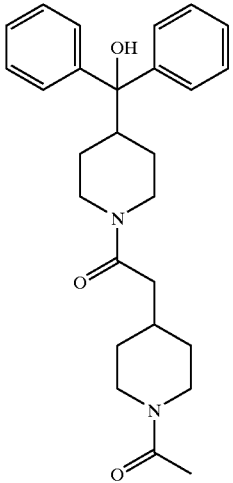 | LCMS: MH⁺ = 435; mp = 76–79° C. |
| 607 | 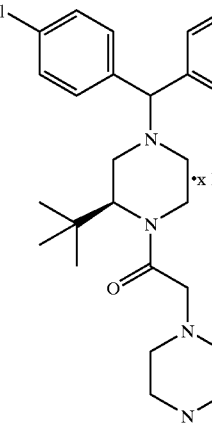 | 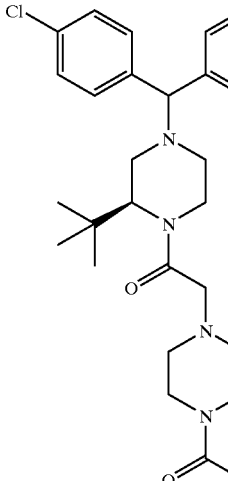 | LCMS: MH⁺ = 545; mp = 97–101° C. |
| 608 | 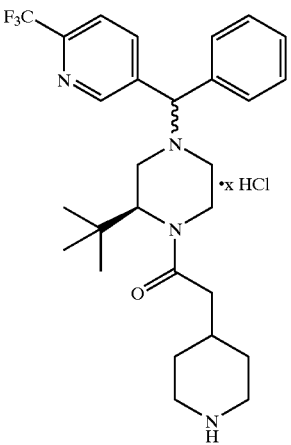 | 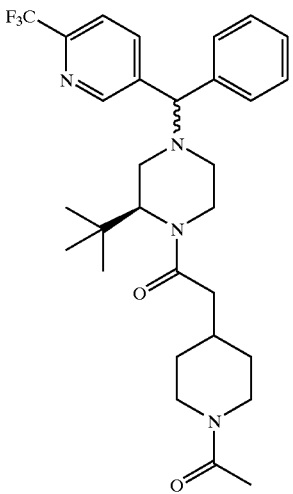 | LCMS: MH⁺ = 545; mp = 65–68° C. |

TABLE 15-continued
| Ex. | Column 2 | Column 3 | CMPD |
|---|---|---|---|
| 608.1 | 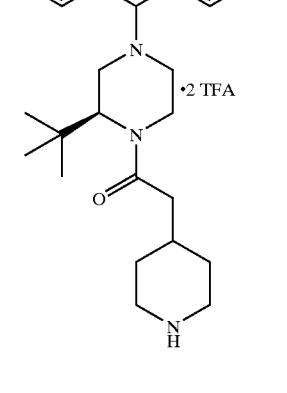 | 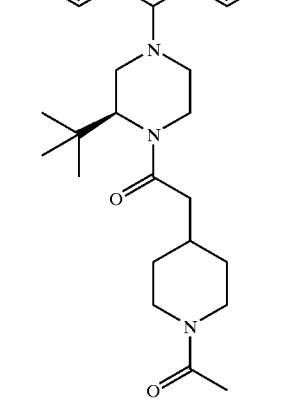 | LCMS: MH+ = 645; mp = 66–72° C. |
| 608.2 | 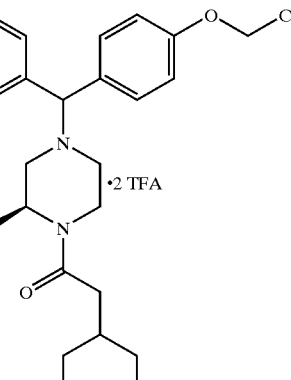 | 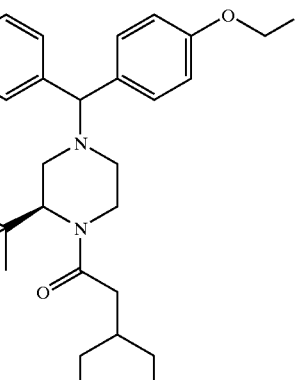 | LCMS: MH+ = 574; mp = 87–92° C. |
| 608.21 | 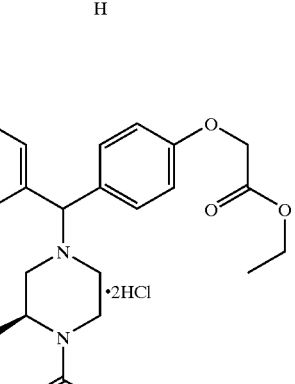 | 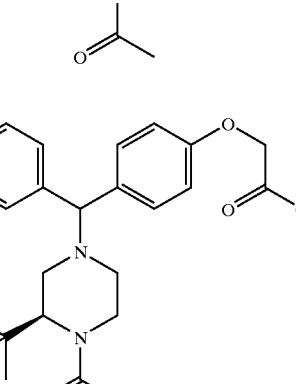 | LCMS: MH+ = 564; mp = 65–69° C. |

TABLE 15-continued
| Ex. | Column 2 | Column 3 | CMPD |
|---|---|---|---|
| 608.22 | 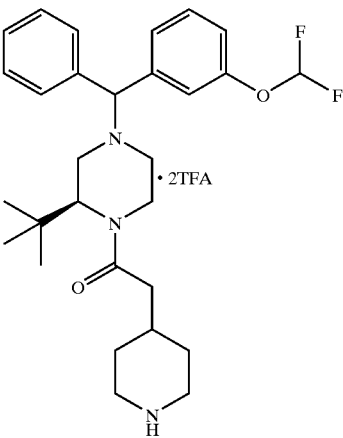 | 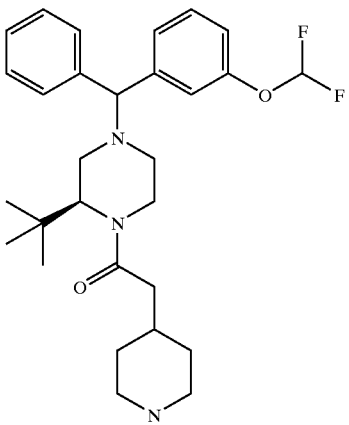 | LCMS:<br>MH+ = 586;<br>mp = 73–77° C. |
| 608.23 | 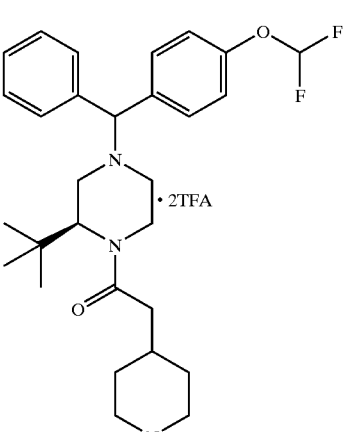 | 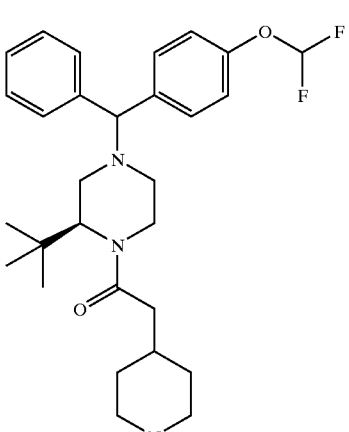 | LCMS:<br>MH+ = 542;<br>mp = 81–84° C. |
| 608.25 | 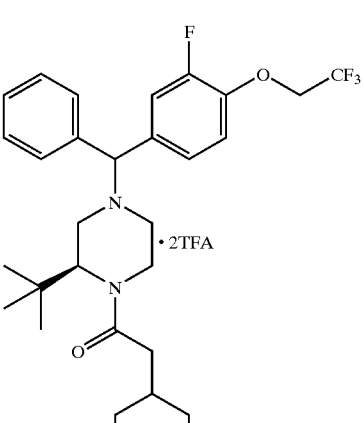 | 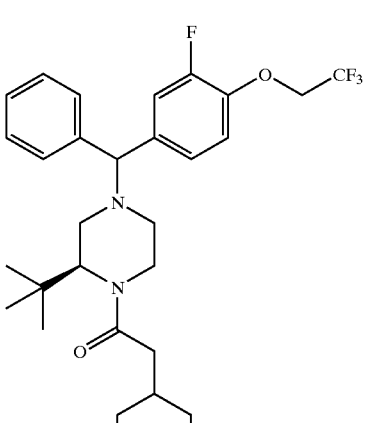 | LCMS:<br>MH+ = 592;<br>mp = 85–91° C. |

TABLE 15-continued
| Ex. | Column 2 | Column 3 | CMPD |
|---|---|---|---|
| 608.26 | 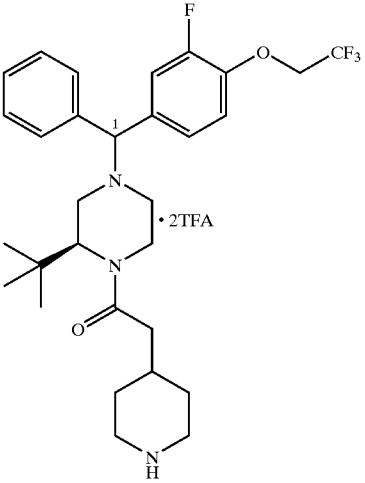 | 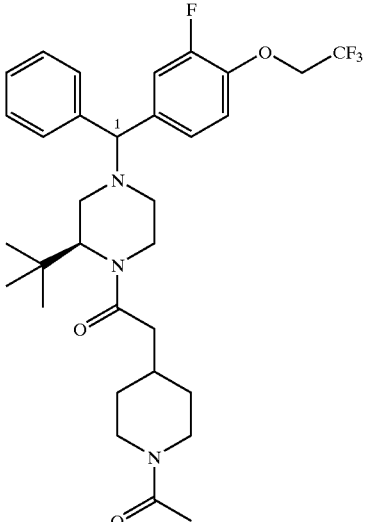 | LCMS:<br>MH+ = 592;<br>mp = 74–80° C. |
| 608.27 | 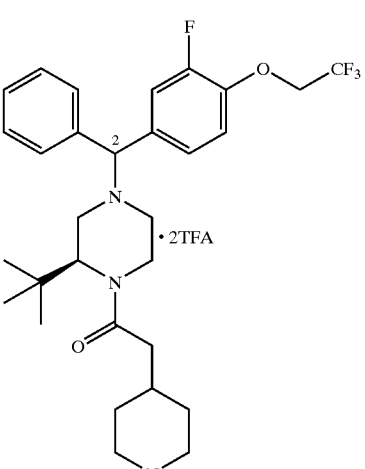 | 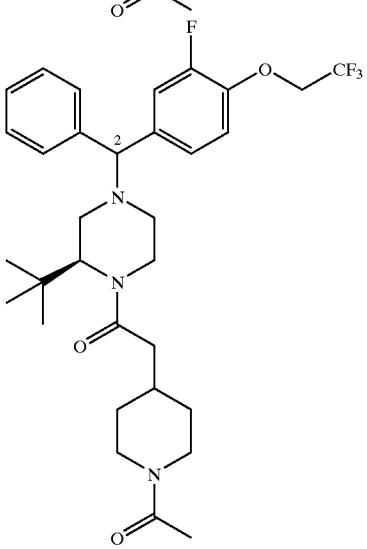 | LCMS:<br>MH+ = 586;<br>mp = 82–85° C. |
| 608.28 | 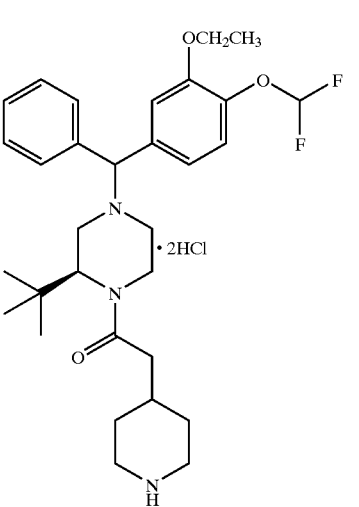 | 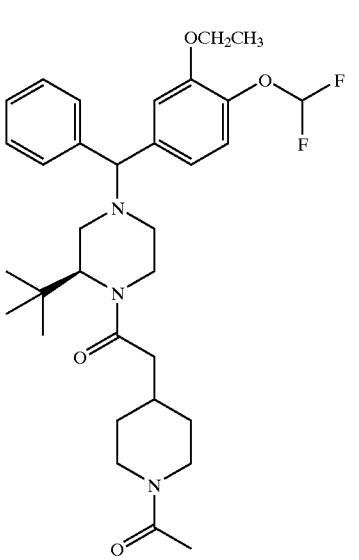 | LCMS:<br>MH+ = 586;<br>mp = 76–80° C. |

TABLE 15-continued
| Ex. | Column 2 | Column 3 | CMPD |
|---|---|---|---|
| 608.29 | 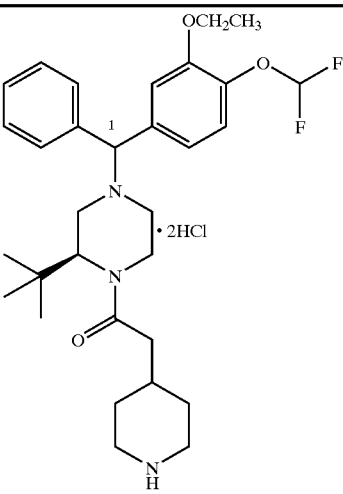 | 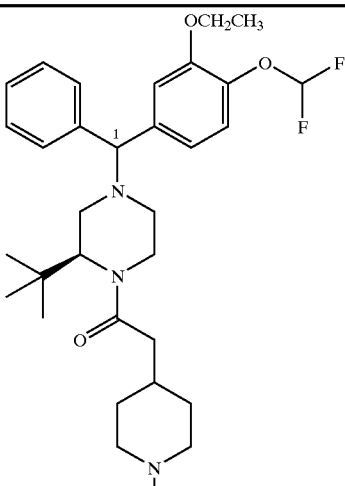 | LCMS:<br>MH+ = 586;<br>mp = 48.7–49.8° C. |
| 608.30 | 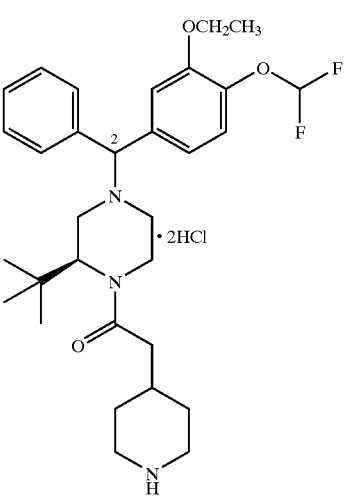 | 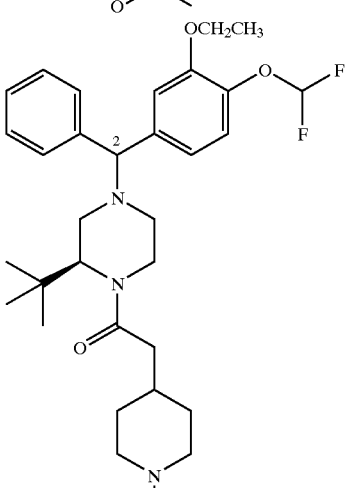 | LCMS:<br>MH+ = 586;<br>mp = 70–73° C. |
| 608.31 | 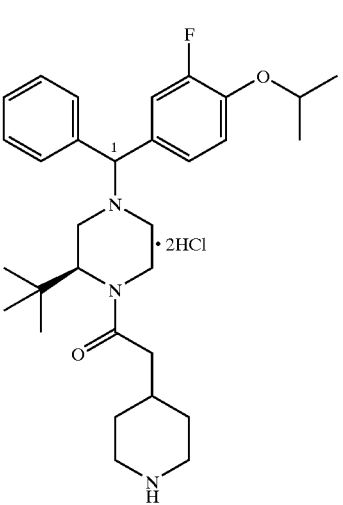 | 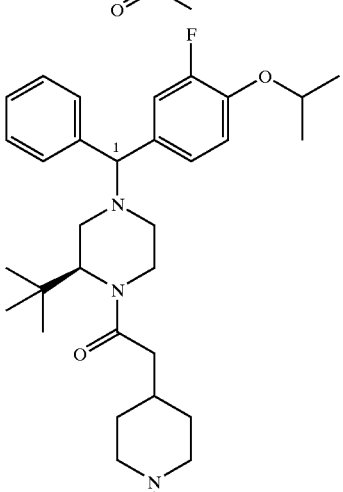 | LCMS:<br>MH+ = 552;<br>mp = 48–51° C. |

TABLE 15-continued

| Ex. | Column 2 | Column 3 | CMPD |
|---|---|---|---|
| 608.32 | | | LCMS: MH$^+$ = 552; mp = 75–79° C. |
| 608.33 | | | LCMS: MH$^+$ = 564; mp = 76–81° C. |
| 608.34 | | | LCMS: MH$^+$ = 564; mp = 75–78° C. |

TABLE 15-continued

| Ex. | Column 2 | Column 3 | CMPD |
|---|---|---|---|
| 608.35 | | | LCMS:<br>MH+ = 615;<br>mp = 97–104° C. |
| 608.36 | | | LCMS:<br>MH+ = 615;<br>mp = 105–110° C. |

US 6,903,102 B2
339                                                                                                              340
TABLE 15-continued
| Ex. | Column 2 | Column 3 | CMPD |
|---|---|---|---|
| 608.37 | 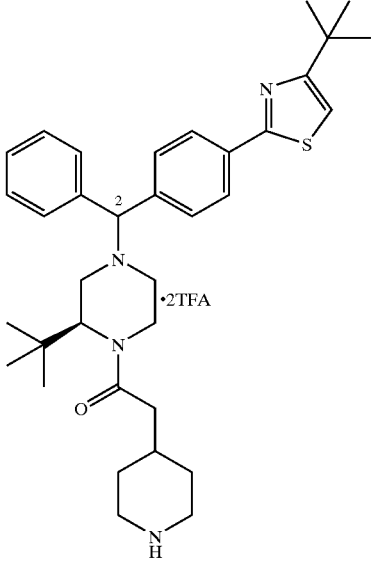 | 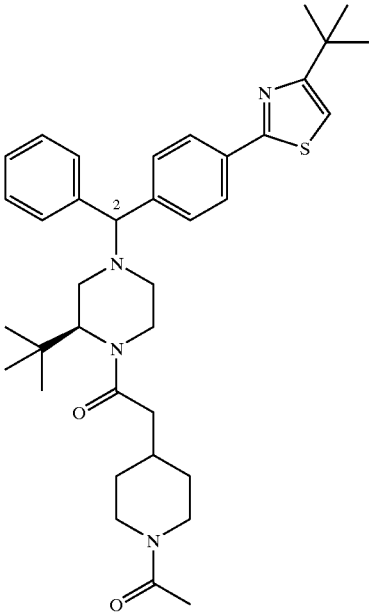 | LCMS:<br>MH$^+$ = 615;<br>mp = 100–106° C. |
| 608.38 | 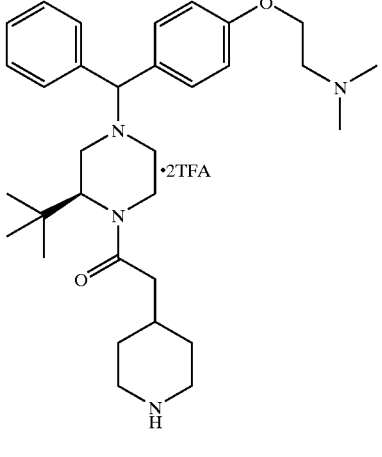 | 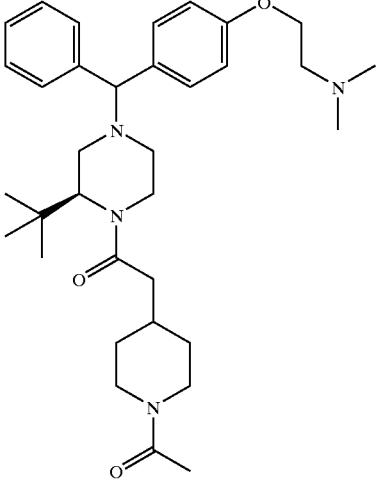 | LCMS:<br>MH$^+$ = 563;<br>mp = 70–73° C. |
| 608.39 | 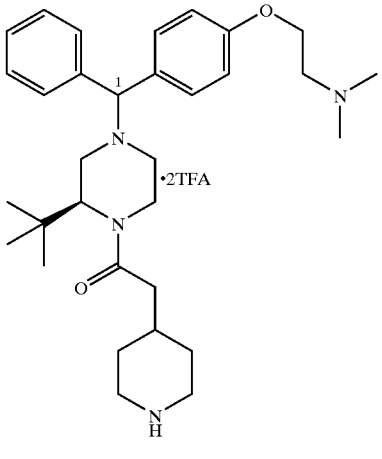 | 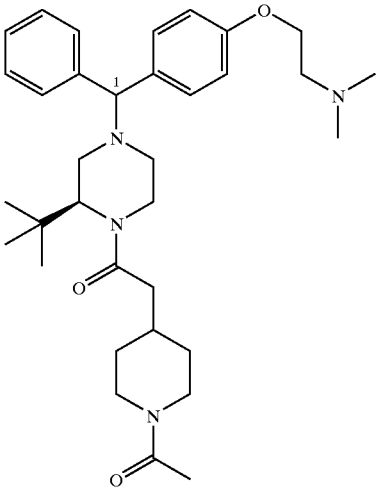 | LCMS:<br>MH$^+$ = 563;<br>mp = 64–66° C. |

TABLE 15-continued
| Ex. | Column 2 | Column 3 | CMPD |
|---|---|---|---|
| 608.40 | 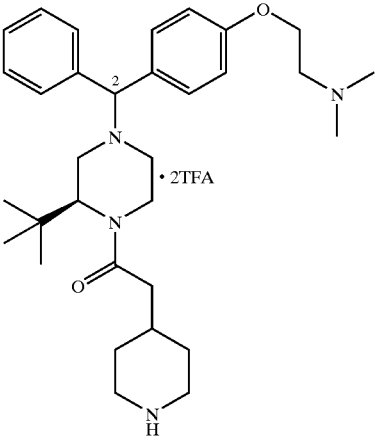 | 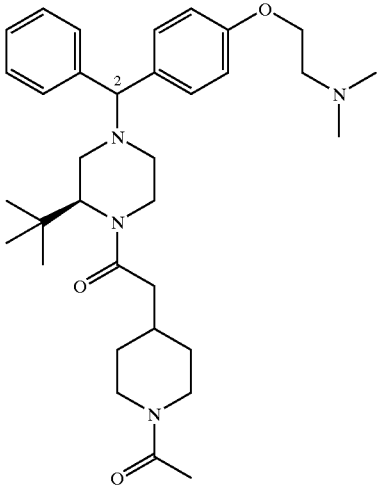 | LCMS:<br>MH+ = 563;<br>mp = 71–73° C. |
| 608.41 | 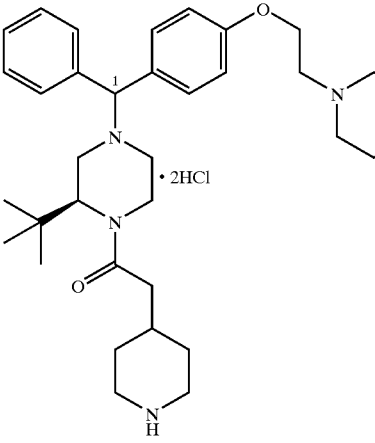 | 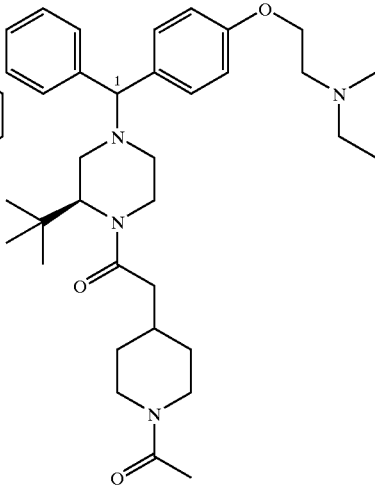 | LCMS:<br>MH+ = 603;<br>mp = 58–63° C. |
| 608.42 | 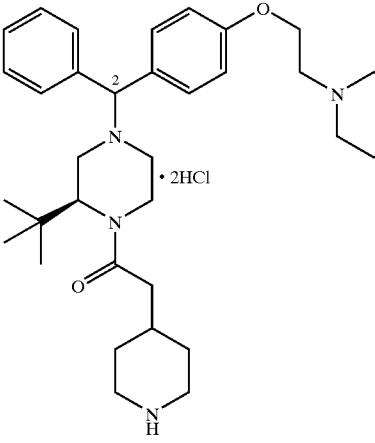 | 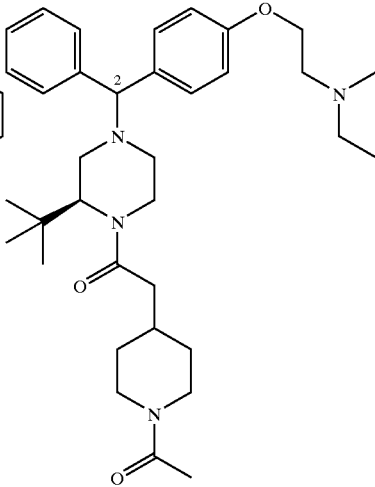 | LCMS:<br>MH+ = 603;<br>mp = 83–86° C. |

TABLE 15-continued
| Ex. | Column 2 | Column 3 | CMPD |
|---|---|---|---|
| 608.43 | 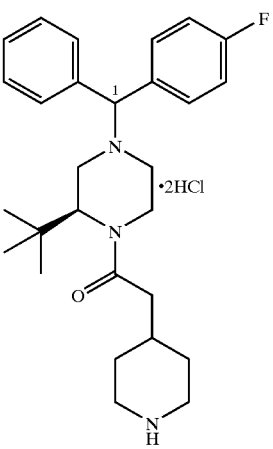 •2HCl | 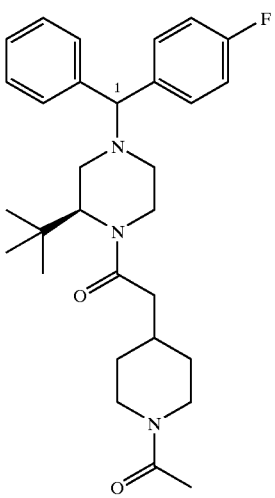 | LCMS:<br>MH$^+$ = 494;<br>mp = 64–67° C. |
| 608.44 | 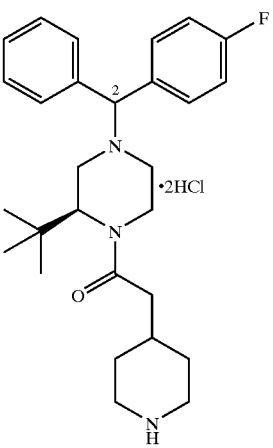 •2HCl | 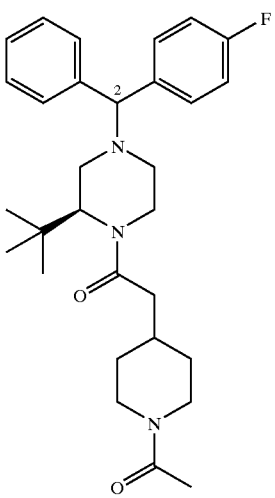 | LCMS:<br>MH$^+$ = 494;<br>mp = 78–81° C. |
| 608.45 | 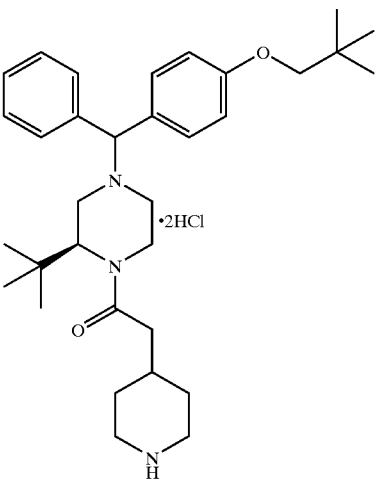 •2HCl | 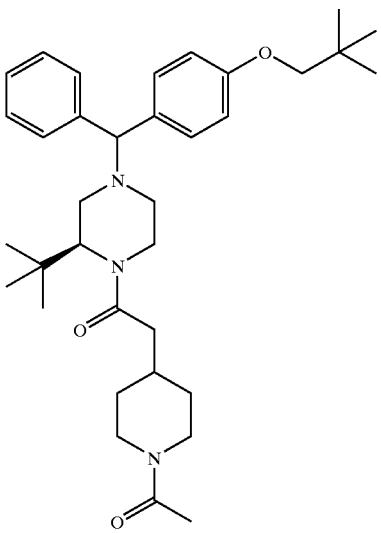 | LCMS:<br>MH$^+$ = 562;<br>mp = 57–60° C. |

TABLE 15-continued
| Ex. | Column 2 | Column 3 | CMPD |
|---|---|---|---|
| 608.46 | 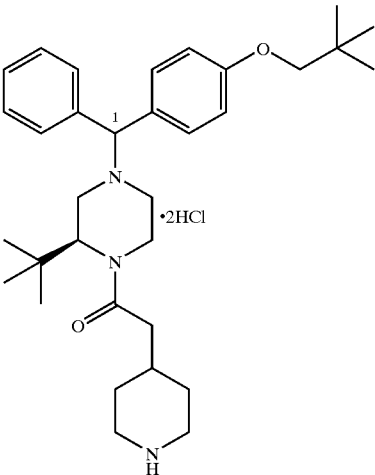 | 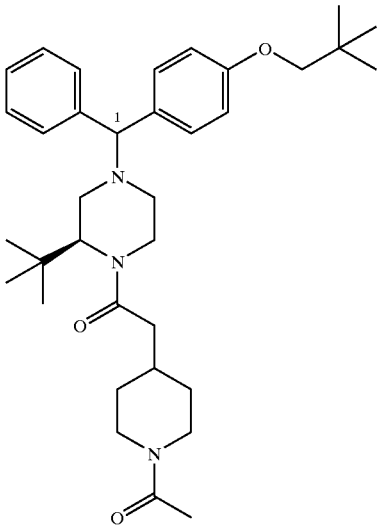 | LCMS: MH+ = 562; mp = 89–91° C. |
| 608.47 | 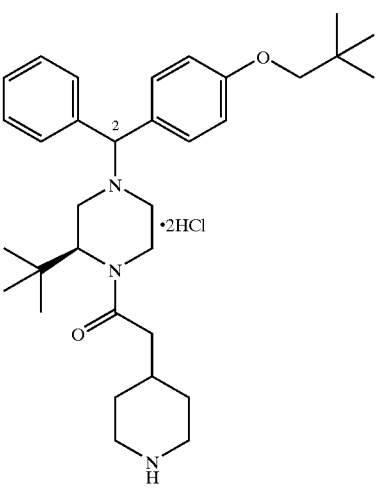 | 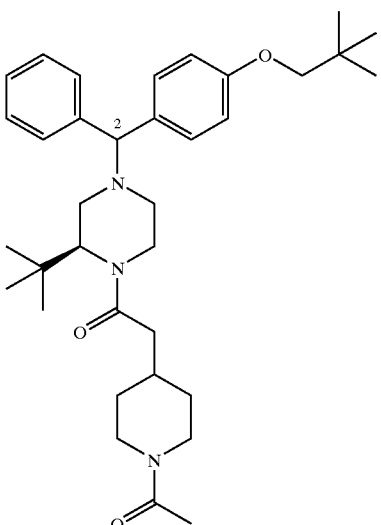 | LCMS: MH+ = 562; mp = 78–82° C. |
| 608.48 | 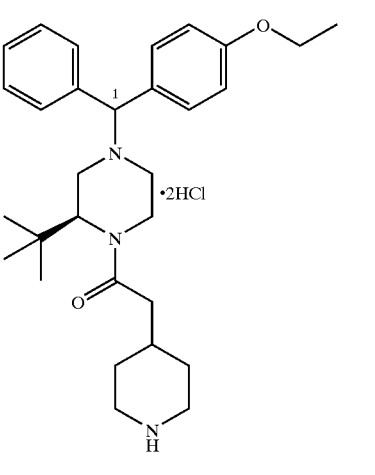 | 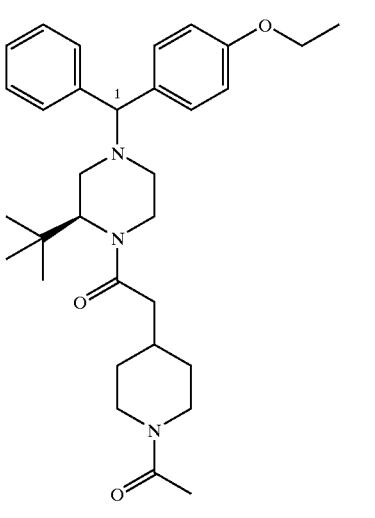 | LCMS: MH+ = 520; mp = 50–52° C. |

TABLE 15-continued

| Ex. | Column 2 | Column 3 | CMPD |
|---|---|---|---|
| 608.49 | | | LCMS:<br>MH⁺ = 520;<br>mp = 42–44° C. |
| 609.50 | | | LCMS:<br>MH⁺ = 575;<br>mp = 131–135° C. |
| 609.51 | | | LCMS:<br>MH⁺ = 623;<br>mp = 73–84° C. |

TABLE 15-continued
| Ex. | Column 2 | Column 3 | CMPD |
|---|---|---|---|
| 609.52 | 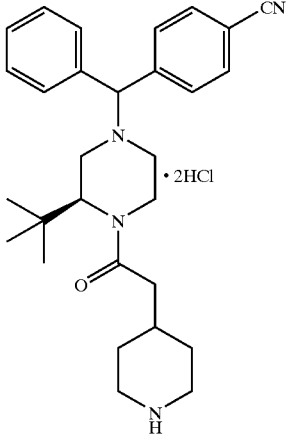 | 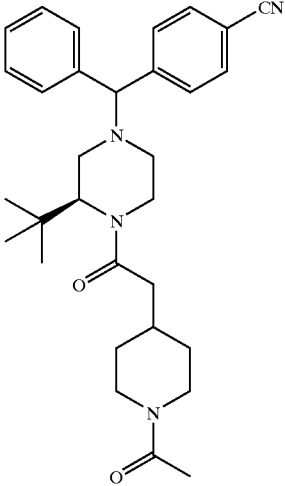 | LCMS: MH+ = 501; mp = 88–90° C. |
| 609.53 | 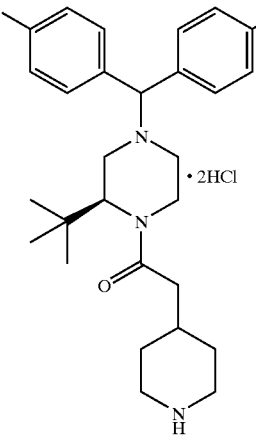 | 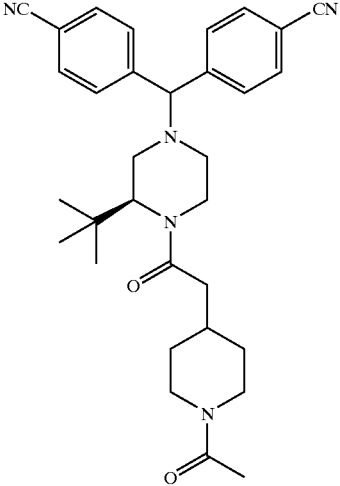 | LCMS: MH+ = 526; mp = 110–112° C. |
| 609.54 | 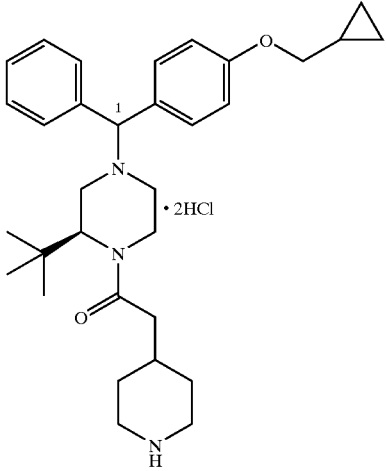 | 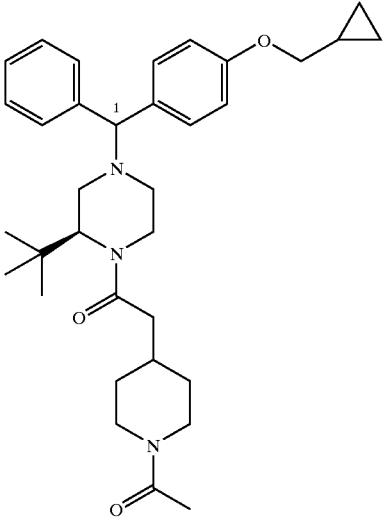 | LCMS: MH+ = 546; mp = 100–104° C. |

TABLE 15-continued
| Ex. | Column 2 | Column 3 | CMPD |
|---|---|---|---|
| 609.55 | 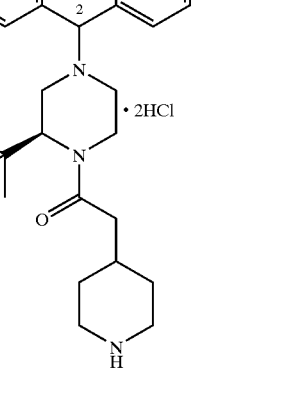 | 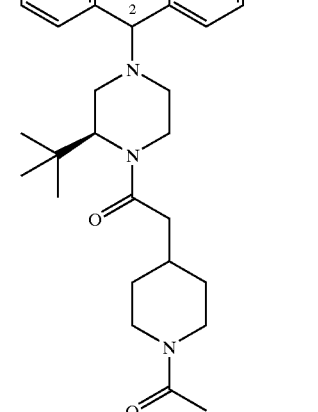 | LCMS:<br>MH+ = 546;<br>mp = 85–87° C. |
| 609.56 | 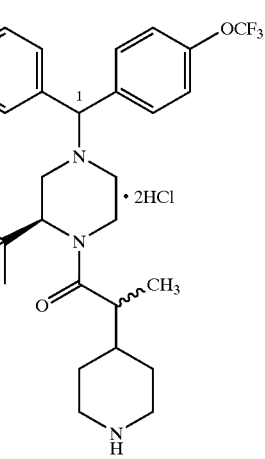 | 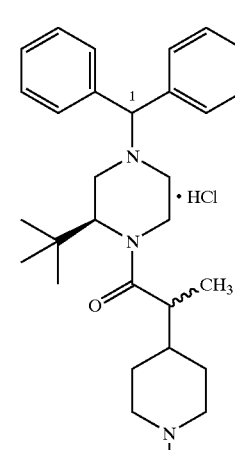 | LCMS:<br>MH+ = 574;<br>mp = 63–70° C. |
| 609.57 | 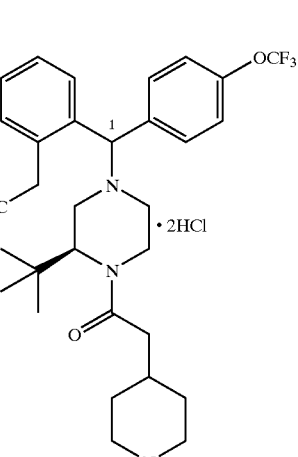 | 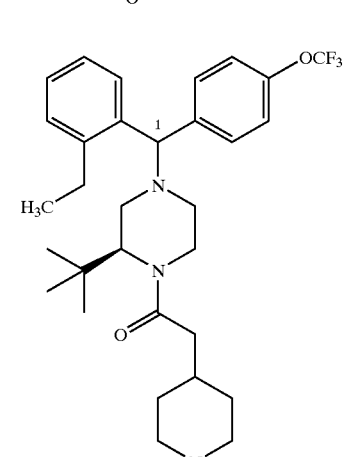 | LCMS:<br>MH+ = 588;<br>mp = 67–75° C. |

TABLE 15-continued
| Ex. | Column 2 | Column 3 | CMPD |
|---|---|---|---|
| 609.58 | 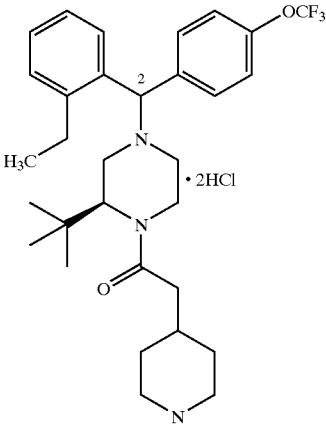 | 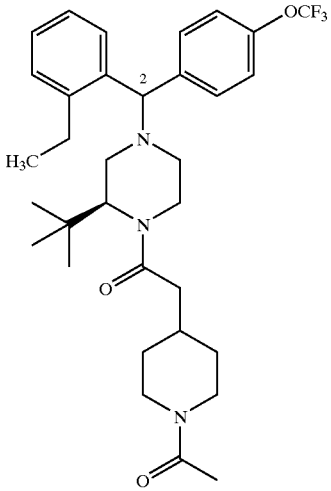 | LCMS: MH+ = 588; mp = 66–88° C. |
| 609.59 | 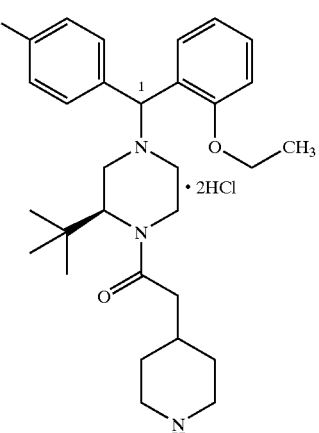 | 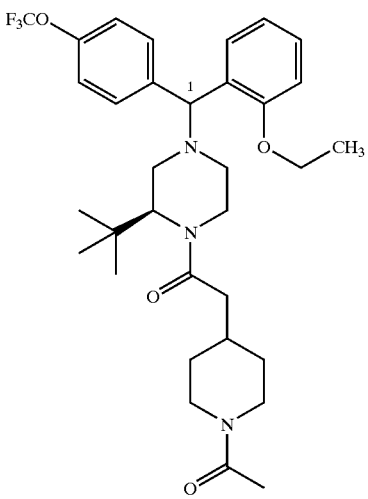 | LCMS: MH+ = 604; mp = 53–71° C. |
| 609.60 | 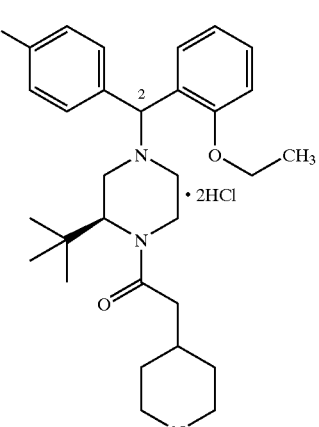 | 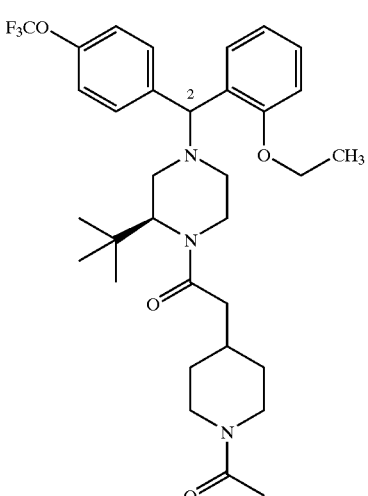 | LCMS: MH+ = 604; mp = 55–72° C. |

US 6,903,102 B2
355 356
TABLE 15-continued
| Ex. | Column 2 | Column 3 | CMPD |
|---|---|---|---|
| 609.61 | 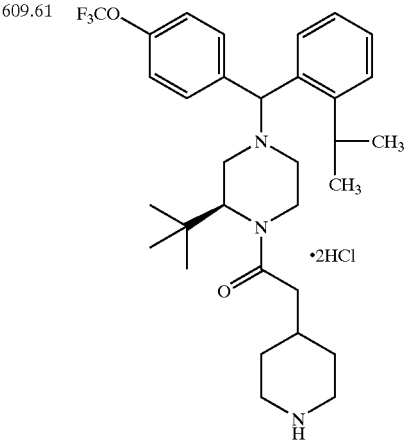 | 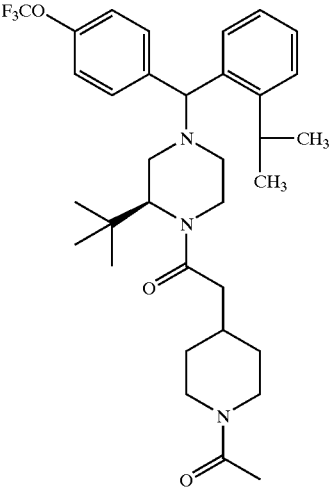 | LCMS: MH$^+$ = 602 |
| 609.62 | 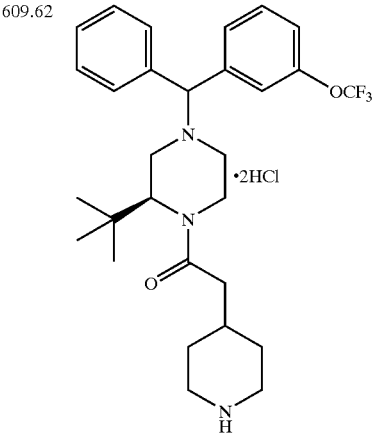 | 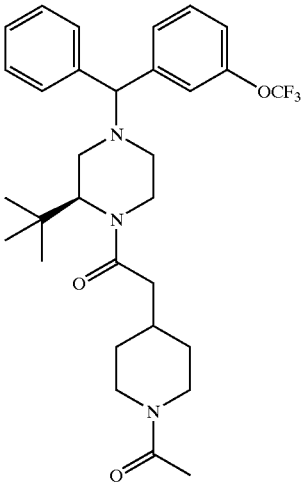 | LCMS: MH$^+$ = 560; mp = 65–68° C. |
| 609.63 | 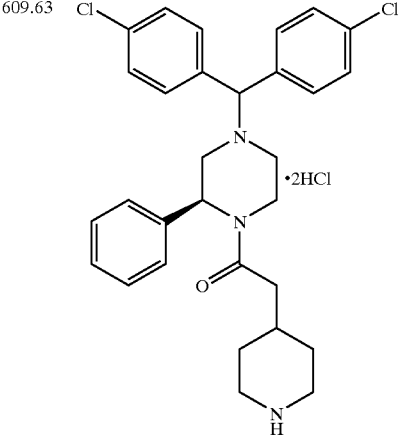 | 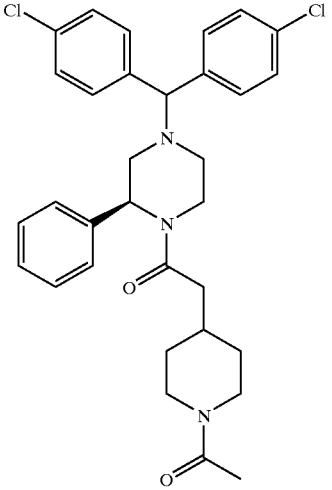 | LCMS: MH$^+$ = 565; mp = 45–48° C. |

TABLE 15-continued
| Ex. | Column 2 | Column 3 | CMPD |
|---|---|---|---|
| 609.64 | 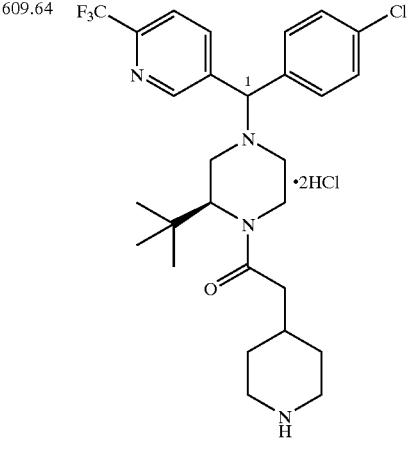 | 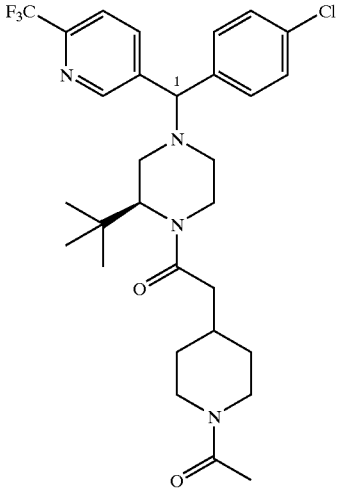 | LCMS: MH$^+$ = 579; mp = 101–104° C. |
| 609.65 | 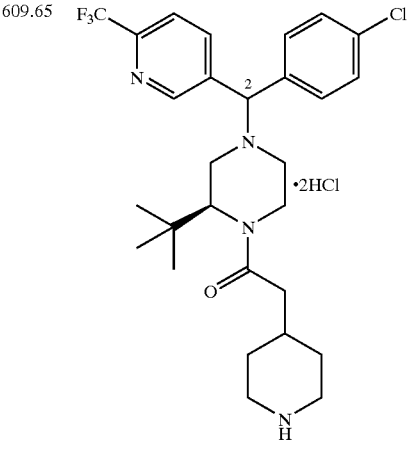 | 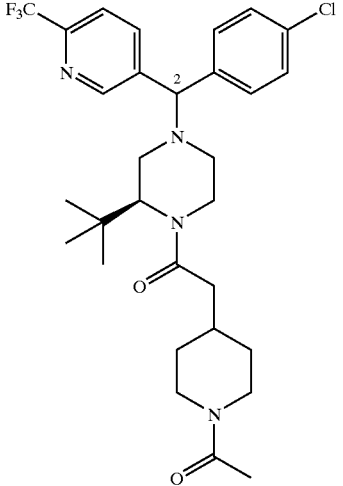 | LCMS: MH$^+$ = 579; mp = 96–101° C. |
| 609.66 | 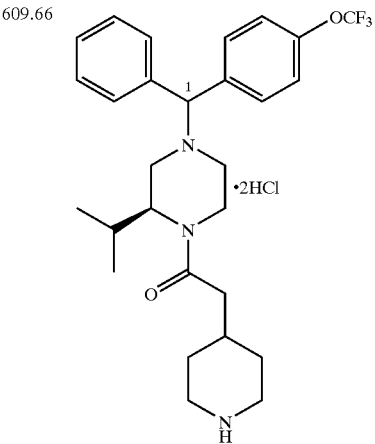 | 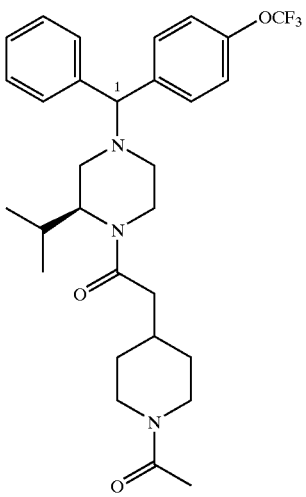 | LCMS: MH$^+$ = 546; mp = 69–74° C. |

TABLE 15-continued

| Ex. | Column 2 | Column 3 | CMPD |
|---|---|---|---|
| 609.67 | | | LCMS: MH+ = 546; mp = 65–69° C. |
| 609.68 | | | LCMS: MH+ = 478; mp = 63–68° C. |

EXAMPLES 609.69 AND 609.70

By essentially the same procedure set forth in Example 559, using the compounds shown in Column 2 of Table 15.1, the products shown in Column 3 of Table 15.1 (CMPD) were prepared:

TABLE 15.1

| Ex. | Column 2 | Column 3 | CMPD |
|---|---|---|---|
| 609.69 | | | LCMS: MH+ = 573; mp = 50–85° C. |

TABLE 15.1-continued

| Ex. | Column 2 | Column 3 | CMPD |
|---|---|---|---|
| 609.70 | | | LCMS: MH⁺ = 573; mp = 90–97° C. |

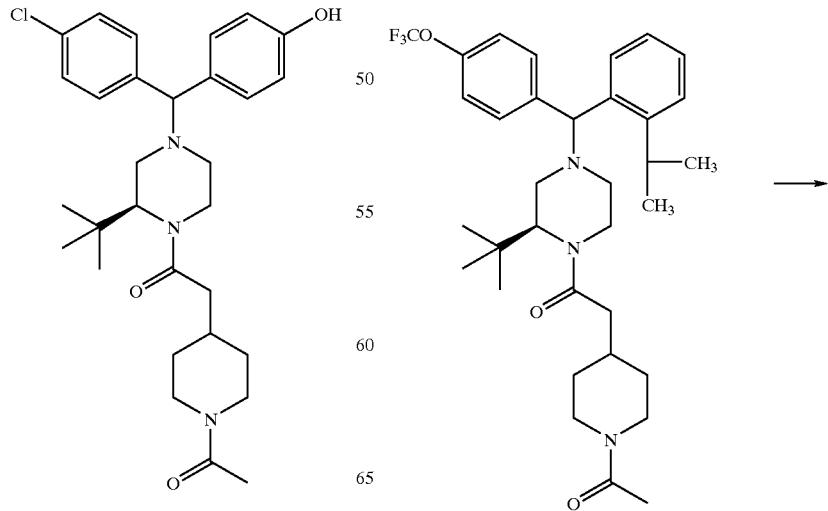

EXAMPLE 609

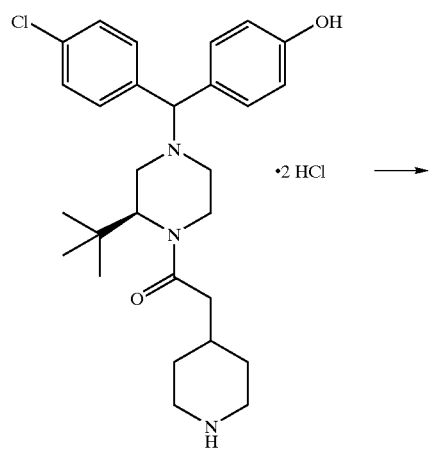

The product from Preparative Example 238 (0.20 g, 0.41 mmol) in $CH_2Cl_2$ (4.0 mL) was treated with $Ac_2O$ (0.038 mL, 1.0 eq) and TEA (0.057 mL, 1.0 eq.) and the resulting solution stirred at room temperature 5 hours. The reaction was quenched by the addition of saturated $NaHCO_3$ and extracted with $CH_2Cl_2$. The combine organics were purified by flash chromatography using a 2.5% to 5% (10% $NH_4OH$ in MeOH) in $CH_2Cl_2$ solution as eluent to give the diacetate (0.12 g, 50% yield). This product was dissolved in MeOH (5.0 mL) and treated with 1N NaOH. The resulting solution was stirred at room temperature 5 hours. The reaction mixture was concentrated under reduced pressure and the crude residue purified by preparative thin layer chromatography (TLC) using a 5% (10% $NH_4OH$ in $CH_2Cl_2$ solution as eluent (0.053 g, 53% yield). LCMS: MH⁺=526; mp=132–137° C.

EXAMPLE 609.71 AND 609.72

EXAMPLES 609.73 AND 609.74
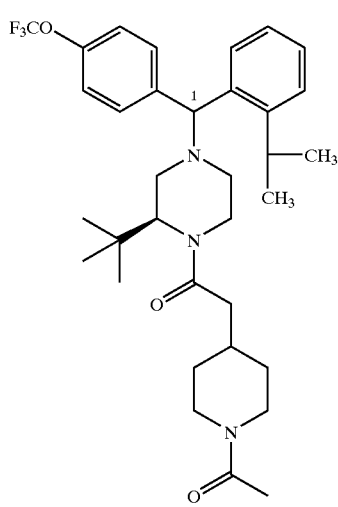
+
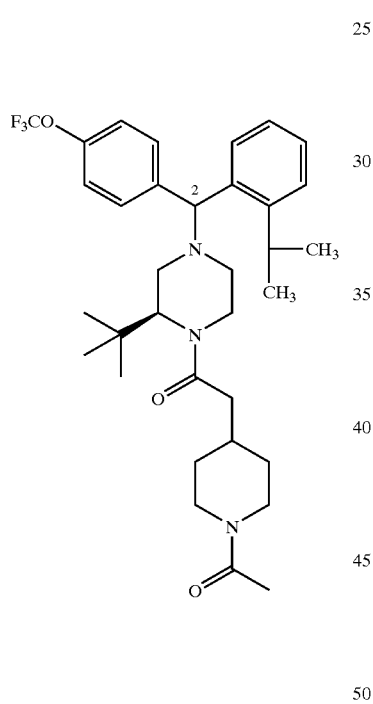
The above compounds were prepared through the separation of diastereomers of the compound from Example 609.60 using preparative HPLC with a CHIRALPAK AD column using a 95:5 hexanes:IPA mix with 0.1% DEA as eluent:
Example 609.61 (first eluting isomer): LCMS: MH$^+$=602.
Example 609.62 (second eluting isomer): LCMS: MH$^+$=602.
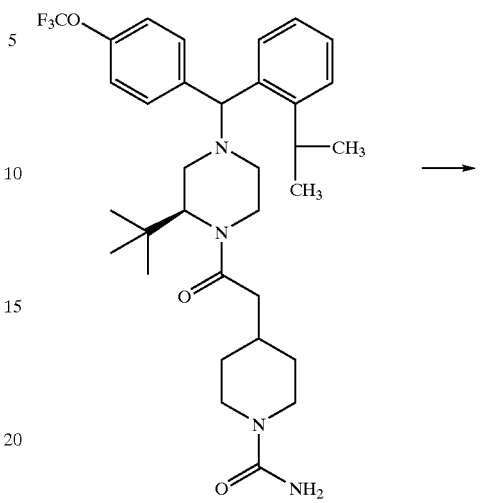
→
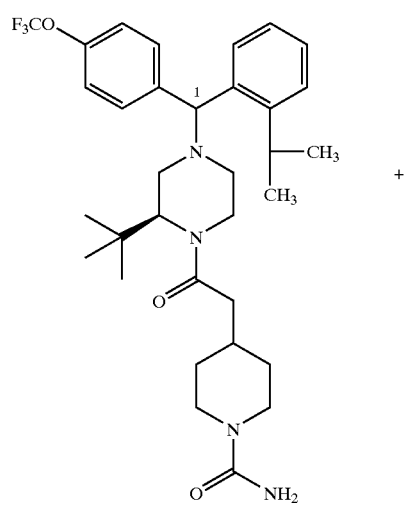
+
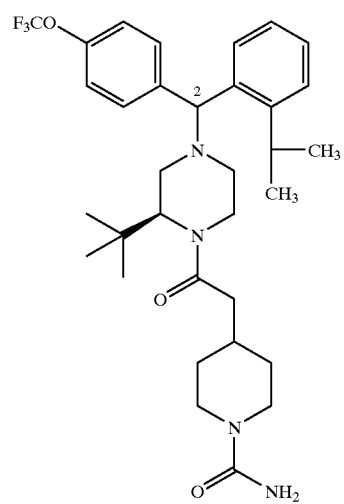

365

The above compounds were prepared through the separation of diastereomers of the compound from Example 609.60 using preparative HPLC with a CHIRALPAK AD column using a 95:5 hexanes:IPA mix with 0.1% DEA as eluent:

Example 609.63 (first eluting isomer): LCMS: MH+=603.

Example 609.64 (second eluting isomer): LCMS: MH+=603.

EXAMPLE 609.75

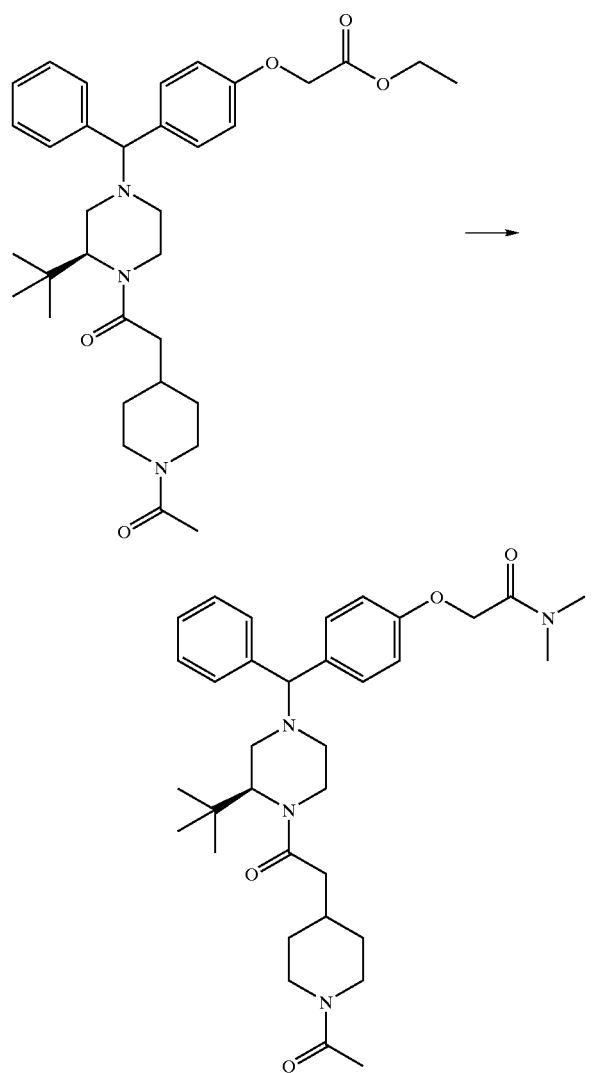

A solution of the compound from Example 608.21 (0.053 g, 0.09 mmol) was stirred in MeOH (1.0 mL) and 1N NaOH (0.1 mL) at room temperature overnight. The reaction mixture was concentrated under reduced pressure. The crude product was dissolved in $CH_2Cl_2$ (1 mL) and HOBt (0.010 g), dimethylamine hydrochloride (0.015 g), DEC (0.015 g) and TEA (0.06 mL) were added and the resulting mixture stirred at room temperature overnight. The reaction mixture was quenched by the addition of saturated $NaHCO_3$ and the resulting mixture was extracted with $CH_2Cl_2$. The combined organics were dired over $Na_2SO_4$, filtered, and concentrated under reduced pressure. The crude product was purified by flash chromatography using a 10% (10% $NH_4OH$ in MeOH solution) in $CH_2Cl_2$ as eluent (0.019 g, 54% yield): LCMS: $MH^+=577$; mp=64–68° C.

366

EXAMPLE 610

The product from Example 609 (0.05 g, 0.10 mmol) in acetone (2.0 mL) was treated with MeI (0.01 mL, 1.1 eq.) and $K_2CO_3$ (0.066 g, 5 eq.) and the resulting solution stirred at room temperature overnight. The reaction mixture was concentrated under reduced pressure and the crude product purified by flash chromatography using a 5% (10% $NH_4OH$ in MeOH) in $CH_2Cl_2$ solution as eluent (0.051 g, 94% yield). LCMS: $MH^+=541$;

mp=64–66° C.

EXAMPLE 611

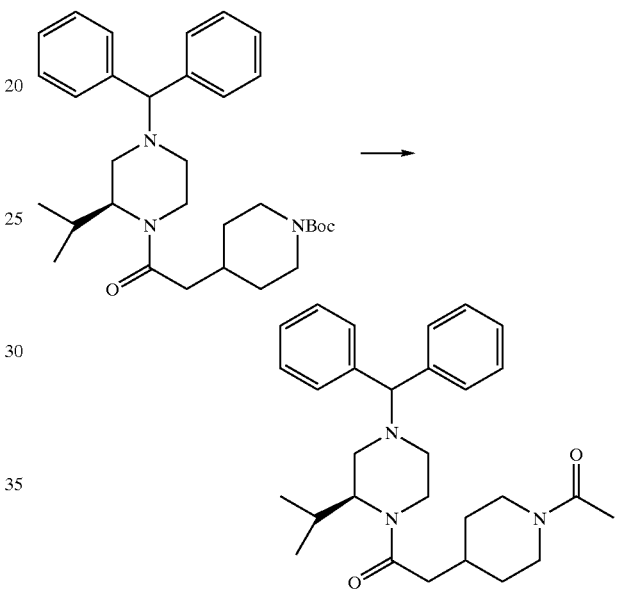

TFA (4.0 mL) was added to a solution of the product from Preparative Example 172 (2.00 g, 3.86 mmol) in anhydrous $CH_2Cl_2$ (40 mL) at 0° C. under $N_2$. The mixture was stirred at 0° C. for 15 min, then 16 mL of TFA was added and the stirring was continued for another 30 min at 0 C. The mixture was poured onto solid $K_2CO_3$ (50 g), $H_2O$ (200 mL) was added, and the mixture was extracted with $CH_2Cl_2$ (4×30 mL). The extracts were dried over $Na_2SO_4$, filtered, and the solvent was evaporated. The sticky solid was dissolved in anhydrous $CH_2Cl_2$ (30 mL), and $Ac_2O$ (0.79 g, 7.7 mmol) and TEA (1.95 g, 19.3 mmol) were added. The mixture was stirred under $N_2$ for 24 hrs, poured into sat. $NaHCO_3$ (50 mL), and extracted with $CH_2Cl_2$ (2×30 mL). The combined extracts were dried over $Na_2SO_4$ and filtered. The residue was purified by flash chromatography using 7% MeOH (10% $NH_4OH$) in $CH_2Cl_2$ to give 1.63 g (92%) of a solid. LCMS: $MH^+=462$; mp=65–71° C.

PREPARATIVE EXAMPLES 611.1–611.24

By essentially the same procedure set forth in Preparative Example 611, using the starting materials in column 2, the products given in column 2 were prepared:

| Prep. Ex. | Column 2 | Column 3 | CMPD |
|---|---|---|---|
| 611.1 | 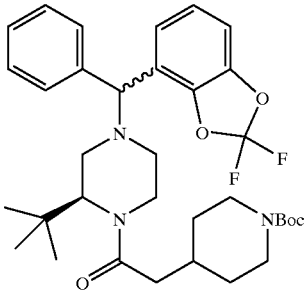 | 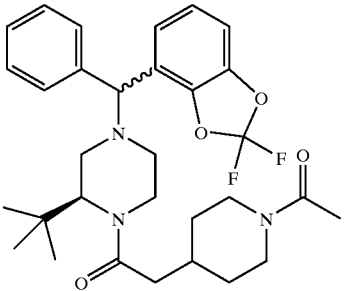 | LCMS: MH+ = 556 Mp = 78–85° C. |
| 611.2 | 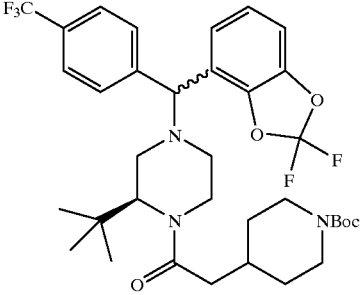 | 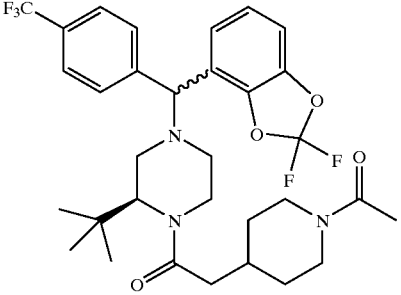 | LCMS: MH+ = 624 Mp = 80–85° C. |
| 611.3 | 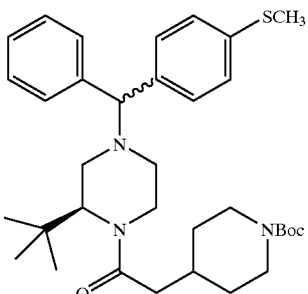 | 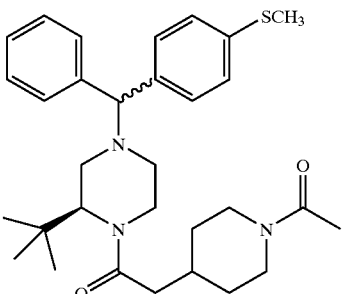 | LCMS: MH+ = 522 Mp = 78–85° C. |
| 611.4 | 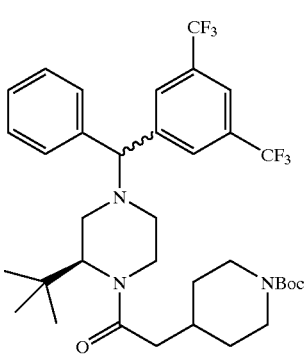 | 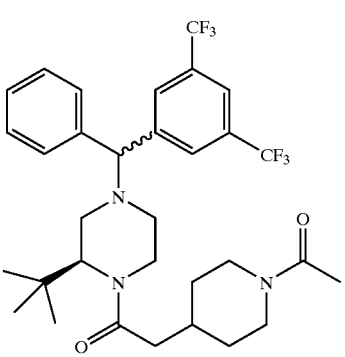 | LCMS: MH+ = 612 Mp = 70–76° C. |
| 611.5 | 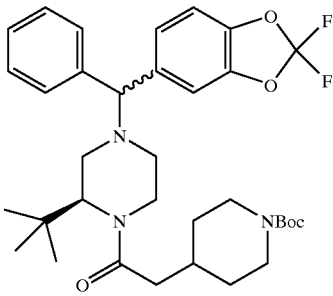 | 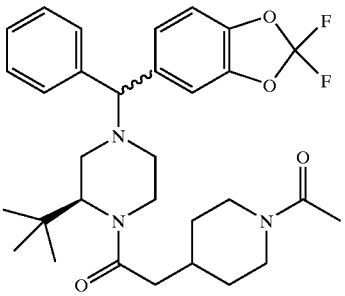 | LCMS: MH+ = 556 Mp = 76–83° C. |

US 6,903,102 B2
-continued
| Prep. Ex. | Column 2 | Column 3 | CMPD |
|---|---|---|---|
| 611.6 | 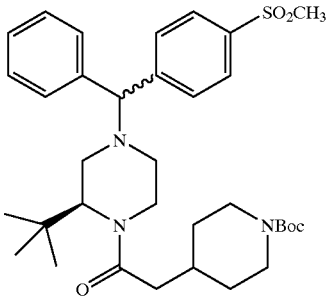 | 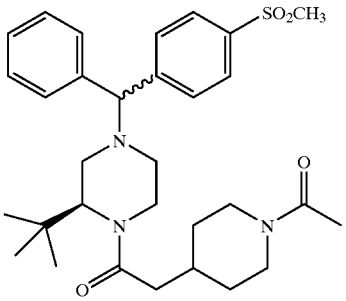 | LCMS: MH+ = 554 Mp = 90–104° C. |
| 611.7 | 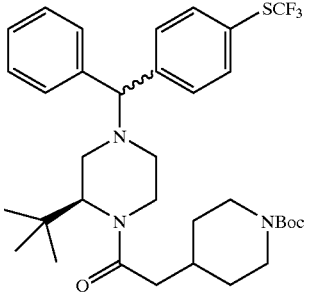 | 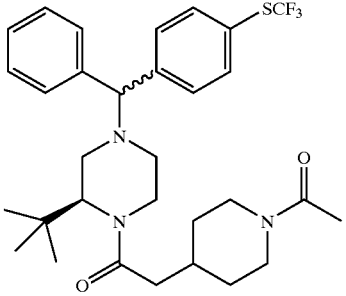 | LCMS: MH+ = 576 Mp = 64–70° C. |
| 611.8 | 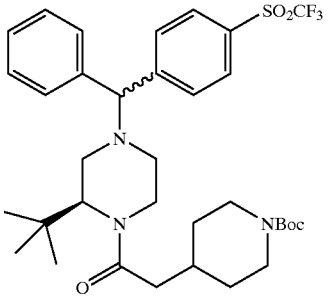 | 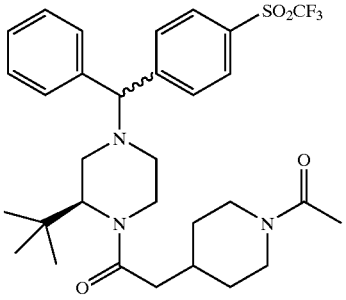 | LCMS: MH+ = 608 Mp = 84–89° C. |
| 611.9 | 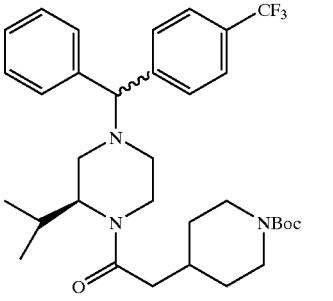 | 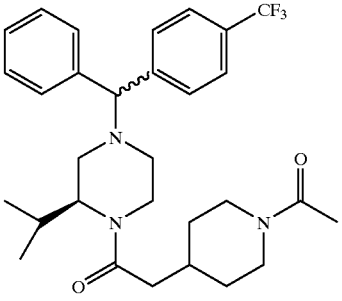 | |
| 611.10 | 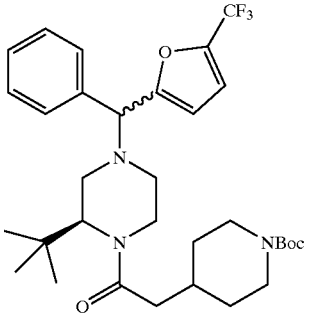 | 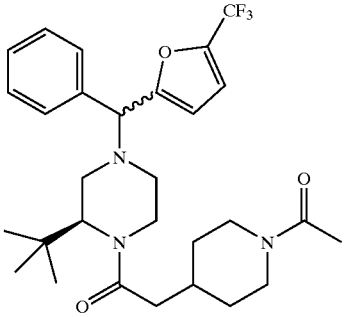 | LCMS: MH+ = 534 Mp = 58–61° C. |

| Prep. Ex. | Column 2 | Column 3 | CMPD |
|---|---|---|---|
| 611.11 | | | LCMS:<br>MH⁺ =<br>Mp = 69–75° C. |
| 611.12 | | | LCMS:<br>MH⁺ = 596<br>Mp = 108–117° C. |
| 611.13 | | | LCMS:<br>MH⁺ = 556<br>Mp = 69–76° C. |
| 611.14 | | | LCMS:<br>MH⁺ = 542<br>Mp = 82–88° C. |
| 611.15 | | | LCMS:<br>MH⁺ = 564<br>Mp = 71–77° C. |

|Prep. Ex.|Column 2|Column 3|CMPD|
|---|---|---|---|
|611.16| | |LCMS:<br>MH⁺ = 554<br>Mp = 95–98° C.|
|611.17| | |LCMS:<br>MH⁺ = 554<br>Mp = 93–96° C.|
|611.18| | |LCMS:<br>MH⁺ = 556<br>Mp = 65–67° C.|
|611.18| | |LCMS:<br>MH⁺ = 556<br>Mp = 70–72° C.|
|611.19| | |LCMS:<br>MH⁺ = 530<br>Mp = 73–76° C.|

| Prep. Ex. | Column 2 | Column 3 | CMPD |
|---|---|---|---|
| 611.20 | | | LCMS:<br>MH+ = 530<br>Mp = 74–77° C. |
| 611.21 | | | LCMS:<br>MH+ = 608<br>Mp = 84–87° C. |
| 611.22 | | | LCMS:<br>MH+ = 608<br>Mp = 91–94° C. |
| 611.23 | | | LCMS:<br>MH+ = 596<br>Mp = 92–96° C. |
| 611.24 | | | LCMS:<br>MH+ = 596<br>Mp = 107–110° C. |

PREPARATIVE EXAMPLE 612

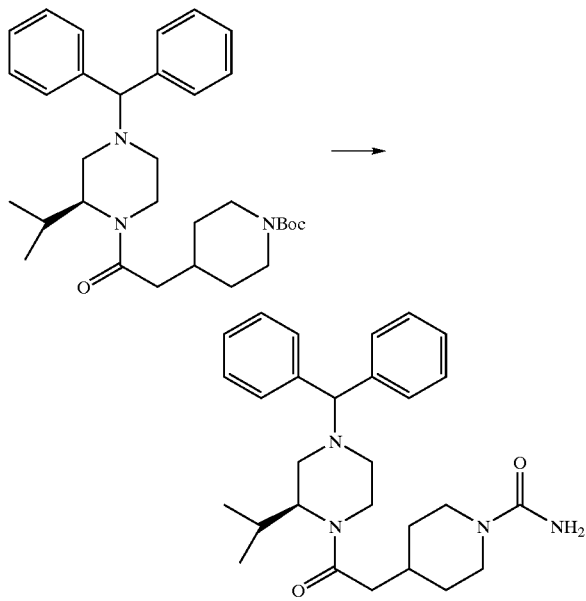

TFA (4.0 mL) was added to a solution of the product from Preparative Example 172 (2.00 g, 3.86 mmol) in anhydrous $CH_2Cl_2$ (40 mL) at 0° C. under $N_2$. The mixture was stirred at 0° C. for 15 min, then 16 mL of TFA was added and the stirring was continued for another 30 min at 0° C. The mixture was poured onto solid $K_2CO_3$ (50 g), $H_2O$ (200 mL) was added and the mixture was extracted with $CH_2Cl_2$ (4×30 mL). The extracts were dried over $Na_2SO_4$, filtered, and the solvent was evaporated. The sticky solid was dissolved in anhydrous $CH_2Cl_2$ (30 mL), and TEA (1.95 g, 19.3 mmol) and TMSNCO (4.44 g, 38.6 mmol) were added. The mixture was stirred under $N_2$ for 3 hrs, poured into sat. $NaHCO_3$ (200 mL), and extracted with $CH_2Cl_2$ (2×30 mL). The combined extracts were dried over $Na_2SO_4$, filtered, and the solvent was evaporated. The residue was purified by flash chromatography using 11% MeOH (10% $NH_4OH$) in $CH_2Cl_2$ to give 1.51 g (85%) of a solid. LCMS: $MH^+$=463; mp=100–107° C.

PREPARATIVE EXAMPLES 612.1–612.8

By essentially the same procedure set forth in Preparative Example 61±2, using the starting materials in column 2, the products given in column 3 were prepared:

| Prep. Ex. | Column 2 | Column 3 | CMPD |
|---|---|---|---|
| 612.1 | | | LCMS: $MH^+$ = 557<br>Mp = 108–114° C. |
| 612.2 | | | LCMS: $MH^+$ = 625<br>Mp = 114–120° C. |

-continued

| Prep. Ex. | Column 2 | Column 3 | CMPD |
|---|---|---|---|
| 612.3 | | | LCMS: MH+ = 523<br>Mp = 105–112° C. |
| 612.4 | | | LCMS: MH+ = 613<br>Mp = 104–109° C. |
| 612.5 | | | LCMS: MH+ = 557<br>Mp = 107–113° C. |
| 612.6 | | | LCMS: MH+ = 555<br>Mp = 132–141° C. |
| 612.7 | | | LCMS: MH+ = 577<br>Mp = 98–105° C. |

-continued

| Prep. Ex. | Column 2 | Column 3 | CMPD |
|---|---|---|---|
| 612.8 | (structure with SO₂CF₃, phenyl, piperazine with t-Bu, piperidine-NBoc) | (structure with SO₂CF₃, phenyl, piperazine with t-Bu, piperidine-N-C(O)NH₂) | LCMS: MH⁺ = 609 Mp = 110–115° C. |

EXAMPLE 613

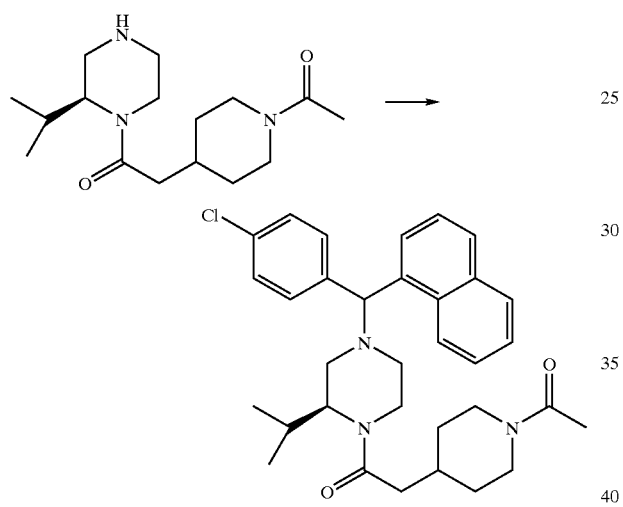

A mixture of the product from Preparative Example 239 (30 mg, 0.10 mmol), the product from Preparative Example 76 (30 mg, 0.11 mmol), NaI (15 mg, 0.10 mmol), and $K_2CO_3$ (60 mg, 0.45 mmol) in anhydrous $CH_3CN$ (1 mL) was stirred and refluxed under $N_2$ for 24 hrs. The mixture was poured into 5% $K_2CO_3$ (30 mL) and extracted with $CH_2Cl_2$ (3×10 mL). The combined extracts were dried over $Na_2SO_4$, the solvent was evaporated, and the residue was purified by flash chromatography using 3% MeOH (10% $NH_4OH$) in $CH_2Cl_2$ to give 36 mg (66%) of a solid. LCMS: MH⁺=546; mp=113–120° C.

EXAMPLES 614–628

By essentially the same procedure set forth in Example 613, using the chlorides in Column 2 of Table 16, the products in Column 3, Table 16 (CMPD) were prepared.

TABLE 16

| Ex. | Column 2 | Column 3 | CMPD |
|---|---|---|---|
| 614 | (pyridine-CH(Cl)-C₆H₄-Cl) | (pyridine-CH-C₆H₄-Cl attached to piperazine-iPr-piperidine-N-acetyl) | LCMS: MH⁺ = 497 |

TABLE 16-continued

| Ex. | Column 2 | Column 3 | CMPD |
|---|---|---|---|
| 615 | | | LCMS: MH⁺ = 546; mp = 110–115° C. |
| 616 | | | LCMS: MH⁺ = 552; mp = 95–100° C. |
| 617 | | | LCMS: MH⁺ = 598; mp = 95–100° C. |
| 618 | | | LCMS: MH⁺ = 502. |
| 619 | | | LCMS: MH⁺ = 503; mp = 82–87° C. |

TABLE 16-continued

| Ex. | Column 2 | Column 3 | CMPD |
|-----|----------|----------|------|
| 620 | | | LCMS: MH+ = 546; mp = 105–109° C. |
| 621 | | | LCMS: MH+ = 547; mp = 115–121° C. |
| 622 | | | LCMS: MH+ = 547; mp = 103–109° C. |
| 623 | | | LCMS: MH+ = 547; mp = 111–117° C. |
| 624 | | | LCMS: MH+ = 596; mp = 95–101° C. |

TABLE 16-continued
| Ex. | Column 2 | Column 3 | CMPD |
|---|---|---|---|
| 625 | 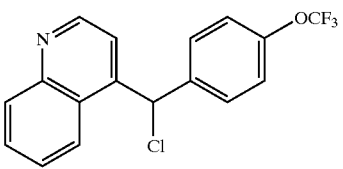 | 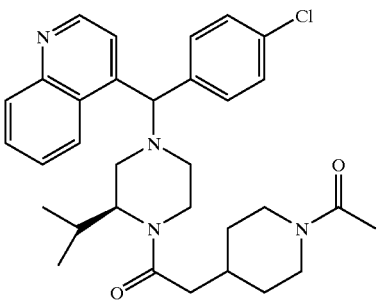 | LCMS:<br>MH$^+$ = 547;<br>mp = 116–122° C. |
| 626 | 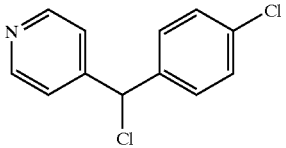 | 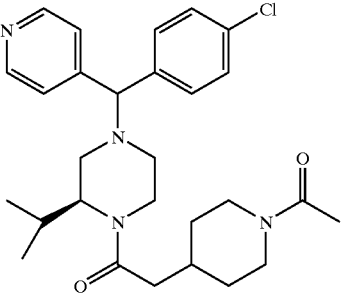 | LCMS:<br>MH$^+$ = 497. |
| 627 | 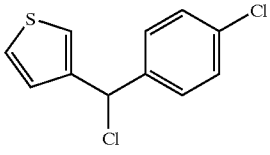 | 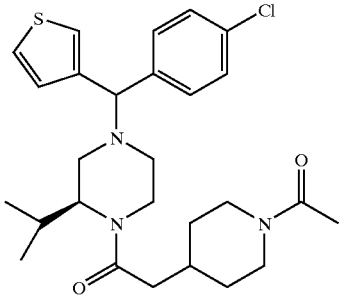 | LCMS:<br>MH$^+$ = 502;<br>mp = 77–85° C. |
| 628 | 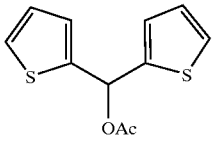 | 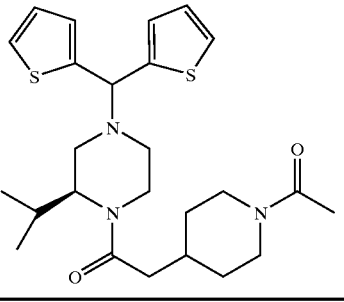 | LCMS:<br>MH$^+$ = 474;<br>mp = 50–56° C. |

EXAMPLE 629

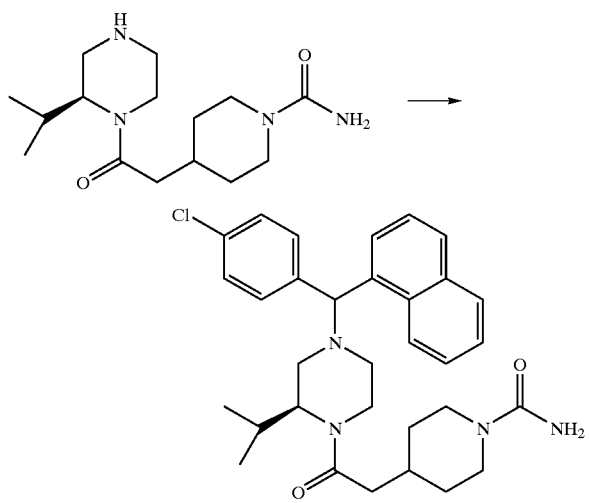

A mixture of the product from Preparative Example 240 (30 mg, 0.10 mmol), the product from Preparative Example 76 (30 mg, 0.11 mmol), NaI (15 mg, 0.10 mmol), and $K_2CO_3$ (60 mg, 0.45 mmol) in anhydrous $CH_3CN$ (1 mL) was stirred and refluxed under $N_2$ for 24 hrs. The mixture was poured into 5% $K_2CO_3$ (30 mL) and extracted with $CH_2Cl_2$ (3×10 mL). The combined extracts were dried over $Na_2SO_4$, the solvent was evaporated, and the residue was purified by flash chromatography using 11% MeOH (10% $NH_4OH$) in $CH_2Cl_2$ to give 27 mg (49%) of a solid. LCMS: $MH^+=547$; mp=128–138° C.

EXAMPLES 630–635

By essentially the same procedure set forth in Example 629, using the chlorides in column 2 of Table 17, the products in column 3, Table 17 (CMPD) were prepared.

TABLE 17

| Ex. | Column 2 | Column 3 | CMPD |
|---|---|---|---|
| 630 | | | LCMS: $MH^+$ = 548; mp = 141–145° C. |
| 631 | | | LCMS: $MH^+$ = 548; mp = 127–135° C. |
| 632 | | | LCMS: $MH^+$ = 548; mp = 143–147° C. |

TABLE 17-continued
| Ex. | Column 2 | Column 3 | CMPD |
|---|---|---|---|
| 633 | 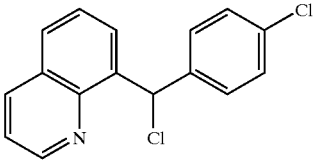 | 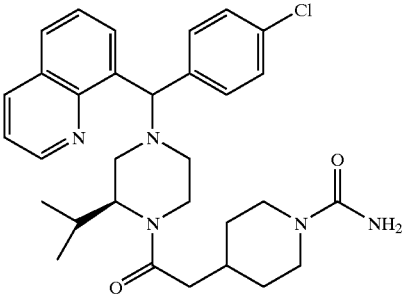 | LCMS:<br>MH⁺ = 548;<br>mp = 136–140° C. |
| 634 | 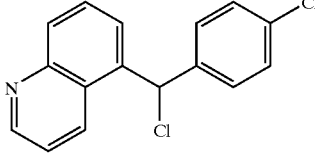 | 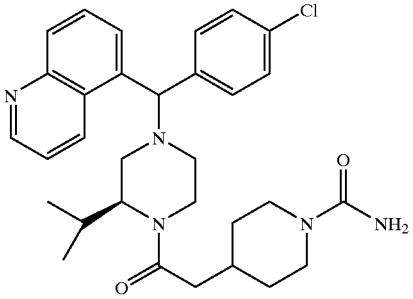 | LCMS:<br>MH⁺ = 548;<br>mp = 135–142° C. |
| 635 | 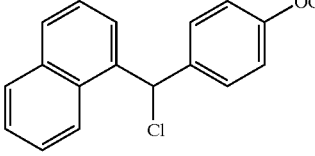 | 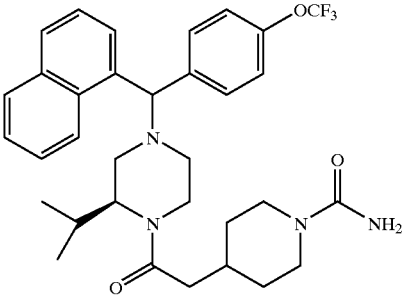 | LCMS:<br>MH⁺ = 597;<br>mp = 122–128° C. |
EXAMPLE 636
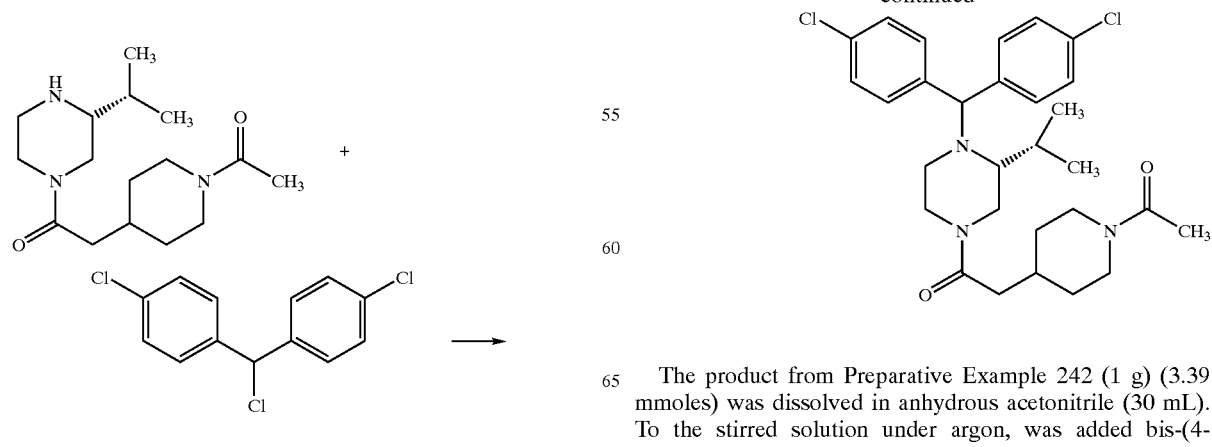
The product from Preparative Example 242 (1 g) (3.39 mmoles) was dissolved in anhydrous acetonitrile (30 mL). To the stirred solution under argon, was added bis-(4- chlorophenyl)methyl chloride (1.04 g (3.39 mmoles), anhydrous potassium iodide (562 mg) (3.39 mmoles) and anhydrous potassium carbonate (468 mg) (3.39 mmoles) and the mixture was stirred at 25° C. for 235 h. The mixture was poured into dichloromethane (800 mL) and extracted with saturated aqueous NaHCO$_3$. The aqueous phase was re-extracted with dichloromethane (300 mL) and the combined dichloromethane layers were dried (MgSO$_4$), filtered and evaporated to dryness. The residue was chromatographed on a silica gel column (25×5 cm) using 1.5% increasing to 6% (10% NH$_4$OH in methanol)-dichloromethane as the eluant to give the product (271.8 mg; 15%): HRFABMS: m/z 530.2329 (MH$^+$), calcd for C$_{29}$H$_{38}$Cl$_2$N$_3$O$_2$ m/z 530.2341; $[\alpha]_D^{25°\,C.}$+33.0° (c=2.600 mg/mL MeOH); $\delta_H$ (CDCl$_3$) 0.89 (3H,d, CH$_3$), 1.07 (3H, d, CH$_3$), 2.08 (3H, s, CH$_3$CON—), 5.22 (1H, s, Ar$_2$CH—) and 7.23–7.35 ppm (8H, m, ArH); $\delta_C$ (CDCl$_3$) CH$_3$: 19.2/19.5, 20.1, 21.7; CH$_2$: 32.2/33.0, 32.2/33.0, 39.2/39.4, 39.2/39.4, 37.8, 41.9/42.2, 43.1/43.7; CH: 26.6/27.0, 33.2, 46.8, 60.0, 66.1, 129.1/129.4, 129.1/129.4, 129.1/129.4, 129.1/129.4, 129.4/129.8, 129.4/129.8, 129.4/129.8, 129.4/129.8; C: 133.2/133.4, 133.2/133.4, 139.4/140.6, 139.4/140.6, 169.0, 170.3/170.6.

PREPARATIVE EXAMPLE 637

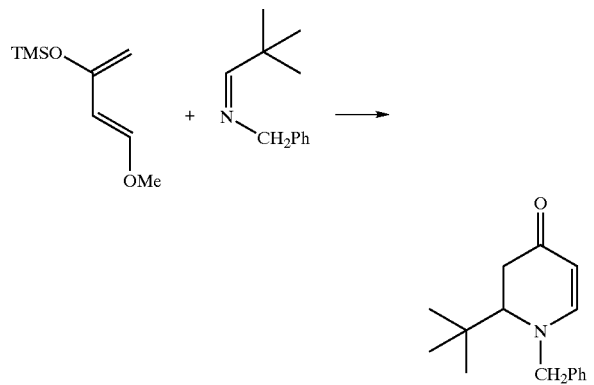

Benzylimine of pivalaldehyde (5.08 g, 29 mmol) was dissolved in anhydrous THF (10 mL), Danishefsky's diene (5.00 g, 29 mmol), then ZnCl$_2$ (0.5 M in THF, 58 mL, 29 mmol) were added under N$_2$. The mixture was stirred at rt for 4 hrs, poured into H$_2$O (500 mL), and extracted with EtOAc (4×50 mL). The combined extracts were washed with brine (100 mL), dried over Na$_2$SO$_4$, filtered, and the solvent was evaporated. Chromatography on silicagel with hexane:EtOAc (1:3) afforded pale yellow oil (2.68 g, 38%).

PREPARATIVE EXAMPLE 638

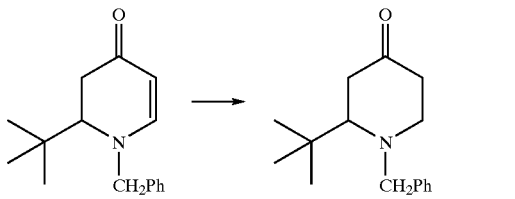

Solution of the product from Preparative Example 637 (2.50 g, 10.3 mmol) in anhydrous THF (50 mL) was stirred under N$_2$ at −78° C. L-Selectride (Aldrich), (1.0 M in THF, 10.3 mL, 10.3 mmol) was added slowly, the mixture was stirred at −78° C. for 1 hr, then at room temperature (rt) for 1 hr after which it was poured into H$_2$O (500 mL) and extracted with CH$_2$Cl$_2$ (4×50 mL). The combined extracts were washed with brine (100 mL), dried over Na$_2$SO$_4$, filtered, and the solvent was evaporated. Chromatography on silicagel with hexane:EtOAc (4:1) afforded a pale yellow solid (1.31 g, 52%).

PREPARATIVE EXAMPLE 639

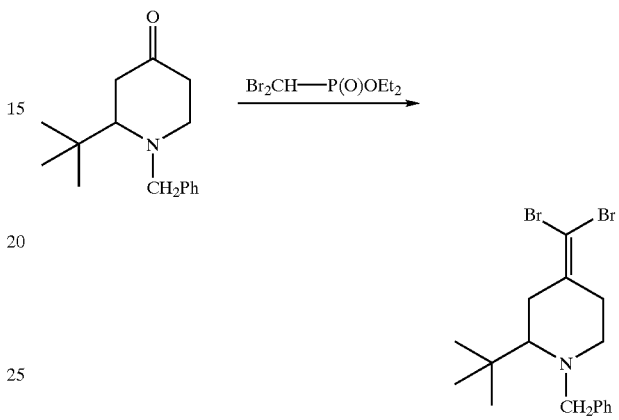

Diethyl(dibromomethyl)phosphonate (1.27 g, 4.10 mol) was dissolved under N$_2$ in anhydrous THF (10 mL) and the solution was cooled to −78° C. Lithium diisopropylamide (2.0 M in THF/heptane 1.70 mL, 3.4 mmol) was added and the solution was stirred at −78° C. for 30 min. Solution of the product from Preparative Example 638 was in dry THF (6 mL) was added and the mixture was stirred at −78° C. for 1 hr, then at rt for 6 days. The mixture was poured into H$_2$O (250 mL) and extracted with CH$_2$Cl$_2$ (3×50 mL). The combined extracts were dried over Na$_2$SO$_4$, filtered and the solvent was evaporated. Chromatography on silicagel with hexane:EtOAc (30:1) afforded a colorless oil (388 mg, 47%).

PREPARATIVE EXAMPLE 640

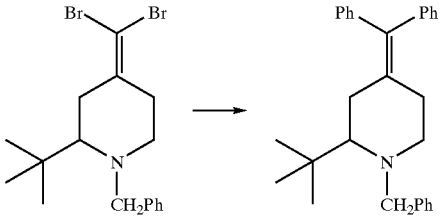

Dimethoxyethane (15 mL) and H$_2$O (3 mL) were added to a mixture of the product from Preparative Example 639 (388 mg, 0.97 mmol), phenylboronic acid (366 mg, 3.00 mmol), PdCl$_2$(PPh$_3$)$_2$ (140 mg, 0.20 mmol), and Na$_2$CO$_3$ (1.06 g, 10.0 mmol) and the mixture was stirred and refluxed under N$_2$ for 24 hr. The mixture was poured into H$_2$O (300 mL) plus brine (30 mL) and extracted with CH$_2$Cl$_2$ (5×40 mL). The combined extracts were dried over Na$_2$SO$_4$, filtered and the solvent was evaporated. Chromatography on silicagel with hexane:EtOAc (30:1) afforded a pale yellow oil (208 mg, 54%).

PREPARATIVE EXAMPLE 641 AND 642

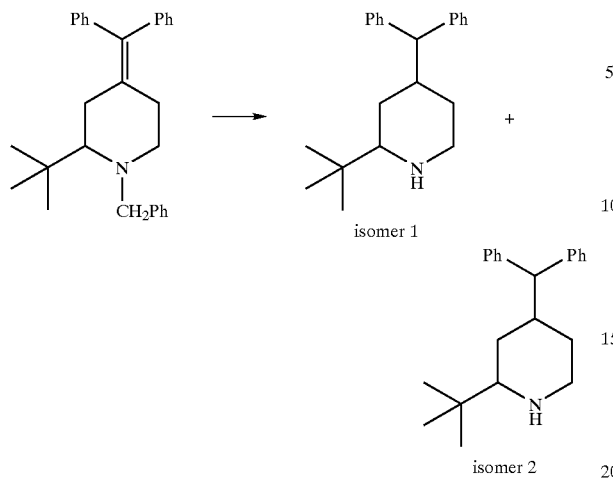

A solution of the product from Preparative Example 640 (208 mg, 0.52 mmol) in anhydrous EtOH (8 mL) and a solution of ammonium formate (756 mg, 12.0 mmol) in anhydrous MeOH (8 mL) were added under $N_2$ to 10% Pd/C (250 mg). The mixture was stirred at rt for 24 hr, then $CH_2Cl_2$ (100 mL) was added, the mixture was filtered through Celite, and the solvent was evaporated. Chromatography on silicagel with 20:1 $CH_2Cl_2$:MeOH/$NH_4OH$ (10/1) afforded 73 mg of a white solid (isomer 1=Preparative Example 641, fast eluting) and 20 mg of a colorless wax (isomer 2=Preparative Example 642, slow eluting). Both diastereomers are racemic.

PREPARATIVE EXAMPLE 643

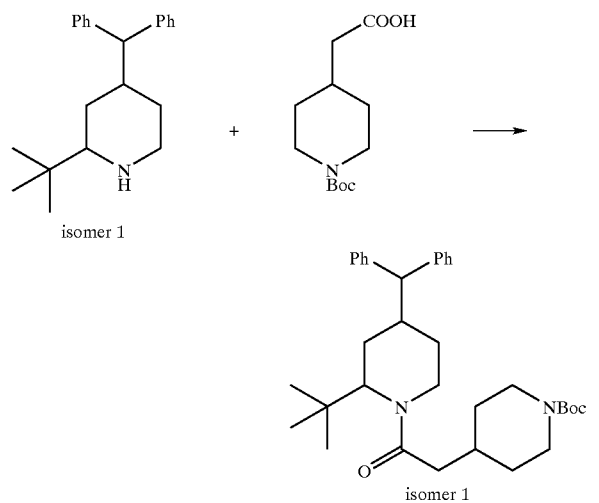

The product shown in the reaction above was prepared using the isomer 1 product of Preparative Example 641 by the procedure that is essentially identical to that described in Preparative Example 19 and afforded a colorless wax.

EXAMPLE 644

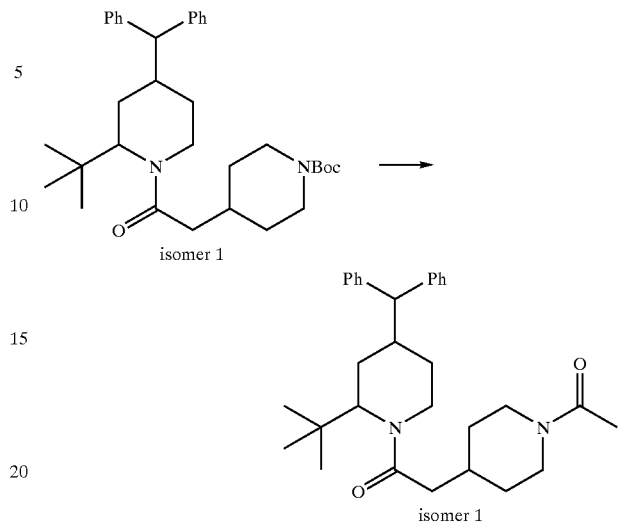

The product shown in the reaction above was prepared using the isomer 1 product from Preparative Example 643 by a procedure that is essentially identical to that described in Preparative Example 611 and afforded a colorless solid. LCMS: $MH^+=475$; mp=61–65° C.

EXAMPLE 645

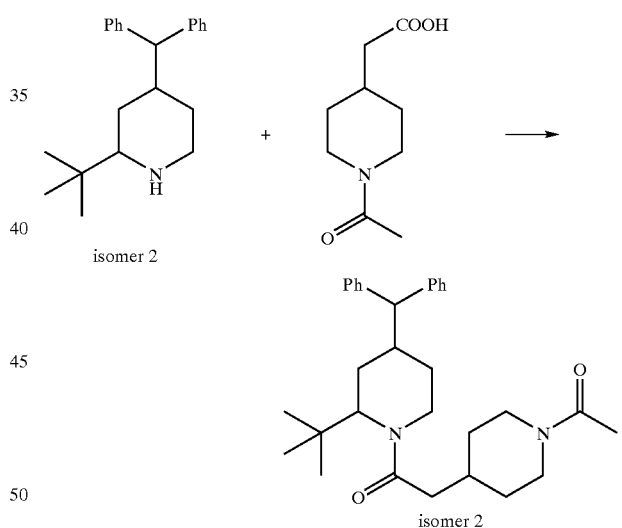

Acetylpiperidine acetic acid (85 mg, 0.50 mmol) was dissolved in anhydrous $PhCH_3$ (1 mL) and TEA (0.06 mL). To the solution was added pivaloyl chloride (0.05 mL) under $N_2$ at 0° C. and the mixture was stirred at 0° C. for 1 hr. A solution of the isomer 2 product from Preparative Example 642 (18 mg, 0.058 mmol) in anhydrous $PhCH_3$ (0.5 mL) was added, followed by TEA (0.10 mL) and the mixture was stirred at rt for 4 days. The mixture was poured into saturated aqueous $NaHCO_3$ (40 mL) and extracted with $CH_2Cl_2$ (4×15 mL). The combined extracts were dried over $Na_2SO_4$, filtered and the solvent was evaporated. Chromatography on silicagel with 50:1 $CH_2Cl_2$:MeOH/$NH_4OH$ (10/1) afforded 22 mg (79%) of a colorless solid. LCMS: $MH^+=475$; mp=49–54° C.

PREPARATIVE EXAMPLE 646 AND 647

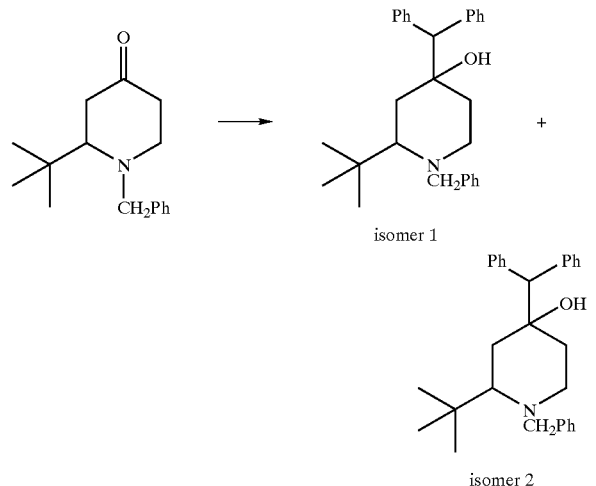

BuLi (2.5 M in hexanes, 3.5 mL, 8.75 mmol) was added under $N_2$ to a solution of diphenylmethane (1.68 g, 10.0 mmol) in anhydrous $Et_2O$ (25 mL). The solution was refluxed for 16 hr, cooled to rt, then a solution of the product from Preparative Example 638 (490 mg, 2.0 mmol) in $Et_2O$ (5 mL) was added and the mixture was stirred at rt for 6 hr. The mixture was poured into $H_2O$ plus brine and extracted with $CH_2Cl_2$. The combined extracts were dried over $Na_2SO_4$, filtered and the solvent was evaporated. Chromatography on silicagel afforded two colorless solids: first (isomer 1=Preparative Example 646 177 mg, 21%) eluted with 15:1 $CH_2Cl_2$:EtOAc, second (isomer 2=Preparative Example 647, 250 mg, 30%) eluted with 3:1 $CH_2Cl_2$:EtOAc.

PREPARATIVE EXAMPLE 648

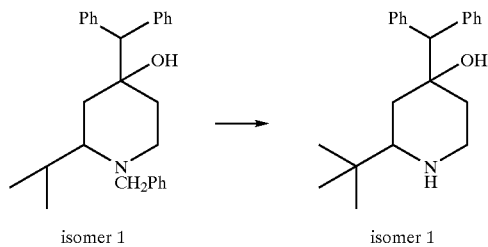

Anhydrous EtOH (3 mL) was added under $N_2$ to a mixture of the isomer 1 product from Preparative Example 646 (90 mg, 0.22 mmol), 10% Pd/C (40 mg) and ammonium formate (200 mg, 3.2 mmol). The mixture was stirred and refluxed for 6 hr, then $CH_2Cl_2$ (30 mL) was added and the mixture was filtered through Celite. The solvent was evaporated and the residue was purified by chromatography on silicagel with 20:1 $CH_2Cl_2$:MeOH/$NH_4OH$ (10/1). A white solid was obtained in an amount of 48 mg (69%).

PREPARATIVE EXAMPLE 649

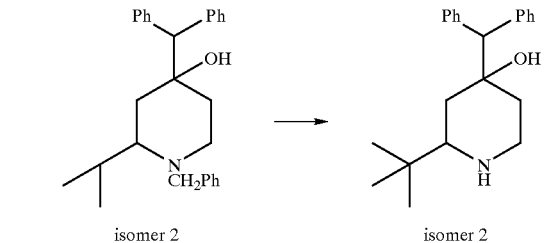

The product shown in the reaction above was prepared using the isomer 2 product of Preparative Example 647 by a procedure that is essentially identical to that described in Preparative Example 648 and afforded a colorless wax.

EXAMPLE 650

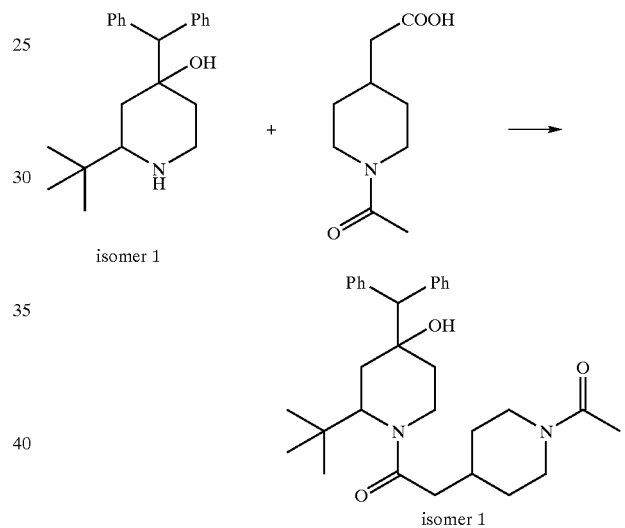

Acetylpiperidine acetic acid (85 mg, 0.50 mmol) was dissolved in anhydrous $PhCH_3$ (1 mL) and TEA (0.10 mL). To the solution was added pivaloyl chloride (0.05 mL) under $N_2$ at 0° C. and the mixture was stirred at 0° C. for 1 hr. A solution of the product from Preparative Example 648 (40 mg, 0.124 mmol) in anhydrous $PhCH_3$ (1.0 mL) was added, followed by TEA (0.30 mL) and the mixture was stirred at rt for 3 days. The mixture was poured into saturated aqueous $NaHCO_3$ (40 mL) and extracted with $CH_2Cl_2$ (4×15 mL). The combined extracts were dried over $Na_2SO_4$, filtered and the solvent was evaporated. The residue was dissolved in MeOH (5 mL), $H_2O$ (0.5 mL) was added, then KOH (250 mg) and the mixture was stirred at rt for 4 hr. The mixture was poured into saturated aqueous $NaHCO_3$ (40 mL) and extracted with $CH_2Cl_2$ (4×15 mL). The combined extracts were dried over $Na_2SO_4$ and the solvent was evaporated. Chromatography on silicagel with 30:1 $CH_2Cl_2$:MeOH/$NH_4OH$ (10/1) afforded 31 mg (51%) of white solid. LCMS: $MH^+$=491; mp=100–106° C.

EXAMPLE 651

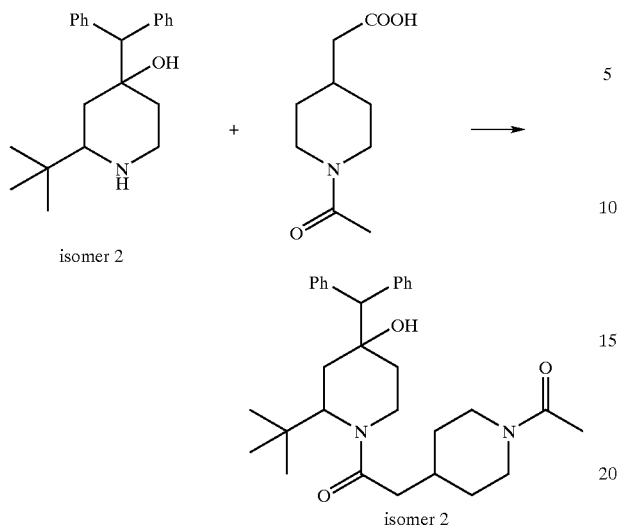

isomer 2

The product shown in the reaction above was prepared using the isomer 2 product of Preparative Example 649 by the procedure that is essentially identical to that described in Example 650 above and afforded a white solid. LCMS: MH$^+$=491; mp=108–115° C.

What is claimed is:

1. A compound of the formula (I):

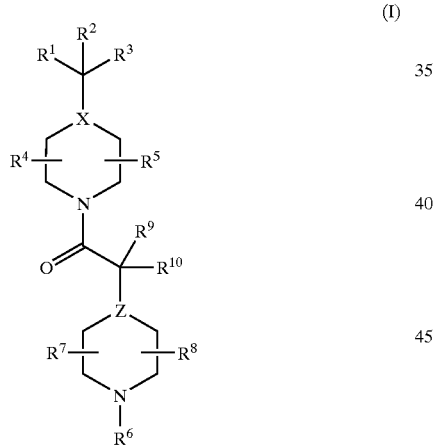

(I)

or a pharmaceutically acceptable salt of said compound wherein, $R^1$ and $R^2$ are the same or different and are independently selected from the group consisting of aryl, heteroaryl, arylalkyl and heteroarylalkyl, each optionally substituted with one to six groups selected from the group consisting of:

a) halogen;
b) —OCF$_3$ or —OCHF$_2$;
c) —CF$_3$;
d) —CN;
e) alkyl or R$^{18}$-alkyl;
f) heteroalkyl or R$^{18}$-heteroalkyl;
g) aryl or R$^{18}$-aryl;
h) heteroaryl or R$^{18}$-heteroaryl;
i) arylalkyl or R$^{18}$-arylakyl;
j) heteroarylalkyl or R$^{18}$-heteroarylalkyl;
k) hydroxy;
l) alkoxy;
m) aryloxy;
n) —SO$_2$-alkyl;
o) —NR$^{11}$R$^{12}$;
p) —N(R$^{11}$)C(O)R$^{13}$,
q) methylenedioxy;
r) difluoromethylenedioxy;
s) trifluoroalkoxy;
t) —SCH$_3$ or —SCF$_3$; and
u) —SO$_2$CF$_3$ or —NHSO$_2$CF$_3$;

$R^3$ is H, —OH, alkoxy or alkyl, provided that when X is N, $R^3$ is not —OH or alkoxy;

$R^4$, $R^5$, $R^7$ and $R^8$ are the same or different and are independently selected from the group consisting of H, OH, OR$^{14}$, —NR$^{11}$R$^{12}$, —N(R$^{11}$)C(O)R$^{13}$, alkyl, heteroalkyl, aryl, cycloalkyl, arylalkyl, heteroaryl, heteroarylalkyl, heterocycloalkyl,

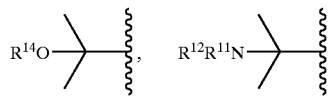

and

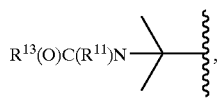

provided that when Z and/or X is N, then $R^4$, $R^5$, $R^7$ and $R^8$ are not OH, OR$^{14}$, —NR$^{11}$R$^{12}$, or —N(R$^{11}$)C(O)R$^{13}$;

$R^6$ is selected from the group consisting of —C(O)R$^{15}$ and —SO$_2$R$^{15}$;

$R^9$ and $R^{10}$ are the same or different and are independently selected from the group consisting of H, F, —CF$_3$, alkyl, cycloalkyl, arylalkyl, heteroalkyl, heteroarylalkyl, heterocycloalkyl, hydroxy, alkoxy, aryloxy, —NR$^{11}$R$^{12}$ and —N(R$^{11}$)C(O)R$^{13}$, provided that when Z is N, then $R^9$ and $R^{10}$ are each not F, hydroxy, alkoxy, aryloxy, —NR$^{11}$R$^{12}$ or —N(R$^{11}$)C(O)R$^{13}$;

$R^{11}$ is selected from the group consisting of H, alkyl, aryl and heteroaryl;

$R^{12}$ is selected from the group consisting of H, alkyl, aryl and heteroaryl;

$R^{13}$ is selected from the group consisting of alkyl, alkoxy and aryloxy;

$R^{14}$ is selected from the group consisting of H, alkyl, aryl and heteroaryl;

$R^{15}$ is selected from the group consisting of —NR$^{16}$R$^{17}$, —OR$^{16}$, alkyl, cycloalkyl, heterocycloalkyl, aryl, arylalkyl and heteroarylalkyl, each optionally substituted with R$^{18}$; R$^{16}$ and R$^{17}$ are the same or different and are independently selected from the group consisting of H, alkyl, aryl, arylalkyl, heteroalkyl and heteroaryl, each optionally substituted with R$^{18}$, provided that when $R^{15}$ is —OR$^{16}$, $R^{16}$ is not H;

$R^{18}$ is one to four substituents each independently selected from the group consisting of lower alkyl, halo, cyano, nitro, haloalkyl, hydroxy, alkoxy, alkoxy carbonyl, carboxy, carboxyalkyl, carboxamide, mercapto, amino, alkylamino, dialkylamino, sulfonyl, sulfonamido, cycloalkyl, heterocycloalkyl, heterocycloalkylalkyl, aryl and heteroaryl; and X is N and Z is C, wherein the term "heteroaryl" refers to 5- or 10-membered single or benzofused aromatic ring consisting of 1 to 3 heteroatoms independently selected from the group consisting of —O—, —S, and —N=, provided that the rings do not possess adjacent oxygen and/or sulfur atoms, wherein said heteroaryl can be unsubstituted or substituted with one, two, or three substituents independently selected from lower alkyl, halo, cyano, nitro, haloalkyl, hydroxy, alkoxy, carboxy, carboxyalkyl, carboxamide, mercapto, amino, alkylamino and dialkylamino; the term "heteroarylalkyl" refers to a heteroaryl group bonded through an alkyl group; the term "heterocycloalkyl" refers to a non-aromatic, heterocyclic ring of 3–7 atoms containing 1–3 heteroatoms selected from N, O and S; and the term "heteroalkyl" refers to an alkyl group containing at least one heteroatom.

2. The compound of claim 1 wherein:

$R^1$ and $R^2$ are the same or different and are independently selected from the group consisting of aryl and heteroaryl, each optionally substituted with one to six groups selected from the group consisting of:

a) halogen;
b) —OCF$_3$;
c) —CF$_3$;
d) —CN;
e) (C1–C20)alkyl or $R^{18}$—(C1–C20)alkyl;
f) heteroalkyl or $R^{18}$-heteroalkyl;
g) aryl or $R^{18}$-aryl;
h) heteroaryl or $R^{18}$-heteroaryl;
i) arylalkyl or $R^{18}$-arylalkyl;
j) heteroarylalkyl or $R^{18}$-heteroarylalkyl;
k) hydroxy;
l) alkoxy;
m) aryloxy;
n) —SO$_2$-alkyl;
o) —NR$^{11}$R$^{12}$;
p) —N(R$^{11}$)C(O)R$^{13}$;
q) methylenedioxy;
r) difluoromethylenedioxy;
s) trifluoroalkoxy;
t) —SCH$_3$; and
u) —SO$_2$CF$_3$;

$R^4$, $R^5$, $R^7$ and $R^8$ are the same or different and are independently selected from the group consisting of H, alkyl, heteroalkyl, aryl, cycloalkyl, arylalkyl, heteroaryl, heteroarylalkyl, heterocycloalkyl, —OR$^{14}$, —NR$^{11}$R$^{12}$,

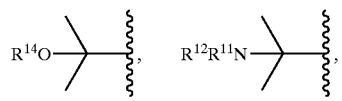

and

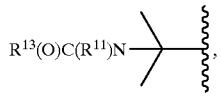

provided that $R^4$, $R^5$, $R^7$ and $R^8$ are each not —OR$^{14}$ or —NR$^{11}$R$^{12}$;

$R^{11}$ is selected from the group consisting of H and alkyl.

3. The compound of claim 1 wherein:

$R^1$ and $R^2$ are the same or different and are independently selected from the group consisting of aryl and heteroaryl, each optionally substituted with one to six groups selected from the group consisting of:

a) halogen;
b) —OCF$_3$;
c) —CF$_3$;
d). trifluoroalkoxy;
e) (C1–C6)alky or $R^{18}$—(C1–C6)alkyl;
f) heteroalkyl or $R^{18}$-heteroalkyl;
g) aryl or $R^{18}$-aryl;
h) arylalkyl or $R^{18}$-arylalkyl;
i) heteroarylalkyl or $R^{18}$-heteroarylalkyl;
j) alkoxy;
k) —SO$_2$-alkyl; and
l) —SO$_2$CF$_3$;

$R^4$, $R^5$, $R^7$ and $R^8$ are the same or different and are independently selected from the group consisting of H, alkyl, heteroalkyl, aryl, cycloalkyl, arylalkyl, heteroaryl, heteroarylalkyl, heterocycloalkyl, —OR$^{14}$, —NR$^{11}$R$^{12}$,

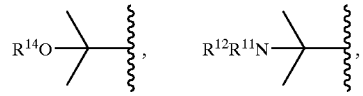

and

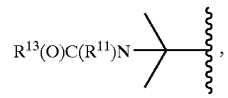

provided that $R^4$, $R^5$, $R^7$ and $R^8$ are each not —OR$^{14}$ or —NR$^{11}$R$^{12}$;

$R^{11}$ is selected from the group consisting of H and alkyl; and

Z is C.

4. The compound of claim 1 wherein, $R^1$ and $R^2$ are the same or different and are independently selected from the group consisting of aryl and heteroaryl, each optionally substituted with one to six groups selected from the group consisting of:

a) halogen;
b) —OCF$_3$;
c) —CF$_3$;
d) alkoxy;
e) trifluoroalkoxy;
f) (C1–C6)alkyl;
g) —SO$_2$-alkyl; and
h) —SO$_2$CF$_3$;

$R^3$ is H or —OH, provided that when X is N, $R^3$ is not —OH;

$R^4$ and $R^5$ are the same or different and are each independently selected from the group consisting of H, (C1–C6)alkyl, heteroalkyl and

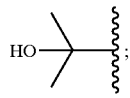

$R^7$ is selected from the group consisting of H, alkyl, —$OR^{14}$ and —$NR^{11}R^{12}$, provided that, $R^7$ is not —$OR^{14}$ or —$NR^{11}R^{12}$;

$R^8$ is selected from the group consisting of H, alkyl, aryl and heteroaryl; and $R^{11}$ is selected from the group consisting of H and alkyl.

5. The compound of claim 1 wherein:

$R^1$ and $R^2$ are the same or different and are independently selected from the group consisting of aryl and heteroaryl, each optionally substituted with one to six groups selected from the group consisting of:
a) halogen;
b) —$OCF_3$;
c) alkoxy;
d) trifluoroalkoxy;
e) —$CF_3$;
f) —$SO_2$-alkyl; and
g) —$SO_2CF_3$;

$R^3$ is H;

$R^4$ and $R^5$ are the same or different and are independently selected from the group consisting of H, (C1–C6)alkyl, heteroalkyl, and

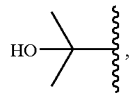

$R^6$ is selected from the group consisting of —C(O)$R^{15}$ and —$SO_2R^{15}$;

$R^7$ is selected from the group consisting of H, alkyl, —$OR^{14}$ and —$NR^{11}R^{12}$, provided that $R^7$ is not —$OR^{14}$ or —$NR^{11}R^{12}$;

$R^8$ is selected from the group consisting of H, alkyl, aryl and heteroaryl; and $R^{11}$ is H or alkyl.

6. The compound of claim 1 wherein, $R^1$ and $R^2$ are the same or different and are independently selected from the group consisting of phenyl and pyridyl, each optionally substituted with one to six groups selected from the group consisting of:
a) Br, F or Cl;
b) —$OCF_3$;
c) —$CF_3$;
d) methoxy;
e) ethoxy;
f) cyclopropylmethoxy;
g) —$OCH_2CF_3$;
h) —$SO_2$-alkyl; and
i) —$SO_2CF_3$ $R^3$ is H;

$R^4$ and $R^5$ are the same or different and are independently selected from the group consisting of H, methyl, ethyl, isopropyl, t-butyl and heteroalkyl;

$R^7$ is selected from the group consisting of H, —$OR^{11}$ and alkyl;

$R^8$, $R^9$, $R^{10}$, $R^{11}$, $R^{12}$ and $R^{14}$ are each independently selected from the group consisting of H and alkyl;

$R^{13}$ is alkyl;

$R^{15}$ is selected from the group consisting of —$NR^{16}R^{17}$, —$OR^{16}$ and alkyl and $R^{16}$ and $R^{17}$ are the same or different and are independently selected from the group consisting of H and alkyl, provided that when $R^{15}$ is —$R^{16}$, $R^{16}$ is not H.

7. A compound, or a pharmaceutically acceptable salt of the compound, said compound being selected from the group consisting of:

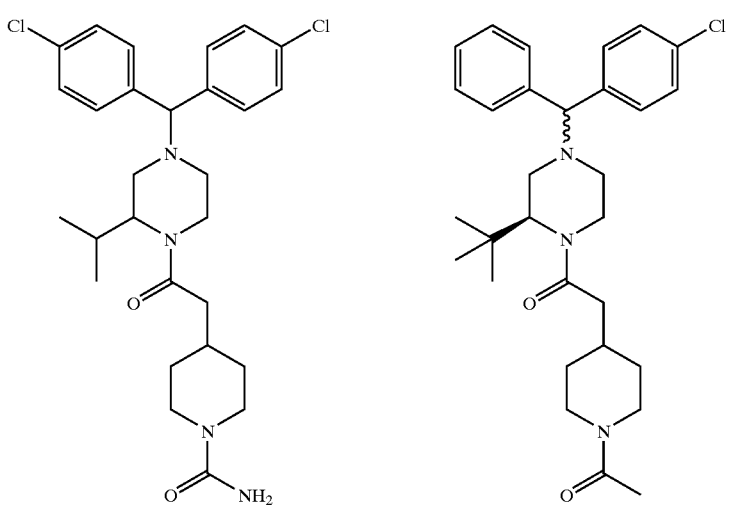

-continued
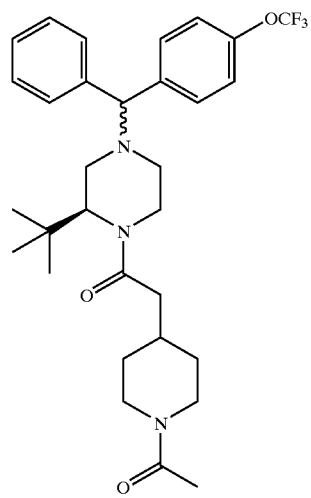 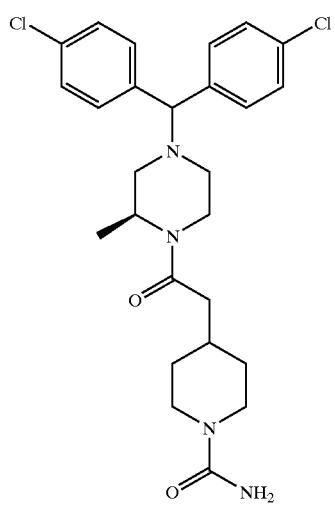
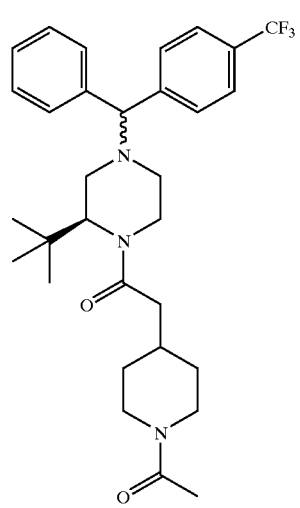 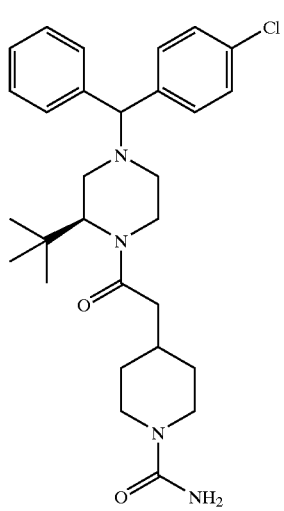
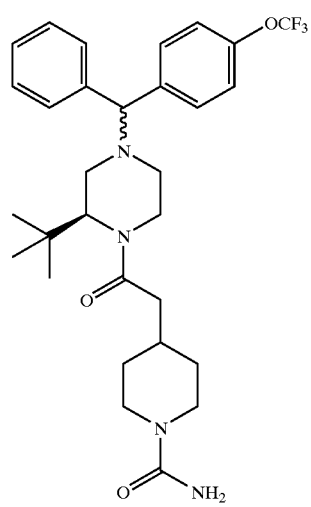 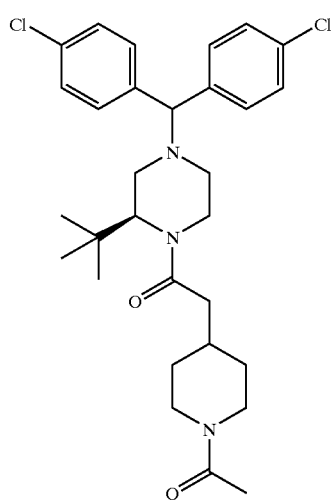

-continued
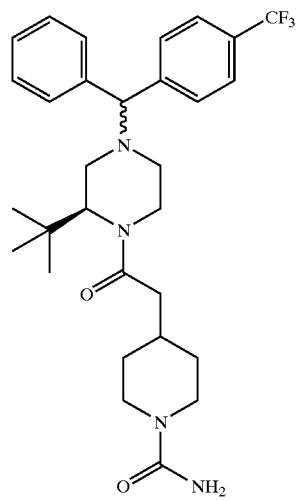 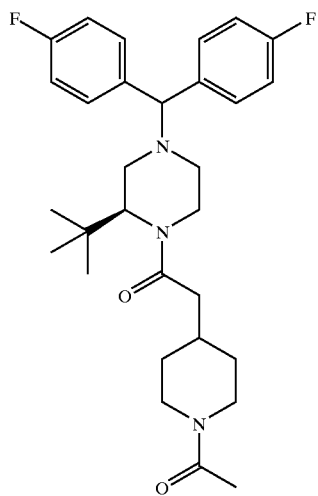
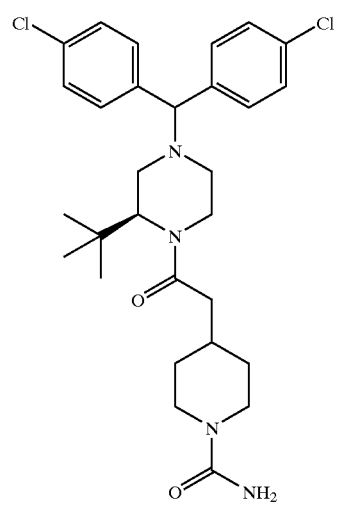 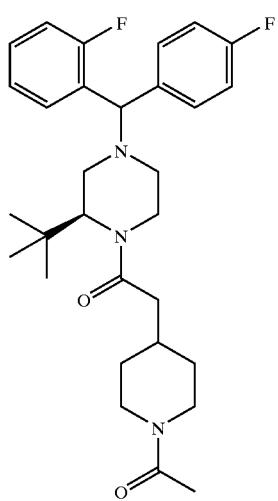
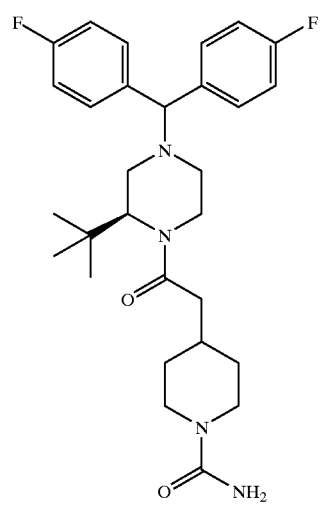 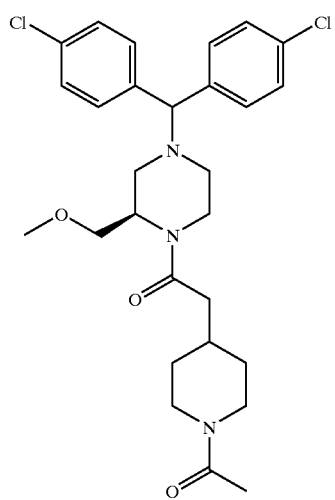

-continued
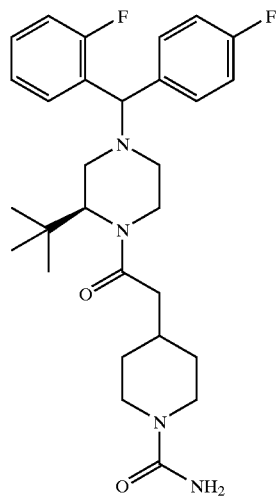
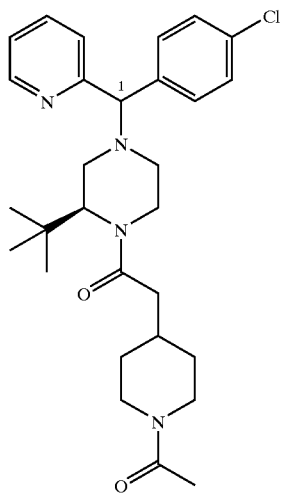
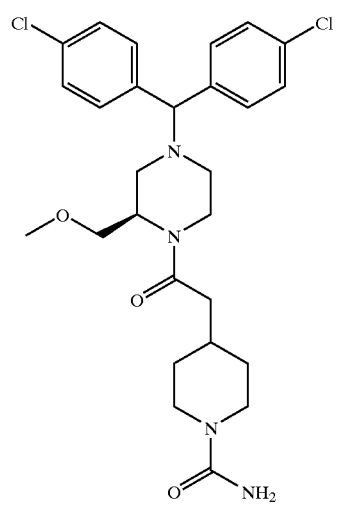
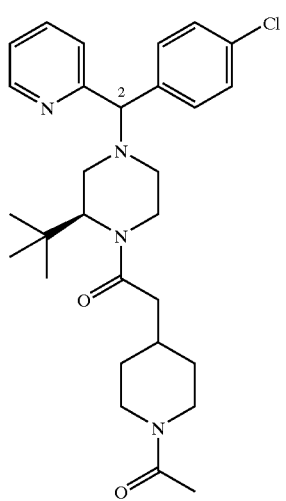
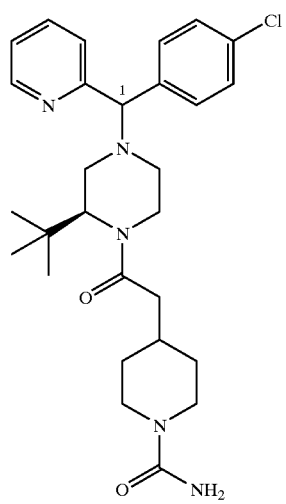
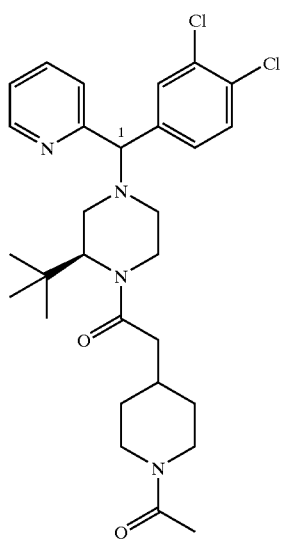

-continued
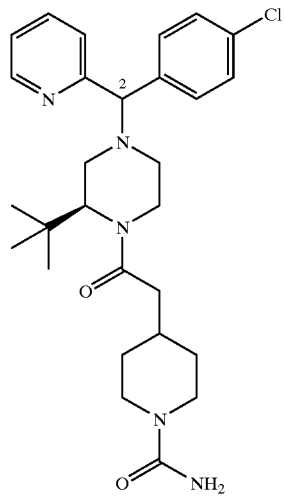
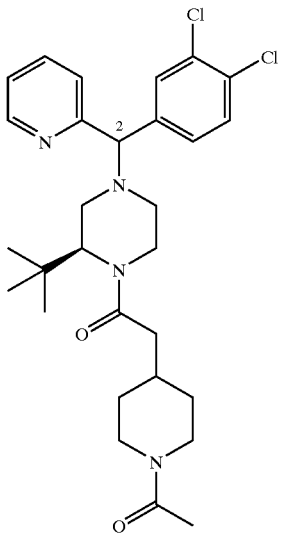
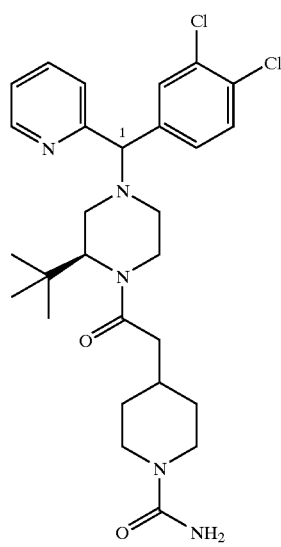
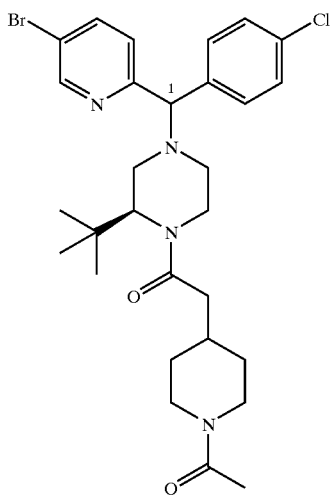
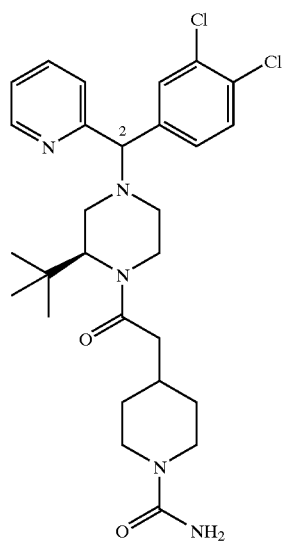
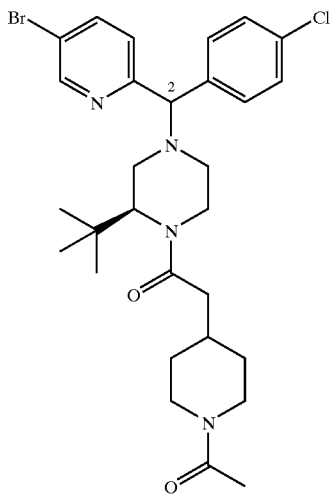

-continued
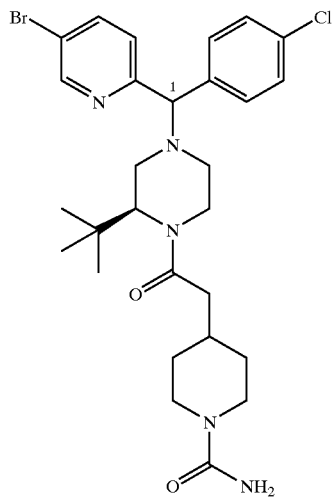 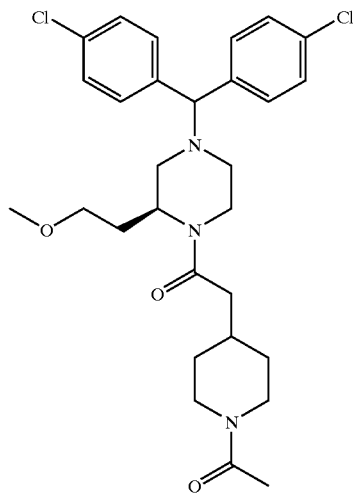
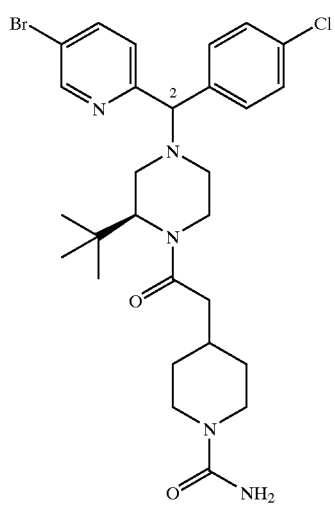 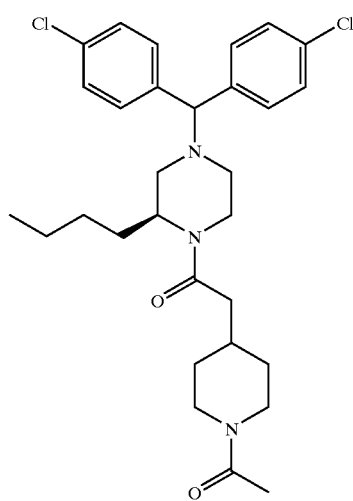
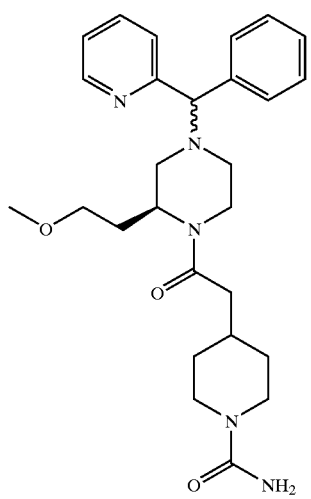 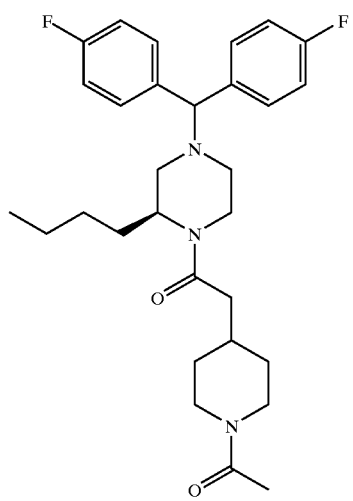

-continued
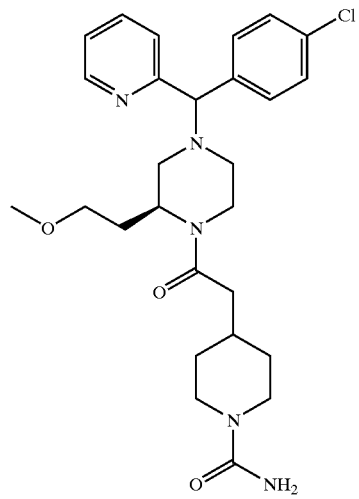 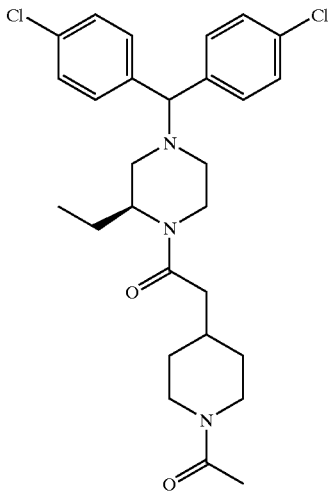
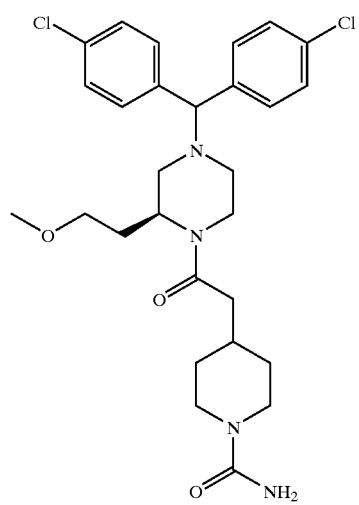 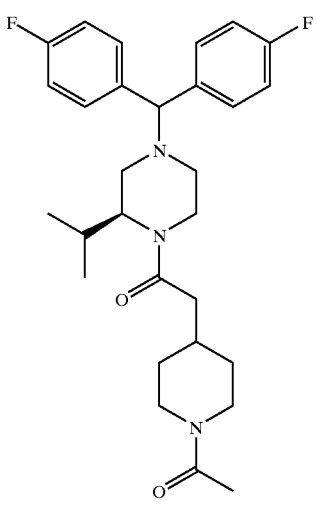
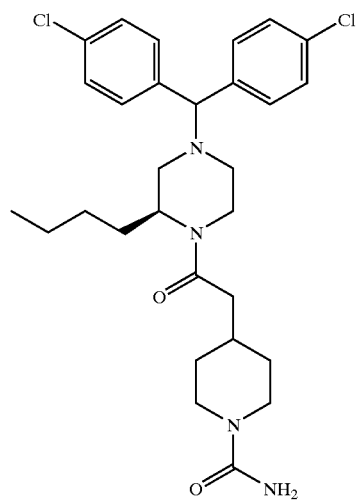 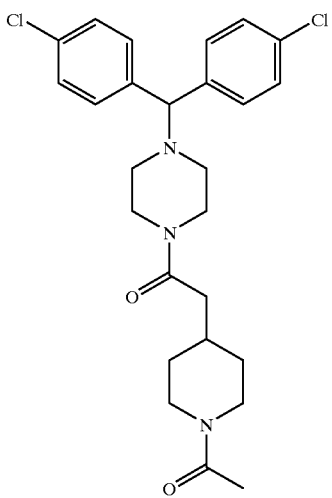

-continued
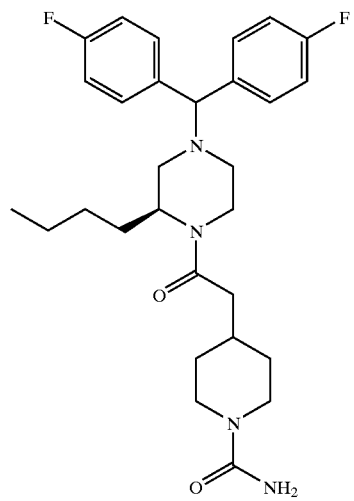 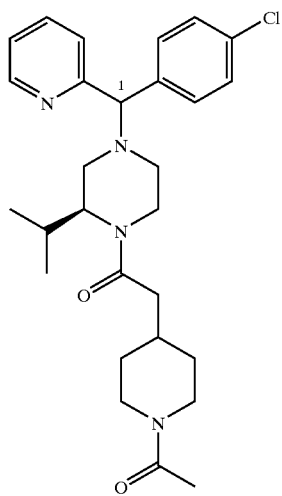
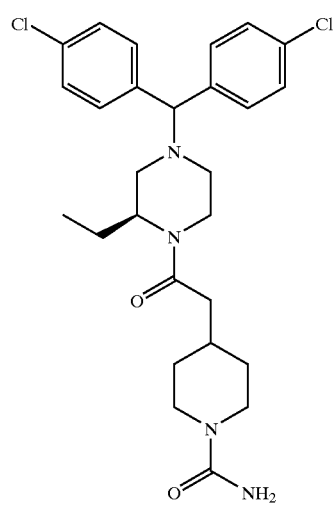 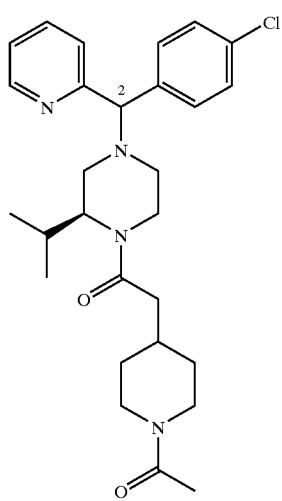
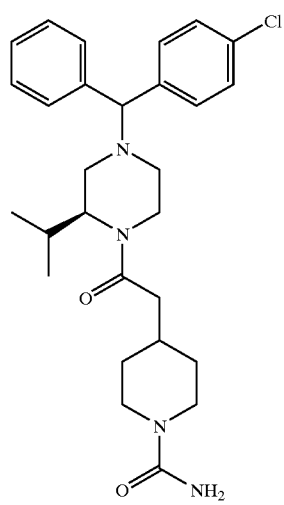 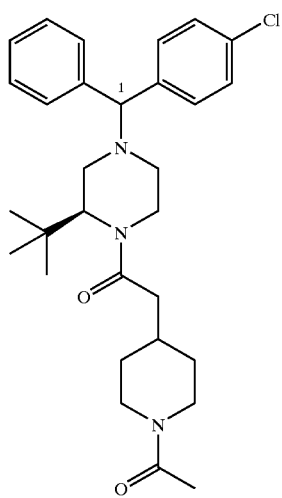

-continued
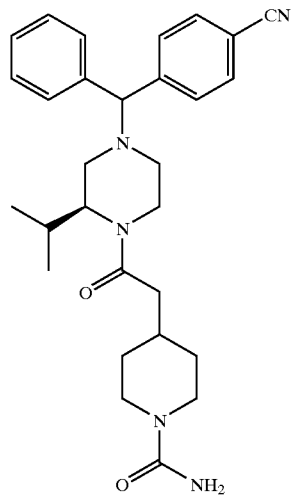
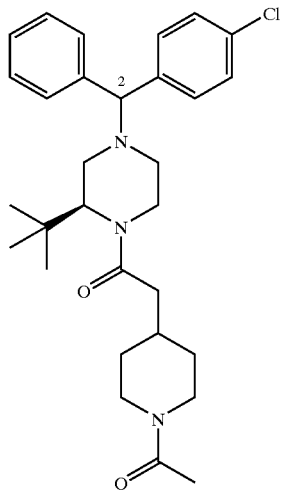
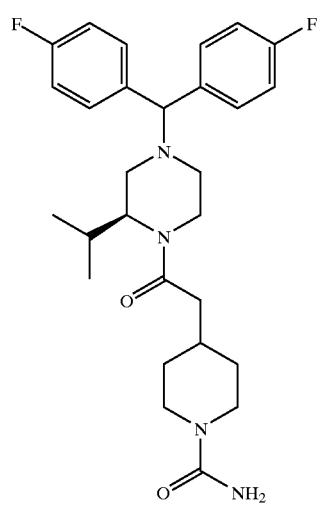
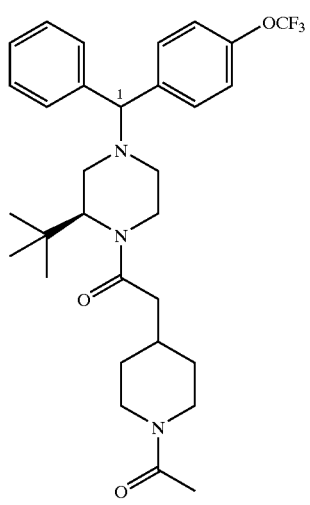
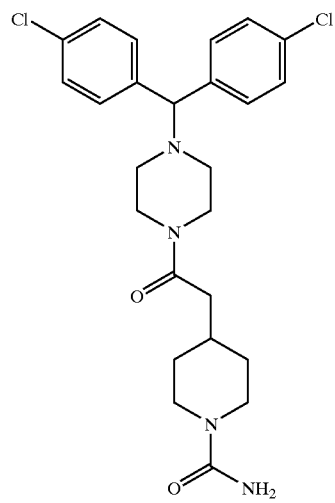
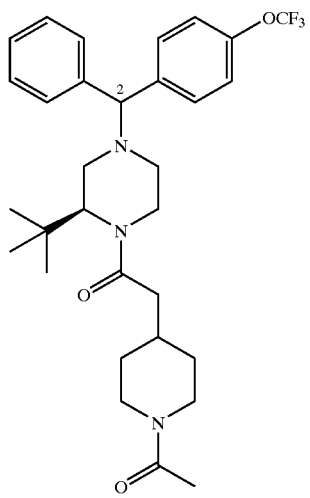

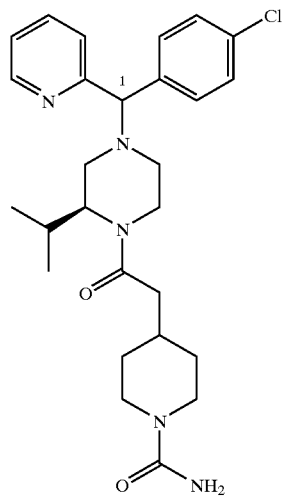
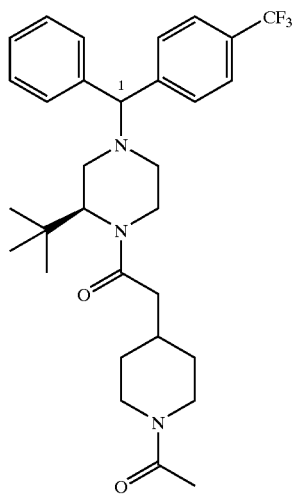
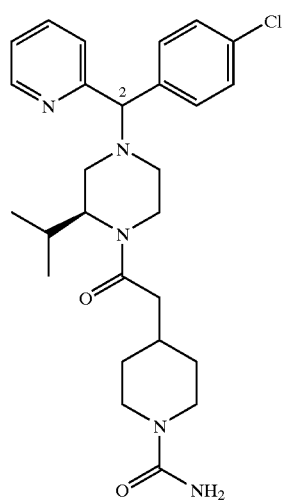
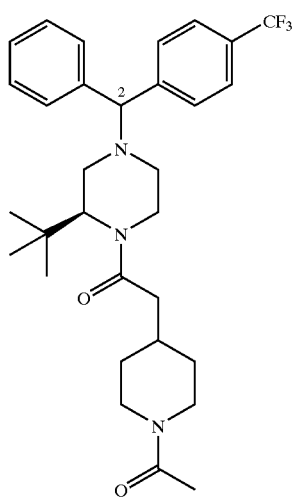
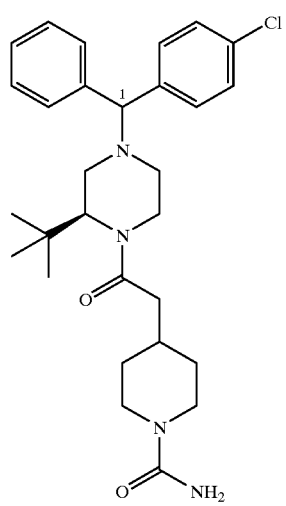
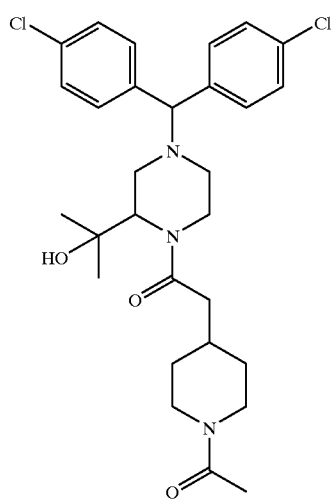

-continued
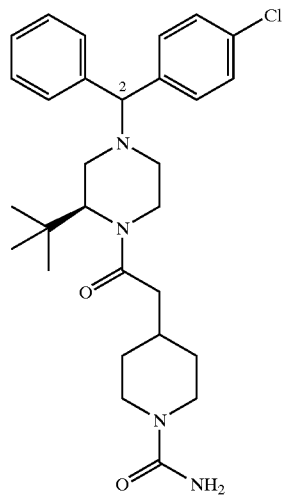
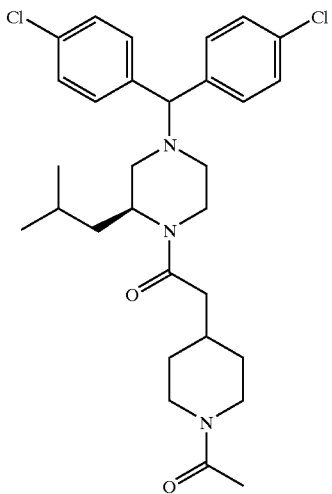
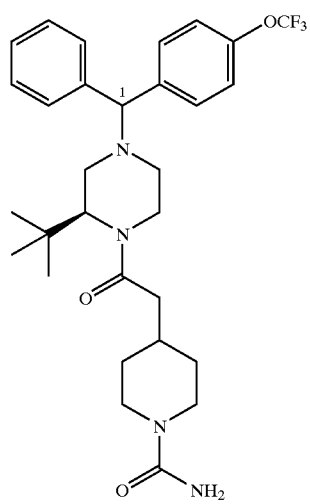
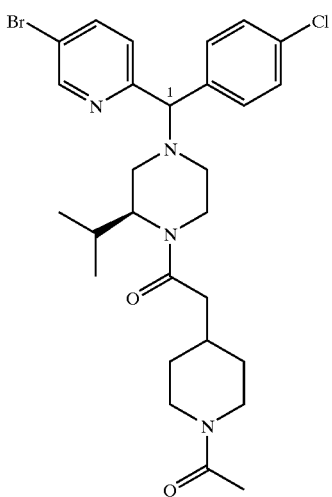
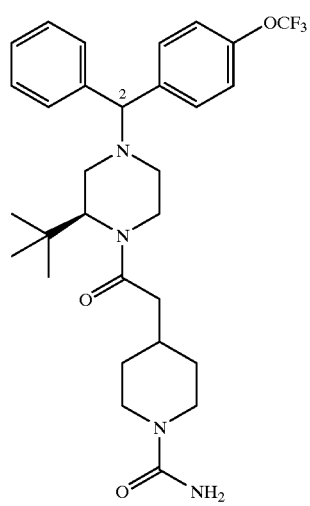
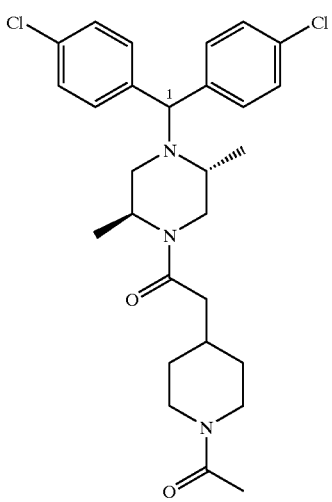

-continued
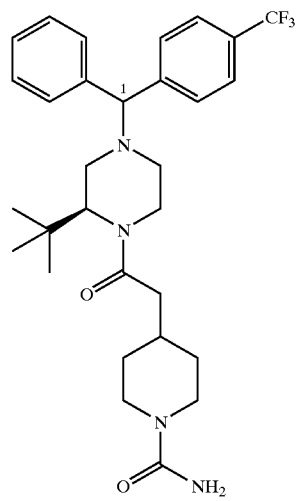
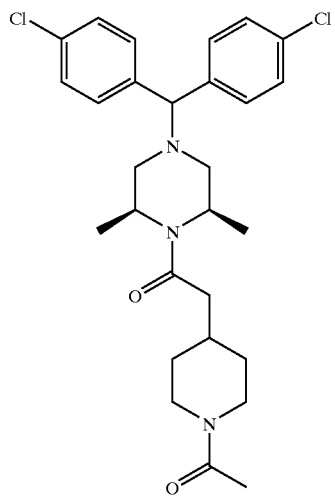
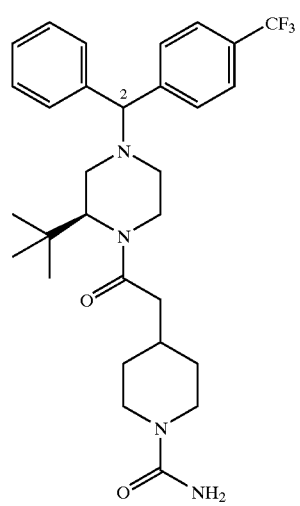
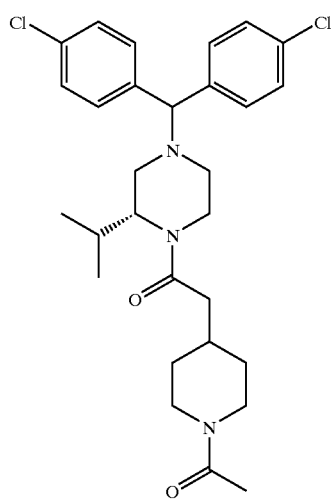
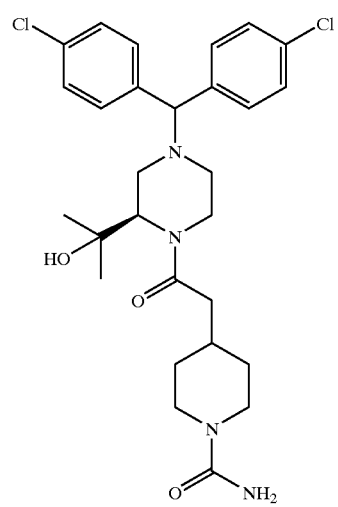
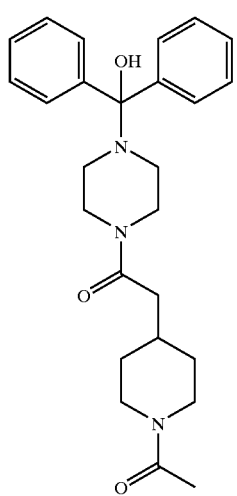

-continued
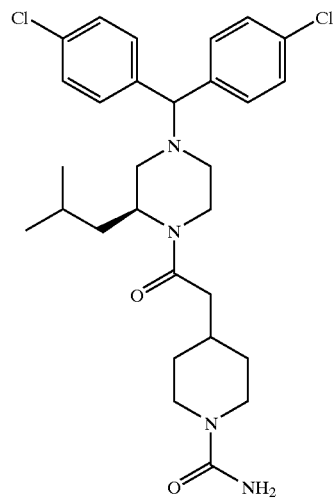
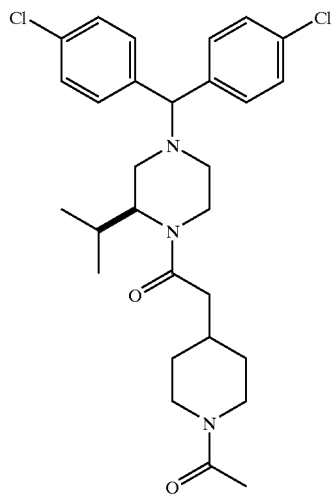
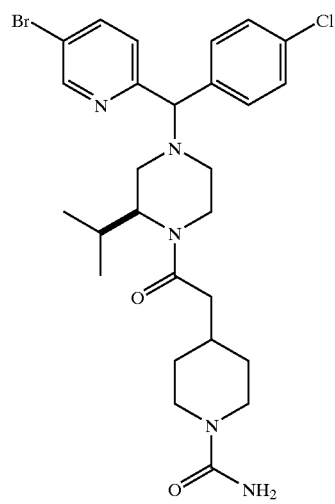
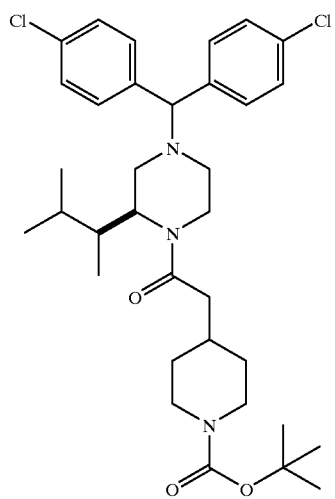
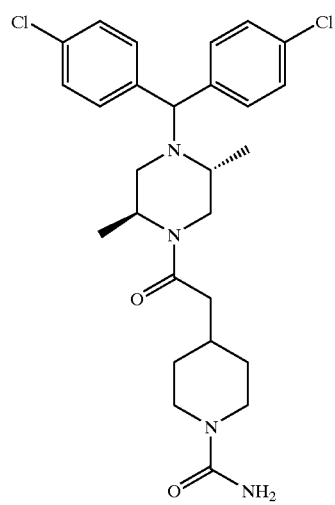
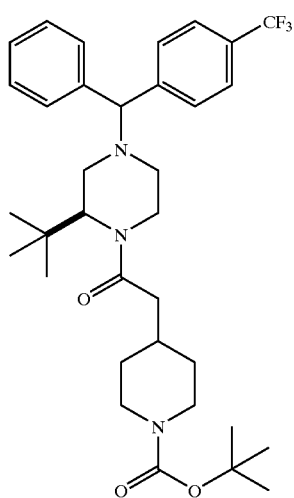

-continued
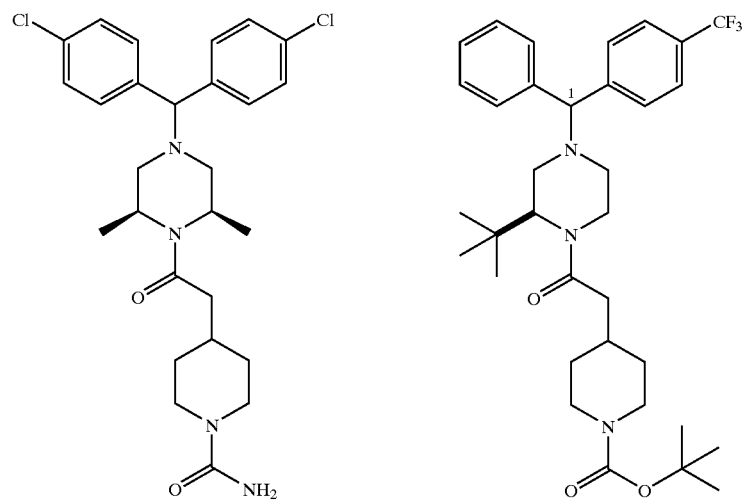
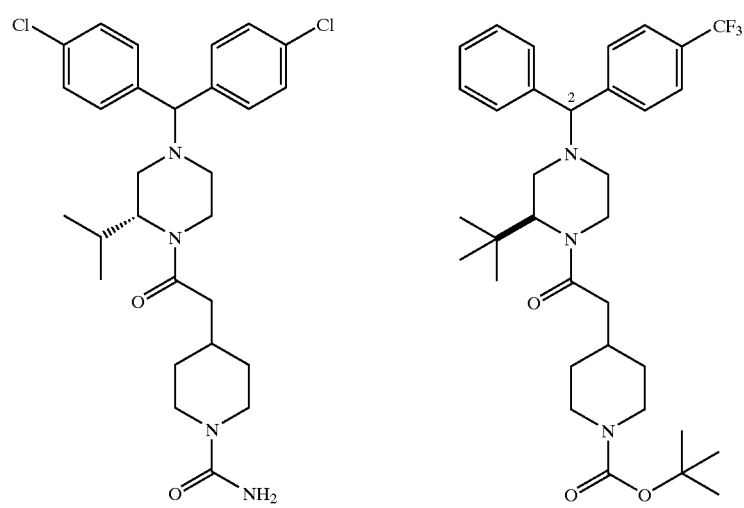
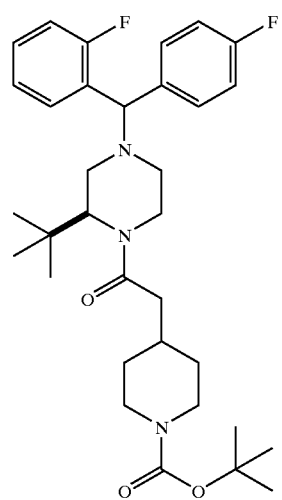

-continued
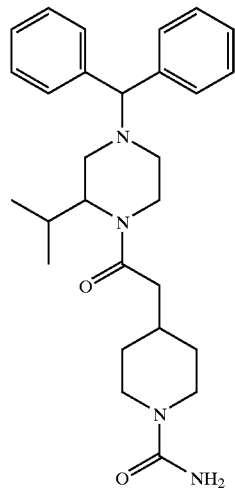 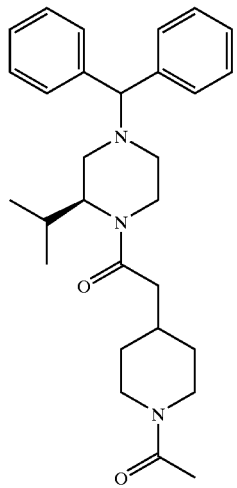
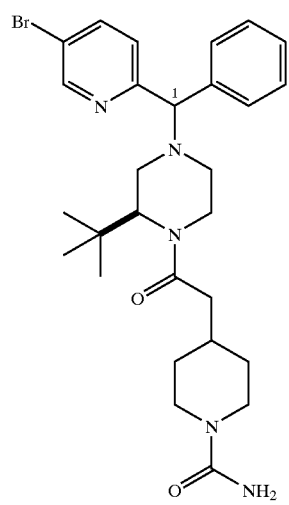 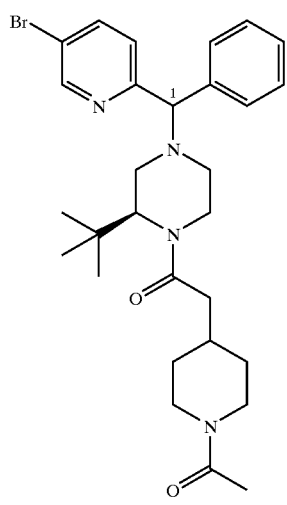
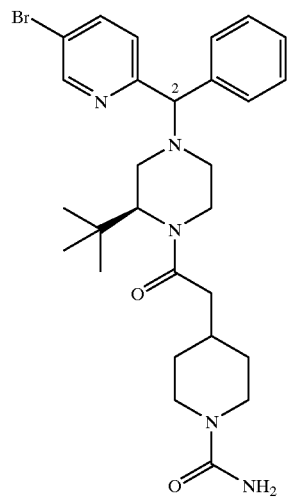 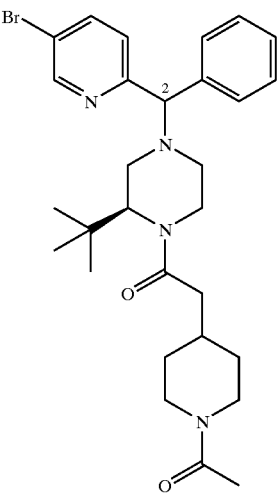

-continued
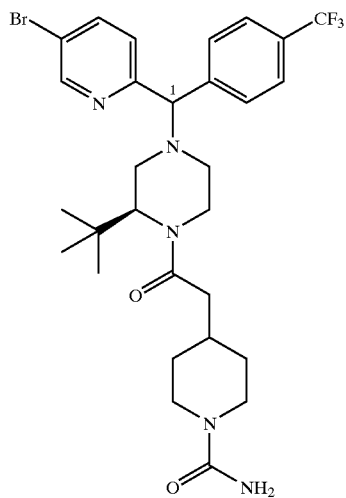
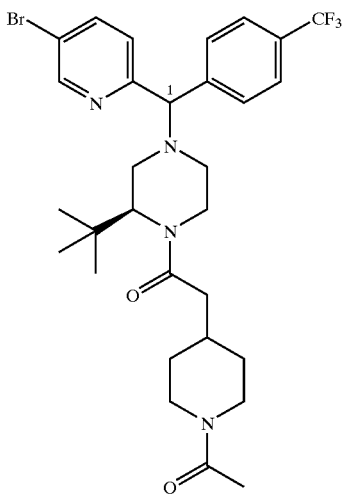
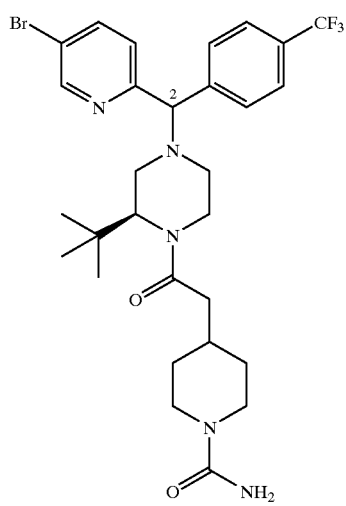
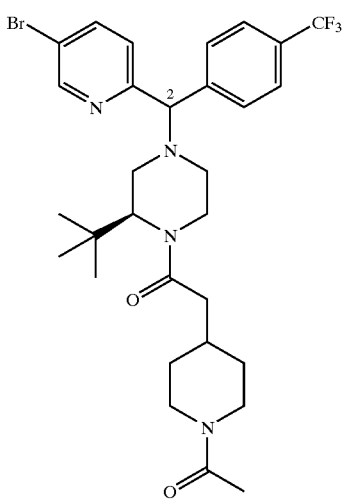
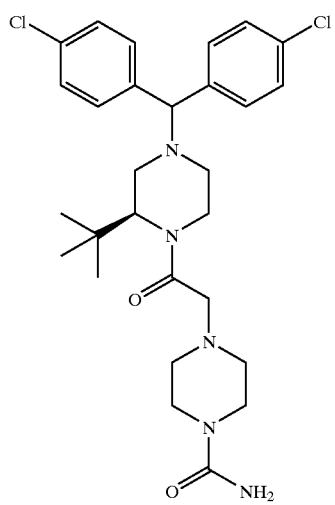
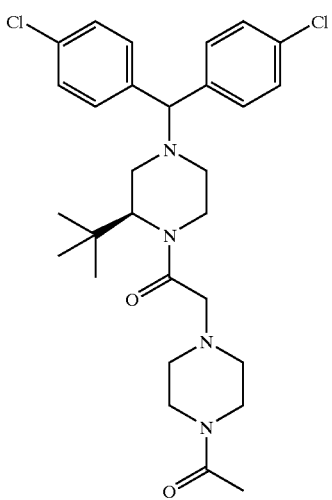

-continued
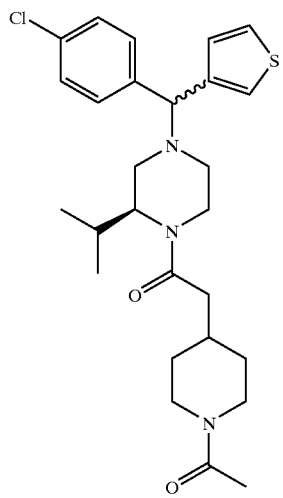 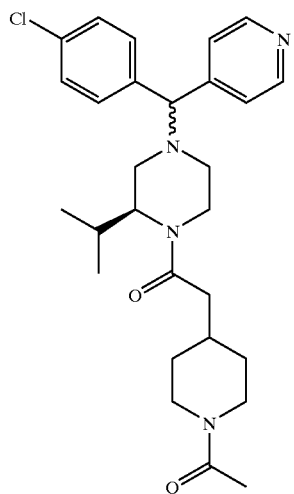
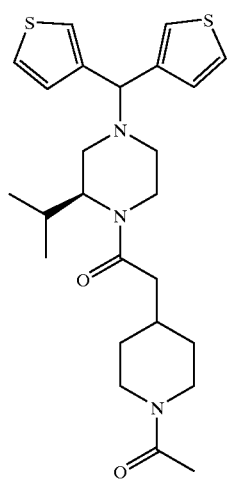 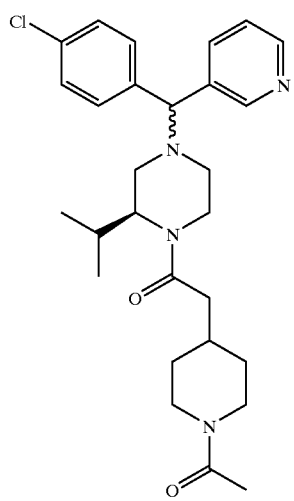
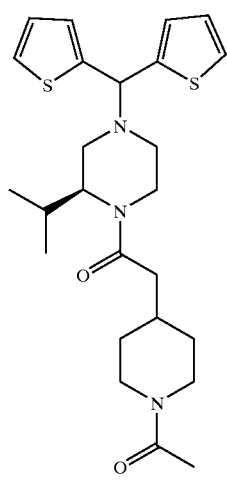 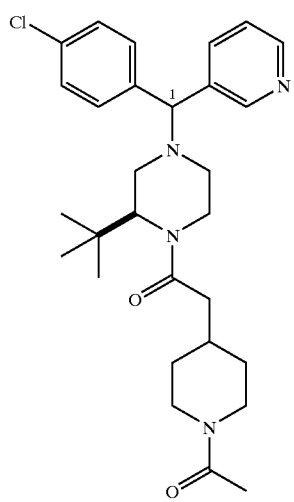

-continued
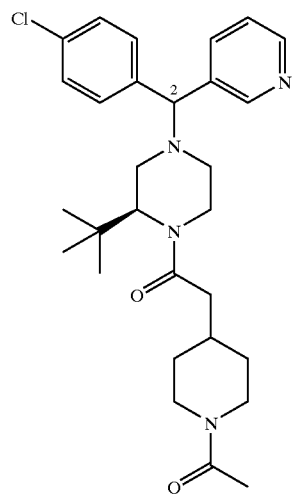
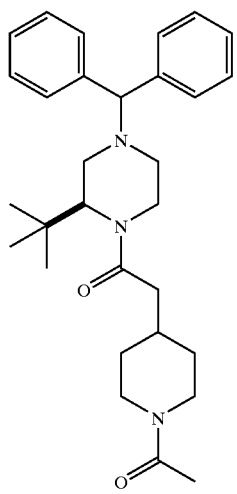
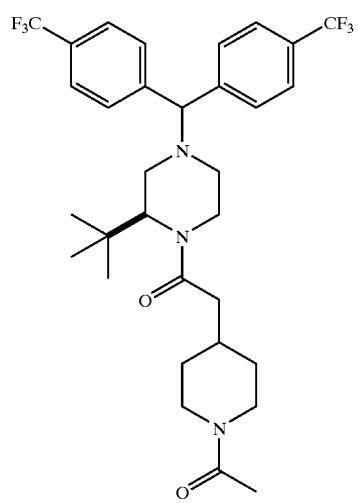
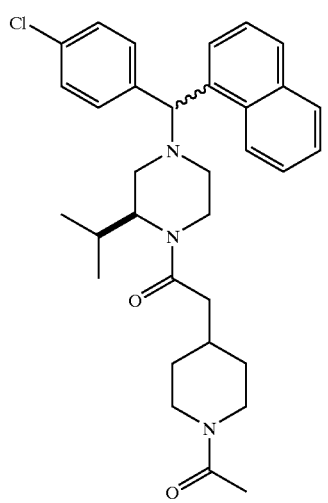
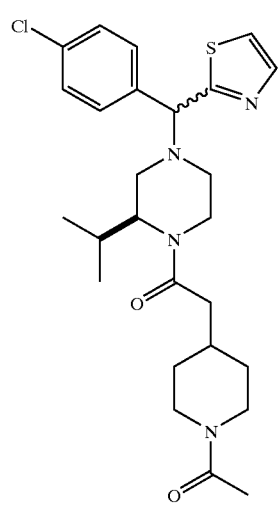
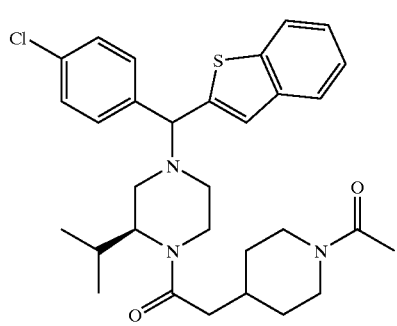

-continued
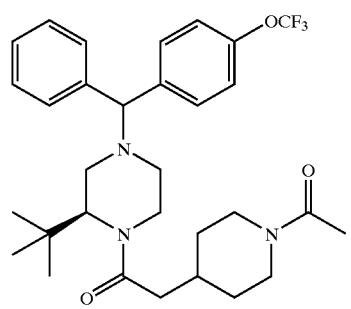
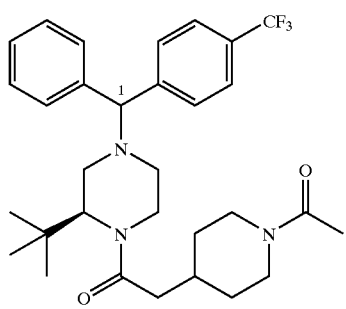
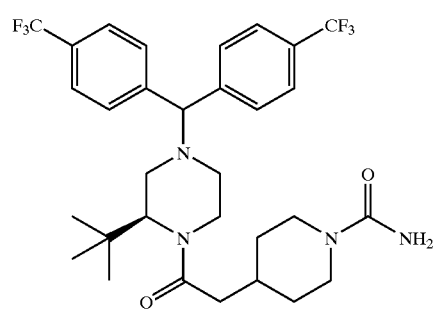
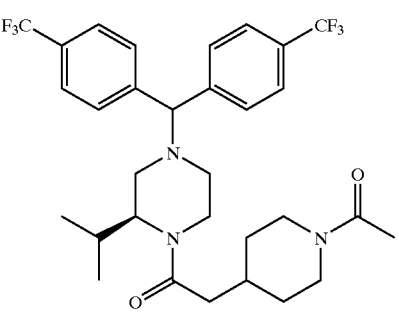
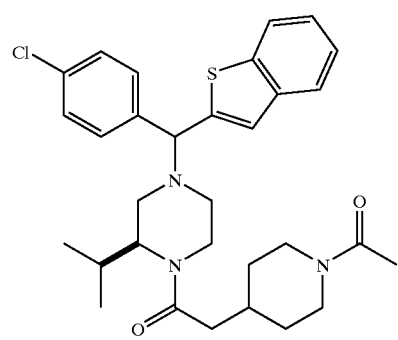
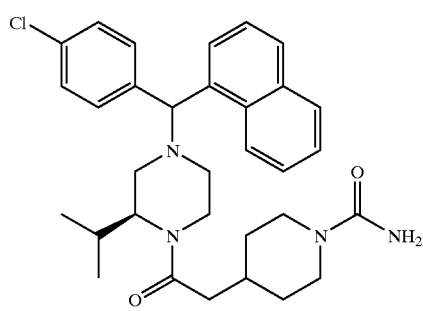
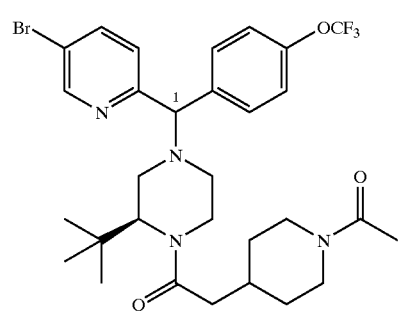
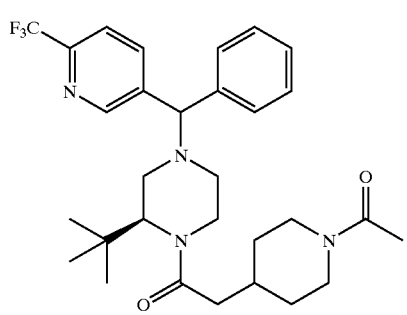
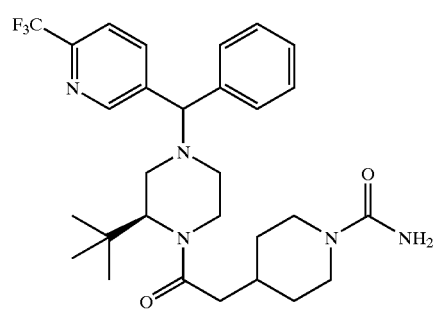
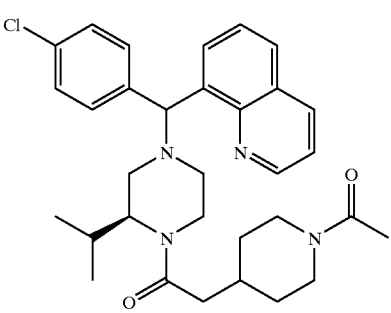

-continued
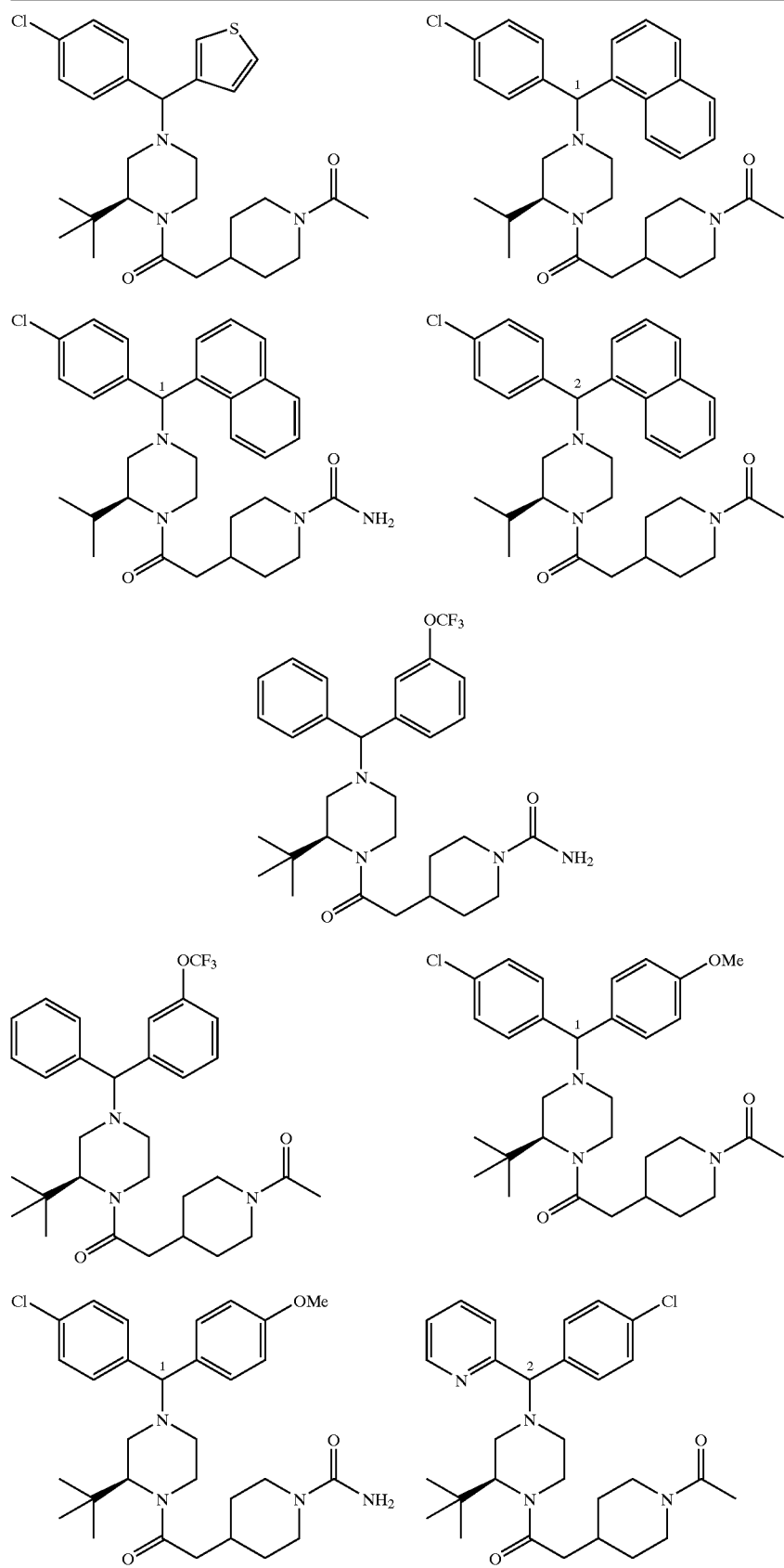

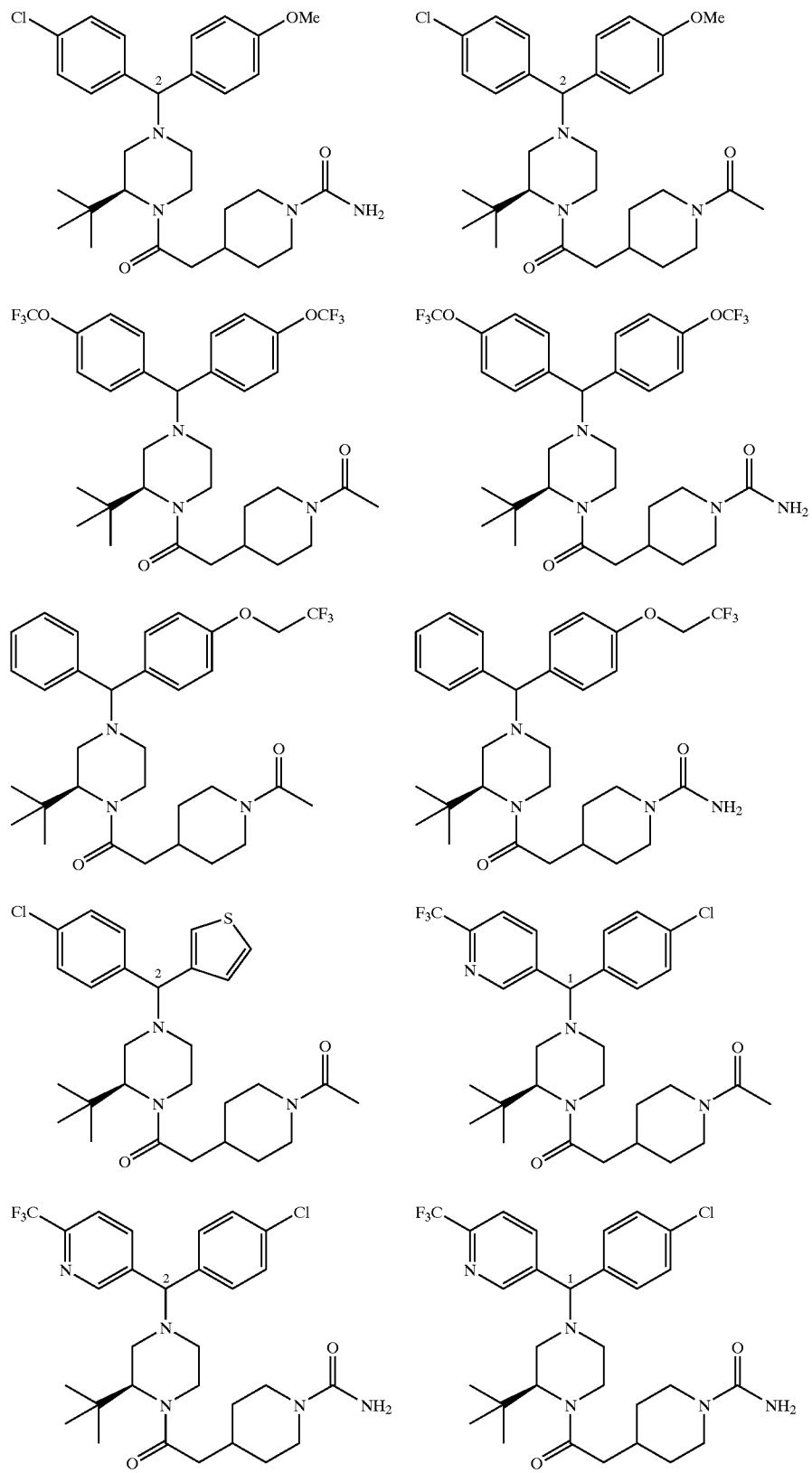

-continued
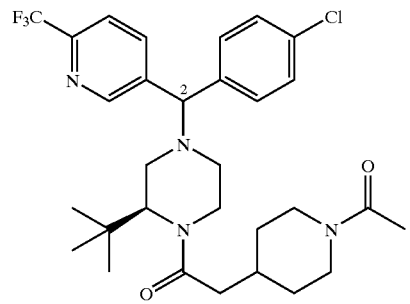 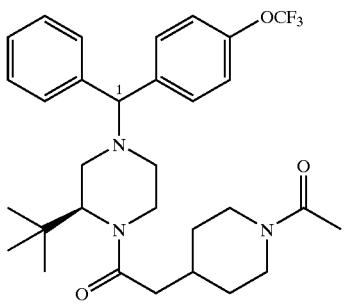
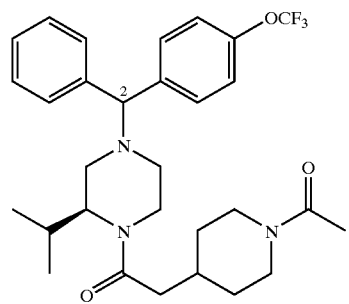 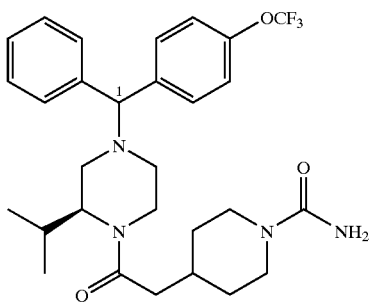
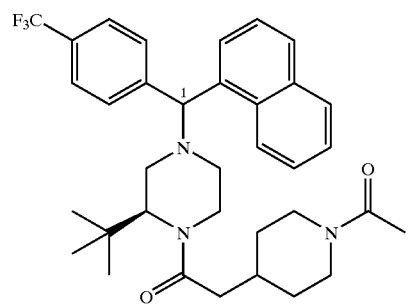 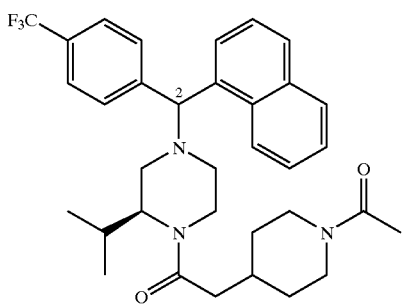
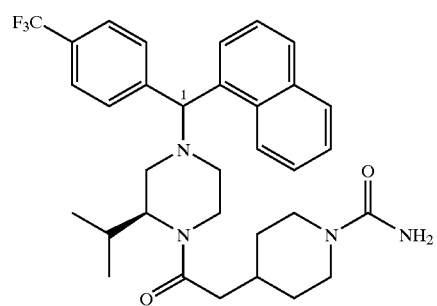 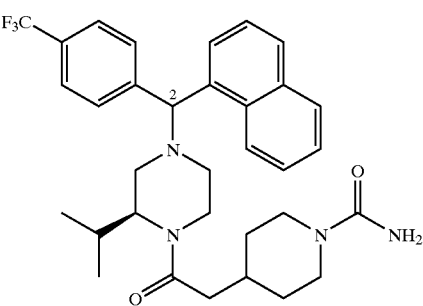
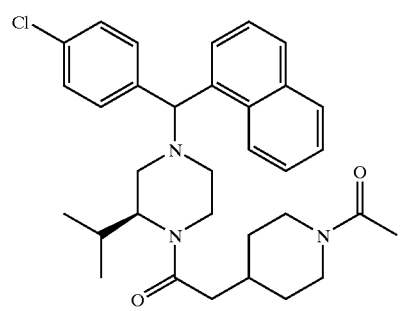

-continued
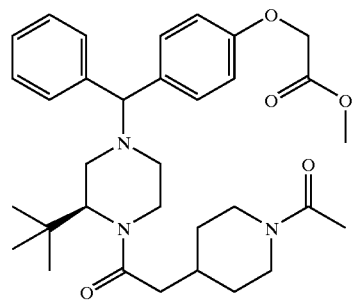 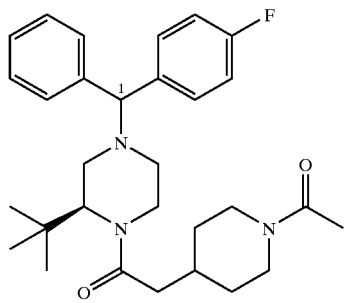
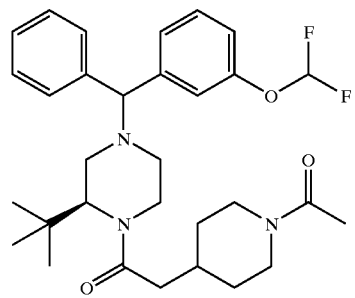 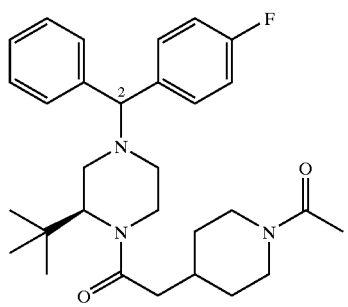
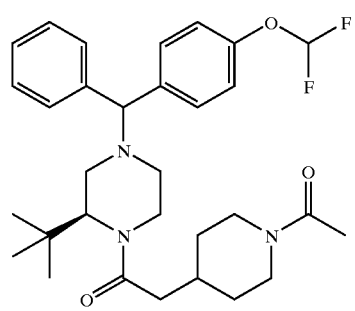 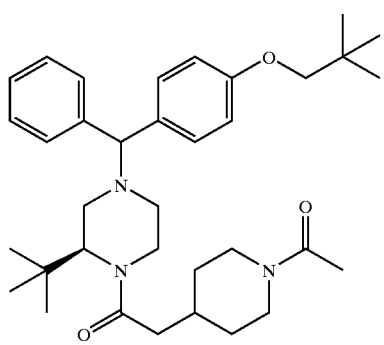
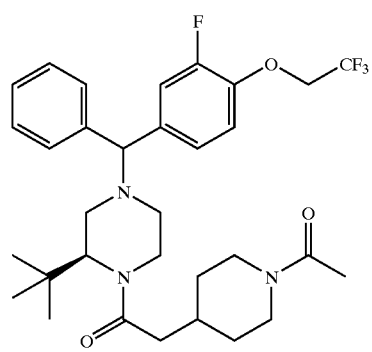 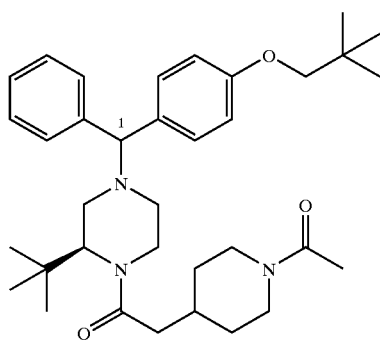

-continued
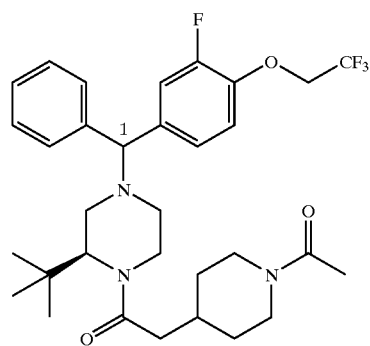
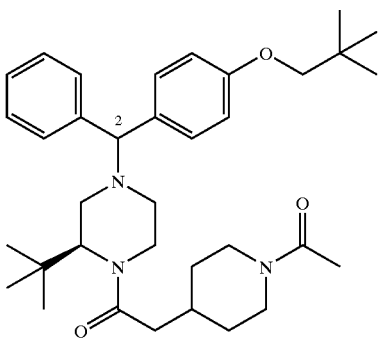
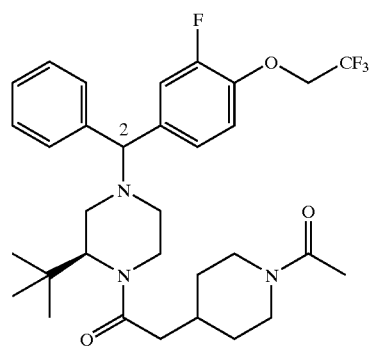
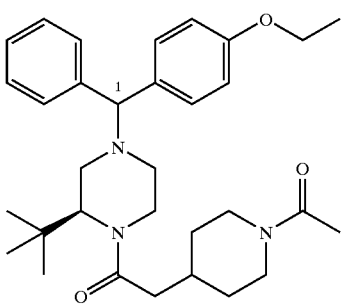
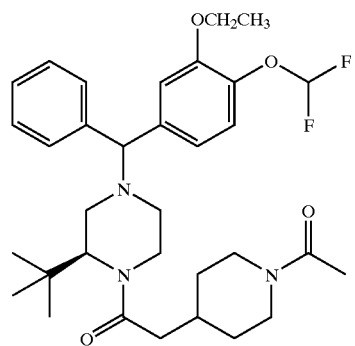
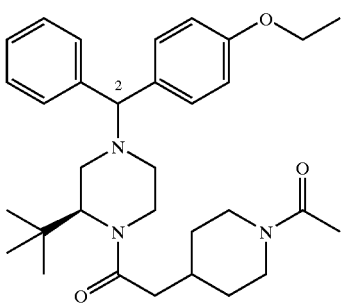
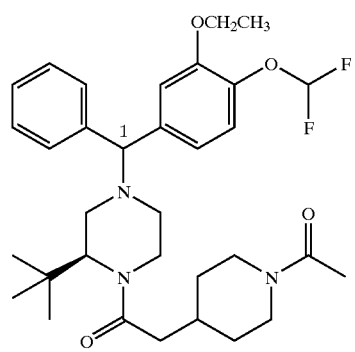
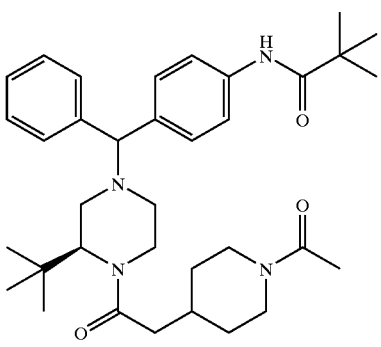

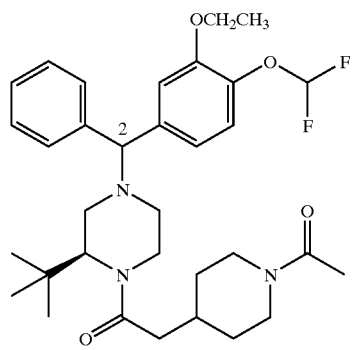
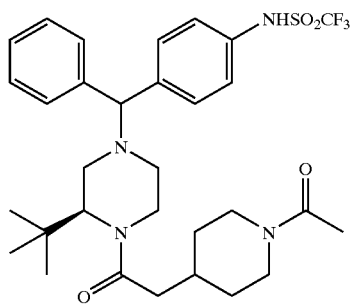
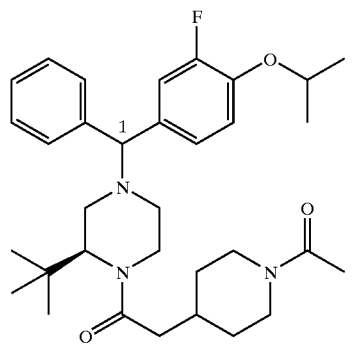
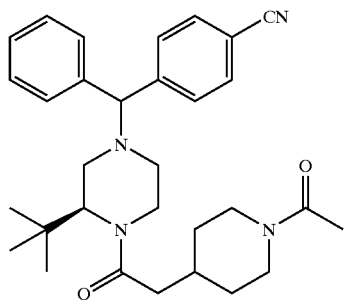
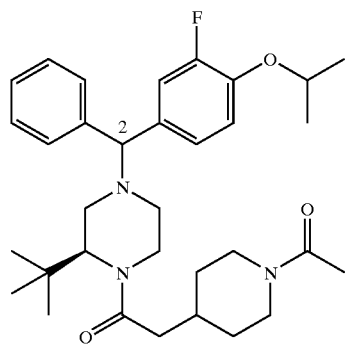
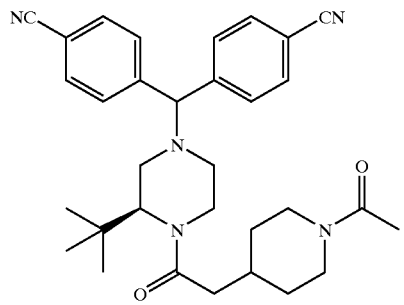
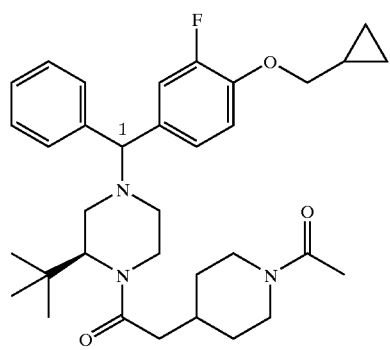
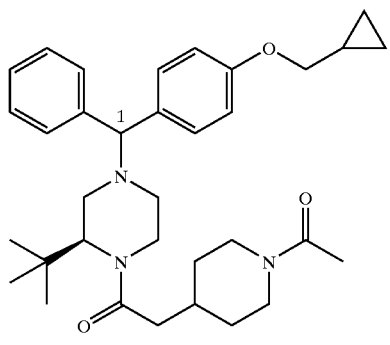

-continued
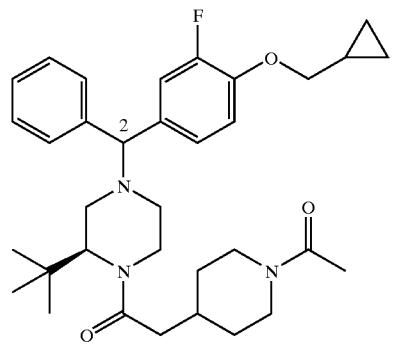
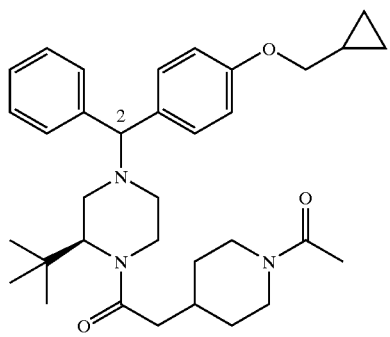
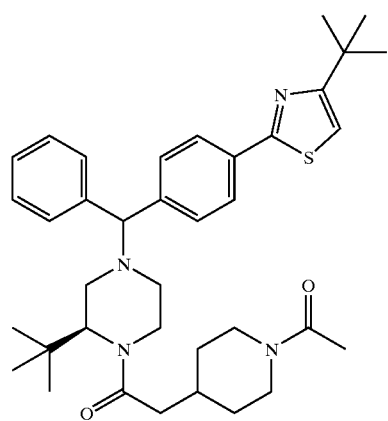
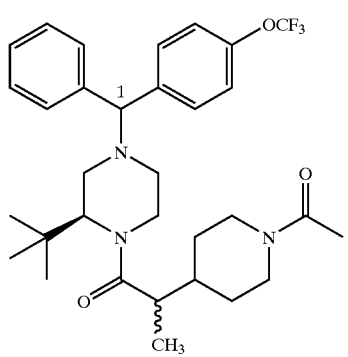
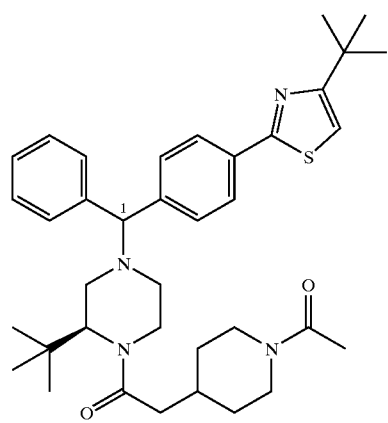
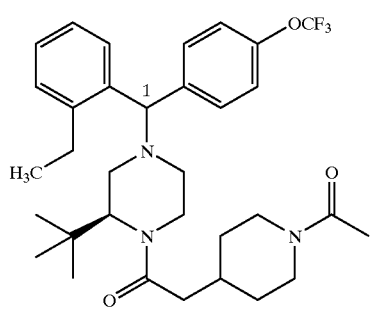
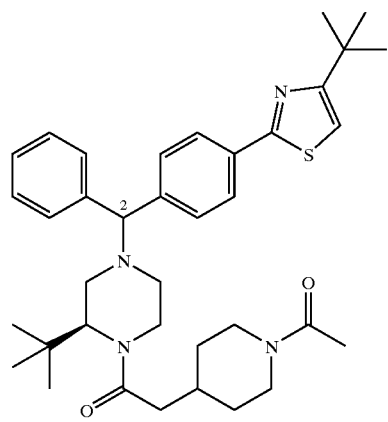
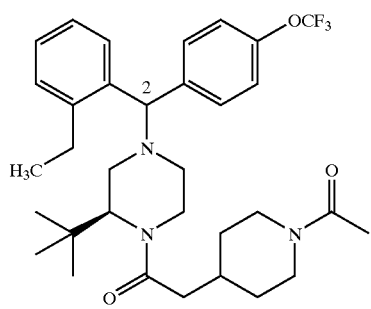

-continued
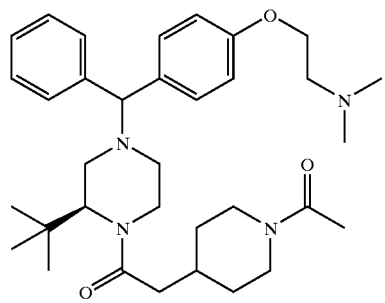 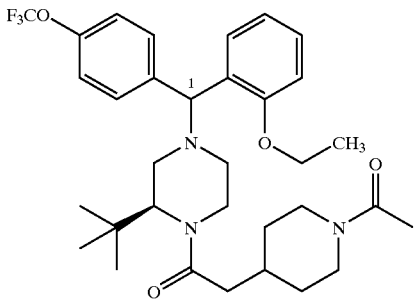
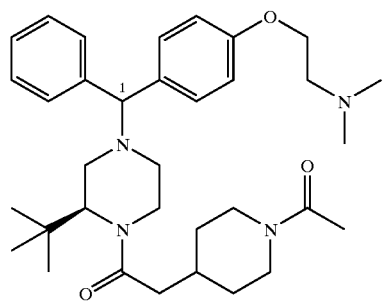 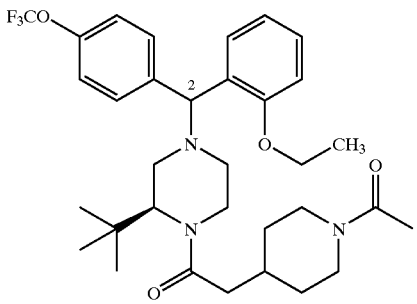
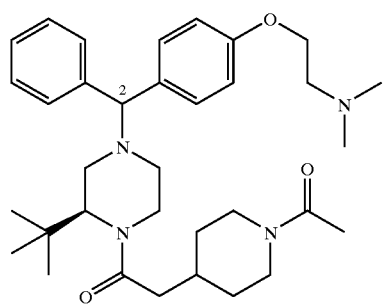 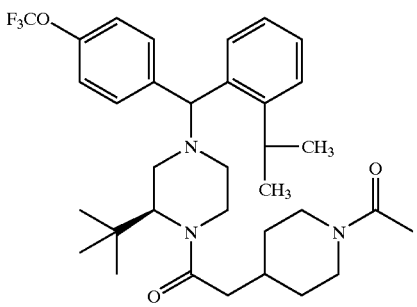
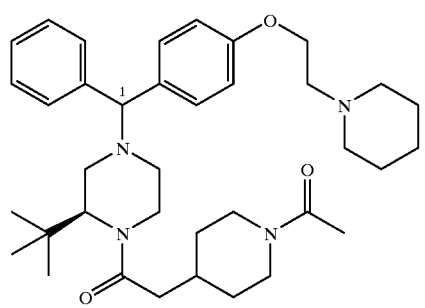 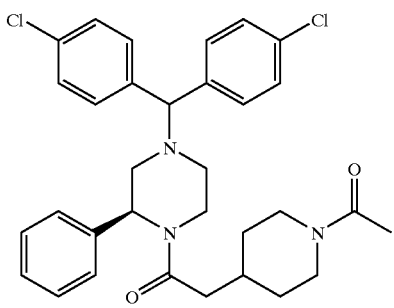
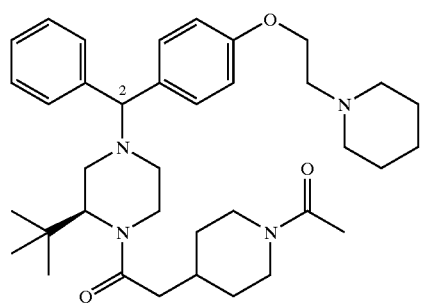 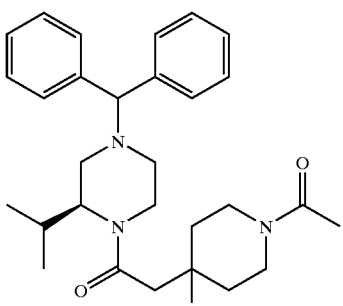

-continued
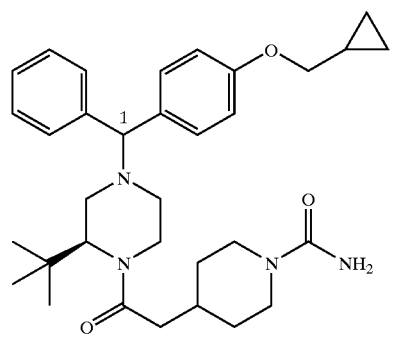 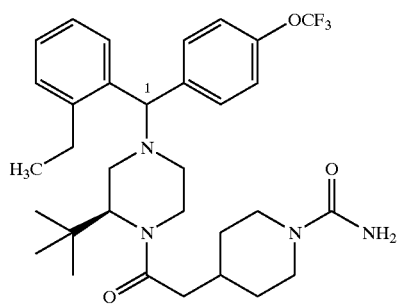
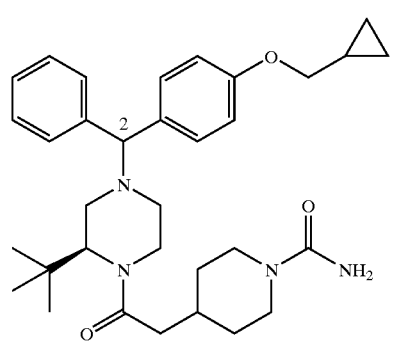 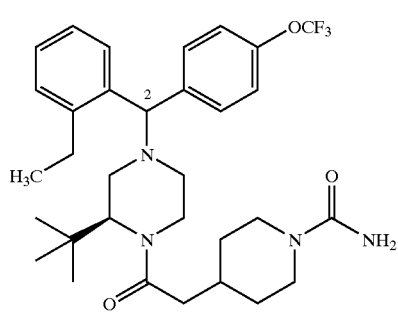
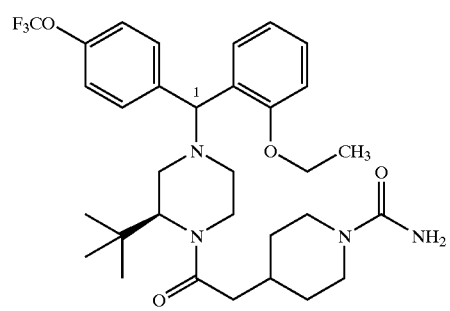 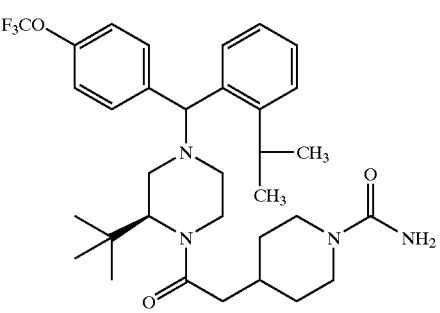
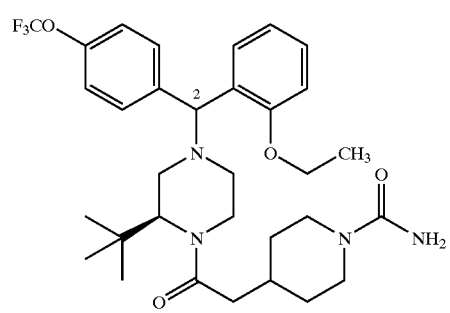 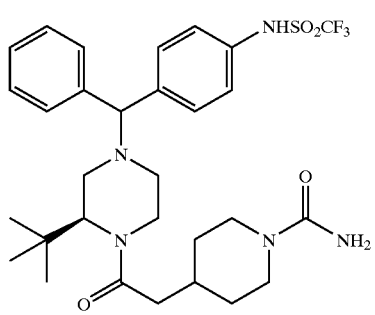
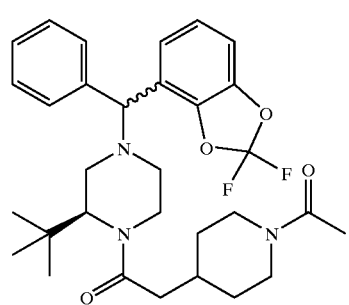 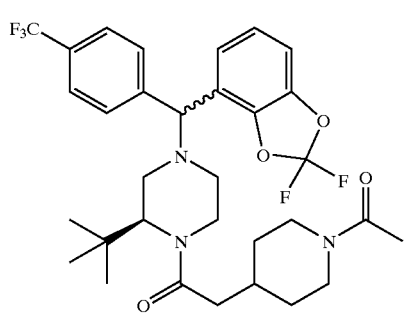

-continued
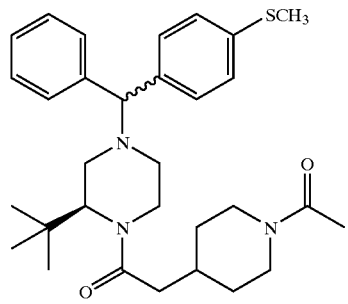 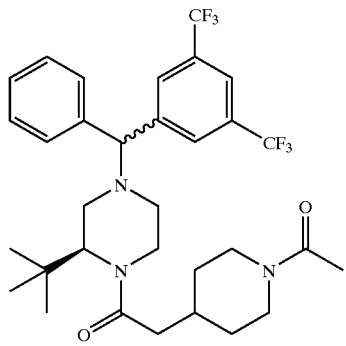
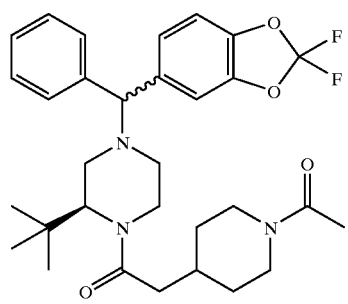 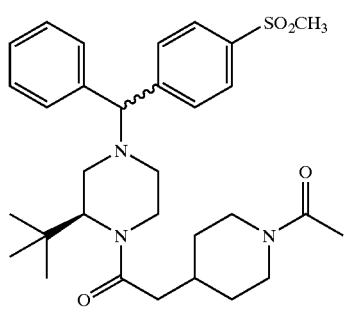
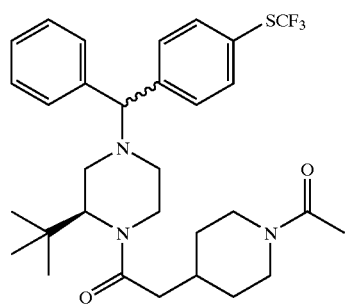 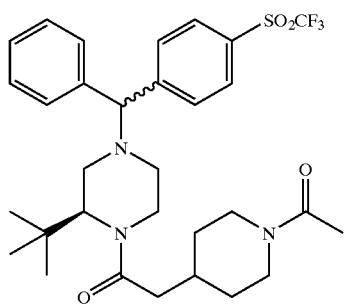
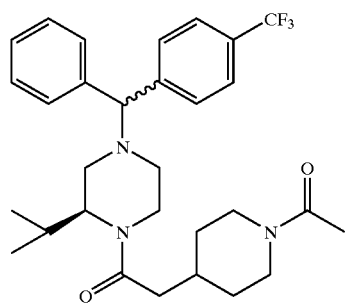 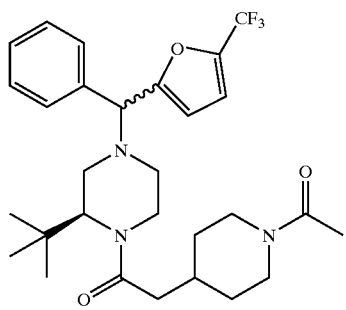
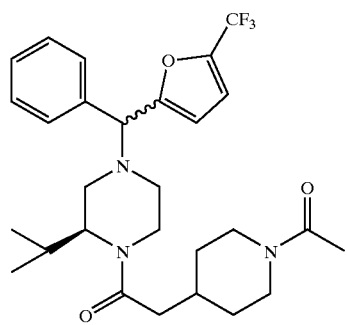 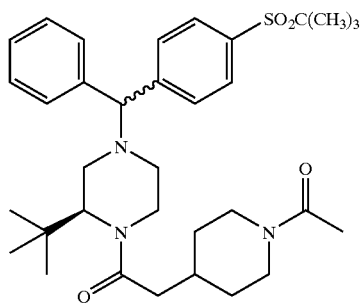

-continued
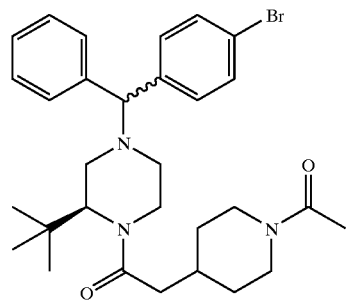 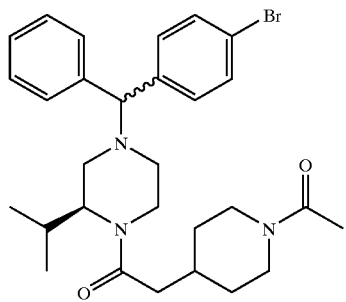
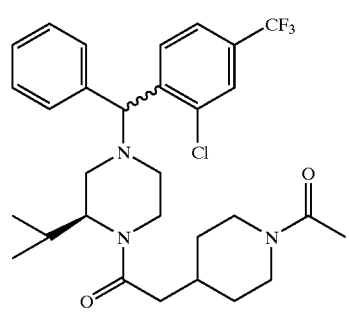 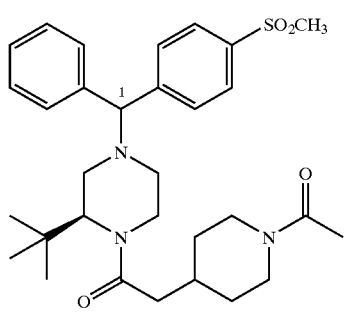
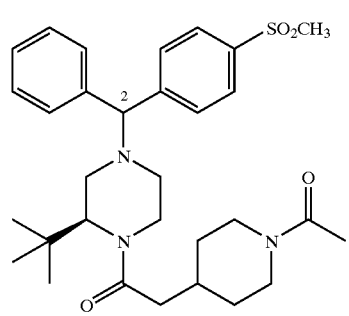 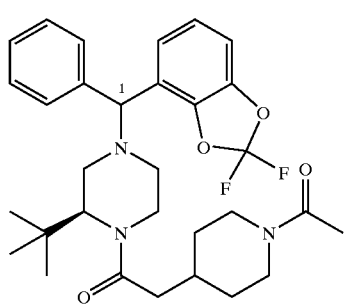
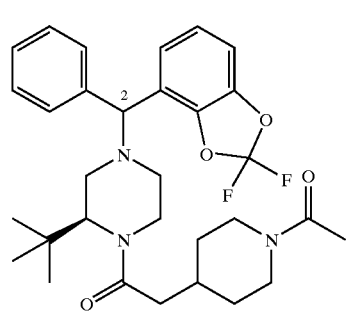 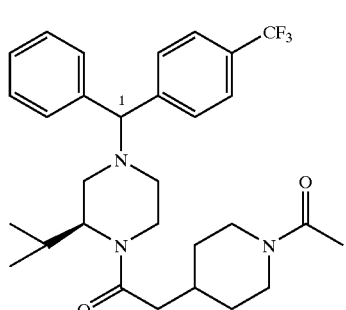
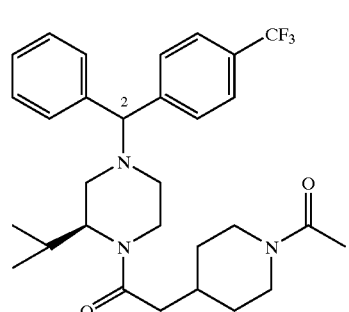 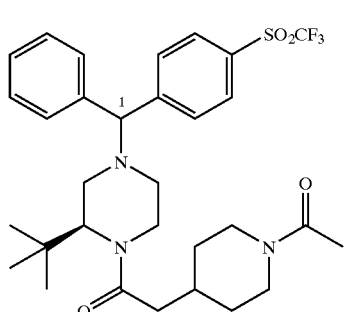

-continued
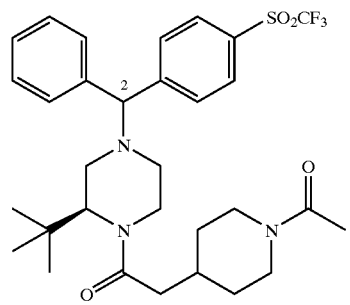
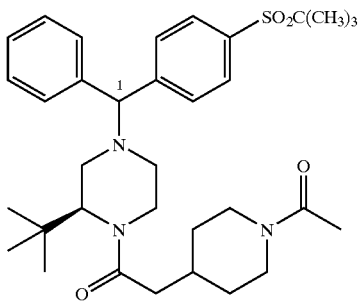
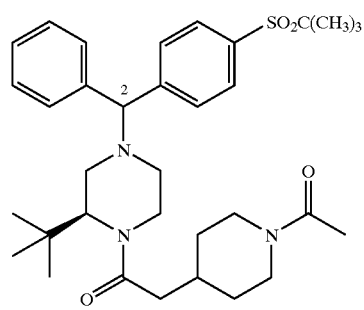
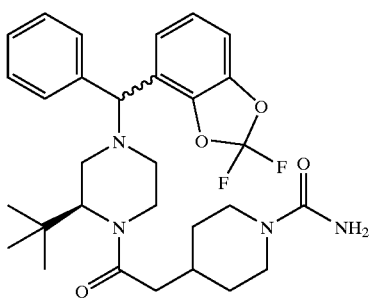
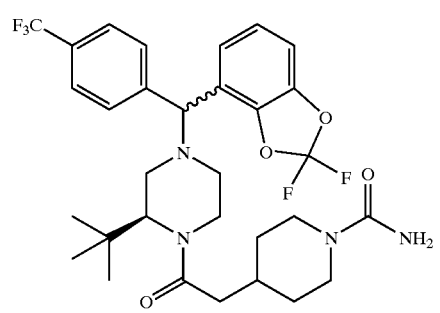
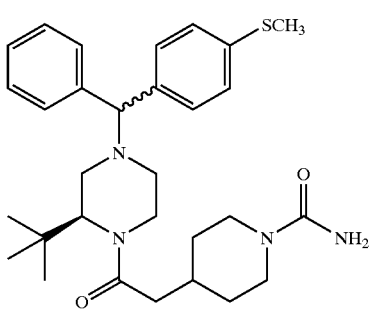
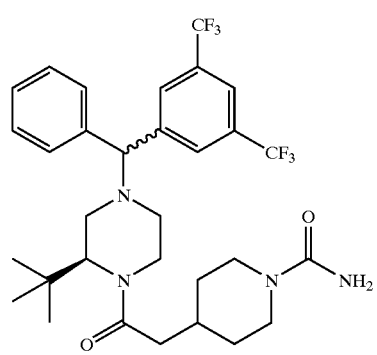
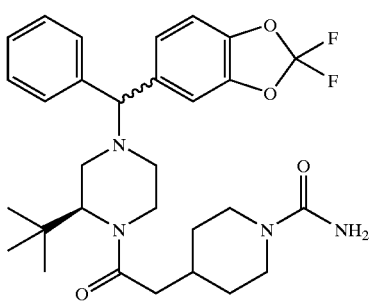
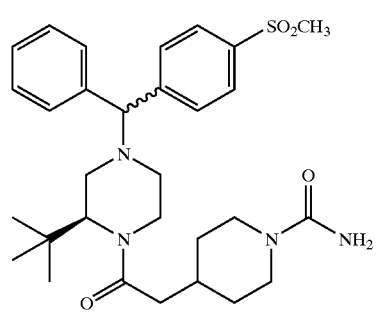
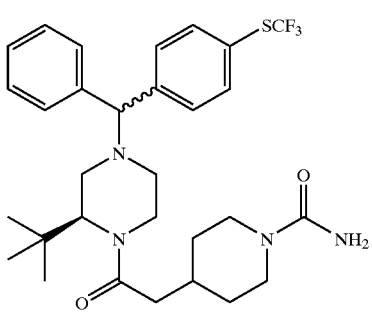

-continued
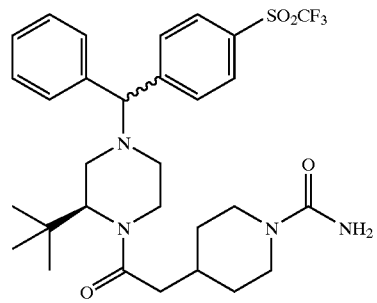
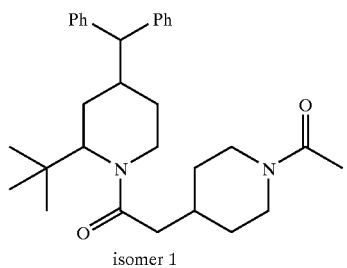
isomer 1
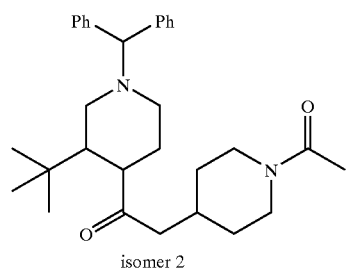
isomer 2
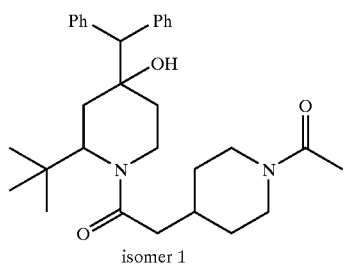
isomer 1
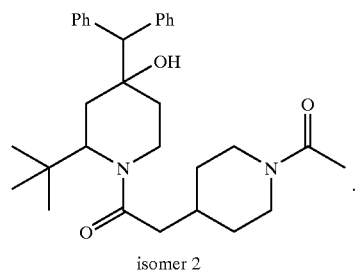
isomer 2
8. A compound, or a pharmaceutically acceptable salt of said compound, said compound being selected from the group consisting of:
-continued
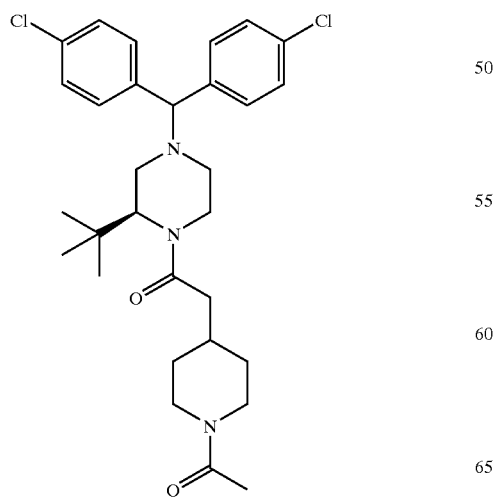
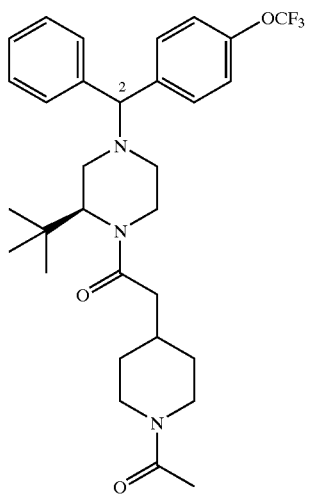

467
-continued
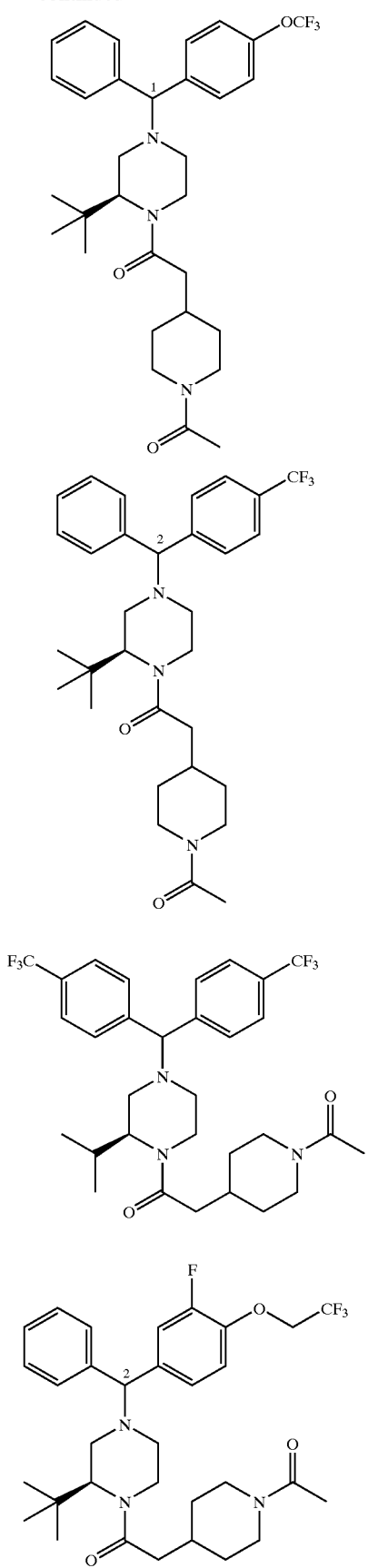
468
-continued
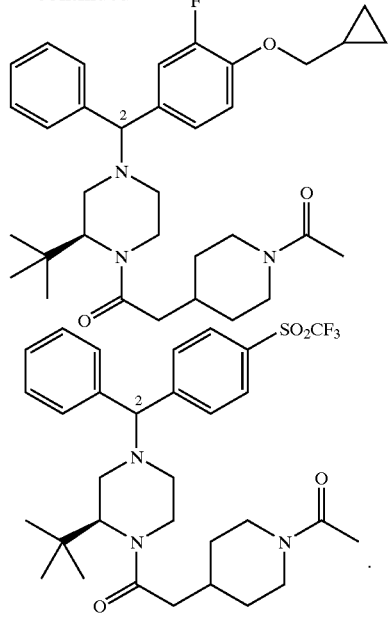
9. The compound according to claim 8, which is:
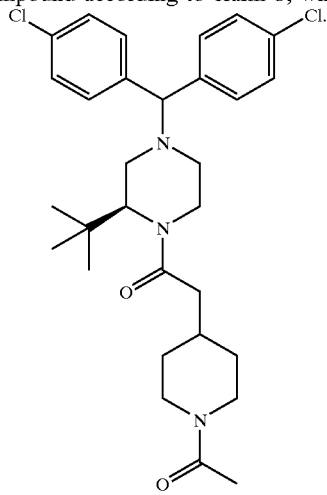
10. The compound according to claim 8, which is:
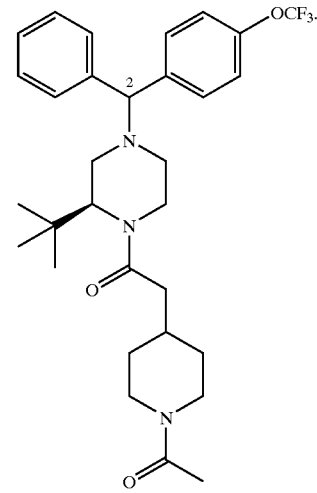

11. The compound according to claim 8, which is:

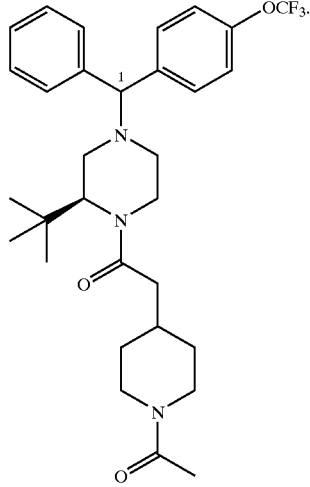

12. The compound according to claim 8, which is:

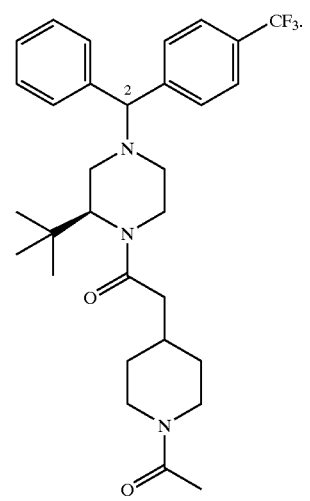

13. The compound according to claim 8, which is:

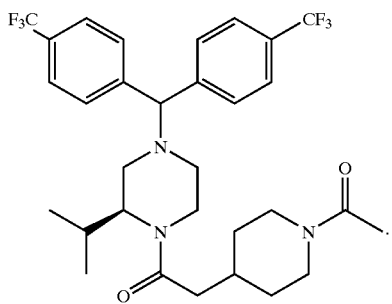

14. The compound according to claim 8, which is:

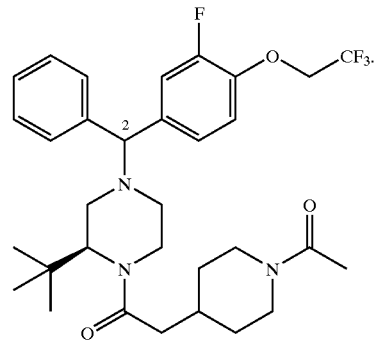

15. The compound according to claim 8, which is:

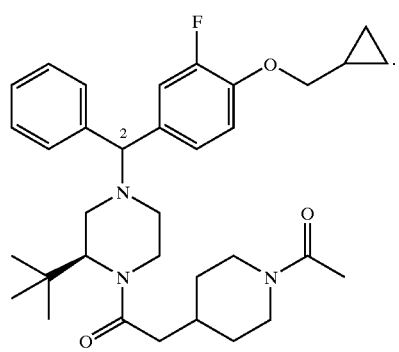

16. The compound according to claim 8, which is:

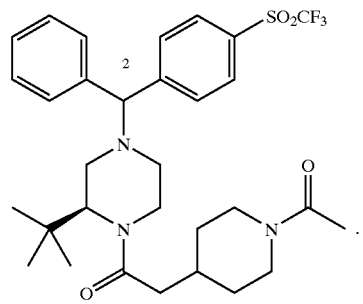

17. A pharmaceutical composition comprising the compound of claim 1, and a pharmaceutically acceptable carrier therefor.

18. A method of treating an androgen dependent disease selected from the group consisting of prostate cancer, benign prostatic hyperplasia, prostatic intraepithelial neoplasia, hirsutism, acne, androgenic alopecia and polcystic ovary syndrome.

19. The method of claim 18, wherein the androgen dependent disease is selected from the group consisting of prostate cancer, benign prostatic hyperplasia and prostatic intraepithelial neoplasia.

20. A method of inhibiting Type 3 17β-hydroxysteroid dehydrogenases, which comprises administering to a patient a therapeutically effective amount of the compound of claim 1, or a pharmaceutically acceptable salt thereof.

21. A method of inhibiting Type 3 17β-hydroxysteroid dehydrogenases, which comprises administering to a patient a therapeutically effective amount of at least one compound, or a pharmaceutically acceptable salt of said compound, said compound being selected from the group consisting of:

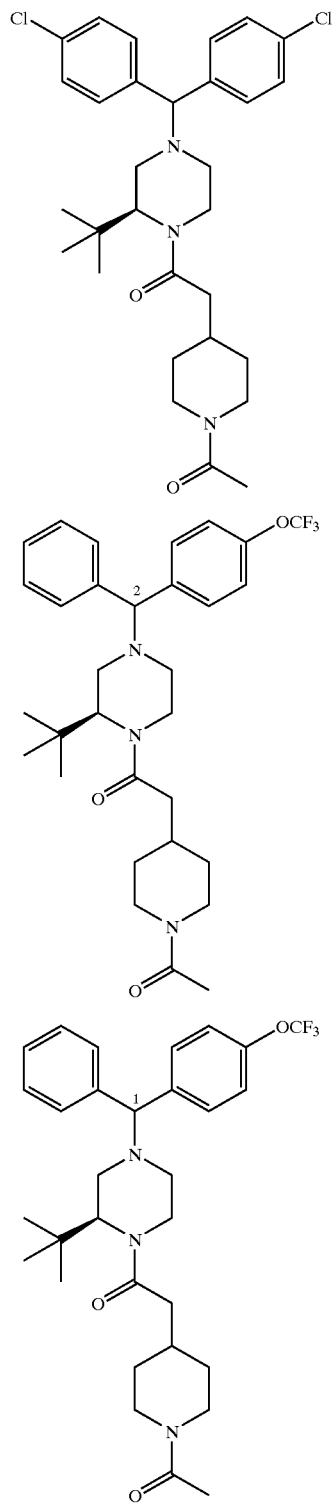

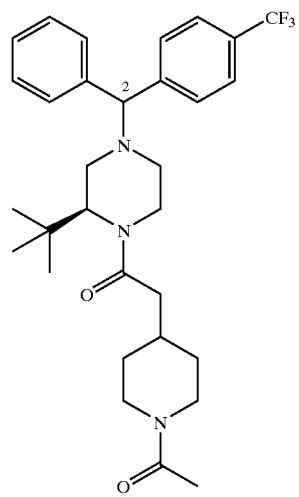

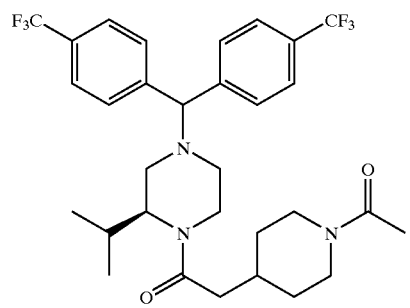

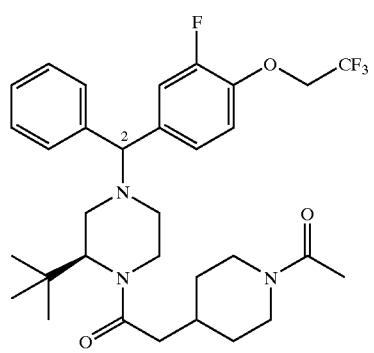

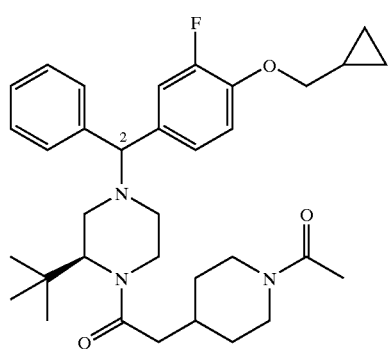

-continued

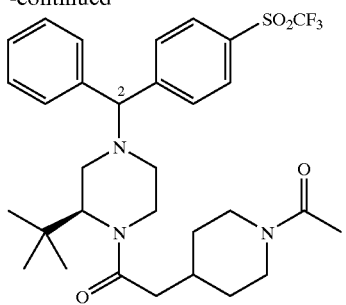

22. A method of inhibiting Type 3 17β-hydroxysteroid dehydrogenases, which comprises administering to a patient a therapeutically effective amount of a compound, or a pharmaceutically acceptable salt of said compound, said compound having the formula:

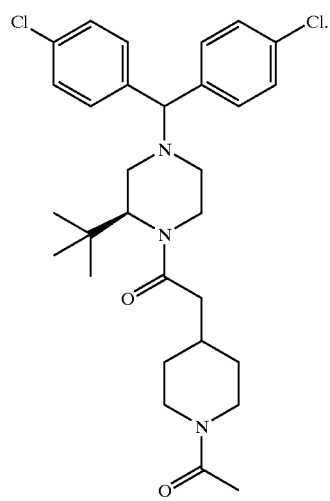

23. A method of inhibiting Type 3 17β-hydroxysteroid dehydrogenases, which comprises administering to a patient a therapeutically effective amount of a compound, or a pharmaceutically acceptable salt of said compound, said compound having the formula:

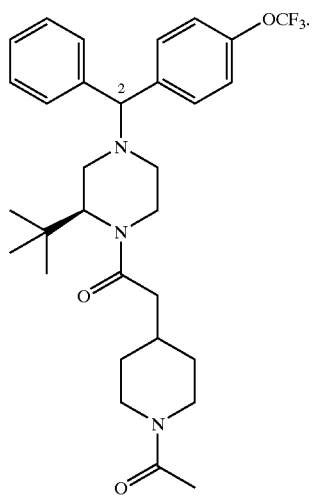

24. A method of inhibiting Type 3 17β-hydroxysteroid dehydrogenases, which comprises administering to a patient a therapeutically effective amount of a compound, or a pharmaceutically acceptable salt of said compound, said compound having the formula:

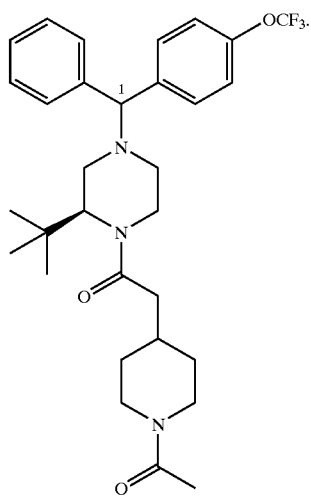

25. A method of inhibiting Type 3 17β-hydroxysteroid dehydrogenases, which comprises administering to a patient a therapeutically effective amount of a compound, or a pharmaceutically acceptable salt of said compound, said compound having the formula:

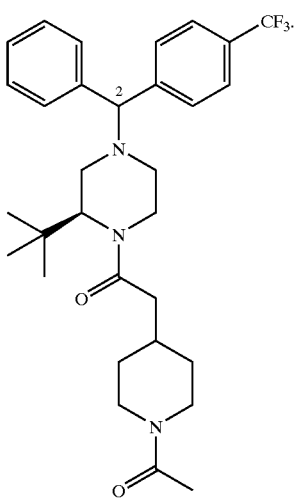

26. A method of inhibiting Type 3 17β-hydroxysteroid dehydrogenases, which comprises administering to a patient a therapeutically effective amount of a compound, or a pharmaceutically acceptable salt of said compound, said compound having the formula:

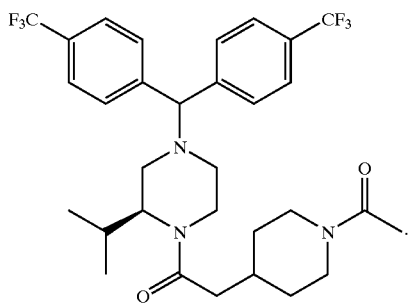

27. A method of inhibiting Type 3 17β-hydroxysteroid dehydrogenases, which comprises administering to a patient a therapeutically effective amount of a compound, or a pharmaceutically acceptable salt of said compound, said compound having the formula:

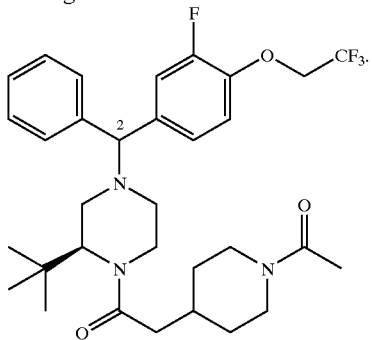

28. A method of inhibiting Type 3 17β-hydroxysteroid dehydrogenases, which comprises administering to a patient a therapeutically effective amount of a compound, or a pharmaceutically acceptable salt of said compound, said compound having the formula:

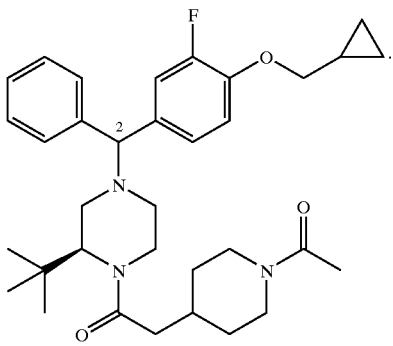

29. A method of inhibiting Type 3 17β-hydroxysteroid dehydrogenases, which comprises administering to a patient a therapeutically effective amount of a compound, or a pharmaceutically acceptable salt of said compound, said compound having the formula:

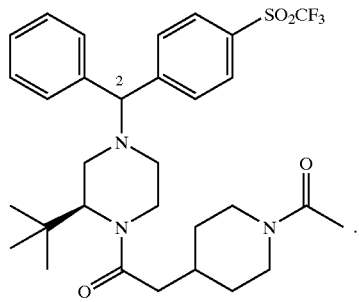

* * * * *

UNITED STATES PATENT AND TRADEMARK OFFICE
CERTIFICATE OF CORRECTION

PATENT NO. : 6,903,102 B2
DATED : June 7, 2005
INVENTOR(S) : Guzi, Timothy J.

It is certified that error appears in the above-identified patent and that said Letters Patent is hereby corrected as shown below:

Title page,
Item [75], Inventors, "Alan K. Mallams" the town should be corrected to
-- Hackettstown, NJ (US) --;
Item [56], References Cited, FOREIGN PATENT DOCUMENTS,
"1 122 242 A1" reference, "JP" should be -- EP --.

Column 428,
First structure should be corrected to:

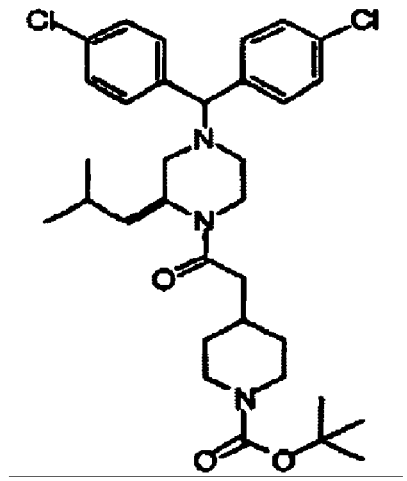

Signed and Sealed this

Thirtieth Day of August, 2005

JON W. DUDAS
*Director of the United States Patent and Trademark Office*